United States Patent
Schaper

(10) Patent No.: US 12,195,423 B1
(45) Date of Patent: Jan. 14, 2025

(54) ENCODED DESIGN INTEGRATED SYNTHESIS OF NUCLEIC ACIDS, AND PHOSPHOLIPIDS, AND RELATED PHARMACEUTICAL PRODUCTS

(71) Applicant: Charles Schaper, Vernon, CT (US)

(72) Inventor: Charles Schaper, Vernon, CT (US)

(*) Notice: Subject to any disclaimer, the term of this patent is extended or adjusted under 35 U.S.C. 154(b) by 0 days.

(21) Appl. No.: 18/641,122

(22) Filed: Apr. 19, 2024

Related U.S. Application Data

(60) Provisional application No. 63/534,831, filed on Aug. 27, 2023.

(51) Int. Cl.
- *C07C 43/23* (2006.01)
- *C07C 25/22* (2006.01)

(52) U.S. Cl.
CPC ............. *C07C 43/23* (2013.01); *C07C 25/22* (2013.01)

(58) Field of Classification Search
CPC ................................. C07C 43/23; C07C 25/22
See application file for complete search history.

(56) References Cited

U.S. PATENT DOCUMENTS

2009/0162693 A1* 6/2009 Ionkin ............. H05B 33/14 570/183

FOREIGN PATENT DOCUMENTS

| KR | 10-9019-0017274 | * | 2/2019 | ......... | H01L 51/0035 |
| WO | WO-2008120808 A1 | * | 10/2008 | ............ | C07C 13/62 |

OTHER PUBLICATIONS

Schaper, "Endogenous Binding of Steroid Molecules to DNA Nucleotides by a Ca2+/PO4− Process to Enable Gene Transcription," *ChemRxiv*, pp. 1-22 (2020). Retrieved online: https://doi.org/10.26434/chemrxiv.11868261.v2.

Schaper, "Intermolecular Enzymatic Encoding of Nucleic Acid, Steroid Complexes: A New Theory on the Chemical Origin of Life Based on Evidence of Structural Symmetry," *ArXiv*, pp. 1-43 (2020). Retrieved online: https://arxiv.org/abs/2006.06429.

Schaper, "New Code for DNA Nucleotide Sequences," *ChemRxiv*, pp. 1-16 (2020). Retrieved online: https://doi.org/10.26434/chemrxiv.12003786.v1.

Schaper, Structural Symmetry of DNA Nucleotides and Steroid Hormones, *ChemRxiv*, pp. 1-17 (2020). Retrieved online: https://doi.org/10.26434/chemrxiv.11991567.v1.

Wise et al., "Photoinduced Oxygen Transfer Using Nitroarenes for the Anaerobic Cleavage of Alkenes," *J. Am. Chem. Soc.*, 144(34):15347-15442 (2022).

Yu et al., "Palladium-Catalyzed Ring-Closing Reaction via C—N Bond Metathesis for Rapid Construction of Saturated N-Heterocycles," *J. Am. Chem. Soc.*, 142:18341-18345 (2020).

\* cited by examiner

*Primary Examiner* — Rosalynd A Keys

(74) *Attorney, Agent, or Firm* — Greenberg Traurig

(57) ABSTRACT

Provided herein are reactive aromatic molecules (e.g., substituted chrysene heterodimers) encodable as base-four sequences for the design and integrated synthesis of nucleic acids (e.g., DNA, RNA, hybrid DNA/RNA) and associated phospholipid bilayers (e.g., cellular membranes). For example, 3,6,9,12-tetrasubstituted chrysene is coupled with 6,12-disubstituted chrysene through π-electron stacking to form a base-four heterodimer. The orientation of the ring structure of the tetrasubstituted chrysene in this heterodimer comprises a base-two (binary) structure and the relative alignment of the ring structure of the disubstituted chrysene to the tetrasubstituted chrysene comprises a second independent base-two (binary) structure. This collectively results in a base-four (quaternary) complex composed of four independent reaction environments. Methods of using and forming these molecules and systems associated therewith are also described.

9 Claims, 83 Drawing Sheets

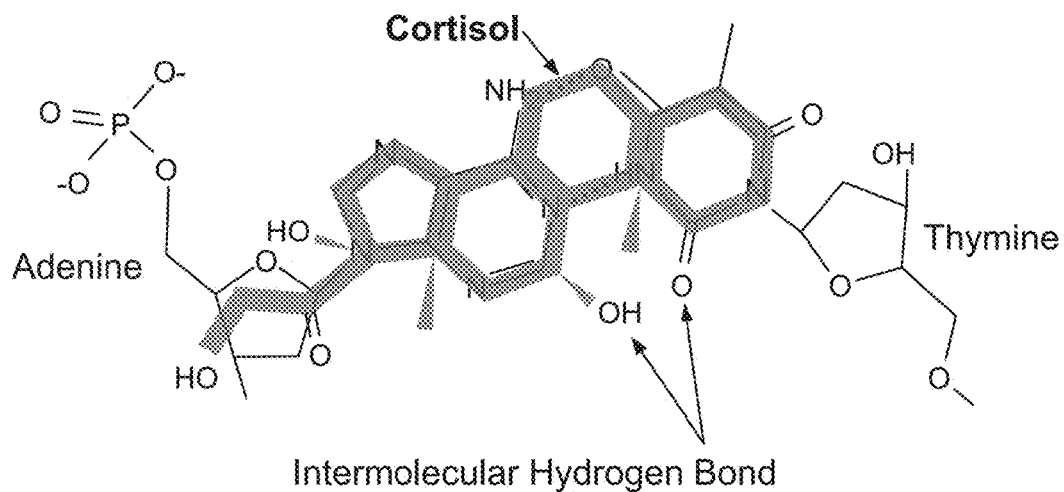
FIG. 1(f)
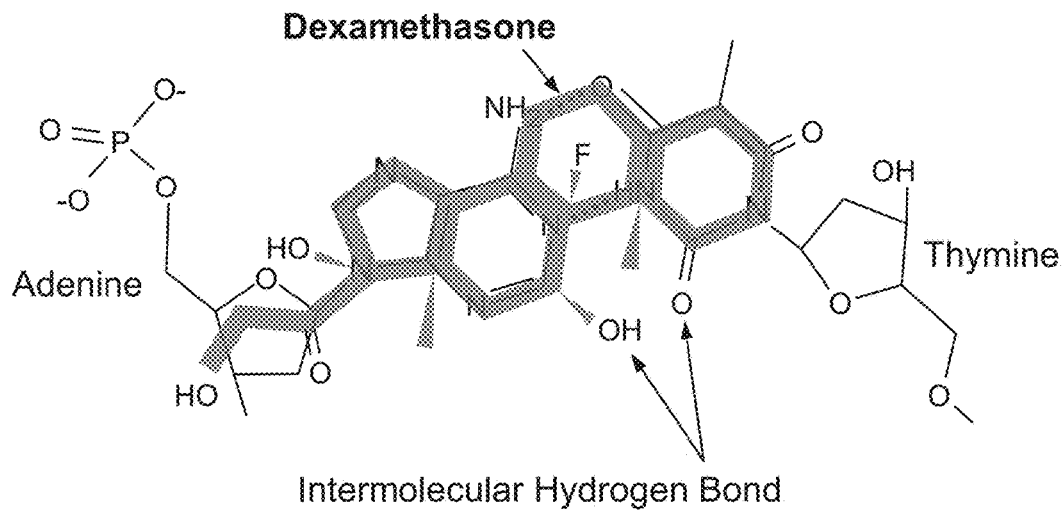
FIG. 1(g)
| Catalyst: Molecule 1 | Substrate: Molecule 2 | |
|---|---|---|
| Encoding Bit 1 (Endocrine) | Encoding Bit 2 (Common Structure) | |
| Intermolecular Relation | L-to-R Orientation | R-to-L Orientation |
| No Hydrogen Bond at ≈11 position | G-C | C-G |
| Hydrogen Bond at ≈11 position | A-T | T-A |
FIG. 1(h)

| Core | DNA | RNA | DNA | RNA |
|---|---|---|---|---|
|  | CU RD / CU LD | CU RR / CU LR | CU RD / CU LD | CU RR / CU LR |
| F/F | DNA-T:DNA-A | RNA-A:RNA-U | DNA-T:RNA-A | RNA-A:DNA-T |
| B/F | DNA-C:DNA-G | RNA-G:RNA-C | DNA-C:RNA-G | RNA-G:DNA-C |
| B/B | DNA-A:DNA-T | RNA-U:RNA-A | DNA-A:RNA-U | RNA-U:DNA-A |
| F/B | DNA-G:DNA-C | RNA-C:RNA-G | DNA-G:RNA-C | RNA-C:DNA-G |
|  | CU RD / CU LD | CU RR / CU LR | CU RR / CU LR | CU RD / CU LD |
| Core | DNA | RNA | RNA | DNA |

FIG. 5(c)

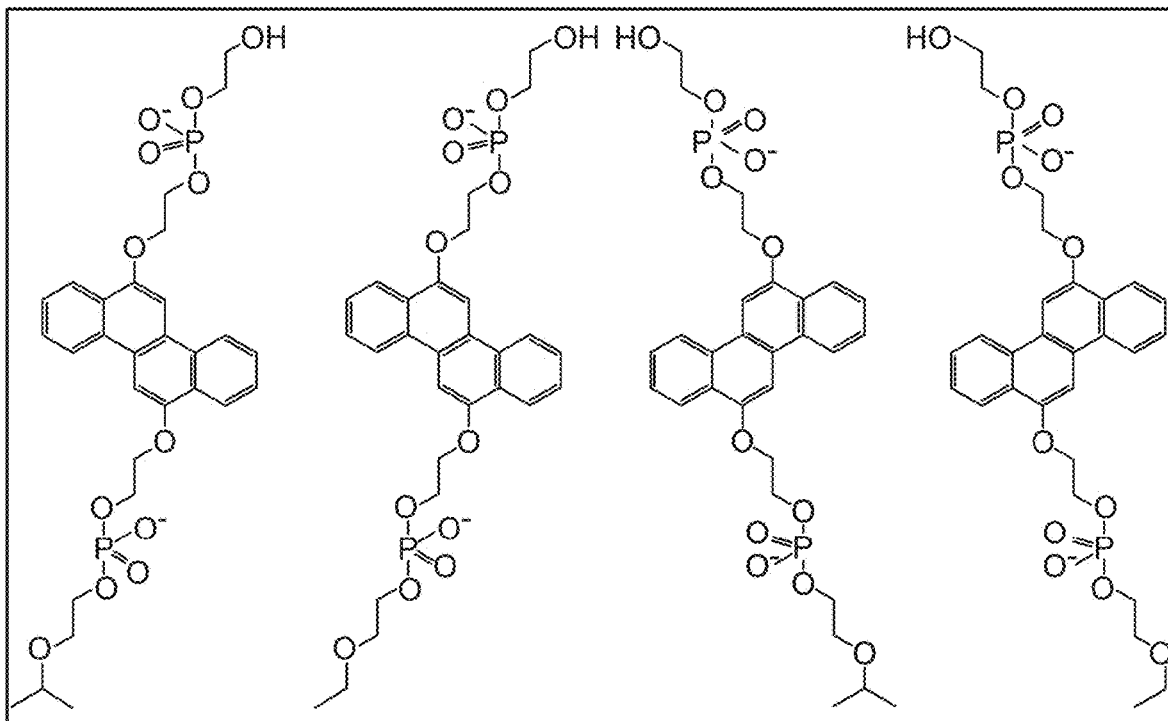
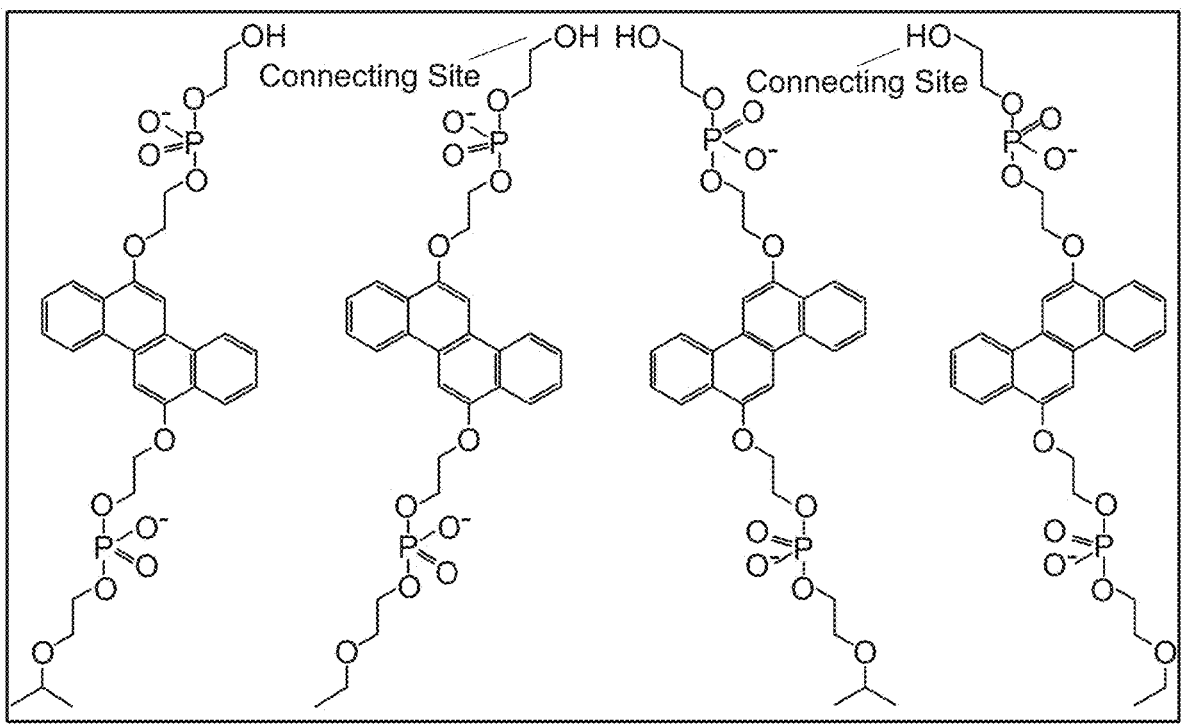
FIG. 9(b)

| Feature | Percent | Description |
|---|---|---|
| Atom economy of phosphorus | 100% | In constructing the substituted chrysene heterodimer, four atoms of phosphorus are used. After synthesis, two phosphorus atoms comprise the phosphodiester linkage of the nucleic acid chain and the other two phosphorus atoms comprise the phospholipid bilayer. |
| Atom economy of carbon | 100% | The 38 and 39 carbon atoms comprising AUCG RNA or ATCG DNA nucleotides, respectively, are all derived from 3,6,9,12-tetraethoxylated chrysene, with the remainder of the SCH substrate and catalyst enabling hydrophilic heads and hydrophobic tails of associated phospholipid bilayer molecules. |
| External requirement of carbon | 0% | In forming the nucleic acid and phospholipid molecules, no external carbon atoms are needed. The entire assembly of SCH units is self-sufficient and thus opens the possibility where the carbon utilized in the construction of the SCH sequence may be uniquely altered in some useful fashion (for example, improved regioselective reactivity). |
| External requirement of nucleic acids | 0% | The SCH assembly through a frameless sequencing encoding mechanism has capability to produce DNA, RNA, hybrid DNA/RNA within the same assembly and thus does not require external nucleic acid to self-replicate after synthesis. |
| External requirement of a cell | 0% | The SCH produces both the nucleic acids and the phospholipids through synthesis and self-separation, and thus a cellular construct externally provided is not required |
| Natural starting materials | 100% | Chrysene is a naturally derived compound individually, and also may be derived through flakes of graphite/graphene, of which the structure associated with the directions of 3,9 and 6,12 achievable via orthogonal crack propagation. |
| Encoding | 100% | The SCH is formed through an encoding method and means relating the substituted chrysene orientation and alignment into base four map for nucleic acids and phospholipids. Thus, both genetic components of DNA and RNA, as well as cell membrane components, are completely encodable. |

FIG. 17

ENCODED DESIGN INTEGRATED SYNTHESIS OF NUCLEIC ACIDS, AND PHOSPHOLIPIDS, AND RELATED PHARMACEUTICAL PRODUCTS

CROSS REFERENCE TO RELATED APPLICATIONS

The present application claims priority to and the benefit of U.S. Application No. 63/534,831, filed Aug. 27, 2023, the entire contents of which are incorporated herein by reference.

FIELD OF DISCLOSURE

The present disclosure is related to reaction vessels capable of encoding one of four pieces of information. These reaction vessels may be used to transmit information, similarly to DNA/RNA. These reaction vessels may also be used to synthesize nucleic acid pairs and sequences thereof. Additionally, information from these reaction vessels provides for actives with polycyclic cores having increased efficacy due to promotion of various binding effects.

BACKGROUND

As the carrier of genetic information and instruction set, DNA is central to cellular function of biological systems. DNA is a complex polymeric molecule comprised of pairs of nucleotides organized as nucleobases and deoxyribose sugars arranged along phosphodiester strands to form a base-four sequence. Methods for de novo synthesis of short fragments of DNA are processed through directed placement of monomers to build a single strand of DNA, which are then converted to double strand DNA through enzymatic methods.

While such methods are useful to build polynucleotides, there is limitation as to the number of bases synthesized. In addition, synthesis strategies for direct production of other nucleic acids, such as RNA and hybrid DNA/RNA, particularly as it relates to rRNA and tRNA, are not apparent. Synthesis techniques do not use molecules for DNA that are significantly different than the final form, but generally work from monomeric versions, and thus will have limitations in handling the materials like the final molecule. Synthesis methods for nucleic acids that offer longer genomes and utilize materials that provide enhanced handling and transport mechanisms would be of significant benefit in biological research and product development.

Current synthesis techniques for DNA and the cell generally employ molecules or monomers individually and piece them together to form the resultant oligonucleotide. Alternative synthesis schemes that aim for a deeper understanding of DNA and the cell as it pertains to their origins generally consider the two entities separately. Moreover, DNA syntheses starting from fundamental precursors generally ignore the inherent base-four encoding scheme. Instead, these strategies often seek a random occurrence wherein molecules randomly self-organize to eventually synthesize as to a DNA molecule, which in turn randomly couples with a phospholipid cellular membrane to propagate via gene expression. Initiation of gene expression is also considered as a random occurrence. These random events provide unknown variability and ambiguity in DNA and cellular production.

Furthermore, DNA requires an interactive cellular construct for biological implementation, of which DNA synthesis strategies do not address. There is a distinct relationship between DNA and the cell in many types of diseases and disorders. For example, DNA mutations impact neoplastic progression, affecting cellular processes of growth, survival, and repair, as a hallmark of cancer. The replicative potential of the cell is affected by proto-oncogenes and tumor suppressor genes responsive to DNA damage. Although the relation is clear between DNA and the cell, de novo synthesis methods consider DNA and cell separately. A synthesis method that considers DNA, or more generally nucleic acids, and its phospholipid cellular enclosure concurrently would be a significant advancement to the biological sciences.

It is therefore an object of this disclosure to address these problems associated with current DNA synthesis and information transmission in a biological system. An integrated synthesis strategy for concurrent DNA and phospholipids that explicitly utilizes the information content of DNA expressed through a base-four encoding system would provide a significant benefit for research and development of DNA and the cell from fundamental precursors, which can have application in regenerative medicine, genetic engineering, and other fields.

SUMMARY

In accordance with the foregoing objectives and others, the present disclosure provides such integrated synthesis strategies. The integrated synthesis strategy of the present disclosure involves leveraging relative molecular orientations to encode the standard coding sequences of DNA and RNA. A common molecular structure, which may be comprised of a fusion of four-rings in the shape of a steroid molecule, is identified within the structure of each nucleotide pair. Orientation of this common structure can be used to chemically retain and encode the relevant genetic information of DNA and RNA. Via chemical syntheses, often involving cascade mechanisms, compounds coupled (e.g., via covalent conjugation, dimerization) in specific relative orientations from a set of substituents of the common molecular structure can be used to construct the base pairs, and strands of DNA/RNA. Additionally, through the use of different conjugation patterns on the common structure, scaffolds are created, which may form the DNA/RNA base pairs, and others which form phospholipids present in cellular membranes.

The base-four DNA molecule may be characterized by two base-two molecules as follows:
 (1) a first base-two molecule as a tetra-ring molecule providing a molecular shape common to each DNA nucleotide pair composing the base-four characteristic of DNA to differentiate between purine and pyrimidine along one strand ((A-T; G-C) versus (T-A; C-G));
 (2) a second base-two molecule as a tetra-ring molecule providing intermolecular connectivity with the unpaired ketone of thymine in the adenine-thymine nucleotide pair to differentiate hydrogen-bonding capacity ((A-T;T-A) versus (G-C;C-G)).

In this aspect, collectively the two tetra-ring base-two molecules encompass the information content of the base-four DNA molecule because of the one-to-one correspondence between the two base-two molecules (comprising a set of four possible orientations) and the—resultant base-four molecules of DNA (comprising a set of four possible base pairings in DNA).

The base-two molecules may be synthesized from a polycyclic (e.g., polyaromatic) molecule such as chrysene, which is of four aromatic rings arranged in a manner consistent with the common shape of DNA nucleotide pairs.

Compounds (e.g., the base-two molecule, compounds used for synthesis of the base-two molecule) are provided which may have the structure:

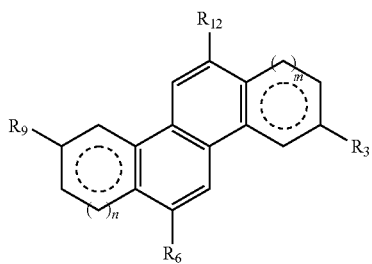

wherein the dotted circles independently indicate optional aromaticity, m and n are independently 0 (i.e., a bond) or 1, $R_3$, $R_6$, $R_9$, and $R_{12}$ are independently hydrogen, halogen (e.g., F, Cl, Br), hydroxylalkyl (e.g., $C_{1-6}$ hydroxylalkyl) optionally substituted with hydroxy or —COOH, hydroxylalkoxy (e.g., optionally unsubstituted $C_{1-6}$ hydroxyalkoxy such as hydroxyethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), —OCH$_2$COOH, —OCOCH$_2$OH, —O(CH$_2$)$_{1-6}$OPO(OH)$_2$, —O(CH$_2$)$_{1-6}$O(P(O)(OH)(O))$_{0-6}$(CH$_2$)$_{1-6}$OR, and at least one (e.g., at least two, at least three) of $R_3$, $R_6$, $R_9$, and $R_{12}$ is not hydrogen, or $R_6$ and/or $R_{12}$ may be optionally:

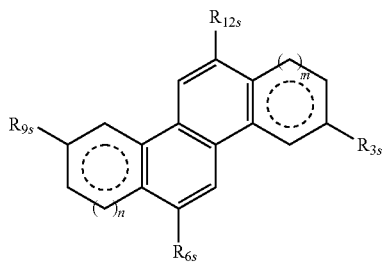

$R_{3s}$, $R_{6s}$, $R_{9s}$, and $R_{12s}$ are independently hydrogen, halogen (e.g., F, Cl, Br), hydroxylalkyl (e.g., $C_{1-6}$ hydroxyalkyl) optionally substituted with hydroxy or —COOH, hydroxylalkoxy (e.g., optionally unsubstituted $C_{1-6}$ hydroxyalkoxy such as hydroxyethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), —OCH$_2$COOH, —OCOCH$_2$OH, —O(CH$_2$)$_{1-6}$OPO(OH)$_2$, —O(CH$_2$)$_{1-6}$O(P(O)(OH)(O))$_{0-6}$(CH$_2$)$_{1-6}$OR; and R is independently at each occurrence hydrogen, alkyl (e.g., lower alkyl, $C_{1-6}$ alkyl), or acyl (e.g., $C_{1-20}$ acyl, $C_{1-6}$ acyl); or salts (e.g., alkali salts such as sodium salts or lithium salts, alkaline earth salts, quaternary ammonium salts, pyridinium salts) thereof. In various embodiments, $R_3$, $R_6$, $R_9$, and $R_{12}$ are independently hydrogen, hydroxylalkyl (e.g., $C_{1-6}$ hydroxyalkyl), hydroxylalkoxy (e.g., $C_{1-6}$ hydroxyalkoxy such as hydroxyethoxy), or hydroxylpolyethyleneoxy (e.g., —O(CH$_2$CH$_2$O)$_n$OH, where n is from 1 to 20 or from 1 to 8 or from 1 to 6). In certain aspects, $R_6$ and $R_{12}$ are not hydrogen. In some implementations, $R_9$ is not hydrogen. In some embodiments, $R_3$ and/or $R_9$ are hydrogen. In some aspects, $R_3$, $R_6$, $R_9$, and $R_{12}$ are hydroxylalkoxy (e.g., $C_{1-6}$ hydroxyalkoxy such as hydroxyethoxy). In certain implementations, $R_{3s}$ and $R_{9s}$ are hydrogen. For example, the compound may be:

2,2'-(chrysene-6,12-diylbis(oxy))bis(ethan-1-ol),
2,2',2"-(chrysene-3,6,12-triyltris(oxy))tris(ethan-1-ol),
2,2',2",2'''-(chrysene-3,6,9,12-tetrayltetrakis(oxy))tetrakis(ethan-1-ol),
6,12-dibromochrysene,
3,6,12-tribromochrysene, or
3,6,9,12-tetrabromochrysene.

The compounds may be used for forming a π-electron stacked sequence of molecules to contain a base two or base four information set, wherein each member of the information set is determined by the relative intramolecular spatial positioning of the aromatic rings.

Systems (e.g., for encoding information, for synthesizing DNA/RNA and hybrids thereof, for synthesizing phospholipids and cellular membranes) such as reaction vessels of the present disclosure are also provided which may comprise a first compound comprising a first polycyclic aromatic ring structure and a second compound comprising a second polycyclic aromatic ring structure, wherein the π structures of the first and second polycyclic aromatic rings interact (e.g., overlap, bond) to form a heterodimer, wherein the interaction between the π structures can have at least two different orientations of the heterodimer (e.g., Aligned, Unaligned). In some embodiments, the first compound has the structure:

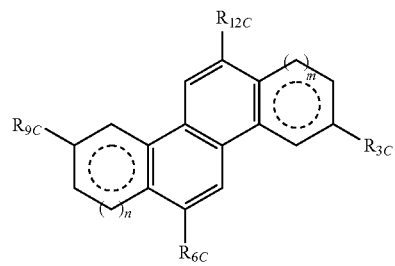

wherein the dotted circles independently indicate optional aromaticity, m and n are independently 0 (i.e., a bond) or 1, $R_{3c}$, $R_{6c}$, $R_{9c}$, and $R_{12c}$ are independently hydrogen, halogen (e.g., F, Cl, Br), hydroxylalkyl (e.g., $C_{1-6}$ hydroxylalkyl) optionally substituted with hydroxy or —COOH, hydroxylalkoxy (e.g., optionally unsubstituted $C_{1-6}$ hydroxyalkoxy such as hydroxyethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), —OCH$_2$COOH, —OCOCH$_2$OH, —O(CH$_2$)$_{1-6}$OPO(OH)$_2$, —O(CH$_2$)$_{1-6}$O(P(O)(OH)(O))$_{0-6}$(CH$_2$)$_{1-6}$OR, and at least three of $R_{3c}$, $R_{6c}$, $R_{9c}$, and $R_{12c}$ is not hydrogen, R is independently at each occurrence hydrogen, alkyl (e.g., lower alkyl, $C_{1-6}$ alkyl), or acyl (e.g., $C_{1-20}$ acyl, $C_{1-6}$ acyl); or salts (e.g., alkali salts such as sodium salts or lithium salts, alkaline earth salts, quaternary ammonium salts, pyridinium salts) thereof, and the second compound has the structure:

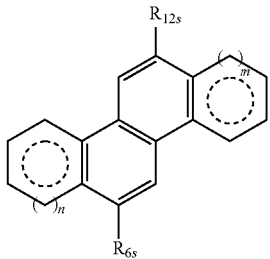

wherein $R_{3s}$, $R_{6s}$, $R_{9s}$, and $R_{12s}$ are independently hydroxylalkyl (e.g., $C_{1-6}$ hydroxyalkyl) optionally substituted with hydroxy or —COOH, hydroxylalkoxy (e.g., optionally unsubstituted $C_{1-6}$ hydroxyalkoxy such as hydroxylethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), oxalate (—OC(O)C(O)OH), —OCOCH$_2$OH, or —O(CH$_2$)$_{1-6}$(OP(O)(OH))$_{0-3}$O(CH$_2$)$_{1-6}$OR, and R is independently at each occurrence hydrogen, alkyl (e.g., lower alkyl, $C_{1-6}$ alkyl), or acyl (e.g., $C_{1-20}$ acyl, $C_{1-6}$ acyl); or salts (e.g., alkali salts such as sodium salts or lithium salts, alkaline earth salts, quaternary ammonium salts, pyridinium salts) thereof. In some embodiments, the first compound is 2,2',2"-(chrysene-3,6,12-triyltris(oxy))tris(ethan-1-ol), or 2,2',2",2'"-(chrysene-3,6,9,12-tetrayltetrakis(oxy))tetrakis(ethan-1-ol), and the second compound is 2,2'-(chrysene-6,12-diylbis(oxy))bis(ethan-1-ol).

In some embodiments, the heterodimer is a first heterodimer and the system further comprises a second heterodimer, wherein the π structures of the first and second heterodimer interact (e.g., overlap, bond) such that the interaction between the π structures of the first and second heterodimers can have at least four different orientations between the heterodimers (e.g., Aligned, Forward; Aligned, Backward; Unaligned, Forward; and Unaligned, Backward).

Methods of creating the information for a base two or base four code sequence are also provided comprising orienting a first molecule comprising a first polycyclic aromatic ring structure with a second molecule comprising a second polycyclic aromatic ring structure such that π structures of the first and second polycyclic aromatic rings interact (e.g., overlap, bond) to form a heterodimer, wherein the interaction between the π structures can have at least two different orientations of the heterodimer; and each member of the base two or base four code sequence is created by one of the at least two different orientations of the heterodimer. In various implementations, the first and second polycyclic aromatic ring structure each comprise four planar fused aromatic rings and no plane of symmetry perpendicular to the planar fused aromatic rings (e.g., $C_{2h}$ symmetry), the first polycyclic aromatic ring structure being substantially parallel to the second polycyclic aromatic ring structure in the heterodimer, and one of the at least two different orientations of the heterodimer, if viewed from a plane parallel to the planar fused aromatic rings, is a) the first molecule oriented with two rings above and to the left and two rings at the bottom and to the right, and the second molecule oriented with two rings at the top and to the right and two rings toward the bottom and to the left (e.g., G-C, C-G);

b) the first molecule oriented with two rings at the top and to the left and two rings toward the bottom and to the right, and the second molecule oriented with two rings at the top and to the left and two rings toward the bottom and to the right (e.g., U-A, A-U).

The first molecule may be 2,2'-(chrysene-6,12-diylbis(oxy))bis(ethan-1-ol) or analog thereof and the other molecule may be 2,2',2",2'"-(chrysene-3,6,9,12-tetrayltetrakis(oxy))tetrakis(ethan-1-ol) or analog thereof. In some embodiments, a base four code sequence is created by the relative orientations of two adjacent heterodimers. In various implementations, the first molecule is 2,2'-(chrysene-6,12-diylbis(oxy))bis(ethan-1-ol) or analog and the second molecule is 2,2',2"-(chrysene-3,6,12-triyltris(oxy))tris(ethan-1-ol) or analog, and the positional orientation of the 3' hydroxyethanoxy sidechain of the second molecules sets the base four code and the relative orientation of the adjacent heterodimer (e.g., the 5' direction the next heterodimer in a DNA or RNA sequence).

The base four molecule may be DNA. In certain embodiments, at least one member of the two nucleotide pairs is thymine, wherein the DNA is formed through a rotation of the nucleotide pair such that the motion of the methyl group of thymine ejects the catalyst from between the two nucleotide pairs. The substituent at the 3 or 12 position of each heterodimer may be phosphorylated and conjugated to the adjacent heterodimer via the 3 or 12 position via a sugar ring.

The base four molecule may be RNA. In various implementations, the base four molecule is RNA formed through the hydroxylation of the 2' carbon of the sugar ring which results in separation of the nucleotide from the catalyst by strand separation.

The starting materials for a synthesis method of the present disclosure may include substituted ethoxylate alcohols at the (6,12); (3,6,12) and (3,6,9,12) carbon positions of chrysene. These molecules, through π-electron interactions, may form a stacked assembly of molecules comprising an encoded sequence. This stacked assembly of molecules (an "SCH Complex" of the present disclosure) may comprise (6,12)-disubstituted chrysene (a "catalyst" of the present disclosure), coupled in an orientation with a (3,6,9,12)-tetrasubstituted chrysene (a "substrate" of the present disclosure) of which the pair are stacked with equivalent pairs oriented the same or dissimilar.

An encoded sequence of molecules may be formed by association of catalyst and substrate (and by adjacent associations of other catalysts and substrates). In this encoded sequence, the number of orientations involved in the coordination of the catalyst and substrate typically results in four effective reaction vessels constrained spatially due to the π-stacking arrangements of catalyst/substrate and adjacent catalyst/substrate pairs. The reaction vessels may be constrained chemically, with a hydrophobic core (e.g., aromatic ring structure) suspended in a hydrophilic medium (e.g., ethoxylated alcohol functionalization). This chemical constraint may create a driving force to result in aromatic compounds during a polymerization process to form phosphodiester linkages between catalysts and/or substrates. For example, the tetrasubstituted chrysene (e.g., substrate) may interact with the disubstituted chrysene (e.g., catalyst) in a substrate-catalyst relationship involving binding (e.g., non-covalent binding between substrate and binding). These substrate-catalyst pairings including multiple pairings such as substrate/catalyst/substrate/catalyst may be referred to herein as "SCH" or "SCH complex."

Each heterodimer of the intercalated set of heterodimers may be an independent reaction vessel independently used for encoding information, wherein each reaction vessel may have four possible configurations (relative from one of the outermost heterodimers) to form a base four code relative to an initiation sequence established by a first heterodimer (e.g., an initiator/catalyst heterodimer), and oxidative cleavage induces a cascade reaction that produces nucleotide pairs in each reaction vessel dependent on the configuration of the reaction vessel and the initiation sequence, in which A-U at 5' is (e.g., Forward, Forward), G-C is (e.g., Backward, Forward), U-A is (e.g., Backward, Backward) and C-G is (e.g., Forward,Backward) for RNA positioning of catalyst and substrate in the sequence, and the opposite code holds for DNA in which T-A is (e.g., Forward, Forward), C-G is (e.g., Backward,Forward), A-T is (e.g., Backward,Backward) and G-C is (e.g., Forward,Backward). The reaction vessels may comprise a set of at least four possible configurations which thereby form a base four code in which DNA and RNA represent a composite hybrid double strand with DNA nucleotides on one strand and RNA nucleotides on the other strand. The two compounds may be a substrate π stacked with a catalyst, wherein in the substrate, $R_3$, $R_6$, $R_9$, and $R_{12}$ are each not hydrogen and, in the catalyst, $R_3$ and $R_9$ are hydrogen, wherein the catalyst is phosphorylated at $R_6$ and $R_{12}$ and the catalyst separated from the substrate forms a phospholipid bilayer following the reaction and/or the substrate is phosphorylated at the $R_3$, $R_6$, $R_9$, and $R_{12}$ which form a nucleic acid backbone following the reaction.

The encoded sequence may be polymerized (e.g., through the formation of linkages such as phosphodiester linkages between adjacent substrates). Polymers are also provided which may comprise the monomer:

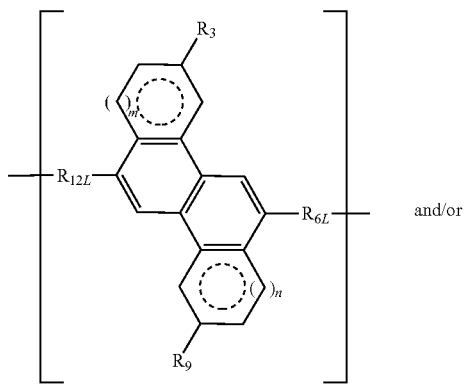

and/or

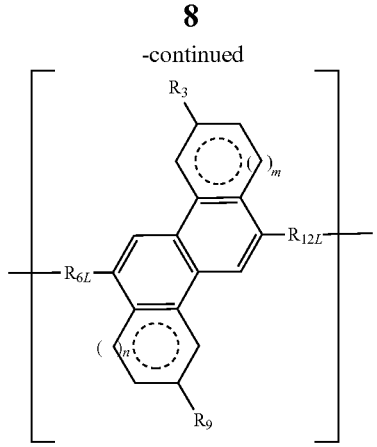

wherein the dotted circle indicates optional aromaticity, m and n are independently 0 (i.e., a bond) or 1, p and q are independently 1-6, $R_{6L}$, and $R_{12L}$ are independently —O(CH$_2$)$_{1-6}$O—, —OCH$_2$COO—, —OCOCH$_2$O—, —O(CH$_2$)$_{1-6}$OP(O)(OH)O(CH$_2$)$_{1-6}$O—, $R_3$ and $R_9$ are independently hydrogen, halogen (e.g., F, Cl, Br), hydroxylalkyl (e.g., $C_{1-6}$ hydroxyalkyl) optionally substituted with hydroxy or —COOH, hydroxylalkoxy (e.g., optionally unsubstituted $C_{1-6}$ hydroxyalkoxy such as hydroxylethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), —OCH$_2$COOH, —OCOCH$_2$OH, —O(CH$_2$)$_{1-6}$O(P(O)(OH)(O))$_{0-6}$(CH$_2$)$_{1-6}$OR; and R is independently at each occurrence hydrogen, alkyl (e.g., lower alkyl, $C_{1-6}$ alkyl), or acyl (e.g., $C_{1-20}$ acyl, $C_{1-6}$ acyl); or salts (e.g., alkali salts such as sodium salts or lithium salts, alkaline earth salts, quaternary ammonium salts, pyridinium salts) thereof. In some embodiments, the polymer is capped by a tri substituted polycyclic aromatic (e.g., 6, 9, 12 substituted chrysene), wherein the 9 position is conjugated to the polymerized monomer (e.g., to form the two indicated orientations). For example, the polymer may comprise one or more monomers having the structure:

In some embodiments, the polymer comprises one or more monomers having the structure:

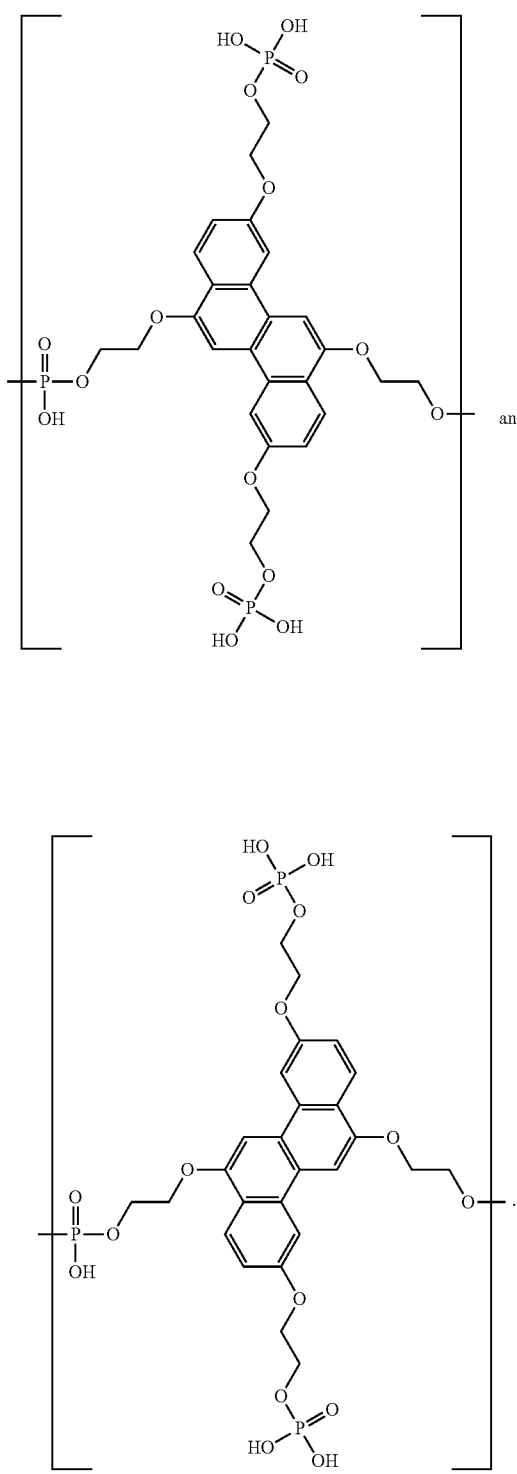

and/or

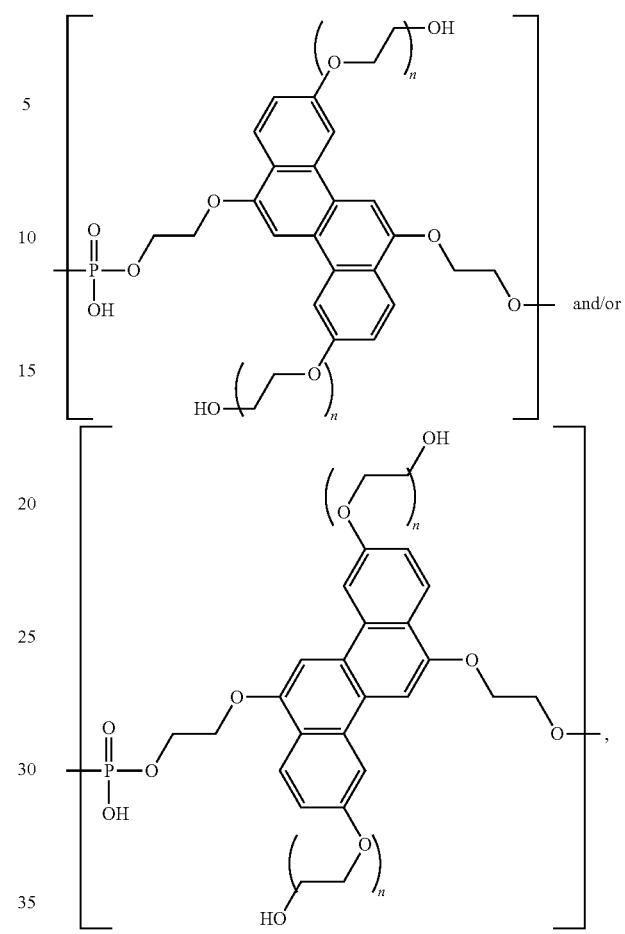

wherein n is independently selected at each occurrence from 1-6.

The synthetic methods of the present disclosure may involve reacting the substrate/catalyst, stack of substrate/catalysts, polymers and other systems of the present disclosure to result in either RNA, DNA, or hybrid DNA/RNA pairings. These pairings may be encoded according to the map of two base-two precursor tetra-ring aromatic molecules having the equivalency of one base-four molecule (e.g., A, T, G, C, U). In one embodiment, a reaction of the substrate/catalyst complex may be initiated that provides a stepwise reaction wherein oxidative cleavage breaks the four rings of the substrate open in a regioselective manner; followed by carbon-carbon bonding to produce sugar-rings on both sides of the substrate. Nitrogen insertions across alkenes may follow and ultimately result in closed-ring structures.

These reactions may result in RNA, DNA, or hybrid DNA/RNA based upon the sequence of stacked substrates/catalysts in the SCH complex. The sequence in the SCH complex may be identified by the orientation of the substrate and the alignment of the catalyst to the substrate. In some embodiments, the substrate/catalyst may provide relative orientations from a set of four possibilities (e.g., within the SCH complex). Association of side-groups of ketone or amines during synthesis to each reaction vessel may produce adenine-thymine, adenine-uracil, and/or cytosine-guanine pairings. The association of these side groups may be contingent on the relative orientation of the catalyst to the substrate (e.g., Aligned or Unaligned as described herein). The association of the substrate as to a purine or pyrimidine may be contingent upon the orientation of the substrate within the general sequence of all substrates (e.g. of the SCH complex).

A method of producing a base four molecule is also provided, wherein the method comprises:
inducing reaction from a heterodimer or from an intercalated or conjugated set of heterodimers each formed by π stacking of one compound (e.g., a molecule comprising substrate and catalyst moieties when $R_6$ and $R_{12}$ are conjugated to one another), two compounds (e.g., substrate and catalyst which form intramolecular bonds), or a system of the present disclosure, wherein the reaction comprises at least one of:
a) oxidative cleavage,
b) formation of carbon carbon rings (e.g., for closure of sugar-rings),
c) nitrogen insertions,
d) formation of N—C bonds for closure of inner rings,
e) oxygen and/or nitrogen side group modifications, and
f) catalyst-substrate separations.

The heterodimer may be formed from orienting 2,2'-(chrysene-6,12-diylbis(oxy))bis(ethan-1-01) or analog thereof with 2,2',2'',2'''-(chrysene-3,6,9,12-tetrayltetrakis(oxy))tetrakis(ethan-1-ol) or analog thereof. In some embodiments, the set of intercalated heterodimers is formed from orienting 2,2',2''-(chrysene-3,6,12-triyltris(oxy))tris(ethan-1-ol) or analog thereof with 2,2'-(chrysene-6,12-diylbis(oxy))bis(ethan-1-ol) or analog thereof to form a first heterodimer;
orienting 2,2'-(chrysene-6,12-diylbis(oxy))bis(ethan-1-ol) or analog thereof with 2,2',2'',2'''-(chrysene-3,6,9,12-tetrayltetrakis(oxy))tetrakis(ethan-1-ol) or analog thereof to form a second heterodimer, and
inducing π-stacking between the first and second heterodimer. In particular embodiments, the base four molecule is DNA or RNA or hybrid DNA/RNA,
the intercalated set of heterodimers is formed by pi stacking a tri or tetra substituted aromatic ring from one heterodimer with a di substituted aromatic ring from the adjacent heterodimer, and
the reaction is initiated by oxidative cleavage of the tri or tetra substituted aromatic ring system of two adjacent heterodimers, and reaction proceed via a reaction cascade to produce at least two nucleotide pairs having a catalyst comprising di substituted aromatic polycyclic ring system intercalated therebetween.

The catalyst for the RNA molecule formation may be released through strand separation by hydroxylation of the 2' carbon on one of the sugar-rings produced between substrates.

For DNA formation, the SCH complex may result in DNA nucleotides arranged in an inverted fashion. Catalyst release may be induced via this inversion, wherein rotation of the nucleotide pairings into a right-handed double helix releases the catalyst intercalated between reacted substrates. Mechanistically, the one additional methyl group of thymine (as compared to cytosine or uracil) may assist in the rotation and ejection of catalyst during DNA synthesis.

The catalyst, such as ejected catalyst or catalyst ejected from the SCH complex, may form phospholipids. For example, the catalyst may result in a phospholipid molecule with one hydrophobic head containing remnants of the nucleotide formation process.

The SCH complex may be capped with a regulatory molecule which may help regulate and define the orientations throughout the SCH complex. This regulatory molecule may be, for example, a tri-substituted polycyclic compound. For example, in one embodiment, a regulatory molecule is (3,6,12)-trisubstituted chrysene molecule. The regulatory molecule may initiate the reaction (e.g., the cascade and/or polymerization reaction resulting in DNA and/or RNA synthesis) in the 5' direction to 3' direction (of the resultant molecule comprising a sugar ring). Typically, the reaction does not propagate the polymerization in the 3' to 5' direction due to a missing sidechain of the regulatory molecule.

The regulatory molecule (and corresponding sequences) may determine the class (e.g., DNA vs RNA) and direction of nucleic acid (e.g., 5' to 3' direction). In one embodiment, the regulatory molecules are specified for RNA to form the first instruction set for cellular divisions, for RNA/DNA hybrids to form the ribosomal units comprising the genetic code, and for DNA for the instruction set after the first few cellular divisions. In one embodiment, the reaction mechanisms applied to the reaction vessel comprise chemistry procedures involving nitroarenes directed towards the substrate from the catalyst in a regioselective manner to achieve oxidative cleavage. In another embodiment, chemical pathways involving oxidative cleavage (particularly regioselective oxidative cleavage) may occur with substrate/catalyst pairings via ozonolysis or reaction with, for example, $KMnO_4$ or $OsO_4$. Oxidative cleavage may initiate the cascade reaction resulting in formation of DNA/RNA. In a preferred embodiment, features of the method comprise more than 90% (e.g., 100%) efficiency in atom economy for phosphorous atoms (e.g., from phosphoric acid) and/or more than 90% (e.g., 100%) efficiency in atom economy for carbon atoms; and/or no external requirement for carbon, nucleic acids, or phospholipid cells (e.g., the reaction includes only the SCH complex, a reactant to induce the oxidative cleavage, and optionally ammonia, sulfuric acid, nitric acid, water, phosphoric acid, and a metal or metal oxide such as zinc oxide or magnesium). In one embodiment, there is more than 90% (e.g., 100%) encoding of the complex of substituted chrysene heterodimers (e.g., each reaction vessel comprising substituted chrysene substrate/catalyst pairs results in more than 90% conversion to acid base pairs). In a preferred embodiment, the SCH complex results (e.g., via a cascade reaction initiated by oxidative cleavage) in DNA of a specific sequence and an associated phospholipid bilayer.

Leveraging the primers of the present disclosure (and possible associated hydrogen bonding implications thereof), pharmacological activity of various biological molecule can be achieved in direct or altered form. In addition to the direct form of the precursor molecular structure, synthetic compounds of an altered form may result in increased activity (as compared to compounds with a similar steroid core). These actives may be formulated in a pharmaceutical compositions. For example, active may have the structure:

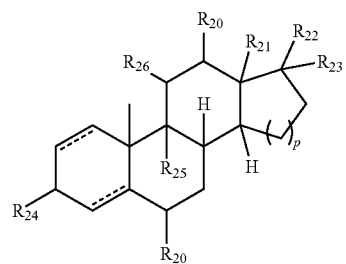

wherein the dashed lines represent optionally double bonds, and at least one of the dashed bonds is a double bond;

p is 0 (i.e., it is a bond) or 1;

$R_{20}$ is independently at each occurrence hydrogen, hydroxylalkoxy (e.g., $C_{1-6}$ hydroxyalkoxy such as —OCH$_2$CH$_2$OH or —OCH$_2$CH$_2$CH$_2$OH), or —OCH$_2$CH$_2$OP(O)OHOR; wherein at least one $R_{20}$ group is not hydrogen;

$R_{21}$ is hydrogen, methyl or —OH;

$R_{22}$ is hydrogen, —OH, or —C(O)CH$_2$OH;

$R_{23}$ is hydrogen or —OH;

$R_{24}$ is =O (there is no geminal hydrogen on the carbon) or hydroxylalkoxy (e.g., $C_{1-6}$ hydroxyalkoxy such as —OCH$_2$CH$_2$OH or —OCH$_2$CH$_2$CH$_2$OH);

$R_{25}$ is hydrogen or fluorine;

$R_{26}$ is hydrogen or —OH, and

R is alkyl (e.g., $C_{1-4}$ alkyl) optionally substituted with —OH; or pharmaceutically acceptable salts thereof. In various implementations, the compound has the structure:

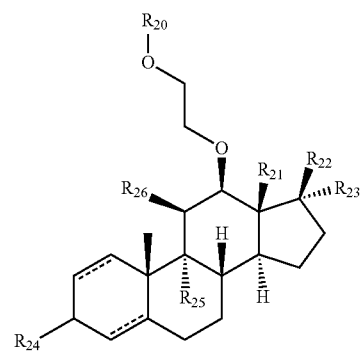

For example, the compound may have the structure:

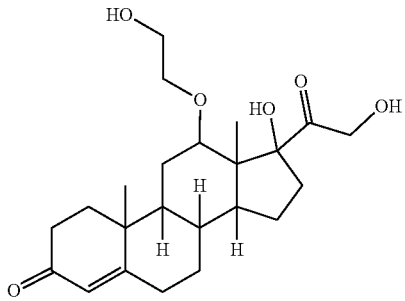

17-hydroxy-17-(2-hydroxyacetyl)-12-(2-hydroxy-ethoxy)-10,13-dimethyl-1,2,6,7,8,9,10,11,12,13,14,15,16,17-tetradecahydro-3H-cyclopenta[a]phenanthren-3-one

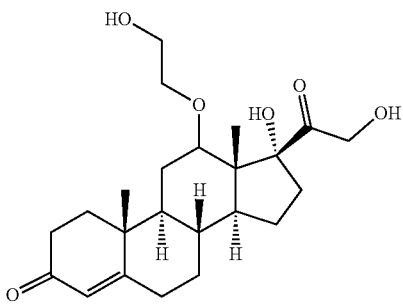

(8R,9S,10R,13R,14S,17R)-17-hydroxy-17-(2-hydroxyacetyl)-12-(2-hydroxyethoxy)-10,13-dimethyl-1,2,6,7,8,9,10,11,12,13,14,15,16,17-tetradecahydro-3H-cyclopenta[a]phenanthren-3-one

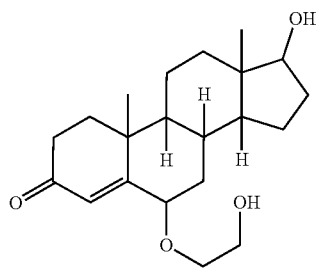

17-hydroxy-6-(2-hydroxyethoxy)-10,13-dimethyl-1,2,6,7,8,9,10,11,12,13,14,15,16,17-tetradecahydro-3H-cyclopenta[a]phenanthren-3-one

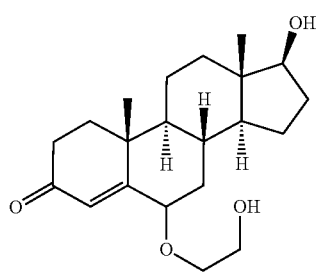

(8R,9S,10R,13S,14S,17S)-17-hydroxy-6-(2-hydroxyethoxy)-10,13-dimethyl-1,2,6,7,8,9,10,11,12,13,14,15,16,17-tetradecahydro-3H-cyclopenta[a]phenanthren-3-one Additional compounds which may be useful for pharmaceutical applications may include reduced forms of the steroid core. For example, the compound may have the structure:

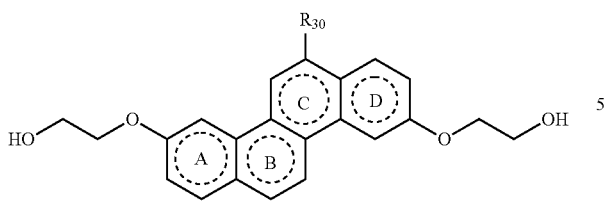

wherein rings A, B, C, and D are each independently saturated or unsaturated (e.g., each are optionally aromatic), and $R_{30}$ is hydrogen or —OCH$_2$CH$_2$OH. In some embodiments, at least one of rings A, B, C, or D is not aromatic (e.g., then number of double bonds is decreased with respect to the aromatic version in at least one ring). In various implementations, the compound may have the structure:

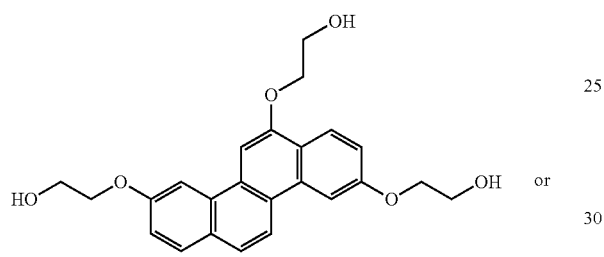

or

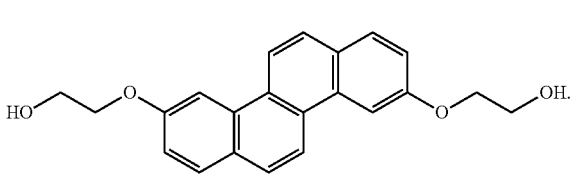

In a preferred embodiment, chrysene forms a self-assembled sequence through n-electron coupling of adjacent molecules. The carbon positions of the sidechains may be based on symmetric coupling of the two encoding molecules and based on the natural occurrence of the sidechain positions when synthetically halogenated to induce functionality. For example, each sidechain may be—consistent with phosphodiester and sugar-ring coupling, as well as the need for solubility.

As shown herein, the catalysts of the present disclosure may be intercalated between substrates and such intercalation results in the base four encoding systems. However, during syntheses, such as those to form DNA/RNA or hybrids thereof, to form sugar rings, or to polymerize adjacent reaction vessels, the catalysts may be ejected from their intercalated positions. These ejected catalysts may form phospholipids which may result in bilayers and cellular membranes. For example, the disclosure also includes compounds having the structure:

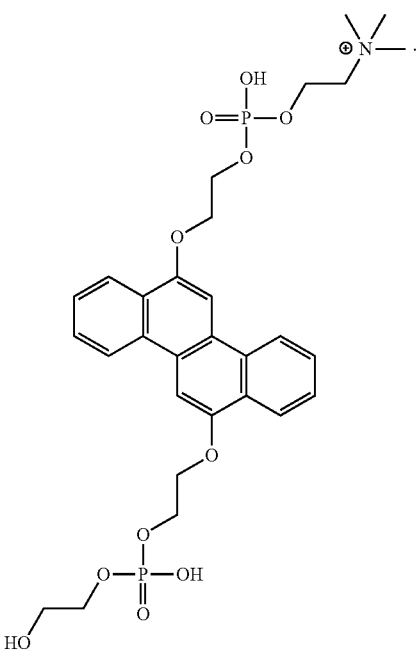 [SMILES: C[N+](C)(C)CCOP(=O)(O)OCCOc1cc2c3ccccc3c(OCCOP(=O)(O)OCCO)cc2c2ccccc12]

During RNA synthesis, specific substrate core containing moieties may be formed which conjugate to the lipid bilayer via RNA adenines. These compounds may have the structure:

$$X_1-(B^L)_{n1}-(I^L)_{m1}-(B^L)_{n2}-(I^L)_{m2}-X_2$$

wherein n1 and n2 are independently 0-15;

m1 and m2 are independently at each occurrence 0-15 and at least one of m1 or m2 is greater than 1;

$B^L$ has the structure:

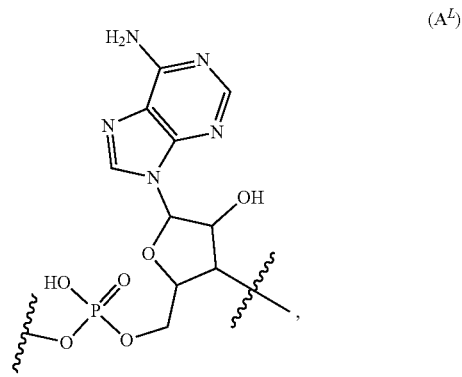

$(A^L)$ $I^L$ has the structure:
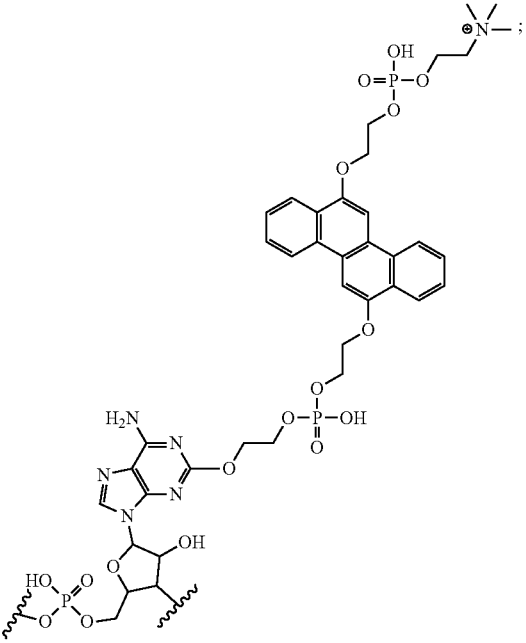 [SMILES: *OP(=O)(O)OCC1OC(n2cnc3c(N)nc(OCCOP(=O)(O)OCCOc4cc5c6ccccc6c(OCCOP(=O)(O)OCC[N+](C)(C)C)cc5c5ccccc45)nc32)C(O)C1*]
$X_1$ has the structure:
(G<sup>L</sup>)
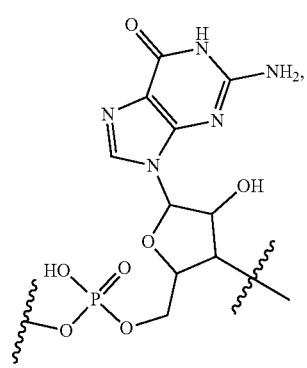
(T<sup>L</sup>)
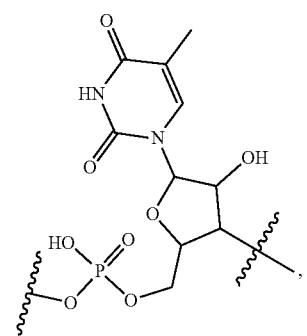
(C<sup>L</sup>)
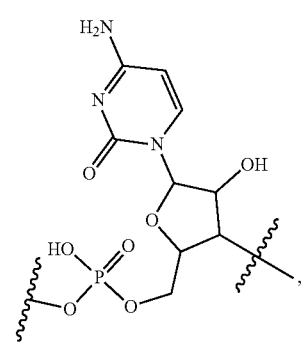
(A₁)
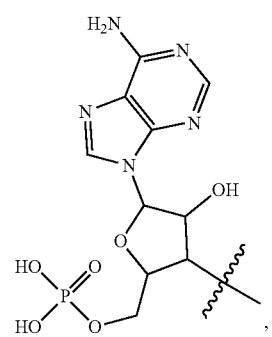
(U<sup>L</sup>)
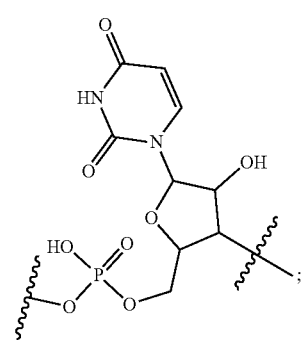
(G₁)
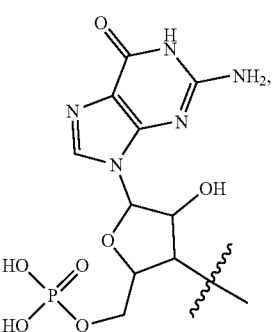

-continued
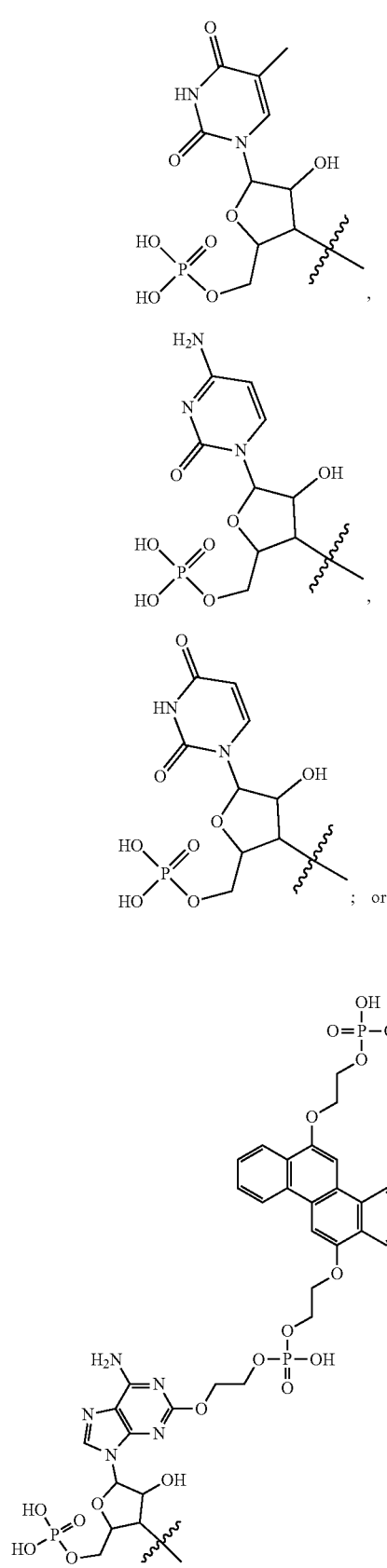
(T₁), (C₁), (U₁), (I₁)
$X_2$ has the structure:
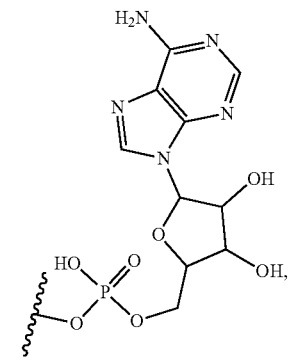
(A₂)
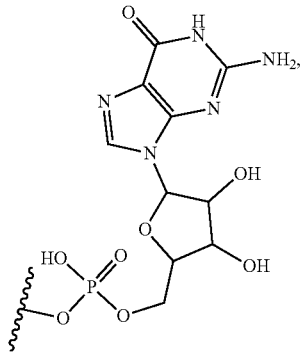
(G₂)
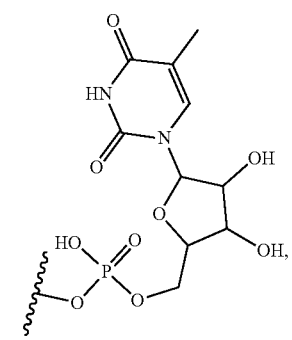
(T₂)
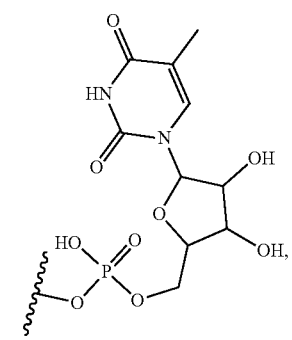
(C₂)
; and

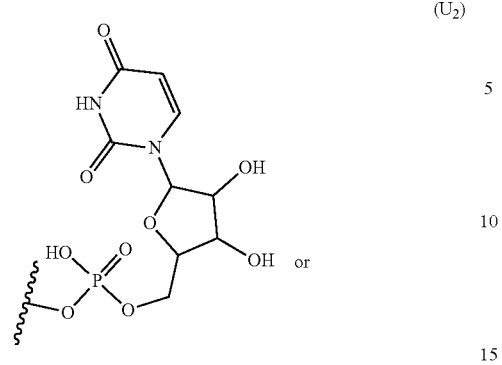
(U₂)
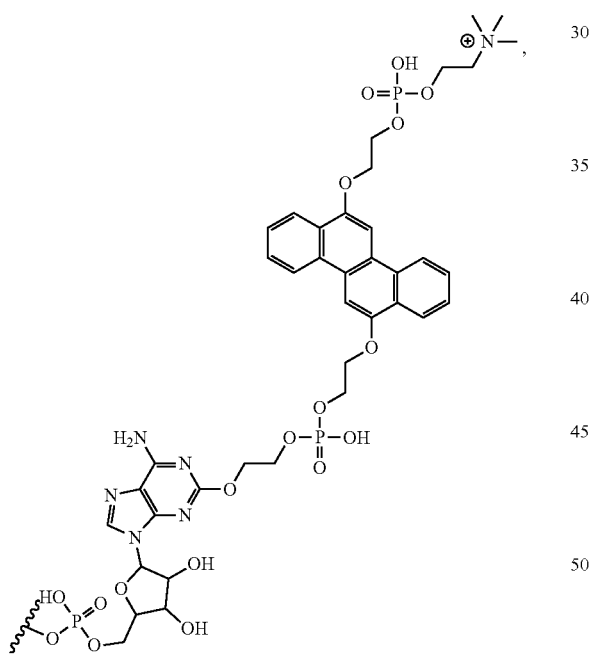
(I₂)
where the wavy bond indicates conjugation to the adjacent moiety;
or pharmaceutically acceptable salts thereof. In some embodiments, m1+m2+n1+n2 is less than or equal to 16. In particular embodiments, the compound has the structure $(I_1-(C^L)_2-I_2)$:

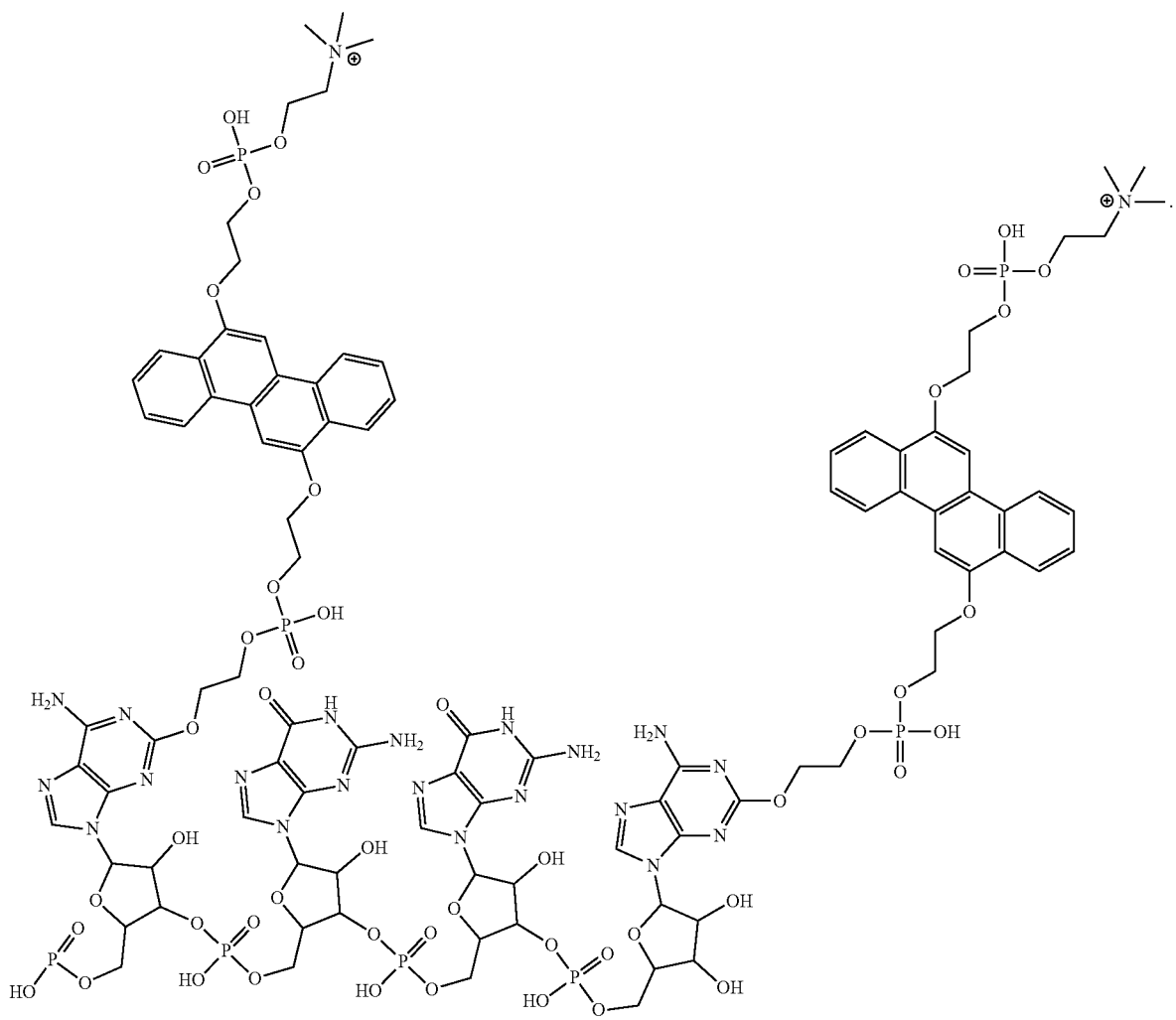

BRIEF DESCRIPTION OF FIGURES

FIG. 1 (FIG. 1(a)-(h)) identifies similarities between nucleotide base pairs hydrogen bonded to one another by illustrating common molecular primers overlayed on their structures. FIG. 1(f) shows the AT pairing with cortisol overlayed thereon. FIG. 1(g) shows the AT pairing with dexamethasone overlayed thereon. FIG. 1(h) is a table correlating catalyst and substrate information to specific orientations of each nucleotide pairing.

4(f) provides an exemplary catalyst/substrate unaligned pairing for formation of a reaction vessel. FIGS. 4(g) and (h) illustrate initiators that may establish RNA encoding in 5'→3' direction or 3'→5' direction and FIGS. 4(i) and (j) illustrate initiators that may establish DNA encoding in 5'→3' direction or 3'→5' direction when in a stack of reaction vessels.

FIG. 5 (FIG. 5(a)-(c)) provides an exemplary code mapping reaction vessels to the DNA/RNA nucleotide pairings. FIG. 5(c) provides a summary of the exemplary codes between stacked reaction vessels and DNA/RNA possible where CA represents catalyst aligned; CU represents catalyst unaligned; RD represents Right 5' DNA position; LD represents left 5' DNA position; RR represents right 5' RNA position; and LR, represents left 5' RNA position.

FIG. 7 (FIG. 7(a)-(j)).

FIG. 9 (FIG. 9(a)-(c)) outlines possible construction of phospholipids is an exemplary schematic illustrating the conversion of the intercalated catalysts into phospholipids. FIG. 9(b) illustrates catalyst phospholipids that may be formed following removal from the intercalated position between substrates (or any nucleobases formed during syntheses).

FIG. 11 (FIG. 11(a)-(e)) provides illustrations of various reaction vessels and stacked reaction vessels.

FIG. 15 (FIG. 15(a)-(c)) illustrates possible catalyst remnants produced during the syntheses described herein for substrate/catalyst pairs particularly suited in RNA encoding of phospholipid layers prior to DNA cellular takeover.

FIG. 17 is a table describing the possible atom economy of various synthetic schema described in the present application.

FIG. 19 (FIG. 19(a)-(f)) details various pharmacological effects and efficacy relationships afforded by comparing the substrates and catalysts with steroid molecules.

FIG. 20 (FIG. 20(a)-(f)) illustrates possible catalyst remnants produced during the syntheses described herein for substrate/catalyst pairs particularly suited in RNA encoding of phospholipid layers prior to DNA cellular takeover.

FIG. 23 (FIG. 23(a)-(b)) details a possible use for the reaction vessels of the present disclosure.

FIG. 24 (FIG. 24(a)-(b)) provide detail regarding the construction of a chosen sequence.

FIG. 25 (FIG. 25(a)-(d)) provides a model to illustrate the two different reaction vessel configurations corresponding to aligned ring structures of the substrate relative to the catalyst or unaligned ring structures of the substrate relative to the catalyst.

DETAILED DESCRIPTION

Figure 1A:
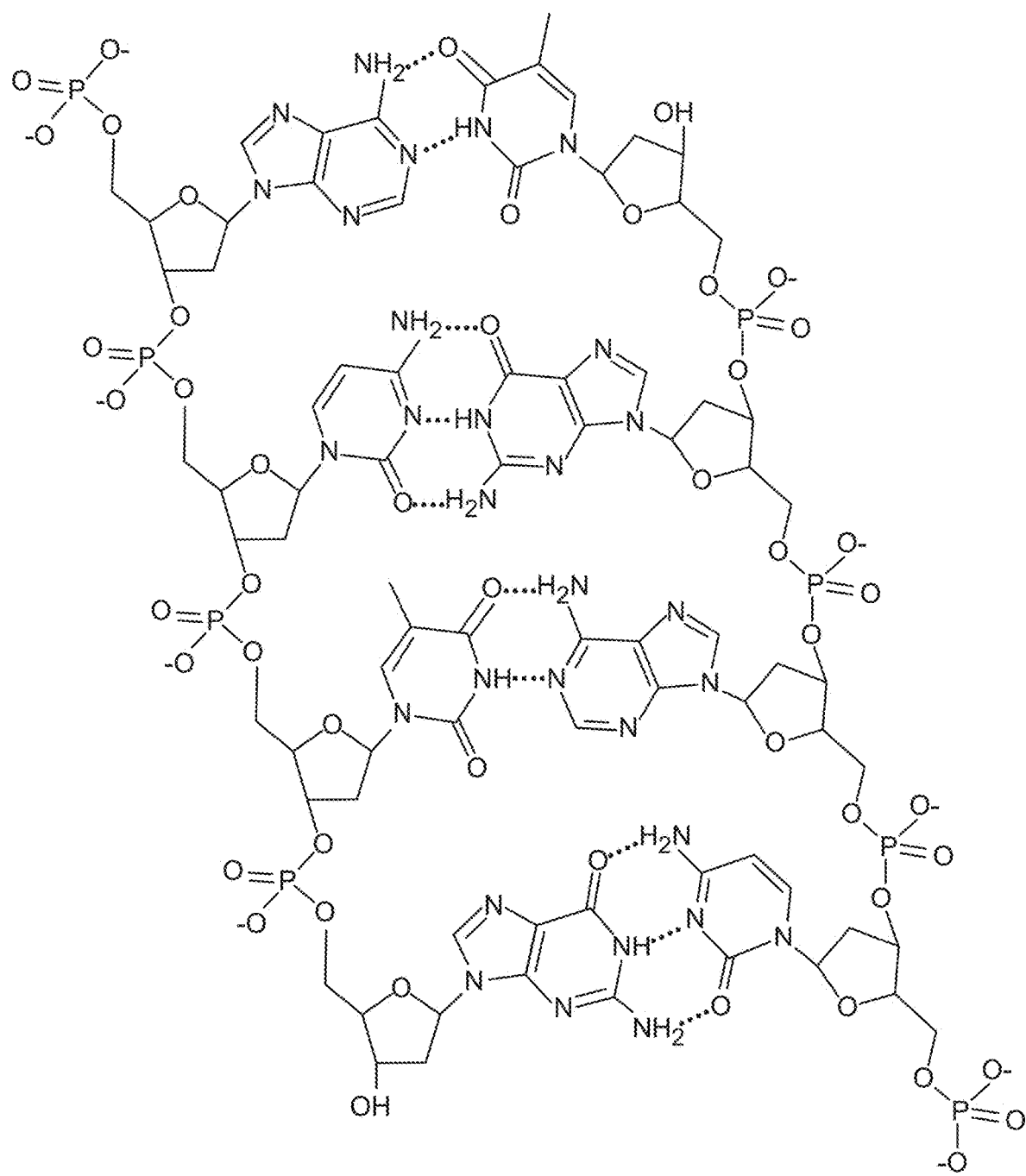
FIG. 1(a) provides the two nucleotide pairs of DNA in the four possible orientations.

Detailed embodiments of the present disclosure are disclosed herein; however, it is to be understood that the disclosed embodiments are merely illustrative of the disclosure that may be embodied in various forms. In addition, each of the examples given in connection with the various embodiments of the disclosure is intended to be illustrative, and not restrictive.

All terms used herein are intended to have their ordinary meaning in the art unless otherwise provided. All concentrations are in terms of percentage by weight of the specified component relative to the entire weight of the topical composition, unless otherwise defined.

As used herein, "a" or "an" shall mean one or more. As used herein when used in conjunction with the word "comprising," the words "a" or "an" mean one or more than one. As used herein "another" means at least a second or more.

As used herein, all ranges of numeric values include the endpoints and all possible values disclosed between the disclosed values. The exact values of all half-integral numeric values are also contemplated as specifically disclosed and as limits for all subsets of the disclosed range. For example, a range of from 0.1% to 3% specifically discloses a percentage of 0.1%, 1%, 1.5%, 2.0%, 2.5%, and 3%. Additionally, a range of 0.1 to 3% includes subsets of the original range including from 0.5% to 2.5%, from 1% to 3%, from 0.1% to 2.5%, etc. It will be understood that the sum of all weight % of individual components will not exceed 100%.

Throughout this description, various components may be identified having specific values or parameters, however, these items are provided as exemplary embodiments. Indeed, the exemplary embodiments do not limit the various aspects and concepts of the present disclosure as many comparable parameters, sizes, ranges, and/or values may be implemented. Unless otherwise specified, the terms "first," "second," and the like, "primary," "secondary," and the like, do not denote any order, quantity, or importance, but rather are used to distinguish one element from another.

By "consist essentially" it is meant that the ingredients include only the listed components along with the normal impurities present in commercial materials and with any other additives present at levels which do not affect the operation of the disclosure, for instance at levels less than 5% by weight or less than 1% or even 0.5% by weight.

The term "hydrocarbon" refers to a radical or group containing carbon and hydrogen atoms. Examples of hydrocarbon radicals include, without limitation, alkyl, alkenyl, alkynyl, aryl, aryl-alkyl, alkyl-aryl, and any combination thereof (e.g., alkyl-aryl-alkyl, etc.). As used herein, unless otherwise indicated, hydrocarbons may be monovalent or multivalent (e.g., divalent, trivalent) hydrocarbon radicals. A radical of the form $-(CH_2)_n-$, including a methylene radical, i.e., $-CH_2-$, is regarded as an alkyl radical if it does not have unsaturated bonds between carbon atoms. Unless otherwise specified, all hydrocarbon radicals (including substituted and unsubstituted alkyl, alkenyl, alkynyl, aryl, aryl-alkyl, alkyl-aryl, etc.) may have from 1-45 carbon atoms (e.g., $C_1$-$C_{30}$, $C_1$-$C_{20}$, $C_1$-$C_{10}$, $C_5$-$C_{15}$, $C_5$-$C_{30}$, $C_5$-$C_{40}$, $C_{10}$-$C_{40}$, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$). In certain embodiments, hydrocarbons will have from 5-35 or from 1-20 or from 1-12 or from 1-8 or from 1-6 or from 1-3 carbon atoms, including for example, embodiments having one, two, three, four, five, six, seven, eight, nine, or ten carbon atoms. For example, hydrocarbons may have from 2 to 70 atoms or from 4 to 60 atoms or from 4 to 20 atoms.

Typically, alkyl groups described herein refer to a branched or straight-chain monovalent saturated aliphatic hydrocarbon radical of 1-30 carbon atoms (e.g., 1-16 carbon atoms, 6-20 carbon atoms, 8-16 carbon atoms, or 4-18 carbon atoms, 4-12 carbon atoms). In some embodiments, any hydrocarbon of the present disclosure may be an unsaturated alkyl (e.g., alkenyl, alkynyl). In some embodiments, the alkyl or unsaturated alkyl group may be substituted with 1, 2, 3, or 4 substituent groups as defined herein. Alkyl or unsaturated alkyl groups may have from 1-26 carbon atoms. In other embodiments, alkyl or unsaturated alkyl groups will have from 6-18 or from 1-8 or from 1-6 or from 1-4 or from 1-3 carbon atoms, including for example, embodiments having one, two, three, four, five, six, seven, eight, nine, or ten carbon atoms. Examples of alkyl groups include methyl, ethyl, propyl, butyl, pentyl, hexyl, heptyl, octyl, nonyl, decyl, undecyl, and dodecyl groups, and unsaturated versions of these groups are considered within the scope of the disclosure. Heteroalkyl groups may refer to branched or straight-chain monovalent saturated aliphatic hydrocarbon radicals with one or more heteroatoms (e.g., N, O, S, etc.) in the carbon chain. In some embodiments, any hydrocarbon of the present disclosure may be an unsaturated heteroalkyl (e.g., heteroalkenyl, heteroalkynyl). Heteroalkyl or unsaturated hetoralkyl groups may have 1-30 carbon atoms (e.g., 1-16 carbon atoms, 6-20 carbon atoms, 8-16 carbon atoms, or 4-18 carbon atoms, 4-12 carbon atoms) with one or more heteroatoms replacing the carbon atom in the carbon chain. In some embodiments, the heteroalkyl group may be substituted with 1, 2, 3, or 4 substituent groups as defined herein. Heteroalkyl or unsaturated hetoralkyl groups may have from 1-26 carbon atoms. In other embodiments, heteroalkyl groups will have from 6-18 or from 1-8 or from 1-6 or from 1-4 or from 1-3 carbon atoms, including for example, embodiments having one, two, three, four, five, six, seven, eight, nine, or ten carbon atoms. In some embodiments, the heteroalkyl group can be substituted with 1, 2, 3, or 4 substituent groups as described herein. Examples of heteroalkyl groups are an alkoxy. Alkoxy substituent groups or alkoxy-containing substituent groups may be substituted by, for example, one or more alkyl groups. Cycloalkyl or heterocycloalkyl groups described herein typically to saturated cyclic alkyl or cyclic heteroalkyl groups having at least one ring structure such as being monocyclic or polycyclic (e.g., bicyclic, polycyclic). Cyclo groups may be unsaturated such as cycloalkenyl or heterocycloalkenyl. Cycloalkyl groups or unsaturated cycloalkyl groups may be optionally saturated and be, for example $C_3$-$C_{15}$, (e.g., $C_3$-$C_{12}$, $C_3$-$C_{10}$, $C_3$-$C_8$, $C_4$-$C_7$, $C_3$-$C_4$, $C_5$-$C_6$). Heterocycloalkyl or unsaturated hetercycloalkyl groups may be, for example, rings being 3 to 15-membered (e.g., 3-12 membered, 3-10 membered, 3-8 membered, 4-7 membered, 3-4 membered, 5-6 membered). In various implementations the cycloalkyl or heterocycloalkyl groups may be optionally substituted with a substituent as described herein. For these groups may be 1, 2, 3, or 4 substituent groups as described herein. Acyl groups are generally groups conjugated via a carbonyl group. For example, acyl groups of the present disclosure may have the structure $-C(O)R$, wherein R is hydrogen or substituted or unsubstituted alkyl (e.g., $C_{1-25}$ alkyl, $C_{1-15}$ alkyl, $C_{1-8}$ alkyl, $C_{1-4}$ alkyl).

Aryl groups may be aromatic mono- or polycyclic (e.g., bicyclic) radicals of 6 to 12 carbon atoms having at least one aromatic ring. Examples of such groups include, but are not limited to, phenyl, naphthyl, 1,2,3,4-tetrahydronaphthalyl, 1,2-dihydronaphthalyl, indanyl, and 1H-indenyl. Typically, heteroaryls include mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are pyridyl, benzooxazolyl, benzoimidazolyl, and benzothiazolyl.

The term "substituent" refers to a group "substituted" on, e.g., an alkyl, at any atom of that group, replacing one or more hydrogen atoms therein (e.g., the point of substitution). In some aspects, the substituent(s) on a group are independently any one single, or any combination of two or more of the permissible atoms or groups of atoms delineated for that substituent. In another aspect, a substituent may itself be substituted with any one of the substituents described herein. Substituents may be located pendant to the hydrocarbon chain.

A substituted hydrocarbon group may have as a substituent one or more hydrocarbon radicals, substituted hydrocarbon radicals, or may comprise one or more heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (e.g., F, Cl, Br, I, etc.), boron, silicon, etc. In some embodiments, heteroatoms will be selected from the group consisting of oxygen, nitrogen, sulfur, phosphorous, and halogen (e.g., F, Cl, Br, I, etc.). In some embodiments, a heteroatom or group may substitute a carbon (e.g., substituted alkyl may include heteroalkyl). In some embodiments, a heteroatom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo").

In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different (e.g., R may be independently selected at each occurrence from $C_1$-$C_{10}$ alkyl optionally comprising one or more points of substitution).

Unless otherwise noted, all groups described herein (e.g., alkyl, cycloalkyl, heteroalkyl, acyl, heterocycloalkyl, aryl, heteroaryl, alkylene, heteroalkylene, cylcoalkylene, heterocycloalkylene) may optionally contain one or more common substituents, to the extent permitted by valency. Common substituents include halogen (e.g., F, Cl), $C_{1-12}$ straight chain or branched chain alkyl, $C_{2-12}$ alkenyl, $C_{2-12}$ alkynyl, $C_{3-12}$ cycloalkyl, $C_{6-12}$ aryl, $C_{3-12}$ heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as halogen, fluoroalkyl, perfluoroalkyl, perfluroalkoxy, trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, $C_{3-12}$ heteroaryl, or $C_{4-24}$ heteroarylalkyl. Further, as used herein, the phrase optionally substituted indicates the designated hydrocarbon group may be unsubstituted (e.g., substituted with H) or substituted. Typically, substituted hydrocarbons are hydrocarbons with a hydrogen atom removed and replaced by a substituent (e.g., a common substituent).

In some embodiments, any hydrocarbon or substituted hydrocarbon disclosed herein may be substituted with one or more (e.g., from 1-6 or from 1-4 or from 1-3 or one or two or three) substituents $X^{sub}$, where $X^{sub}$ is independently selected at each occurrence from one or more (e.g., 1-20) heteroatoms or one or more (e.g., 1-10) heteroatom-containing groups, or $X^{sub}$ is independently selected at each occurrence from —F, —Cl, —Br, —I, —OH, —OR*, —NH$_2$, —NHR*, —N(R*)$_2$, —N(R*)$_3$*, —N(R*)—OH, —N(→O)(R*)$_2$, —O—N(R*)$_2$, —N(R*)—O—R*, —N(R*)—N(R*)$_2$, —C=N—R*, —N=C(R*)$_2$, —C=N—N(R*)$_2$, —C(=NR*)(—N(R*)$_2$), —C(H)(=N—OH), —SH, —SR*, —CN, —NC, —CHF$_2$, —CCl$_3$, —CF$_2$Cl, —CFCl$_2$, —C(=O)—R*, —CHO, —CO$_2$H, —C(O)CH$_3$, —CO$_2$—, —CO$_2$R*, —C(=O)—S—R*, —O—(C=O)—H, —O—(C=O)—R*, —S—C(=O)—R*, —(C=O)—NH$_2$, —C(=O)—N(R*)$_2$, —C(=O)—NHNH$_2$, —O—C(=O)—NHNH$_2$, —C(=S)—NH$_2$, —(C=S)—N(R*)$_2$, —N(R*)—CHO, —N(R*)—C(=O)—R*, —C(=NR)—OR*, —O—C(=NR*)—R*, —SCN, —NCS, —NSO, —SSR*, —N(R*)—C(=O)—N(R*)$_2$, —CH$_3$, —CH$_2$—CH$_3$, —CH$_2$—CH$_2$—CH$_3$, —C(H)(CH$_2$)$_2$, —C(CH$_3$)$_3$, —N(R*)—C(=S)—N(R*)$_2$, —S(=O)$_{1-2}$—R*, —O—S(=O)$_2$—R*, —S(=O)$_2$—OR*, —N(R*)—S(=O)$_2$—R*, —S(=O)$_2$—N(R*)$_2$, —O—SO$_3$, —O—S(=O)$_2$—OR*, —O—S(=O)—OR*, —O—S(=O)—R*, —S(=O)—OR*, —S(=O)—R*, —NO, —NO$_2$, —NO$_3$, —O—NO, —O—NO$_2$, —N$_3$, —N$_2$—R*, —N(C$_2$H$_4$), —Si(R*)$_3$, —CF$_3$, —O—CF$_3$, —O—CHF$_2$, —O—CH$_3$, —O—(CH$_2$)$_{1-6}$CH$_3$, —OC(H)(CH$_2$)$_2$—OC(CH$_3$)$_3$, —PR*$_2$, —O—P(=O)(OR*)$_2$, or —P(=O)(OR*)$_2$; where, independently at each occurrence, R* may be H or a $C_{1-10}$ or $C_{1-8}$ or $C_{1-6}$ or $C_{1-4}$ unsubstituted hydrocarbon, including without limitation alkyl, alkenyl, alkynyl, aryl (e.g., phenyl), alkylaryl (e.g., benzyl), aryl-alkyl (e.g., toluyl). In some embodiments, $X^{sub}$ may comprise a $C_1$-$C_8$ or $C_1$-$C_6$ or $C_2$-$C_4$ perfluoroalkyl. In some embodiments, X may be a $C_1$-$C_8$ or $C_2$-$C_6$ or $C_3$-$C_5$ heterocycle (e.g., heteroaryl radical). The term "halo" or "halogen" refers to any radical of fluorine, chlorine, bromine or iodine. In certain embodiments, $X^{sub}$ is independently selected at each occurrence from —OH, —SH, —NH$_2$, —N(R*)$_2$, —C(O)OR*, —C(O)NR*R*, —C(O)NR*R*, —C(O)OH, —C(O)NH$_2$, F, or —Cl. In some embodiments, $X^{sub}$ is F. In some embodiments, R* is hydrogen, or lower alkyl (e.g., $C_1$-$C_5$ linear or branched alkyl such as methyl, ethyl, propyl, or isopropyl). In some embodiments, R* is hydrogen, or lower alkoxy (e.g., $C_1$-$C_5$ linear or branched alkoxy such as methoxy, ethoxy, propoxy, or isopropoxy). In some embodiments, $X^{sub}$ is —CF$_3$ or —O—CF$_3$.

It is understood by one of ordinary skill in the chemistry art that substitution at a given atom is limited by valency. The use of a substituent (radical) prefix names such as alkyl without the modifier optionally substituted or substituted is understood to mean that the particular substituent is unsubstituted. However, the use of haloalkyl without the modifier optionally substituted or substituted is still understood to mean an alkyl group, in which at least one hydrogen atom is replaced by halo. Where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon. Additionally, when a structure has less than the required number of functional groups indicated, those carbon atoms without an indicated functional group are bonded to the requisite number of hydrogen atoms to satisfy the valency of that carbon.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gel cap, etc.); for topical administration (e.g., as a cream, gel, lotion, or ointment); for intravenous administration (e.g., as a sterile solution free of particulate emboli and in a solvent system suitable for intravenous use); or in any other formulation described herein (see below).

"Catalyst" as used herein typically is a disubstituted quadracycle (such as 6,12-substituted chrysene), unless otherwise specified. Specific substitutions on the catalysts of the present disclosure include hydroxyalkoxy substitution such as hydroxyethoxy substitution at the two positions.

"Substrate" as used herein typically is a tetra substituted quadracycle (such as 3,6,9,12-substituted chrysene, unless otherwise specified. Specific substitutions on the substrates of the present disclosure include hydroxyalkoxy substitution such as hydroxyethoxy substitution at the four positions.

The "regulatory sequence" typically is present at an end group pairing of the SCH complex and may involve an associated regulatory molecule and catalyst. Regulatory molecules are typically tri substituted quadracycles (such as 3,6,12-substituted chrysene), unless otherwise specified. Specific substitutions on the regulatory molecules of the present disclosure include hydroxyalkoxy substitution such as hydroxyethoxy substitution at the four positions.

"SCH Complex" herein typically refers associated pairings of substrate and catalysts (or catalysts and regulatory molecules). These associations may occur though π stacking of the aromatic ring systems of the substrate/catalyst and regulatory molecule/catalyst. These associations may be in heterodimeric form or through covalent conjugation through the substitutions as described herein. The SCH Complex may also include adjacent substrate/catalyst pairings as well, often associated vi π stacking of the substrate from one heterodimer (or molecule if the substrate is covalently conjugated to the catalyst in one reaction vessel) to the catalyst of another adjacent heterodimer (or molecule if the substrate is covalently conjugated to the catalyst). "SCH Sequences" involve two or more associated heterodimers or molecules which may undergo the reactions described herein to form DNA, RNA, and/or DNA/RNA hybrids.

"Reaction Vessels" as used herein are typically individual pairings of moieties that undergo π stacking with one another. The reaction vessel may include dimerized forms (such as by two compounds having the structure of formula (I), or a molecule having two moieties comprising polycyclic moieties with π systems bonded to one another and oriented in a manner to encode information (e.g., via unaligned or aligned orientations of the π systems).

As used herein, the phrase "pharmaceutically acceptable" generally safe for ingestion or contact with biologic tissues at the levels employed. Pharmaceutically acceptable is used interchangeably with physiologically compatible. It will be understood that the pharmaceutical compositions of the disclosure include nutraceutical compositions (e.g., dietary supplements) unless otherwise specified.

Unit dosage forms, also referred to as unitary dosage forms, often denote those forms of medication supplied in a manner that does not require further weighing or measuring to provide the dosage (e.g., tablet, capsule, caplet, etc.). The compositions of the present disclosure may be present as unit dosage forms. For example, a unit dosage form may refer to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, and gel cap. In certain embodiments, the compounds described herein, including crystallized forms, polymorphs, and solvates thereof, may be present in a unit dosage form.

Useful pharmaceutical carriers, excipients, and diluents for the preparation of the compositions hereof, can be solids, liquids, or gases. These include any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are examples of liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution and rendering the solution sterile. Suitable pharmaceutical excipients include starch, cellulose, chitosan, talc, glucose, lactose, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol;

esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; self-emulsifying drug delivery systems (SEDDS) such as d-atocopherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives can also be used to enhance delivery of the compounds described herein.

The compounds described herein may be present as a pharmaceutically acceptable salt. Typically, salts are composed of a related number of cations and anions (at least one of which is formed from the compounds described herein) coupled together (e.g., the pairs may be bonded ionically) such that the salt is electrically neutral. Pharmaceutically acceptable salts may retain or have similar activity to the parent compound (e.g., an $ED_{50}$ within 10%, etc.) and have a toxicity profile within a range that affords utility in pharmaceutical compositions. For example, pharmaceutically acceptable salts may be suitable for use in contact with the tissues of humans and animals without undue toxicity, irritation, allergic response and are commensurate with a reasonable benefit/risk ratio. Pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecylsulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

Pharmaceutically acceptable acid addition salts of the disclosure can be formed by the reaction of a compound of the disclosure with an equimolar or excess amount of acid. Alternatively, hemi-salts can be formed by the reaction of a compound of the disclosure with the desired acid in a 2:1 ratio, compound to acid. The reactants are generally combined in a mutual solvent such as diethyl ether, tetrahydrofuran, methanol, ethanol, iso-propanol, benzene, or the like. The salts normally precipitate out of solution within, e.g., one hour to ten days and can be isolated by filtration or other conventional methods.

Solvates of the compounds described herein may the aggregate of the compound or an ion of the compound with one or more solvents. Such solvents may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "effective amount" or "therapeutically effective amount" of an agent (e.g the combination of cytokines and quinine derivatives described herein), as used herein, is that amount sufficient to effect beneficial or desired results, such as clinical results, and, as such, an "effective amount" depends upon the context in which it is being applied. In some embodiments, the compounds are administered in an effective amount for the treatment or prophylaxis of a disease disorder or condition. In another embodiment, in the context of administering an agent that is an anticancer agent, an effective amount of an agent is, for example, an amount sufficient to achieve alleviation or amelioration or prevention or prophylaxis of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition (e.g., those associated with infection); and remission (whether partial or total), whether detectable or undetectable, as compared to the response obtained without administration of the agent.

As used herein, the term "subject" refers to any organism to which a composition and/or compound in accordance with the disclosure may be administered, e.g., for experimental, diagnostic, prophylactic, and/or therapeutic purposes. Typical subjects include any animal (e.g., mammals such as mice, rats, rabbits, non-human primates, and humans). A subject in need thereof is typically a subject for whom it is desirable to treat a disease, disorder, or condition as described herein. For example, a subject in need thereof may seek or be in need of treatment, require treatment, be receiving treatment, may be receiving treatment in the future, or a human or animal that is under care by a trained professional for a particular disease, disorder, or condition.

Provided herein are compounds, systems, methods of use, and methods of construction independent reaction vessels, and stacked versions thereof, that may be able to contain information (e.g., base two information, base four information). The information is contained in a the relative orientations of a substrate and catalyst, which, when coupled to adjacent substrate and catalyst pairs contain four independent bits of information. These substrate and catalyst pairs (also referred to herein as reaction vessels), may undergo certain synthetic transformation to result in DNA/RNA or hybrids thereof and/or phospholipids (which may form bilayers and, eventually a cellular membrane).

Primer for Encoding DNA as Coupled Binary Molecular Sequences

Without wishing to be bound by theory, the development of the code and the associated molecular structures to encode DNA and RNA described herein begins with a detailed examination of the DNA molecule.

In FIG. 1(a), a view of the DNA nucleotides is shown for each of the four base pairings: Adenine-Thymine (A-T), Cytosine-Guanine (C-G), Thymine-Adenine (T-A), and Guanine-Cytosine (G-C) (as listed from top to bottom in the figure). Also included in the illustration is the inter-nucleotide hydrogen bonding of the base pairings, of which there are three hydrogen bonds for the C-G and G-C pairs, but only two inter-nucleotide hydrogen bonds for the A-T and T-A base pairs. Of particular importance to this analysis are:
  (1) the carbon two position of thymine, there exists a functional oxygen element, a ketone, but there exists no complementary element on adenine, for example a hydroxyl or amine group, that could offer a link as a hydrogen bond (primarily discussed in this subsection); and
  (2) the angle of the position of the connection of the sugar-ring molecules to the nucleobase (primarily discussed in subsection titled "Code for DNA and RNA").

Figure 1B:
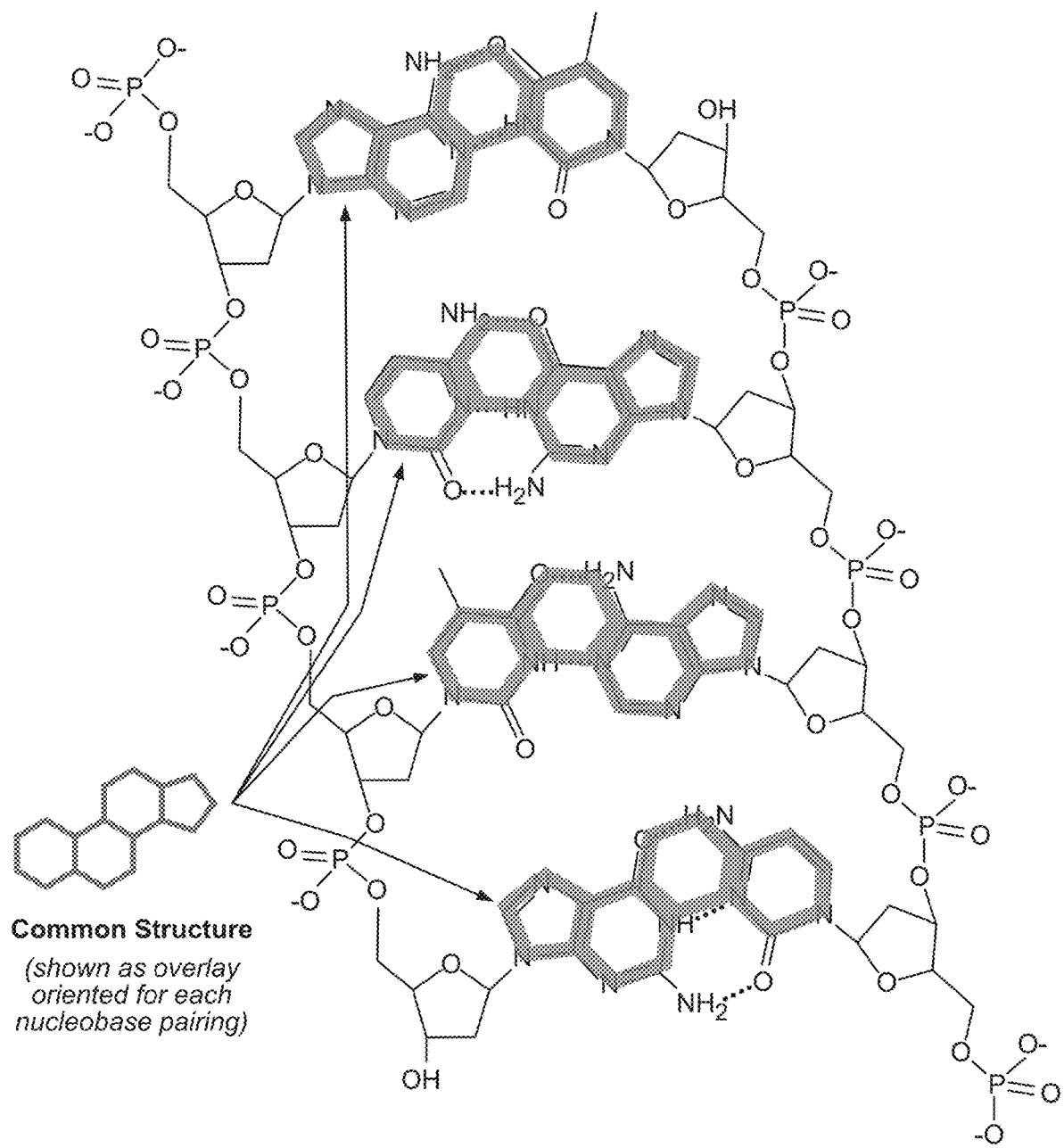
FIG. 1(b) provides, from top to bottom, AT, CG, TA, and GC, with a four ring structure (e.g., steroid core) overlayed on each pair.

Analysis described herein of these pairings identifies a common structure, comprised of a fusion of four-rings in the shape of a steroid molecule, is incorporated within the structure of each nucleotide pair. FIG. 1(b) highlights the common structure (thick grey lines) overlayed over each of the pairings. This overlay is obtained by connecting a total of seventeen oxygen, nitrogen, and carbon elements of each nucleobase pairs in a particular manner. Connecting these seventeen atoms identifies a common four-ring structure for each of the four DNA nucleotide pairs in different orientations. This overlay of a four-ring structure can be achieved for each of the four Watson-Crick pairings of nucleotides. As can be seen, a structural correspondence between the atoms and vertices in each Watson-Crick pairings and the catalyst is present. The orientation of the four-ring molecule (which is of a steroid molecule core) is also in symmetric correspondence when analyzing the A-T and G-C pairings: As can be seen, in the A-T and G-C pairings, a purine moiety is associated on the 5' side, while on the reverse orientation, the same match holds for the T-A and C-G pairings when the pyrimidine molecule starts the 5' pair. For each pairing, there is a lateral stretching of one of the rings in the common structure, where the purine and pyrimidine come into alignment through hydrogen bonding. The common structure, which has structure of a four-ring molecule (e.g., a four-ring steroid molecule) is instructive in developing encoding methods to represent the base four sequence of DNA. In addition, the carbon atom of adenine associated with the unpaired thymine ketone (the 2 position of the purine moiety) is also useful to understanding the primer shape and underlying code described herein.

Figure 1C:
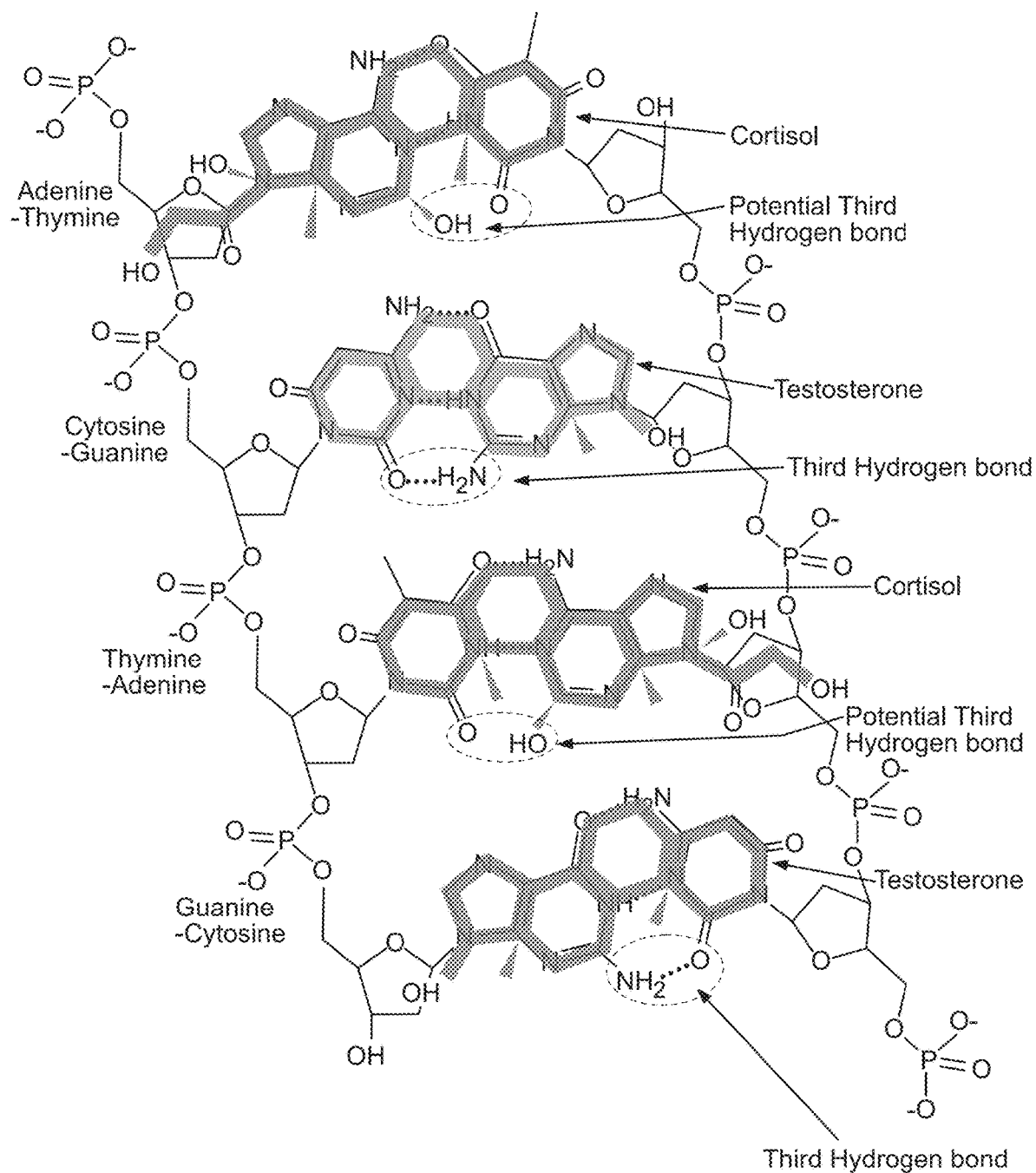
FIG. 1(c) provides the nucleotide pairs having cortisol or testosterone overlayed thereon.

As the common structure of the four nucleotide pairings identified herein generally has a steroid core, the structural correspondence of steroid molecules with each nucleotide pairing is informative. For example, A-T nucleotide pairings possess only two internal hydrogen bonds and C-G pairings which have three internal hydrogen bonds is of considerable importance. In FIG. 1(c), the cortisol molecule, which is a steroid hormone that nominally interacts with DNA through the glucocorticoid receptor, is shown in a one-to-one alignment between the carbon atoms of the steroid core with the vertices of the common structures on the A-T and T-A pairings. The hydroxyl moieties in cortisol are included in the grey overlay. As can be seen, one of the cortisol hydroxyl groups (the 11-hydroxyl) exists in the position where the unpaired hydrogen ketone of thymine would hydrogen bond (if adenine had a group at the appropriate carbon position of its purine moiety). This hydroxyl extends into this "potential space" with the unpaired ketone group of thymine. This match is held on the frontside of A-T and on the backside of the T-A pairing. In addition to the correspondence at the carbon-11 position, the other two side groups of cortisol at carbon-3 and carbon-17 also have positioning of a functional nature in terms of potential electrostatic interaction with the phosphodiester backbone. This relation is not only symmetry but also a complementary match.

An analysis of the C-G pairings, which already have three internal hydrogen bonds, provides a correlation with another type of nuclear steroid hormone. Similarly to the complementary match between cortisol and the A-T dinucleotide, as shown in FIG. 1(c), testosterone aligns with C-G, since the carbon-3 and carbon-17 side-groups are effective with the phosphodiester chain like cortisol with A-T. Interestingly, like cortisol, testosterone also has two methyl groups in the same positions as cortisol, which hinder a hydroxyl association through hydrogen binding with thymine. The orientation also is relevant as the complementary match is met on the front view when purines start the link to the 5' strand, and also on the back with pyrimidine starting the link.

Figure 1D:
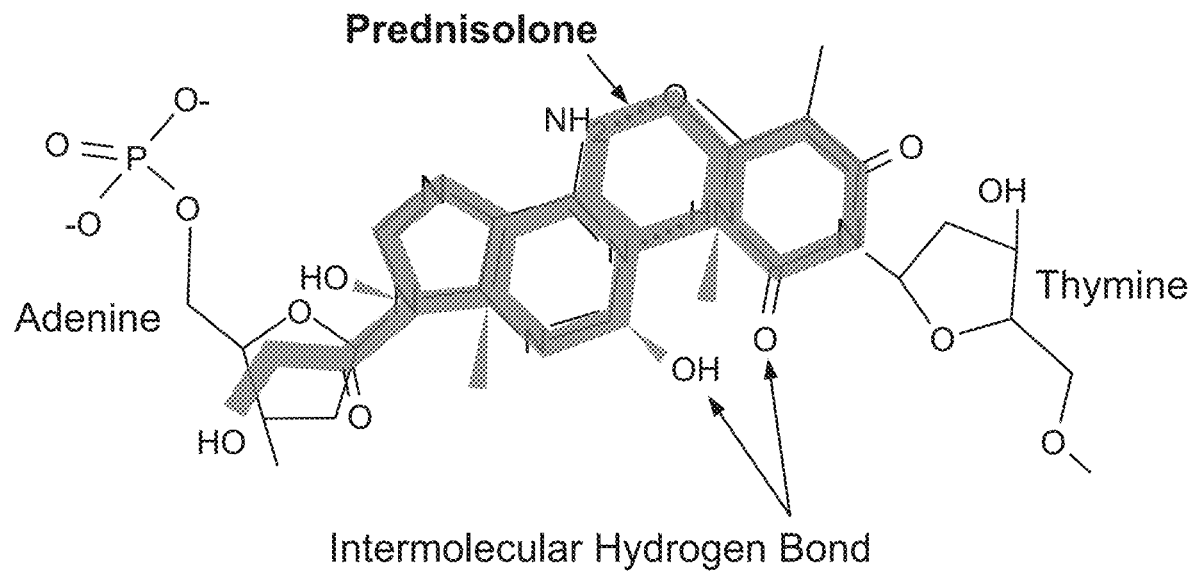
FIG. 1(d) shows the AT pairing with prednisolone overlayed thereon.
Figure 1E:
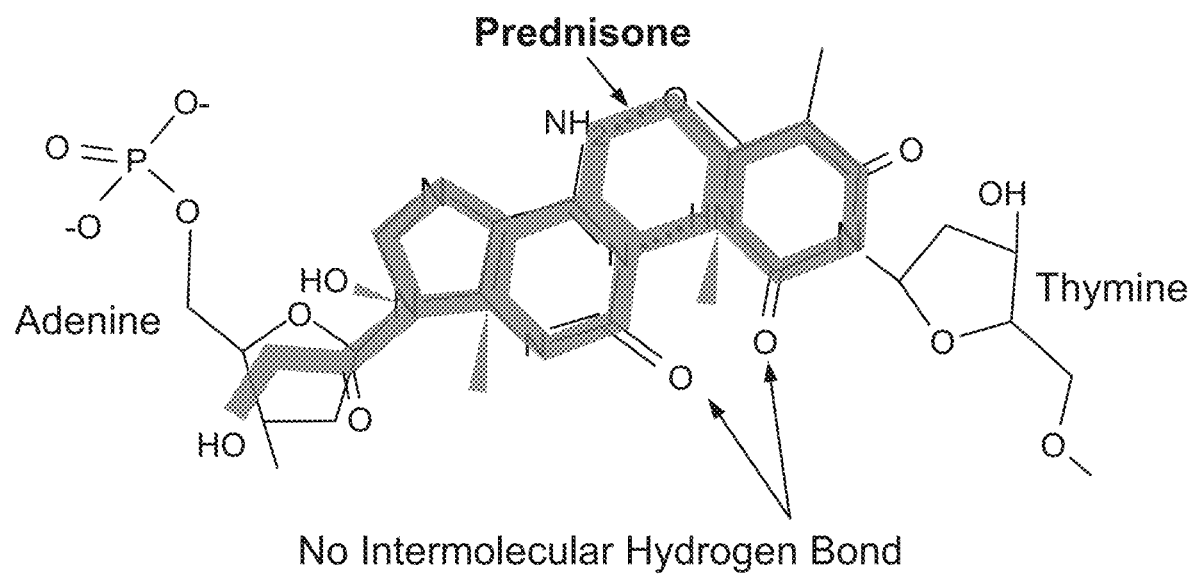
FIG. 1(e) shows the AT pairing with prednisone overlayed thereon.

Without wishing to be bound by theory, the symmetric and complementary relation of the steroid hormones with DNA provides a predictive capability for the pharmacological efficacy of synthetic corticosteroids. In particular, the observation of a structural match to produce the third hydrogen bond with A-T is of a functional nature. The intermolecular strength of the hydrogen bond with the unpaired ketone group of thymine may be examined by comparative assessment of the potency of dexamethasone, prednisolone, prednisone relative to cortisol. The relative activity of dexamethasone:prednisolone:cortisol is approximately 25:4:1 and that prednisone, in its native form, is inactive as it must be converted into prednisolone in the liver before it can be used. By analyzing the strength of the potential hydrogen bond with thymine, the pharmacological efficacy data is predictable. The structural relationship of prednisolone to thymine is shown in FIG. 1(d), in which it is shown that it is possible to form an intermolecular hydrogen bond with thymine using the hydroxyl. However, as shown in FIG. 1(e), the ketone at this same hydroxyl position makes renders it not possible to form a similar intermolecular hydrogen bond between prednisone and thymine. There is just a single atom difference between prednisolone and prednisone despite this dramatically altered activity. This single atom difference is at a critical point in molecule such that the prednisolone hydroxyl group binds to thymine. This precise result is consistent with the efficacy of prednisone, which experimentally shows no activity until it is converted into prednisolone.

Potency is consistent with the hypothesis that the intermolecular bond between endogenous steroids and the A-T dinucleotide is of a functional correlation. Represented in FIG. 1(f), the relationship between the steroid hormone cortisol and thymine illustrates that an intermolecular hydrogen bond can be formed. With respect to prednisolone, the only difference is an extra double bond in a ring of prednisolone as compared to cortisol. The additional double bond may aid in stabilizing the intermolecular hydrogen bond between thymine and prednisolone inducing the increased prednisolone activity. This stabilization may also provide favorable, in relation to potency, structural arrangement in terms of the angle difference induced by the double bond. Further, by examination of the chemical relation of dexamethasone as FIG. 1(g), the correlation between the structural relation of endogenous steroids and DNA nucleotides indicates that activity is also enhanced due to the dexamethasone fluoride group which stabilizes the intermolecular hydrogen bond even more so than prednisolone, thereby increasing its relative activity.

The thymine ketone hydrogen bond is implicated in activity, despite it not forming any hydrogen bonds in nucleotide pairings. Because of both structural and functional correlations, the interaction of a second intercalated molecule with DNA at the unpaired thymine ketone may be the reason for the absence of this ketone hydrogen bonding during the formation of the A-T pairing. Thus, an explanation for the shape of a four-ring structure common to each nucleotide paring and the interaction of this common shape molecule with the A-T pairing and lack of interaction with the C-G pairing constitute the partial premise the present description considers. These similarities are particularly relevant to help provide common structures that are able to provide the same information as DNA and/or RNA and may be used to synthesize DNA/RNA.

An underlying code for DNA using a common structure is shown in FIG. 1(h). By applying two base-two (or "binary") molecules to characterize DNA: the first base-two molecule (or "catalyst") may characterize the intermolecular association between the binary molecules based on the lack of hydrogen bonding capability at the carbon-11 position (such as with the in the testosterone-like molecules) and or presence of hydrogen bonding (such as with cortisol-like molecules); and the second base-two molecule (or "substrate") of the encoding system may characterize the shape affiliated with the common structure. The second molecule generally identifies the substrate as the 5' nucleotide of either purine or pyrimidine. The first molecule is referred to as a catalyst and relates structurally to the missing third hydrogen bond of the A-T/T-A dinucleotide. The catalyst may effectively create a reaction environment that will either induce the third hydrogen bond (e.g., and result in A-T or T-A pairing) or result in a reactive pathway that prevents the formation of the third hydrogen bond (e.g., and result in G-C or C-G pairing). Thus, if the first base-two molecule is capable of forming an effective hydrogen bond onto the second base-two molecule, thereby preventing the formation of the third hydrogen bond, the second base-two molecule encodes either an A or a T. On the other hand, if the first base-two molecule is not capable of forming an effective hydrogen bond onto the second base-two molecule, otherwise, encodes either a C or G.

Consequently, the two binary molecules (e.g., configured as indicated in FIG. 1(h)) can characterize, encode, and provide the same information as nucleotide pairing based on the relative orientations of these two binary molecules. The second base-two molecule in the interactive pair is generally referenced to its observed orientation ("observed orientation" in this context indicating the relative orientations implied by orientations of the molecules in the figures) as the substrate and the first base-two molecule is determined with reference to the second base-two molecule through its intermolecular binding capability.

The relation of the base-two molecules described herein to describe a base-four entity of nucleotide pairings is bijective. The first base-two molecule (or catalyst) describes an intermolecular association of interaction with the second base-two molecule to prevent the formation of the third hydrogen bonding during nucleic acid synthesis, and the second base-two molecule, considered as the substrate, defines a shape that characterizes the spatial orientation of purine and pyrimidine nucleotides. Therefore, the four possible configurations of nucleotide pairings may be directly mapped to relative orientations of substrate/catalyst pairings dependent on the molecular form of the catalyst and substrate.

Source and Starting Molecules

To implement the code outlined in FIG. 1(h), two molecules are required which form a functional pair that produces four reaction vessels from which one of four Watson-Crick nucleotide pairs results in one of the two molecules (the substrate), and the second compound catalyst (non-substrate) molecule may be removed from the nucleotides (and possibly sequence of nucleotides).

The implications of the present disclosure to the origin of DNA also may help construct and identify suitable molecules and reaction vessels. For example, the search for the molecules may be narrowed by considering that a sequence needs to self-assemble (e.g., based on available chemicals and reaction environments encountered at first synthesis). For example, aromatics, particularly polycyclic aromatic hydrocarbons, are readily produced in combustion reactions and present in the atmosphere. Suitable candidates for substrates and catalysts may therefore be aromatic compounds that can achieve $\pi$-electron stacking with one another. Typically, to achieve the common structure identified in nucleotides pairs, a four-ring molecule can be sought (e.g., chrysene, "heterochrysene" which is meant a chrysene core having one or more heteroatom substitutions (e.g., N, O, S) in the four-ring structure core). Furthermore, although not a requirement for the encoding method to work, ideally the molecular basis should be produced by natural occurrences. In research embodiments for reviewing and/or identifying the origin of DNA, then the molecules should meet this requirement. These methods may involve synthesizing a catalyst and substrate, reviewing the self-assembly mechanisms, for the catalyst and substrate, and initiating (or attempting to initiate) a DNA synthesis such as a DNA synthesis cascade initiated by ozonolysis as described herein.

Figure 2A:
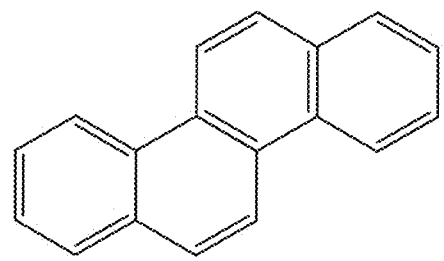
FIG. 2 (FIG. 2(a)-(d)) provides exemplary structures of primer core (2(a)), catalyst (2(b)), initiator (2(c)), and substrate (2(d)) molecules.

Chrysene, shown in FIG. 2(a), meets criteria as a suitable candidate for functionalization to form substrates and catalysts of the present disclosure. It is a four-ring aromatic compound that is capable of $\pi$-stacking. Furthermore, chrysene is similar to the common structure of the four DNA nucleotides shown in FIG. 1(b). Chrysene is a natural product available in free form (e.g., the molecule itself is available as dissolved in suitable solvents and/or as a particulate in air). In addition, chrysene and associated alkene sidechains may be attained from graphene/graphite flakes associated with cracks propagating along principal directions in graphite structures intersect. For example, graphite comprising or formed from AB-type graphene stacking is suitable for production and identification of suitable catalysts and/or substrates. The AB-stacking and/or AA-stacking of bilayer graphene for example, may be directly implicated in the required pi-stacking of the substrates and catalysts as described herein.

It is noted that chrysene is a symmetric molecule, whereas DNA is a non-symmetric molecule in terms of ring structure as shown outlined in FIG. 1. A reaction involving chrysene as the basis material for structure and catalyst requires a transformation reaction from the symmetric four-ring hexagonal structure.

To develop sidechains for chrysene for use as a catalyst and substrate undergoing a reactive transformation, there are also several requirements from the base chrysene material. For example, as chrysene is insoluble in aqueous, and thus to make it soluble, the sidechains may induce hydrophilicity. One method of producing sidechains on chrysene of the present disclosure involves halogenation of chrysene (e.g., at higher temperatures for an extended periods of time to introduce functionalization at the appropriate positions), followed by subsequent conversion of the halogen sidechain to the desired group. During the halogenation process, as shown herein, there is an order of appearance of the sidechains on the aromatic rings. In some environments, the halogenation process will produce multiple halogenated products that occur at different times while transitioning to a final product.

Figure 2B:
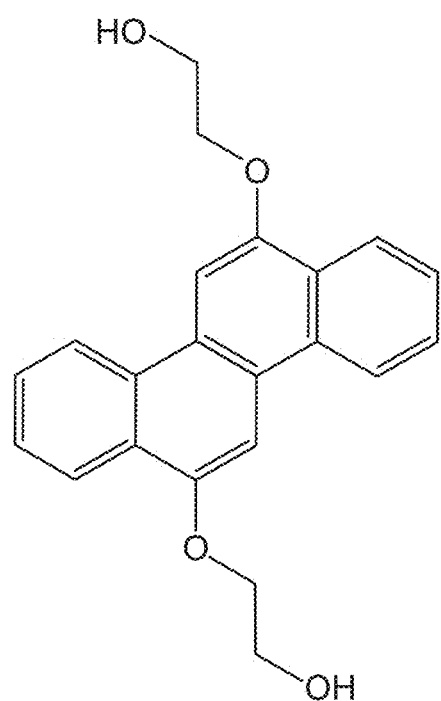
Figure 2C:
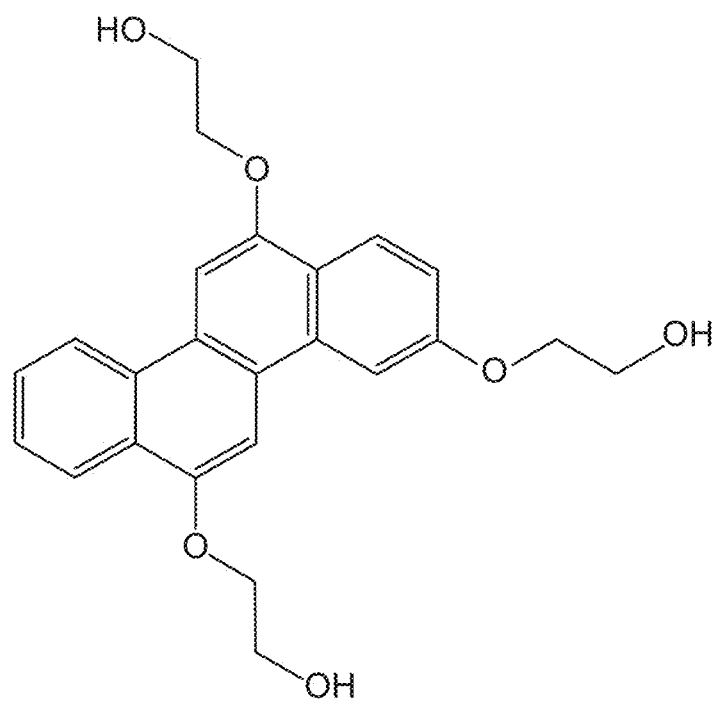
Figure 2D:
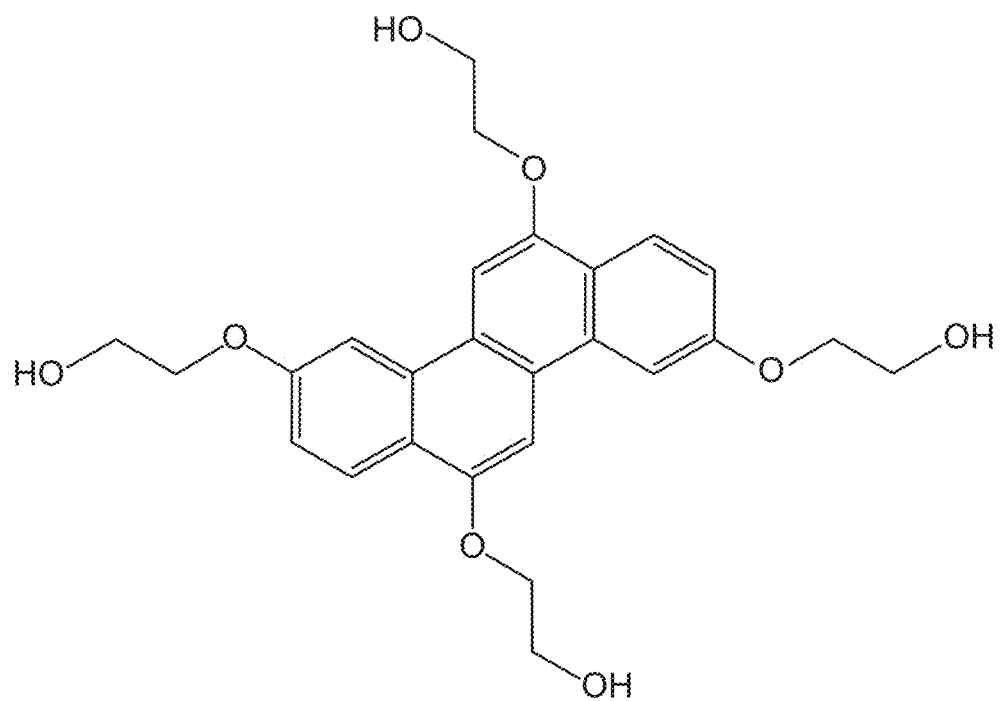

Exemplary molecules of the present disclosure capable of inducing encoded molecular sequences of RNA and DNA (as well as phospholipids for cell membranes) are presented as follows: FIG. 2(b) 2,2'-(chrysene-6,12-diylbis(oxy))bis (ethan-1-ol); FIG. 2(c) 2,2',2"-(chrysene-3,6,12-triyltris (oxy))tris(ethan-1-ol); and FIG. 2(d) 2,2',2",2'''-(chrysene-3, 6,9,12-tetrayltetrakis(oxy))tetrakis(ethan-1-ol). The sidechains are of ethoxylated alcohols, which are commonly deployed as surfactants and generally regarded as excellent nonionic surfactants.

The production of the end groups associated with the starting materials are consistent with natural occurrences as well as synthetic methods. Relevant positions for substrate and catalyst creations on chrysene become brominated sequentially. As shown herein, experimental results of a four-day bromination process of chrysene involving reaction with bromine ($Br_2$) in the presence of trimethyl phosphate show that after approximately one day the (6,12) positions are only brominated and brominated in a simultaneous manner. The bromination process involves the dilution of bromine with trimethyl phosphate to develop a reaction mixture with chrysene (e.g., at an elevated temperature such as 100° C.) for a period of time such as three days. After the formation of the 6,12 substituents, the 3 position becomes brominated to result in (3,6,12) tribromochrysene. Finally, the full (3,6,9,12)-tetrabromochrysene completes the reaction (with the experimental conditions, seventy-two hours of reaction time). The amount of trisubstituted product is low, less than 5% (by mol), with the majority of product disubstituted and tetrasubstituted product. Bromination reactions can occur at high rates with less than 2 mol % chrysene remaining, and with minimal monobromosubstituted chrysene compounds (e.g., less than 2 mol %).

Figure 3:
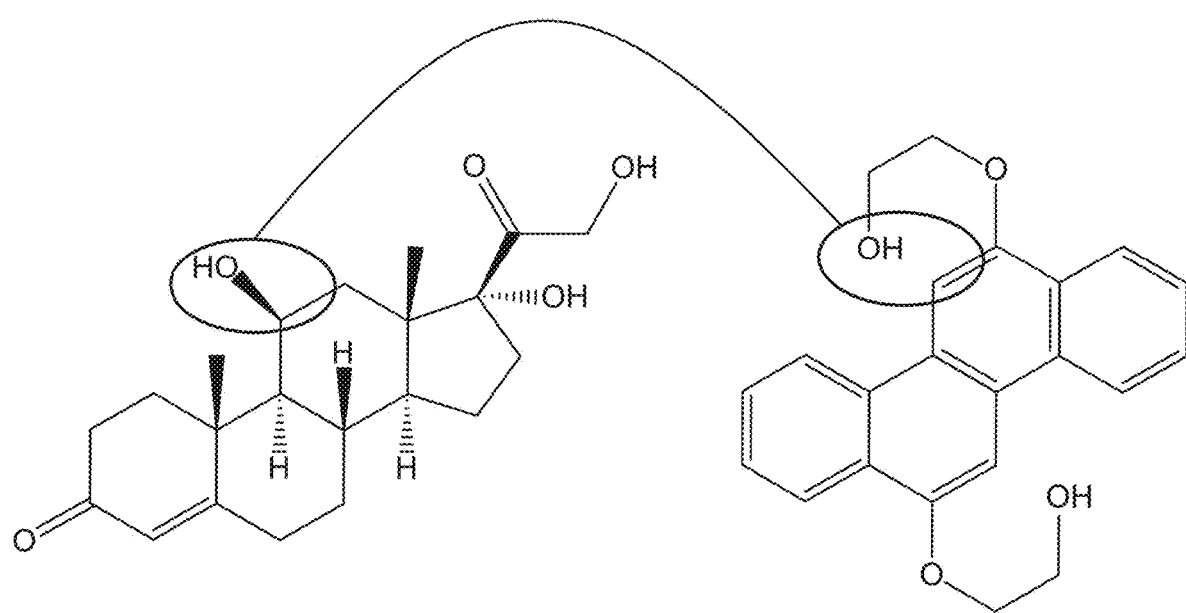
FIG. 3 provides a schematic illustrating the similarities and differences in core functionalization (extendible to catalysts/substrates/initiator) to cortisol.

The halogenated sidechains may be used to install more specific groups such as alkoxy groups on the central polycyclic core consistent with the asymmetries in the substrate and catalyst (particularly in the encoding and the DNA/RNA syntheses described herein). For example, installation of an oxalate-based (e.g., —OC(O)C(O)O—) or ethylene glycol-based sidechain e.g., —OC($R_2$)C($R_2$)O—, wherein R is independently selected at each occurrence from hydrogen or alkyl (e.g., lower alkyl, $C_{1-6}$ alkyl) or two geminal R groups may together form =O),) at the carbon 12 position of chrysene is consistent with the positioning of the hydroxyl group at the carbon-11 position of steroids matching the primer shape identified in FIG. 1 such as cortisol. As shown in FIG. 3, a comparison of the cortisol hydroxyl position, which can induce a third hydrogen bond through intermolecular coupling between the A-T pairing and cortisol, to a possible positioning of a hydroxyl group is shown. When the substrate and catalyst are aligned (having such an oxalate-based sidechain), the hydroxyl end-group of the sidechain of the chrysene carbon-12 position substrate is similarly matched to the chrysene-based catalyst.

The four-ring shape, which relates to the common shape of the primer structure, as well as the positioning of the side-chain elements, and the consistency with the natural appearance of sidechains, suggest that starting materials, such as those in of FIG. 2, are capable of encoding the information content of DNA. Therefore, the three compounds, which are consistent with natural occurrences thereby lowering development efforts, and are capable, as will be developed, of inducing a synthesis of encoded nucleic acids. These syntheses may not require substantive other additive compounds and instead proceed in cascade reactions as described herein. Consequently, substrates and catalysts of the present disclosure (e.g., the molecules of FIG. 2 synthesize DNA, RNA, hybrid DNA/RNA. Additionally, these components and reactions form phospholipid bilayer molecules for cellular enclosure of the genetic materials.

Encoded Sequences by π-Electron Stacking of Substituted Chrysene

Figure 4A:
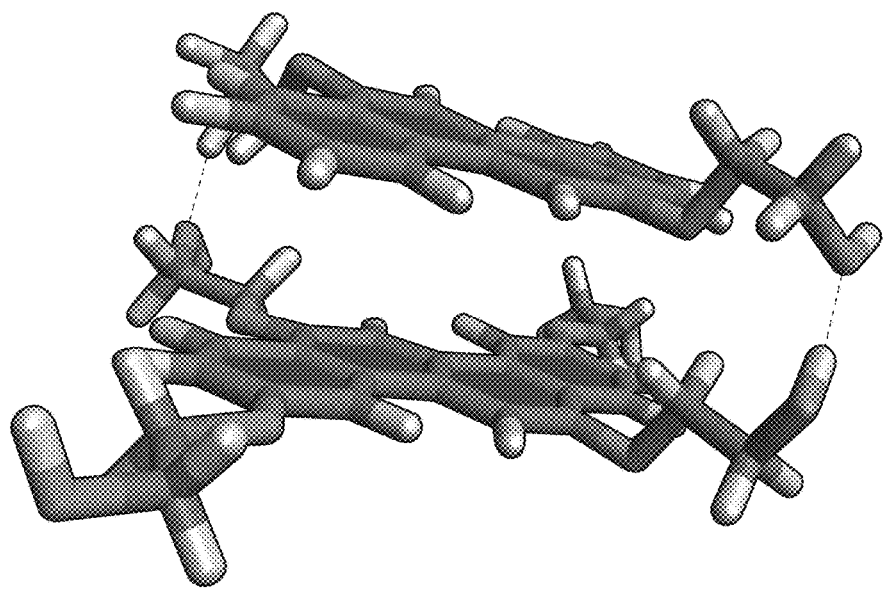
FIG. 4(a) is a 3D model of a substrate/catalyst pairing showing possible π-stacking between each molecule.
Figure 4B:
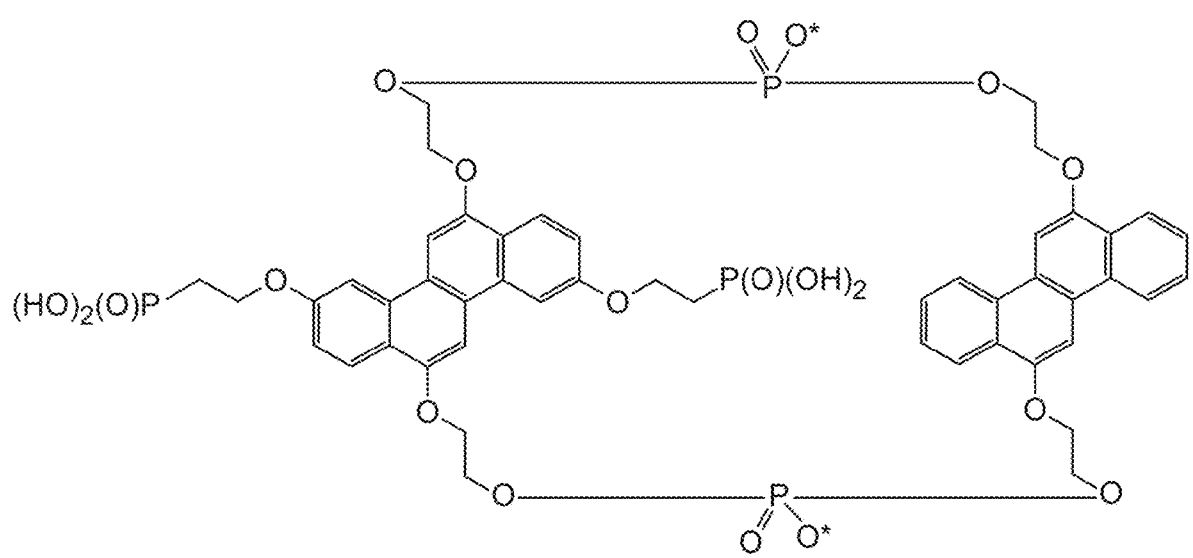
FIG. 4(b) provides a chemical structure of a substrate and catalyst conjugated to one another via covalent phosphodiester bonding of the 6 and 12 positions of the chrysene core in both the substrate and catalyst.

In FIG. 4(a), a model depicts a coupling of chrysene molecules through π-π electron interactions to form an exemplary reaction vessel. The model was constructed using the Avogadro simulation program incorporating a MMFF94 force field with steepest descent convergence algorithm to estimate the planar separation distance, as indicated by the dotted lines, as 3.6 Å in the model—a separation consistent with the base stacking distance of DNA. In FIG. 4(a), the top molecule is a catalyst, having sidechain conjugation at only the 6 and 12 positions, while the bottom molecule is a substrate, having sidechain conjugation at the 3, 6, 9, and 12 positions. In another embodiment, the bottom molecule of the reaction vessel has sidechain conjugation only at the 3, 6, and 12 positions. The core chrysene is hydrophobic, as is DNA, and with the addition of the sidechains, these molecules and reaction vessels may be solubilized with hydrophilic solutions. Furthermore, the dimerized forms may be converted into molecules themselves, conjugation between substrate and catalyst. For example, the heterodimer of FIG. 4(b) shows the pairing of the 6,12-disubstituted chrysene with 3,6,9,12-tetrasubstituted chrysene, connected through two phosphodiester bonds. This compound is a spatially constrained reaction environment (or reactant) combined with a chemically constrained environment having a hydrophobic core contained within hydrophilic surroundings.

Figure 4C:
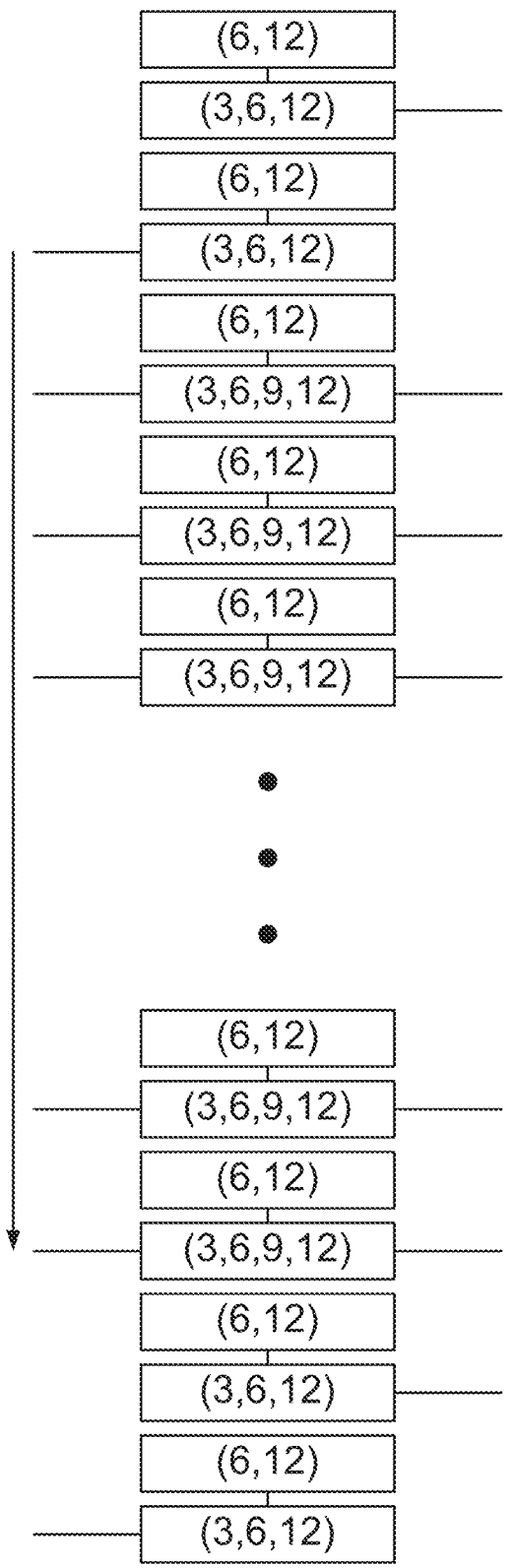
FIG. 4(c) provides an exemplary stacked set of heterodimer pairs (each which may be considered and individual reaction environment). Each rectangle represents a substrate or catalyst (e.g., chrysene) labeled with the functionalized carbon positions ("(6,12)" refers to catalysts, "(3,6,12)" refers to substrates, and "(3,6,12)" refers to initiators). The vertical lines identify the π-stacking within each reaction vessel capable of encoding base four information. The horizontal lines refer to sidechains extending from the 3 or 9 positions which may be used to form conjugations with adjacent reaction vessels. Arrows refer to the 5'→3' direction.

A sequence of heterodimers may form a useful segment of RNA or DNA is depicted in FIG. 4(c). In FIG. 4(c), each square rectangle represents an ordering of catalysts (denoted by (6,12) representing the conjugation positions in chrysene), substrates (denoted by (3,6,9,12) representing the conjugation positions in chrysene), or initiators (represented by (3,6,12)). Each individual π-stacked heterodimer (substrate/catalyst or initiator/catalyst) pair is represented by the a vertical line between each component. The horizontal lines extending from each initiator or substrate represent the functional groups at the 3 and 9 positions extending from the chrysene core. The sequence is predominantly heterodimers presented in an arrangement comprising a long train capped at each end by the 3,6,12-trisubstituted chrysene (or initiator). The initiator(s) is(are) responsible for the initiation and termination of the polymerization process of the phosphodiester linkage between reaction vessels. Furthermore, the relative orientation of the catalyst to the substrate and the spatial orientation of the substrate itself to the 5' direction will define the resultant nucleotide. Using such systems, a code is provided capable of storing information (e.g., base four information). This code may map related spatial orientations of the substrate and catalyst (and initiator and catalyst) to the resultant nucleotide order after synthesis as described herein.

Figure 4D:
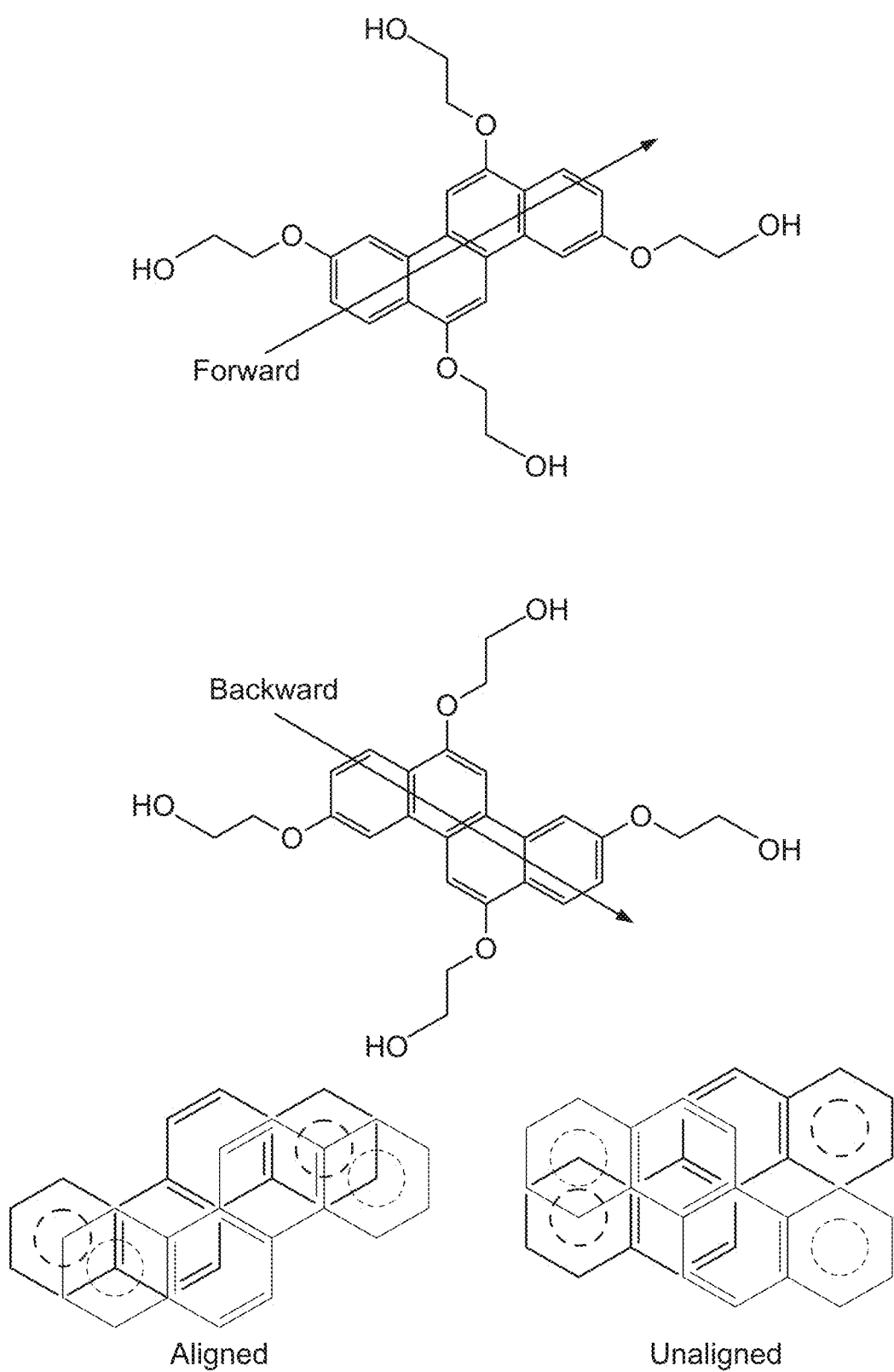
FIG. 4(d) provides two different configurations possible for the substrate (and catalyst): Forward ("F") or Backward ("B") as well as exemplary Aligned and Unaligned configurations when pairing with the catalyst. For the Aligned and Unaligned pairings, the substrate (black) is provided in the Forward orientation, while the catalyst (grey) is alternated between the Forward and Backward orientation.
Figure 4E:
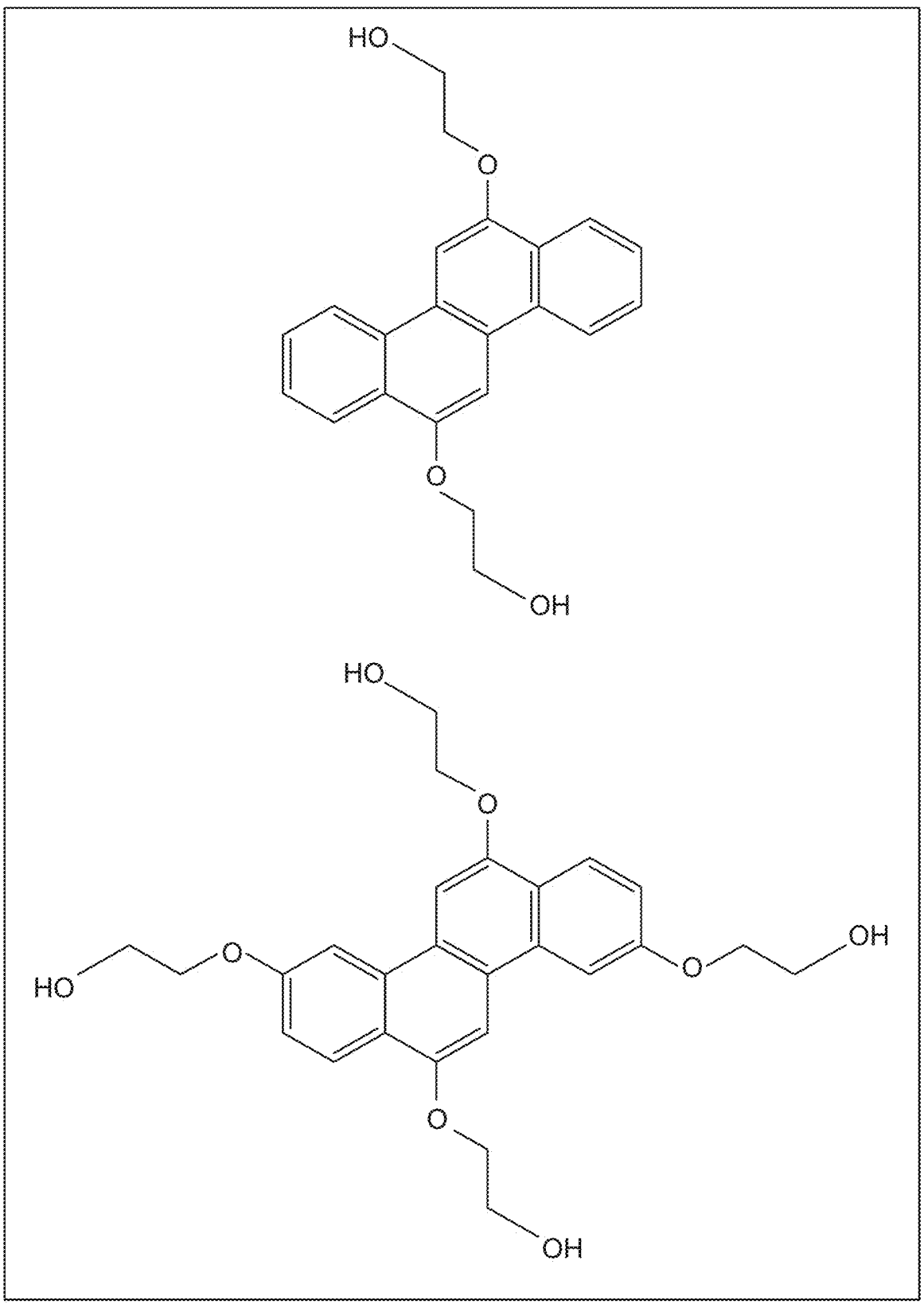
FIG. 4(e) provides an exemplary catalyst/substrate aligned pairing for formation of a reaction vessel. FIG.
Figure 4F:
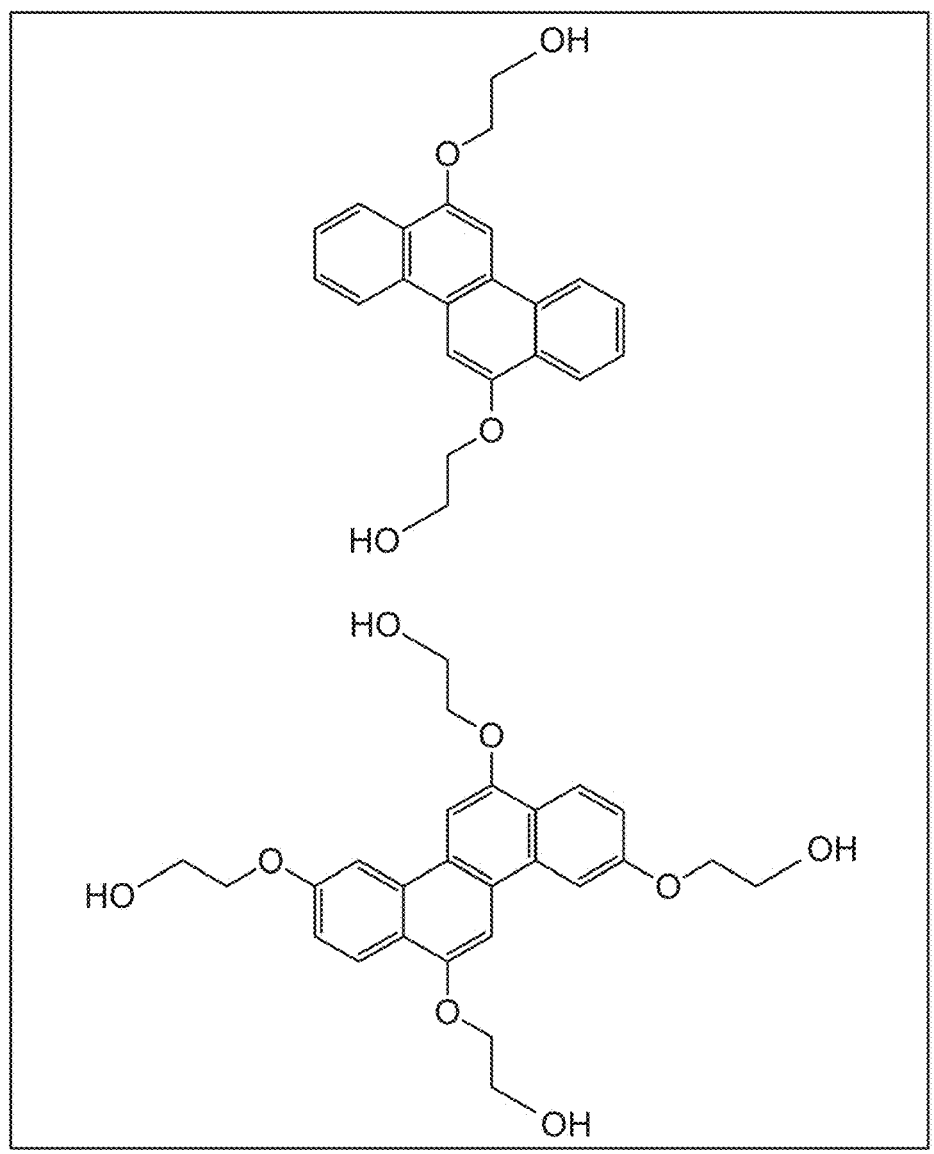
FIG. 4 (FIG. 4(a)-(j)) identifies various substrate/catalyst pairings (via dimerization or conjugation).
FIGS. 4(g)-(j) provide an exemplary initiator compound which is typically used to establish the basis for the relative orientations of the substrates for encoding the base four information in a stack of reaction vessels.

FIG. 4(d) identifies exemplary relative orientations useful for code storage of exemplary substrate molecules. The molecule may be defined as either "Forward" (F) or "Backward" (B) depending upon the orientation of the aromatic ring structures. Due to the symmetry of these tetra substituted chrysene catalysts, of which there are only two possible orientations in the parallel arrangement of molecules due to π-stacking implicated in the reaction vessels of the present disclosure. When π-stacked with a catalyst, the substrate/catalyst pair (formed either via dimerization or conjugation between each moiety), the Forward and Backward alignments result in two different relative configurations for an individual reaction vessel. As used herein, the alignment of the catalyst to the substrate is considered "Aligned" as shown in FIG. 4(d) with π-stacked substrate/catalyst/initiator cores in their "AB" forms (similar to graphite/graphene AB stacking). In FIG. 4(d), a black exemplary core may be the catalyst, with the relative orientation of the grey substrate or initiator π-stacked thereon in both the Aligned and Unaligned configurations. In FIGS. 4(a) and (e), which depicts the Aligned configuration, the π-stacked substrate and catalyst pair have the central polycyclic cores in the same orientation such that there is substantial π orbital overlap. As can be seen, an Aligned orientation refers to when the top catalyst molecule π-stacks with the bottom substrate molecule (as shown in FIG. 4(a)), in the same relative orientation where the central core is in the orientation configuration (e.g., in this case, both are in the Forward direction). In FIG. 4(f), which depicts the "Unaligned" orientation the central core has, the catalyst and substrate are oriented in the configuration depicted, but with π-stacking as shown in FIG. 4(a). The catalyst is in the Backward direction, while the substrate is in the Forward direction and are therefore considered Unaligned. For any substrate/catalyst pair (or initiator/catalyst pair), the Unaligned and Aligned configurations may be considered the local minima on a potential energy surface representing the dimerization of the two molecules. In some embodiments, the Aligned structure is the global minimum on the potential energy surface. Such local minima may help induce the self-assembly of the two molecules into the two orientations and allow for the encoding of information.

The alignment of the catalyst to the substrate typically defines the resultant nucleotide by the production of the three hydrogen or two hydrogen bonds linking the paired resultant nucleobases. The alignment contributes to the formation of the reaction environment from which the nucleobases may be subsequently synthesized. In FIG. 4(e), the alignment is illustrated of the ring structure of the catalyst (6,12-disubstituted chrysene) to the ring structure of the substrate (3,6,9,12-tetrasubstituted chrysene); whereas in FIG. 4(f) the ring structure of the catalyst to that of the substrate are not aligned (or Unaligned).

Figure 4G:
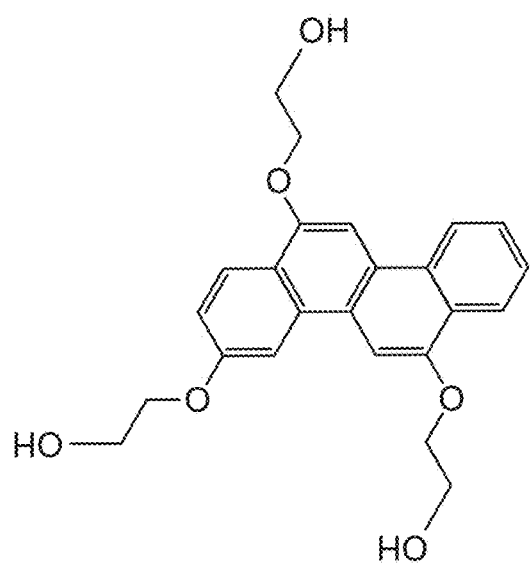
Figure 4H:
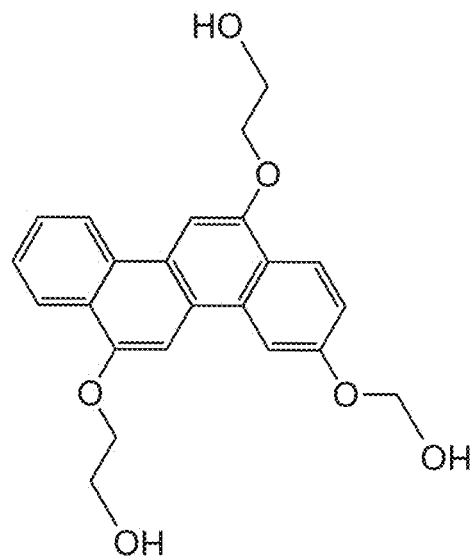
Figure 4I:
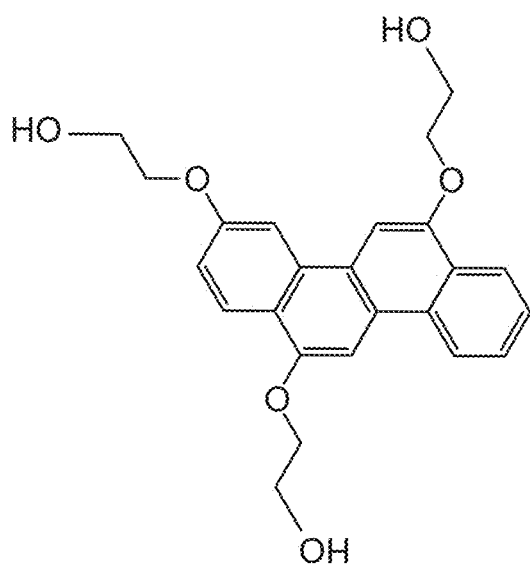
Figure 4J:
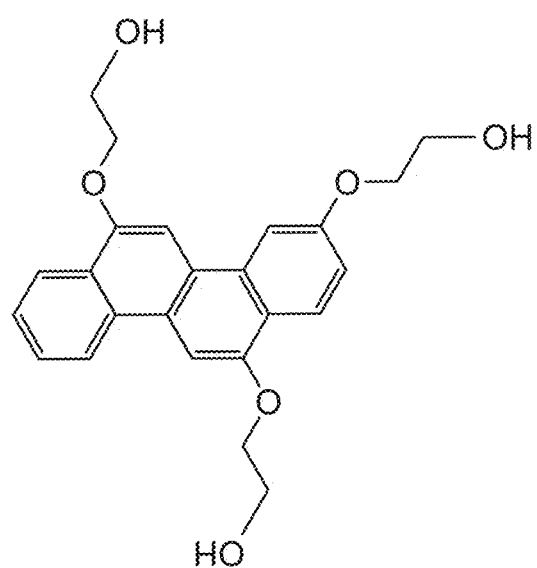

Trisubstituted compounds, such as 3,6,12-trisubstituted chrysene functions as a regulator (or initiator) for the code (and any resultant sequence) as these compounds terminate the polymerization process. Polymerization is terminated due to a lack of a sidechain at the 9 position in the compound, therefore preventing conjugation for any further substrate/catalyst pair. The relative orientation of the regulator (or initiator) compound may also inform the directionality of the encoded sequence. For example, the production of RNA expressed as 3'-5' may be initiated by the orientation of the molecular initiator shown in FIG. 4(i); the production of DNA expressed as 3'-5' orientation may be initiated by the molecule of FIG. 4(j); the production of RNA oriented as 5'-3' may be started by the molecule of FIG. 4(g); and the production of DNA oriented as 5'-3' may be started with the molecule shown in FIG. 4(h). The reason for this distinction relates to the orientation of the entry point for the sugar-ring to the nucleobase in DNA/RNA, which may define the side of the molecule that the phosphodiester chain resides between adjacent nucleotides (or reaction vessels). Therefore, the lack of a functional group for conjugation of adjacent reaction vessels prevents continuance of the polymerization reaction. This can be seen in FIG. 4(c), wherein the initiator molecule does not have a functional group (horizontal line) capable of forming phosphodiester linkages with an adjacent substrate on either the left or right sight of the conjugated set of pairs (e.g., heterodimers, reaction vessels, substrate/catalyst pairs). It will be understood, unless otherwise apparent, in comparing two or more compounds depicted in the figures, their relative orientation is indicated by the orientation identified in the plane of the page.

Code for DNA and RNA

The π-stacked arrangement of reaction vessels (e.g., heterodimers) of catalysts (e.g., 6,12-dihydroxyethoxy chrysene) and substrates (3,6,9,12-tetrahydroxyethoxy chrysene), optionally capped (at one or both ends) with reaction vessels (e.g., heterodimers) comprising initiator (e.g., 3,6,12-trihydroxyethoxy chrysene) and catalyst provides the requisite basis for information. These stacked reaction vessel may define codes which correlate to RNA and/or DNA based on the relative orientation of the four reaction vessels possible of the heterodimers. For the 5'-3' direction in any DNA/RNA synthesized, in FIG. 5(a), an exemplary code based on this encoding system is provided for producing paired RNA nucleotides. In the top table, the catalyst orientation is shown in the left column and the relative substrate orientation is shown in the right column For example, in the top row, which demonstrates the substrate catalyst pairing which may encode the A-U nucleotide pair, the catalyst is shown in the forward direction and the substrate is shown in the forward direction Therefore, A-U along the 5'-3' direction encodes the an adenosine via an aligned reaction vessel. The bottom table summarizes this analysis using the "F" (forward) and "B" (backward) nomenclature. For the 5'-3' direction for DNA nucleotides, FIG. 5(b), provides similar tables for the code producing paired DNA nucleotides. As can be seen, the code may be opposite between DNA and RNA. In various implementations, the synthesis creates the nucleotides and subsequent removal of the catalyst is performed by strand separation for the RNA product, and through ejection by rotation of the DNA nucleotides, as further discussed.

Figure 5A:
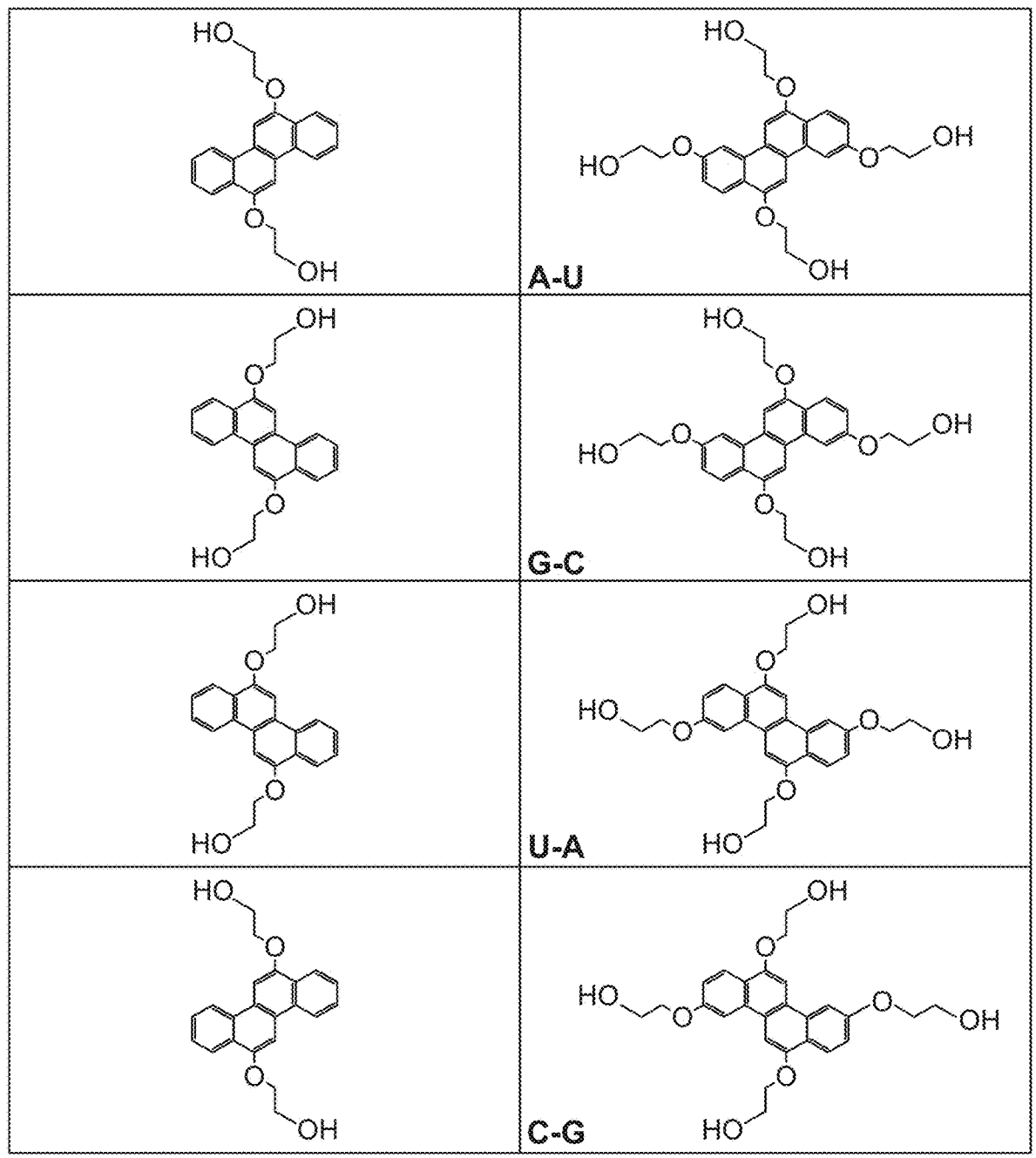
FIG. 5(a) shows catalyst (top table, left column) and substrate (top table, right column) orientations with the respective pair for RNA pairings. The bottom table summarizes these orientations using the Forward ("F") and Backward (B) notation to illustrate the left side nucleotide formed (e.g., the nucleotide formed in the 5'→3' chain).
Figure 5B:
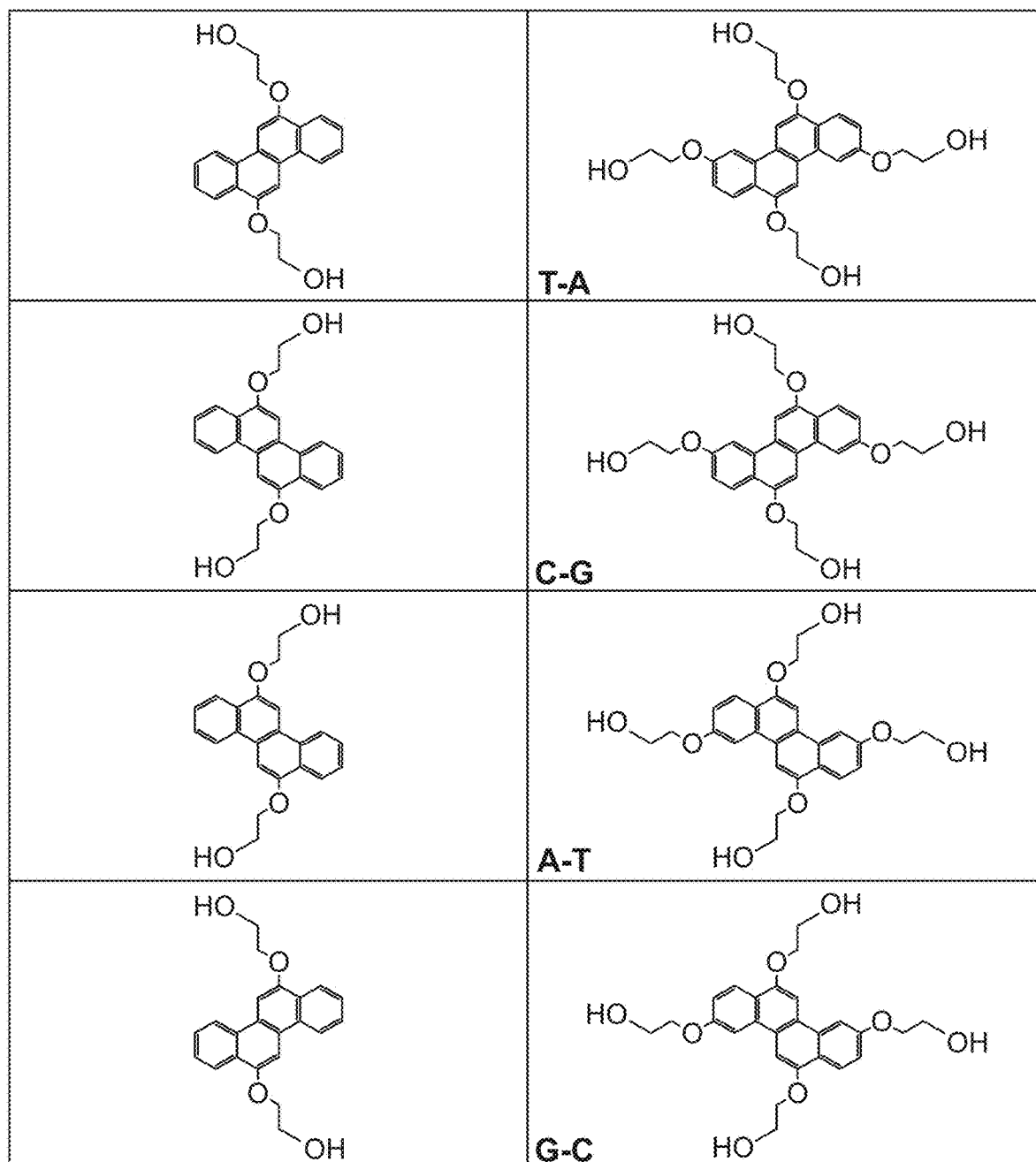
FIG. 5(b) shows catalyst (top table, left column) and substrate (top table, right column) orientations with the respective pair for DNA pairings. The bottom table summarizes these orientations using the Forward ("F") and Backward (B) notation to illustrate the left side nucleotide formed (e.g., the nucleotide formed in the 5'→3' chain).

In FIG. 5(a), an example of the RNA code is presented which may form one strand with sequence 5'-AGUC-3' with an antiparallel strand 5'-GACU-3'. To begin encoding and/or syntheses of these sequences, the substrate and the endcaps (e.g., row 1 in the top table, row 4 in the top table) may be initiators (e.g., trisubstituted chrysene). The beginning portion (row 1) may denote the initiator of the direction and the code, which may be trisubstituted chrysene. The initiator may also terminate the sequence. Initiation and termination may occur simply because there is no sidechain on one side to continue the polymerization process. Sequential trisubstituted chrysenes may also be needed in stacked reaction vessels to halt an antiparallel nature of the polymerization process that may occur (e.g., in a cascade reaction). The right column represents the resultant RNA nucleotide pair after running the reaction within the constrained space defined by the catalyst-substrate assembly. For RNA, the catalyst remains after assembly and is released through strand separation as the 2' carbon becomes hydroxylated. In FIG. 5(b), a comparative code of DNA is indicated. For DNA, the catalyst is typically ejected through a rotation of the paired DNA nucleotides after synthesis. Ejection may effectively convert the DNA from a left-handed helix configuration to a right-handed double helix. Since the placement of the trisubstituted chrysene regulator items are independent, it is possible to have one nucleotide of DNA on one strand and the other nucleotide of RNA on the other strand. Thus, a combination of DNA/RNA may also be a product of this arrangement as a sequence, in which case RNA single-strand separation may be driven by water solution. Cascade reactions on a reaction vessel may be induced to result in formation of a single DNA strand and a RNA strand. In addition to a linear sequence, a circular arrangement of catalyst and substrates is also possible in which the π-stacked sequence of reaction vessels circles back upon itself.

FIG. 5(c) provides a summary of the exemplary codes possible by the stacked reaction vessels of the present disclosure where CA represents catalyst aligned; CU represents catalyst unaligned; RD represents Right 5' DNA position; LD represents left 5' DNA position; RR represents right 5' RNA position; and LR, represents left 5' RNA position.

In some embodiments, the polymerization process takes place between sequential substrates separated with the catalyst without requiring the presence of the regulator. The direction and code may proceed thereby in an indeterminate fashion in terms of the initiating coupling by phosphorylation between adjacent substrates (e.g., 2,2',2",2"'-(chrysene-3,6,9,12-tetrayltetrakis(oxy))tetrakis(ethan-1-ol)). However, certain arrangements of reaction vessels may proceed more rapidly than others depending upon, for example, the physical distance between adjacent sidechains which conduct the polymerization between neighboring substrates. Moreover, the catalyst arrangement between substrates may hamper the polymerization by physically blocking formation of the nascent phosphodiester linkage. Thus, certain arrangements, such as TTTT as compared to TATA have different probabilities of polymerization to initiate and to terminate a sequence. Consequently, the initiator is optional, inasmuch as the substrate (e.g., 2,2',2",2"'-(chrysene-3,6,9,12-tetrayltetrakis(oxy))tetrakis(ethan-1-ol)) may be sufficient to serve as the regulatory and direction encoding compound in certain sequences.

Reaction for Synthesis of Encoded DNA and RNA

The reactive transformation of π-stacked catalysts and substrates (e.g., substituted chrysene) to DNA and RNA may follows Hückel [4n+2] aromaticity. For example, the starting material chrysene has four rings and is aromatic for a total of eighteen ring π-electrons. Initiating a reaction in chrysene (or substituted chrysenes such as the substrate) within a π-stacked framework may induce a stepwise set of reactions in which the end product has regained planarity, aromaticity and π-electron connectivity to the adjacent aromatic catalyst of substituted chrysene. For example, the end-result may be an aromatic substituted purine which has ten ring π-electrons and an aromatic substituted pyrimidine which has six ring π-electrons:

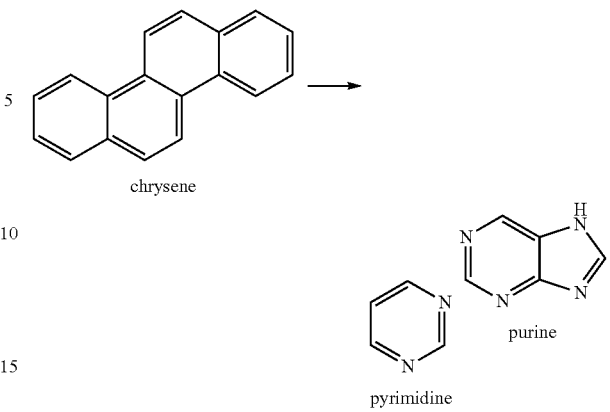

Figure 6:
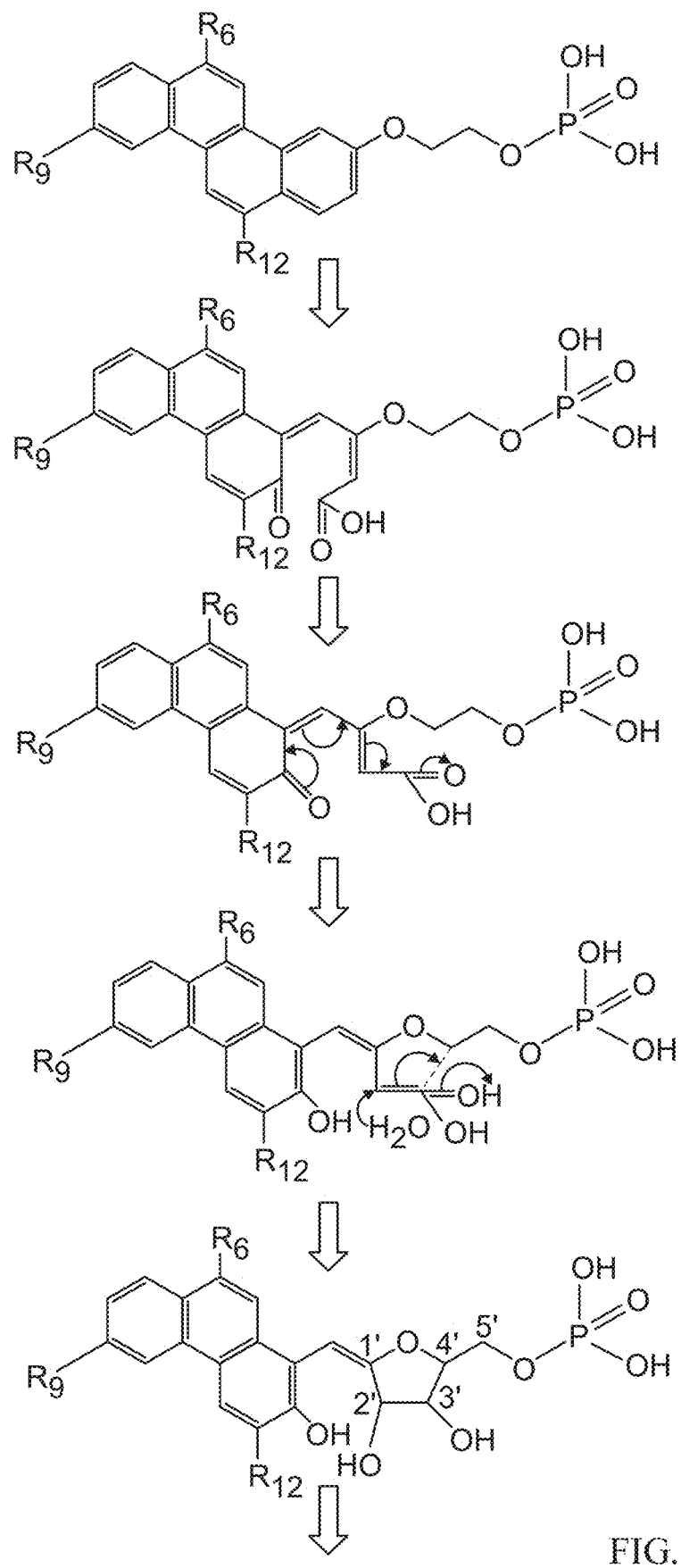
FIG. 6 is an exemplary synthesis of the sugar rings and DNA base pair from an exemplary substrate molecule. $R_6$, $R_9$, and $R_{12}$ may be as defined herein. If separated from the compound (e.g., as a remnant in a reaction), it will be understood that the relevant compound or salt will be formed based on the reaction environment. "- - -" across multiple adjacent bonds indicates a distribution of π electrons across those bonds from a transitional electron pushing mechanistic standpoint.
Figure 6:
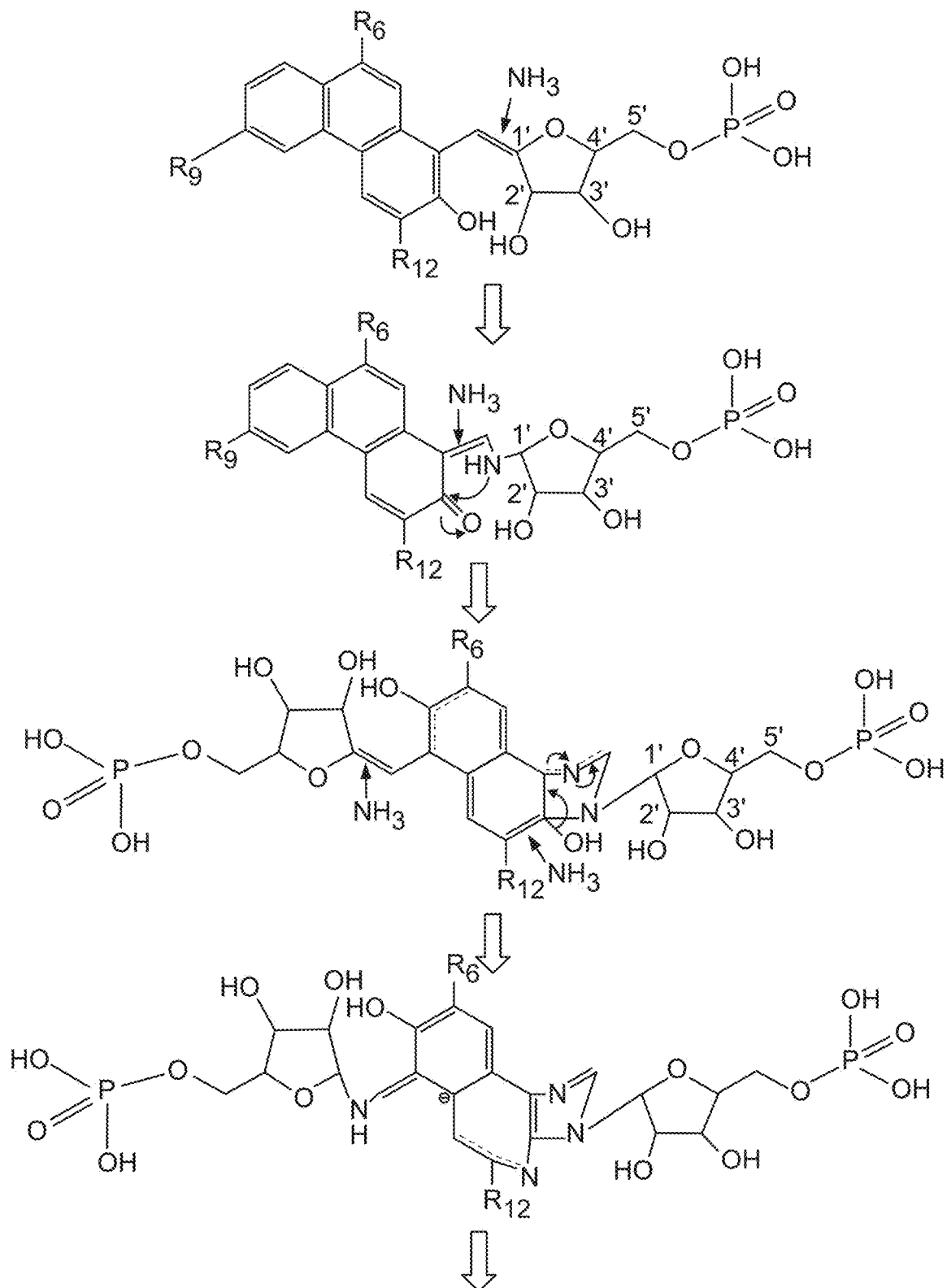
Figure 6:
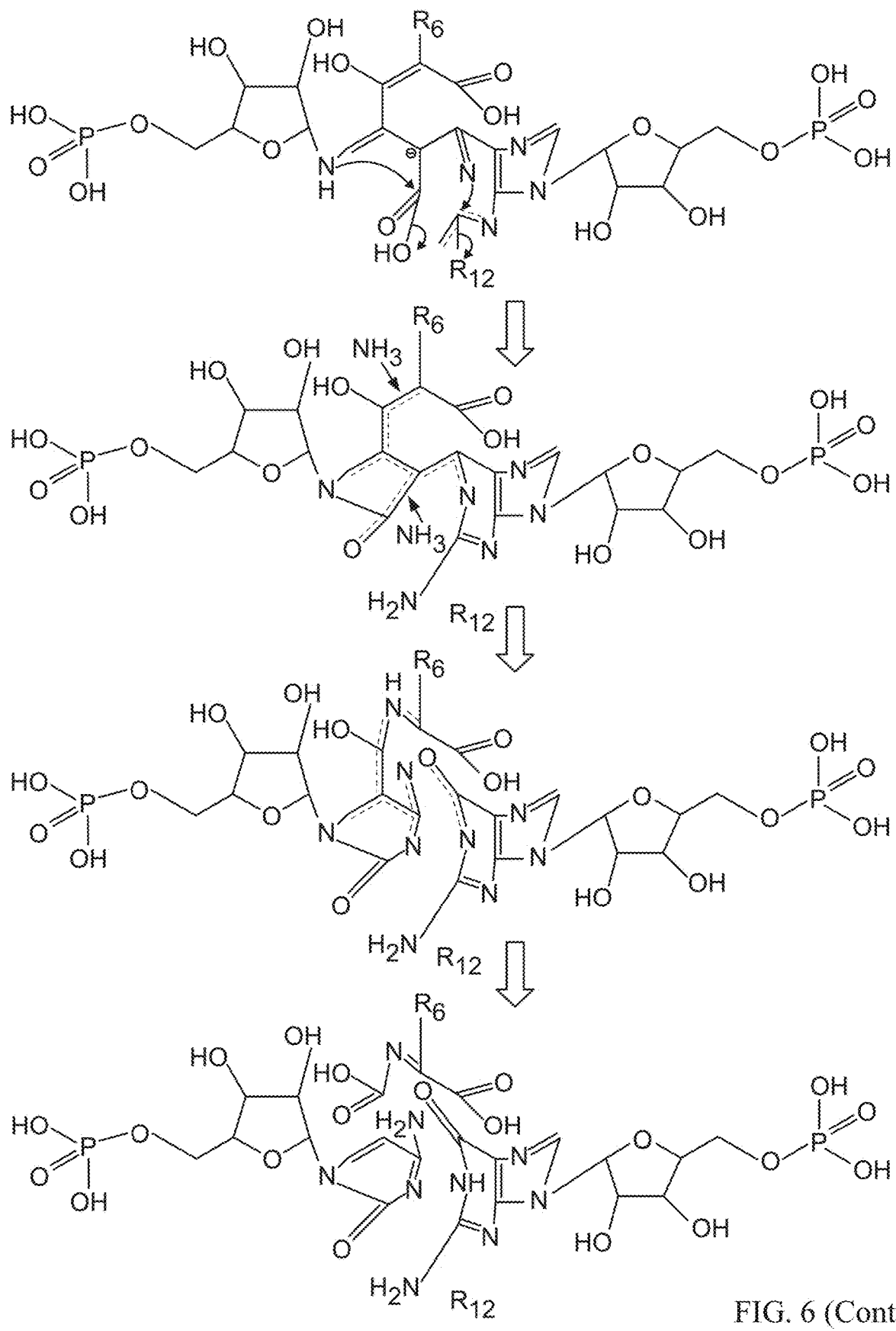
Figure 6:
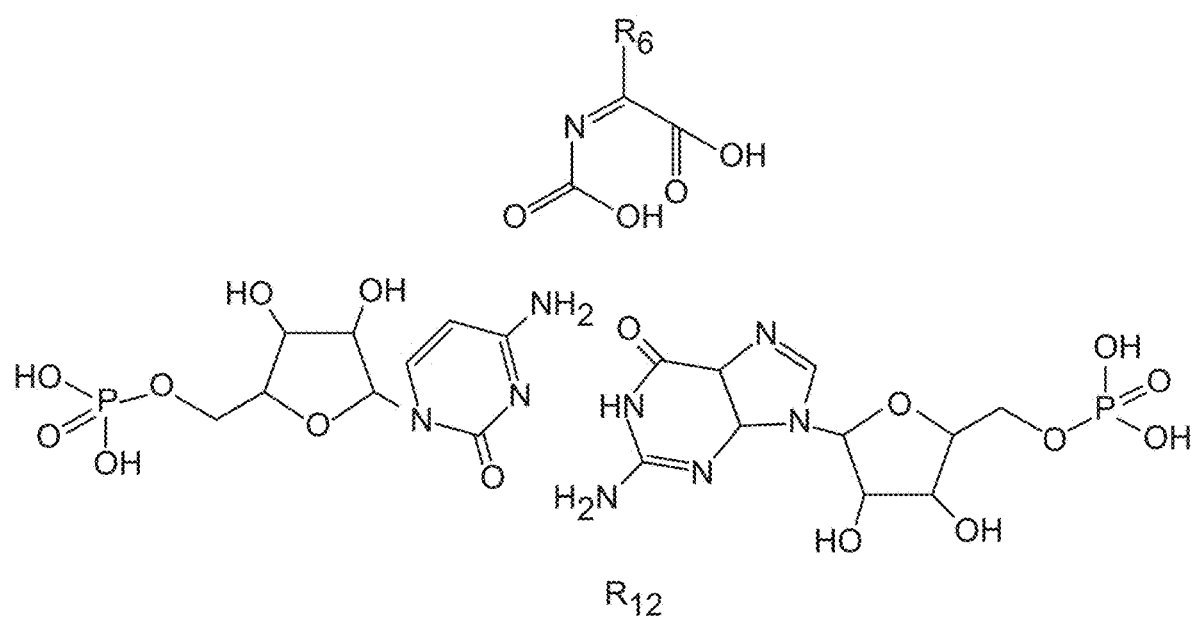

In FIG. 6, an exemplary mechanistic synthesis of nucleoside base pair starting from a substrate, including formation of a sugar-ring, is shown. The first step involves an oxidative cleavage two carbon positions away from the $R_{12}$ sidechain, which in the figure is selectively shown only for one of the two sugar-rings (e.g., $R_9$ may also be —$OCH_2CH_2OPO_3H_2$ and follow a similar synthesis which may occur sequentially or simultaneously with the sugar attachment shown). Electron flow couples a carbon-carbon linkage, reducing a π-bond to a σ-bond connecting what will be the 3'-4' linkage to the sugar. For configurations associated with RNA, a hydroxyl group is incorporated at the 2' position of the sugar. As two π-electrons of the eighteen π-electrons from chrysene are used to form two σ-bonds to connect the sugar-rings, the remaining 16 π-electrons are rearranged along with nitrogen atom insertions (e.g. by ammonia insertion) to ultimately form two aromatic compounds, a purine-pyrimidine, and maintain the continuity of the stacked molecules.

The sequence of steps to produce the internal rings for the cytosine-guanine pairing of RNA is also depicted in FIG. 6. For clarity, a stepwise progression is indicated although a concerted reaction can take place. Nitrogen insertions are used to increase the atoms comprising a ring structure, which is lost due to the formation of the sugar ring for example. Additional oxidative cleavages are applied to break the rings apart and imine-based reactions are applied to form an intramolecular ring. For the formation of the nitrogen elements within the rings, the same sequence holds for C-G/G-C RNA and DNA, as well as T-A/A-T and U-A/A-U. Since the catalyst and substrate are unaligned in the formation of the cytosine-guanine pairing, the side groups of ketone and amine are organized as shown.

Figure 7A:
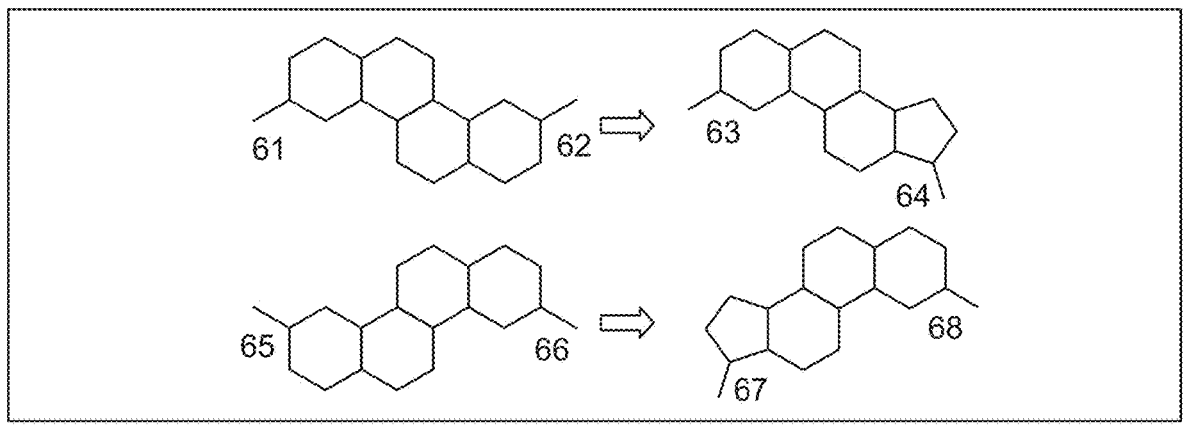
FIG. 7(a) illustrates the transition of the sidechain position of the chrysene ring structure to the nucleobase to sugar-ring connection of RNA.
Figure 7B:
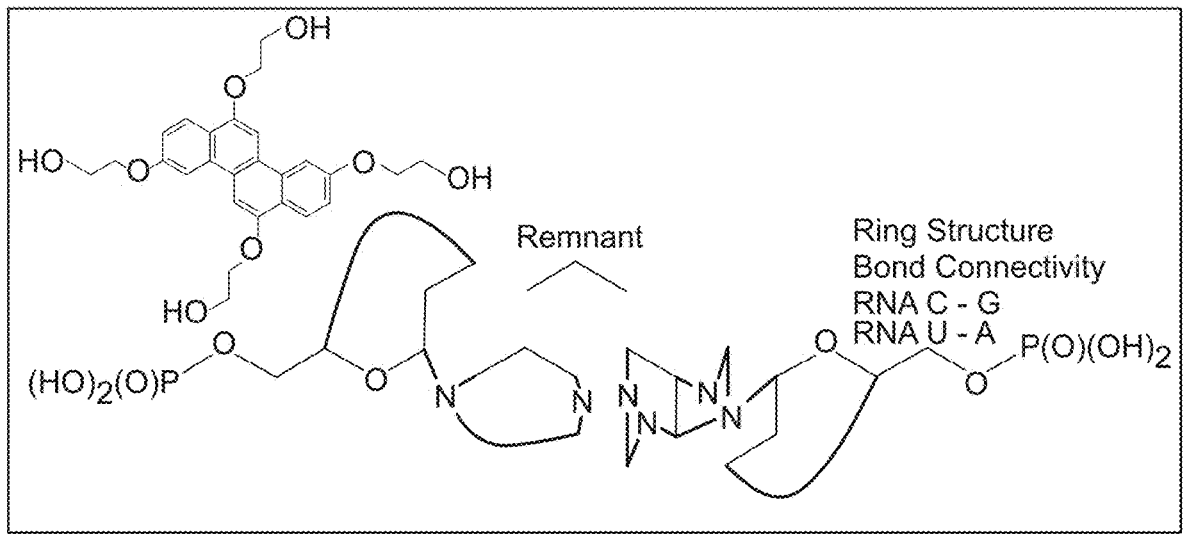
FIG. 7(b) illustrates bond connections relative to the initial positions of the carbon atoms comprising the core chrysene substrate resultant in RNA C-G and RNA U-A.

In FIG. 7(a)-(j), schematics are presented that relate the original position of the carbon atoms of the chrysene-based substrate to the final DNA or RNA nucleic acid structure for the purpose of design and synthesis. The first illustration of FIG. 7(a), presents and overall view of the transformation of the basic ring structure comprising the chrysene substrate to the ring structure circumscribed by paired nucleotides of RNA, pursuant to the description of the common structure (FIG. 1). This illustration is to be compared with FIG. 7(d), which is an equivalent structure presented for complementary DNA nucleotides.

FIG. 7(a) presents for one orientation the sidechains of the chrysene-based substrate as 61 and 62, and the resultant connections to the sugar rings of RNA as 63 and 64. During the transformation process into RNA, the sidechains remain oriented on the 5' strand consistent with the pyrimidine connection and thus relative angle of the sidechains of 61 is equivalent to that of 63. However, for the purine connection, the sidechain of 62 rotates in the formation of the purine, thereby producing a connection with the sugar ring in an orientation consistent with 64.

In FIG. 7(a), the configuration for a purine on the 5' strand is indicated by 65 for the chrysene-based sidechain resultant in the purine connection to the sugar-ring as 67. On the contrary, the correspondence of the purine connection is 66 and 68. Thus, the rotation of the sidechain into a final configuration consistent with RNA occurs through the purine nucleobase with the pyrimidine stationary. In a programming context, the encoding of the chrysene stack can also be developed in terms of the relative positions of the sidechains and would comprise a binary encoding scheme as to purine or pyrimidine as the resultant nucleotide.

Figure 7C:
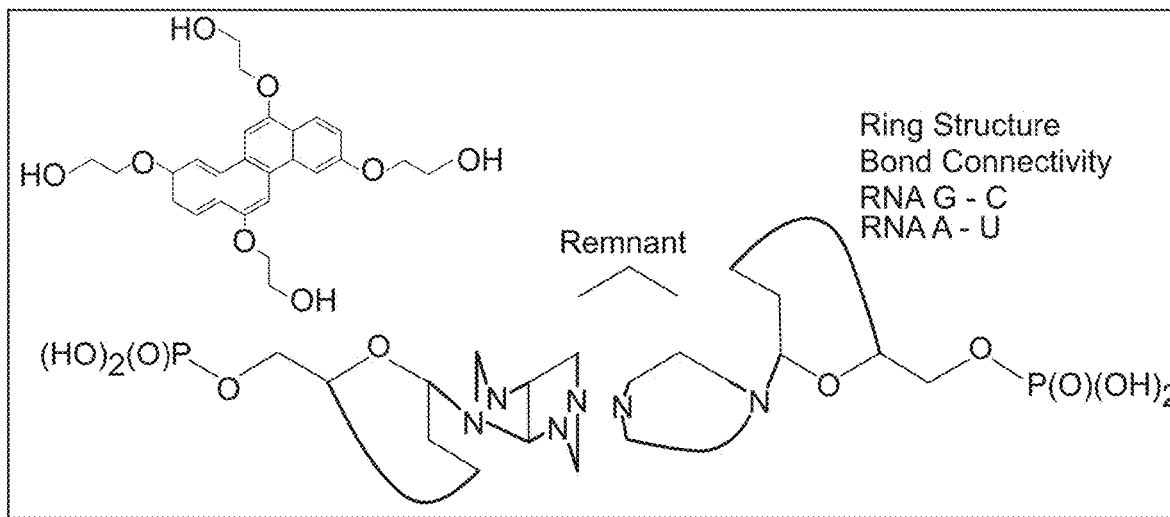
FIG. 7(c) illustrates bond connections relative to the initial positions of the carbon atoms comprising the core chrysene substrate resultant in RNA G-C and RNA A-U.
Figure 7D:
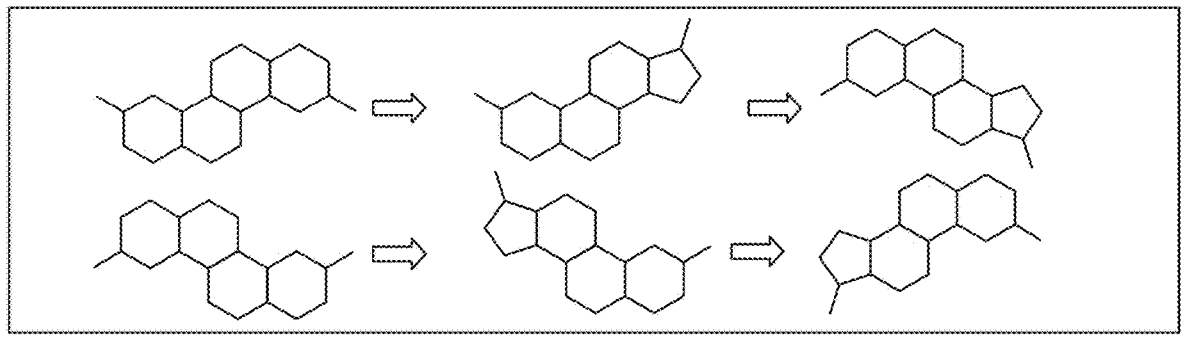
FIG. 7(d) illustrates the transition of the sidechain position of the chrysene ring structure to the nucleobase to sugar-ring connection of DNA indicating conversion to an intermediate structure followed by inversion to the final structure.

Now, the atom mapping is considered for the transformation of the starting molecule of (3,6,9,12)-tetrasubstituted chrysene to RNA and to DNA nucleotides. The general flow of bonds that need to be formed starting from the substrate in Forward orientation (top left) in order to produce the targeted result (without showing the carbonyl or amine side groups) is presented in FIG. 7(b) for the RNA C-G and U-A nucleotide pairs. Similarly, FIG. 7(c) provides the bonds that need to be formed for the RNA G-C and A-U nucleotide pairs with the substrate in the Backward direction (top left corner). As can be seen, bond connections are—the same for all sets, with the only difference being the orientation. The position of the starting material is indicated in the inset figure.

Alternatively, in FIG. 7(c), the schematic of the general morphogenesis for the transformation of the ring structure starting material to DNA nucleotide pairings is shown. In this case, the entry points are positioned in an upward position (or when from above, with a right to left insertion) as an intermediate result. The "left to right" orientations are established through the appropriate initiator (e.g., trisubstituted chrysene) breaking symmetry and providing this orientation. As the relative spatial arrangement of the sugar rings and nucleobases are not of the form associated with a right-handed double helix, a rotation of the nucleobases results, and DNA is formed, which ejects the catalyst. The methyl group on thymine may aid in this rotation process since the action of rotation ejects the catalyst molecule. In RNA the catalyst is typically removed through a dissolution process. A schematic of the four ring outline of the paired nucleotides during the DNA synthesis and repositioning process is presented in FIG. 7(d) for the pyrimidine-purine dinucleotide and the purine-pyrimidine dinucleotide, which shows that the synthesis is performed in the inverted position, and then the final repositioning involves a rotation into the right-handed double helix orientation, which in turn ejects the catalyst.

Figure 7E:
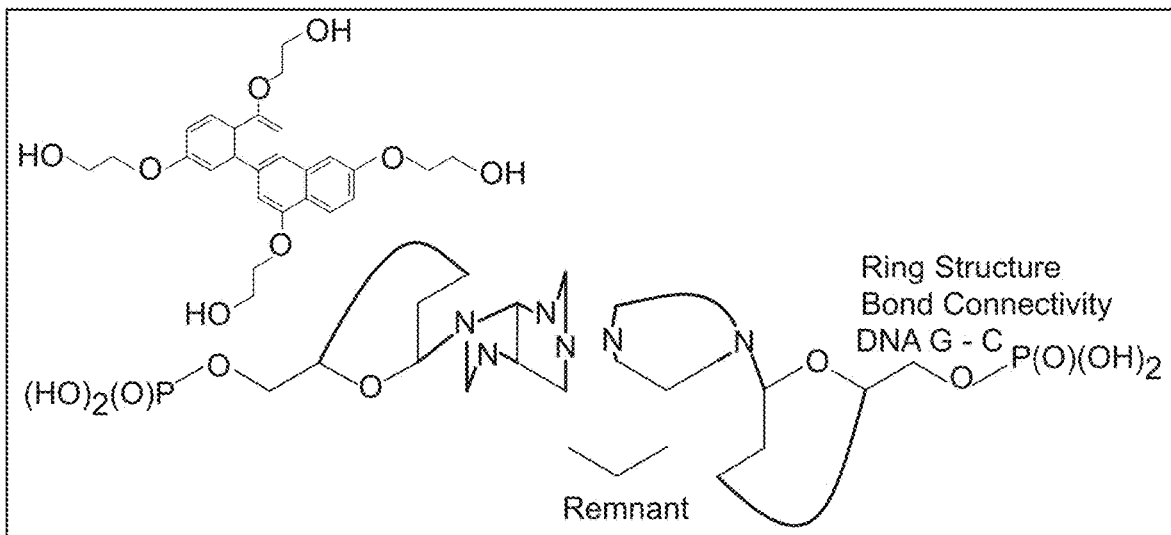
FIG. 7(e) illustrates bond connections relative to the initial positions of the carbon atoms comprising the core chrysene substrate resultant in DNA G-C.
Figure 7F:
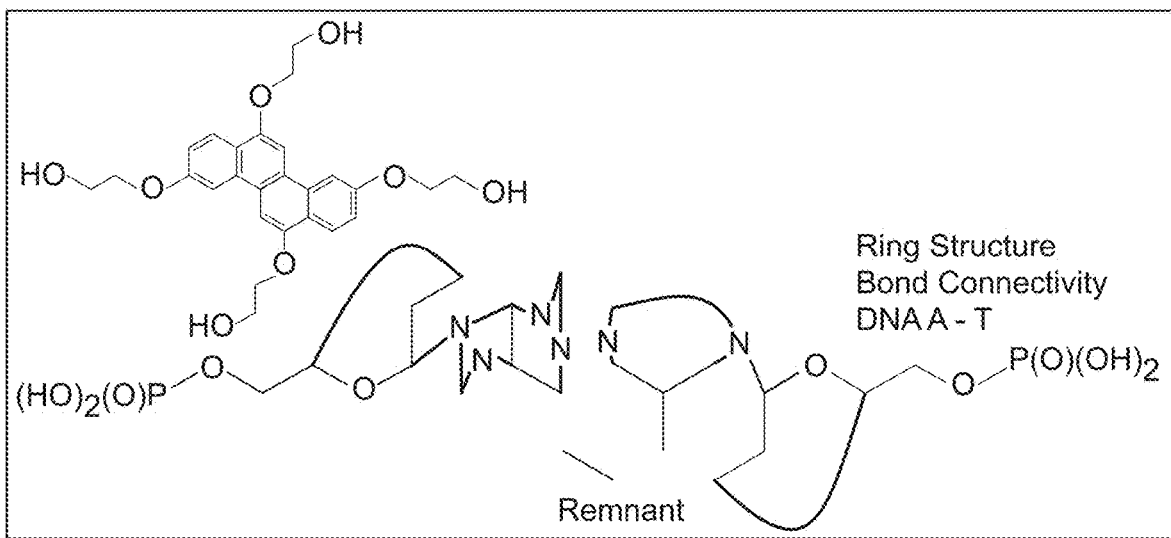
FIG. 7(f) illustrates bond connections relative to the initial positions of the carbon atoms comprising the core chrysene substrate resultant in DNA A-T.

In FIG. 7(e), the bond connectivity of the ring structure is shown from the starting material to the intermediate positioning of the DNA G-C nucleotide pairing prior to inversion. The bonds that are formed starting from the original chrysene substrate to form the core pyrimidine and purine molecules is the same for RNA as DNA. In fact, this bond connectivity pattern of the resultant ring structures is the same for all eight nucleotide pairings, with the only difference being the side groups, which is due to the alignment pattern of the catalyst to the substrate. The DNA A-T general connectivity pattern is shown in FIG. 7(f), in which it is noted that the methyl group is added to thymine simply by the bond cleavage shifting over by one carbon, relative to DNA C-G. A reversible process as to the cleavage point becomes irreversible upon separation of the catalyst and substrate, which is permitted in the case of adenine-thymine bonding through the formation of the methyl group on thymine because the methyl group assists with the ejection of the catalyst since the A-T coupling only has two hydrogen bonds.

Figure 7G:
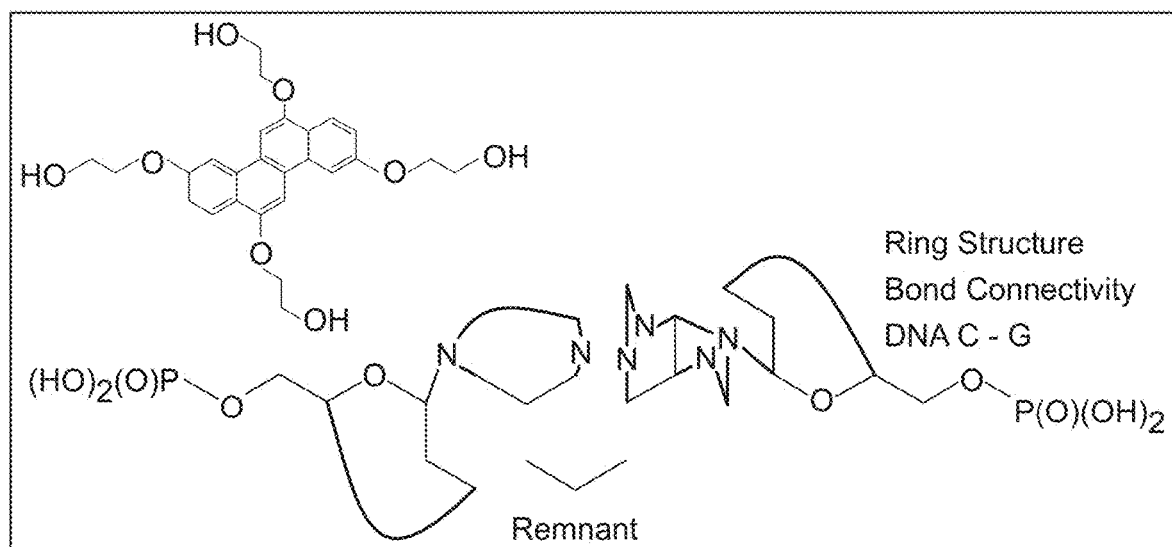
FIG. 7(g) illustrates bond connections relative to the initial positions of the carbon atoms comprising the core chrysene substrate resultant in DNA C-G.
Figure 7H:
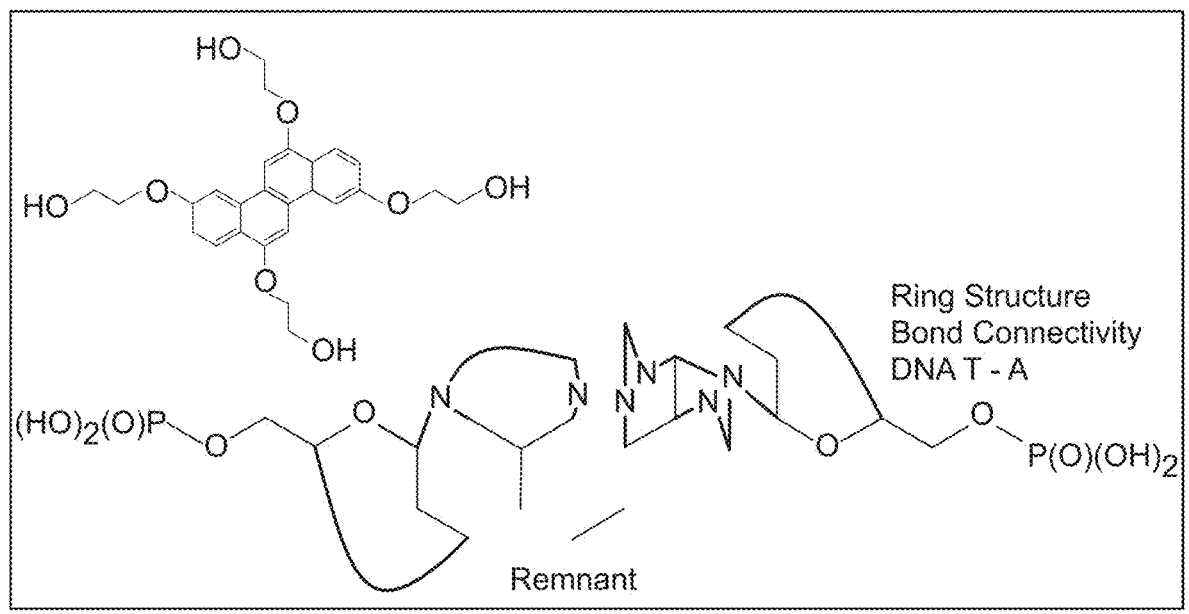
FIG. 7(h) illustrates bond connections relative to the initial positions of the carbon atoms comprising the core chrysene substrate resultant in DNA T-A.

Likewise, the bond connectivity patterns are shown for DNA C-G and DNA T-A in FIG. 7(g) and FIG. 7(h), respectively. Note that the orientation of the remnant, which is taken by the (6,12) catalyst is oriented on the same side albeit opposite for the DNA and RNA pairings.

Figure 7I:
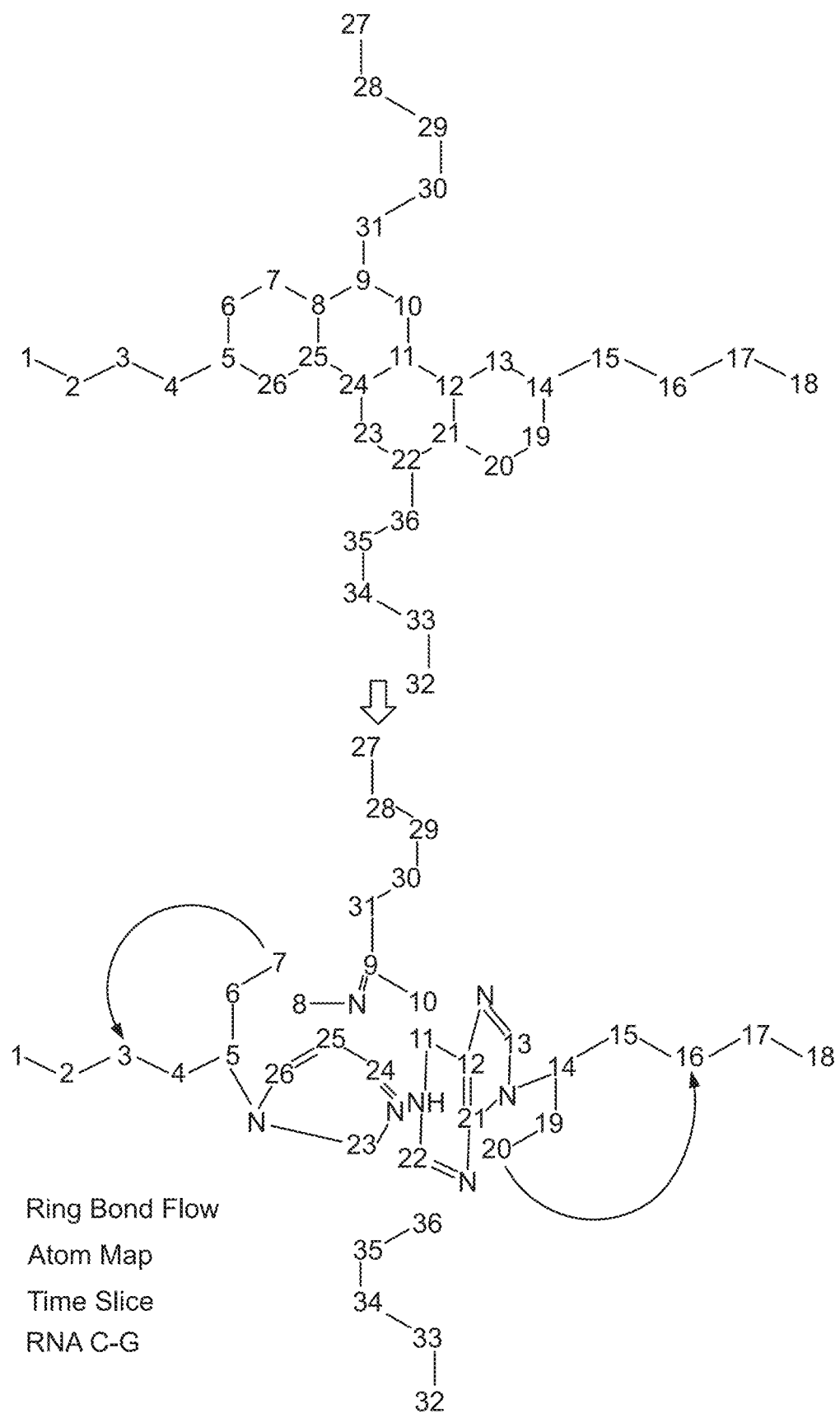
FIG. 7(i) provides the atom mapping from an exemplary substrate during synthesis to form purine and pyrimidine and sugar rings.
Figure 7J:
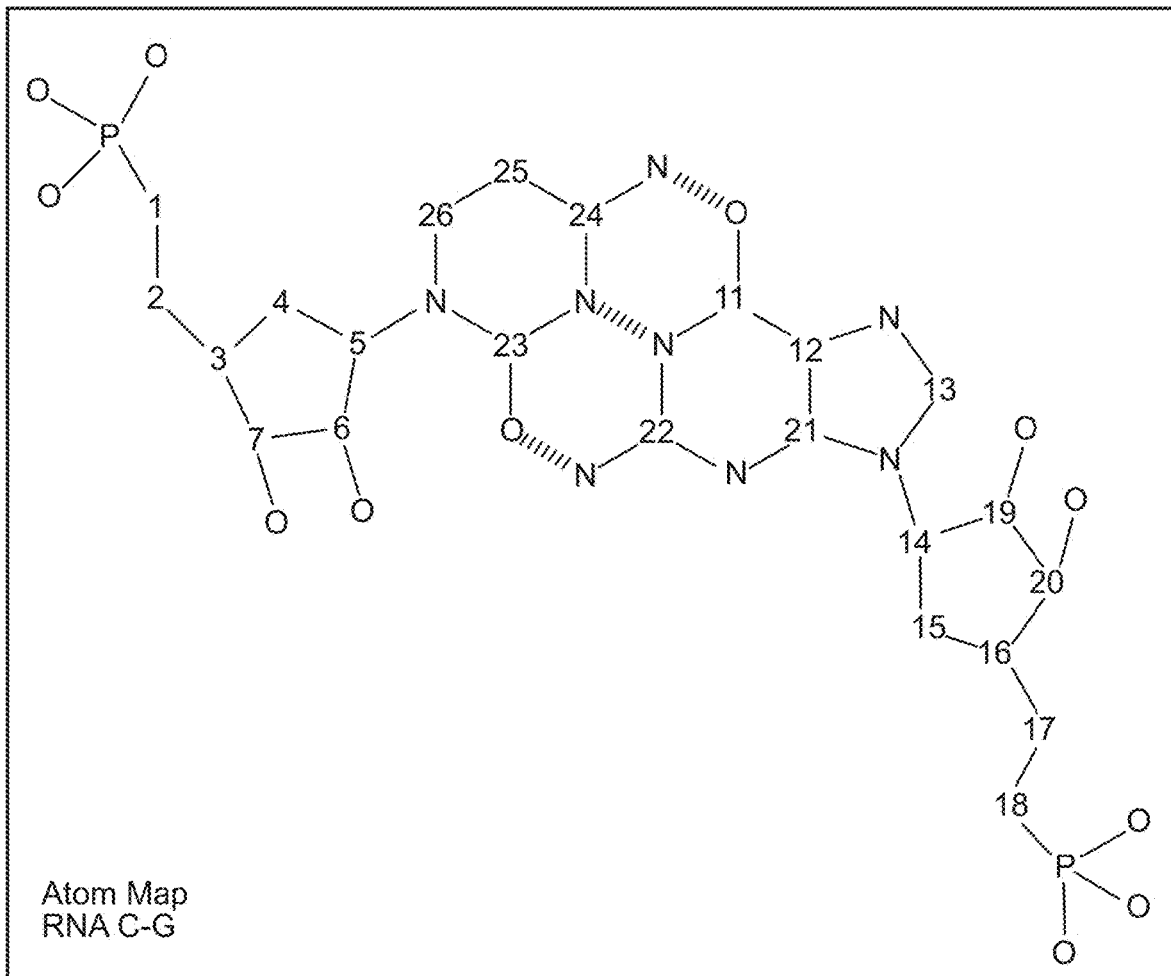
FIG. 7(j) extends that atom mapping to RNA C-G pairing. Unless otherwise indicated, the "Remnant" as referred to herein illustrates the core carbons that may not be incorporated into the nucleobases following reaction. Typically, when using chrysene based substrates, the Remnant for thymine-adenine has two core carbons from the substrate scaffold, while the remnant for all other base pairings has three core carbons. During the reactions described herein, the remnant may be conjugated with the catalyst.

The atom mapping for RNA C-G pairing is shown in FIG. 7(i), along with the end-groups associated with the catalyst which is connected through phosphodiester bonding at atoms 27 and 32, which are both oxygen. The final arrangement of the atoms is shown in FIG. 7(j) for RNA C-G, which depicts the oxygen and nitrogen atoms that are incorporated during the reaction sequence. In the synthetic schema depicted, no external carbon atoms are required for the synthesis from substrate to DNA/RNA pair. Also, in the synthesis, the remnants of the reaction may be conjugated with the catalyst. These remnants conjugated to catalyst may ultimately serve as a phospholipid bilayer upon separation from the complex after nucleic acid formation is complete. After the synthesis steps, the RNA C-G format with atom rearrangement is indicated in FIG. 7(j).

Process Flow

Figure 8:
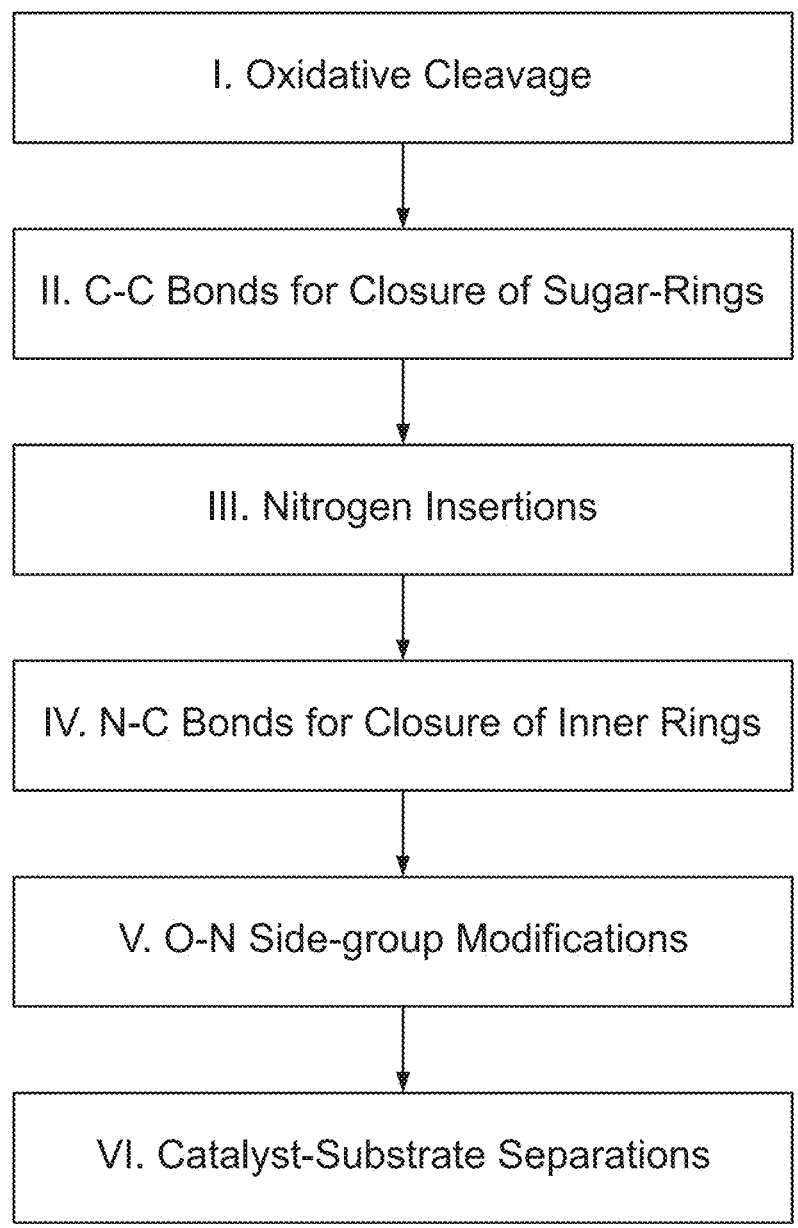
FIG. 8 provides an reaction pathway that may convert substrates (which may be in the reaction vessel of the present disclosure) into nucleotide pairs (with sugar rings).

An exemplary synthetic procedure for the conversion of substrates to nucleotide pairs is provided in FIG. 8. This procedure details exemplary steps that may occur during the synthesis, in an exemplary order of steps. It will be understood that the synthetic procedure may involve these steps in any order and all combinations are within the scope of the present disclosure.

For example, the atom-based reactions that occur to produce the transformation from a chrysene substrate to nucleotides are provided below for various pairings using the atom numbers identified in the upper map of FIG. 7(i). The synthesis may utilize any these synthetic steps. Exemplary types of each of these reactions are illustrated in FIG. 6. Table 1 details the atom positions for oxidative cleavage using the atom numbers identified in the upper map of FIG. 7(i).

TABLE 1

I. Carbon-Carbon Bonds Broken by Oxidative Cleavage

| ID | Atom Numbers | Comment |
|---|---|---|
| 1 | 7-8 | Forms 3'4' sugar-ring by 7-3 binding |
| 2 | 20-21 | Forms 3'4' sugar ring by 20-10 binding |
| 3 | 10-11 | Interior Rings |
| 4 | 11-24 | Interior Rings |
| 5 | 22-23 | Interior Rings |

Table 2 details the atom positions for carbon-carbon bonds formed using the atom numbers identified in FIG. 7(i).

TABLE 2

II. Carbon-carbon bonds formed

| ID | Atom Numbers | Comment |
|---|---|---|
| 6 | 7-3 | Sugar-ring closure |
| 7 | 20-16 | Sugar-ring closure |

Table 3 details the atom positions for nitrogen insertions using the atom numbers identified in FIG. 7(i).

TABLE 3

III. Nitrogen inserted across double bonds

| ID | Atom Numbers | Comment |
| --- | --- | --- |
| 8  | 23-24 | Pyramidine |
| 9  | 5-26  | Pyramidine |
| 10 | 21-22 | Purine |
| 11 | 12-13 | Purine |
| 12 | 13-14 | Purine |

Table 4 details the atom positions for nitrogen formed to close rings using the atom numbers identified in FIG. 7(i).

TABLE 4

IV. Nitrogen bonding to carbon double bond

| ID | Atom Numbers | Comment |
| --- | --- | --- |
| 13 | 11-22 | Closure of six-membered purine ring |
| 14 | 13/14-21 | Closure of five-membered purine ring |
| 15 | 5/26-23 | Closure of six membered pyrimidine ring |

Table 5 details the atom positions for oxygen additions using the atom numbers identified in FIG. 7(i).

TABLE 5

V. Oxygen addition

| ID | Atom Number | Comment |
| --- | --- | --- |
| 16 | 23 | thymine, cytosine, uracil |
| 17 | 11 | thymine, uracil |
| 18 | 6.19 | for RNA, 2' hydroxyl |
| 19 | 7 | 3' hydroxyl from ozonolysis and sugar-ring closure |
| 20 | 20 | 3' hydroxyl from ozonolysis and sugar-ring closure |

Table 6 details the atom positions for amine additions using the atom numbers identified in FIG. 7(i).

TABLE 6

V. Amine addition

| ID | Atom Number | Comment |
| --- | --- | --- |
| 21 | 22 | guanine |
| 22 | 24 | cytosine |
| 23 | 11 | adenine |

Table 7 details the atom positions for carbon-carbon bond release using the atom numbers identified in FIG. 7(i).

TABLE 7

VI. Carbon-carbon bond release

| ID | Atom Number | Comment |
| --- | --- | --- |
| 24 | 8-9 | For Cytosine, Uracil and catalyst-substrate separation |
| 25 | 8-25 | For Thymine and catalyst-substrate separation |
| 26 | 22-36 | catalyst-substrate separation for guanine |

The reaction mechanism may proceed as follows. The first step in the reaction may involve the opening of the outer rings and then the inner rings through an oxidative cleavage process. For example, the reaction may involve the following chemical reaction:

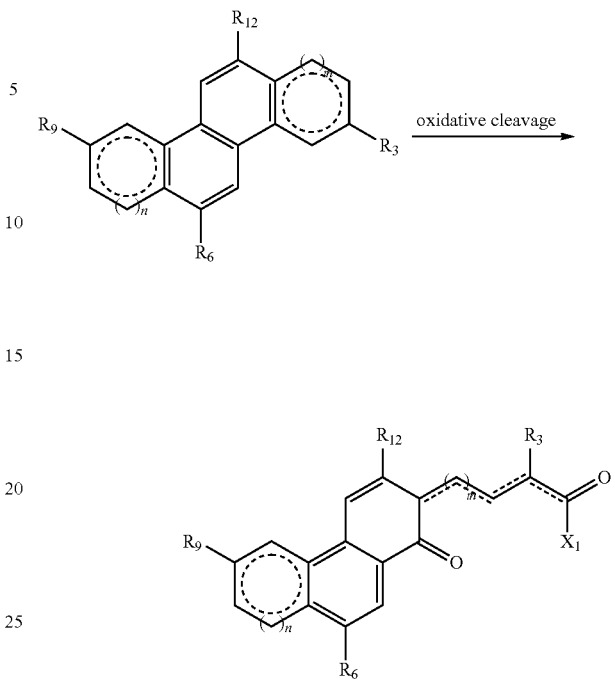

wherein $R_3$, $R_6$, $R_9$, $R_{12}$, m, and n are defined as described herein and $X_1$ is absent (e.g., when the carbon it is attached to is unsaturated such that "- - -" is a double bond at that position) or —OH. Oxidative cleavage may occur, for example, via ozonolysis with ozone ($O_3$) or with other suitable oxidants and/or oxidative catalysts such as $O_2$, permanganates (e.g., $KMnO_4$), chlorites (e.g., $RuCl_3$), nitroarenes (e.g., photoexcited nitroarenes) or $OsO_4$—$NaIO_4$ reaction schema. During this oxidative process, the atoms of the outer ring that are liberated through the cleavage of the bond may be rotated into position through attachment to the 4' carbon on the sidechain. For example, when the original substrate core has at least one terminal six membered aromatic ring (and $X_1$ is —OH), and, $1R_3$ is —$OCH_2CH_2OPO(OH_2)$, the presence of water may induce sugar ring formation:

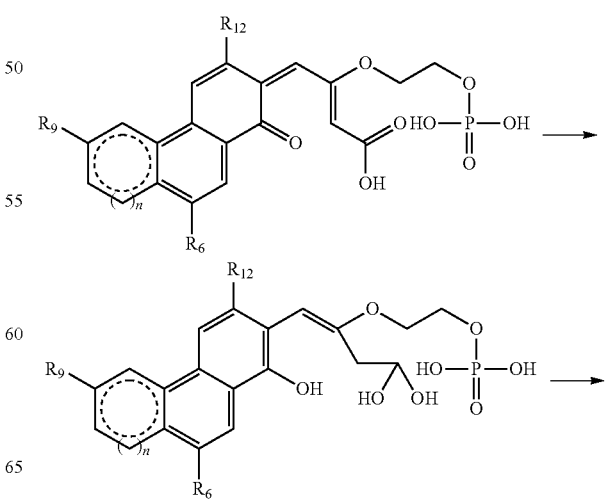

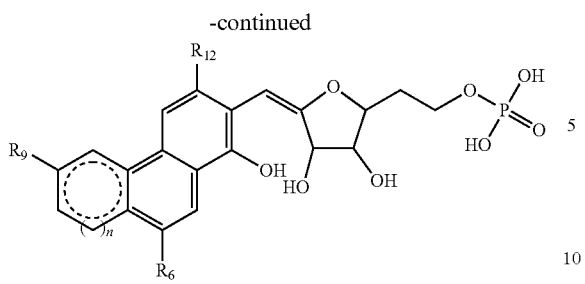

The right-hand ring may undergo a rotational process of the entry point whereby nitrogen is inserted through the double bonds (which may be ascertained based on the directionality of the phosphodiester linkage,). This insertion may occur at both sides of the structure as the flexure of the outer ring into position induces stresses that are relieved through incorporation of nitrogen. In some embodiments, there are a total of five nitrogen insertions throughout the molecule. For example, the synthesis may involve:

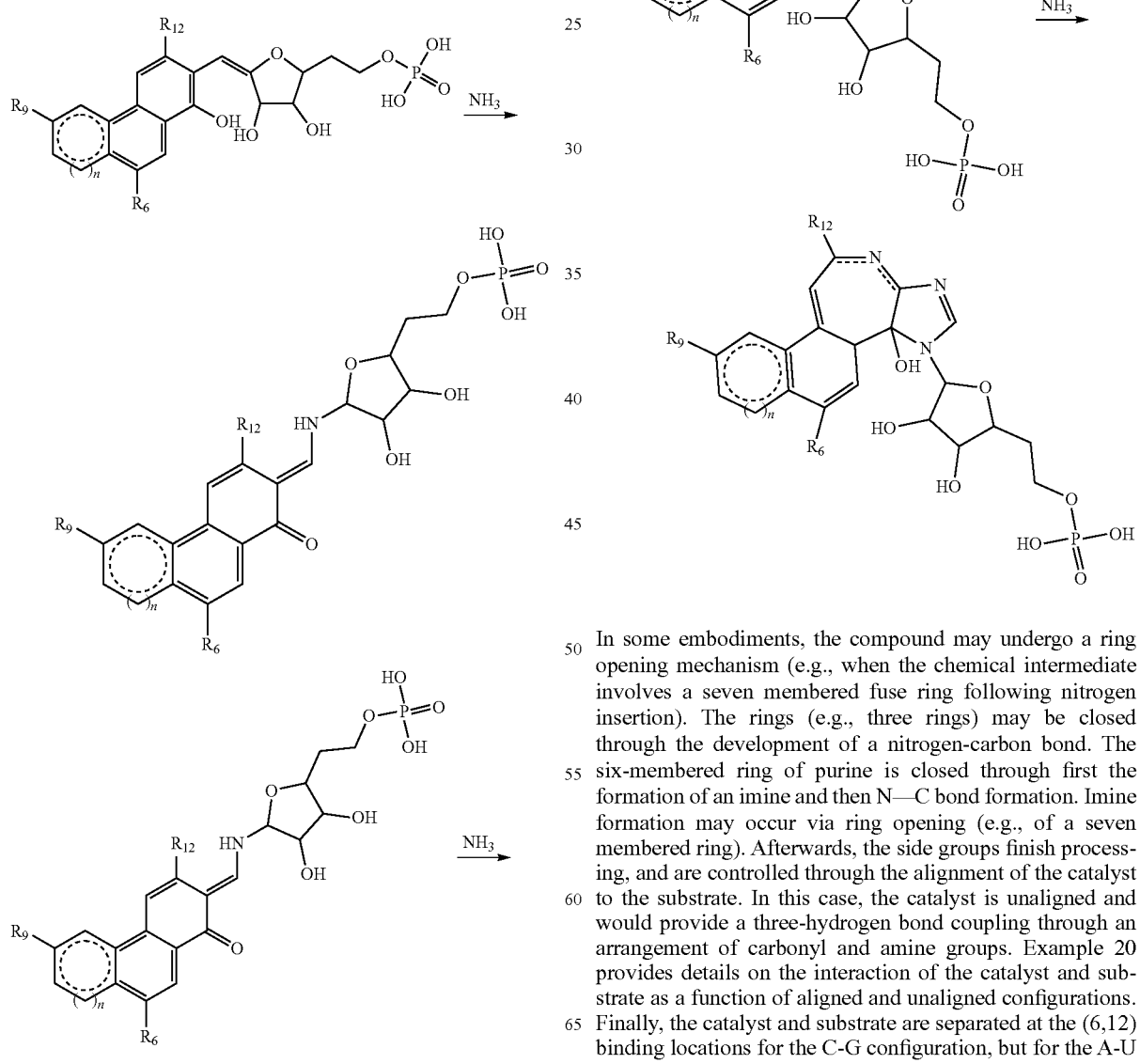

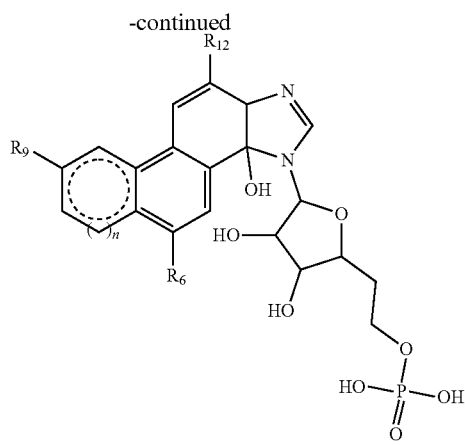

In some embodiments, the compound may undergo a ring opening mechanism (e.g., when the chemical intermediate involves a seven membered fuse ring following nitrogen insertion). The rings (e.g., three rings) may be closed through the development of a nitrogen-carbon bond. The six-membered ring of purine is closed through first the formation of an imine and then N—C bond formation. Imine formation may occur via ring opening (e.g., of a seven membered ring). Afterwards, the side groups finish processing, and are controlled through the alignment of the catalyst to the substrate. In this case, the catalyst is unaligned and would provide a three-hydrogen bond coupling through an arrangement of carbonyl and amine groups. Example 20 provides details on the interaction of the catalyst and substrate as a function of aligned and unaligned configurations. Finally, the catalyst and substrate are separated at the (6,12) binding locations for the C-G configuration, but for the A-U and A-T pairings the catalyst remains attached to adenine.

Conditions for Reactions

There are three steps to form the DNA and RNA nucleotide:
1) provide the substrate/catalyst/initiator (e.g., chrysene-based starting materials),
2) assemble the starting materials into a sequence of π-stacked molecules, and
3) initiate a reaction within the sequence to trigger a cascade of reactive events to form the final product.

To achieve the final product, two approaches are considered: the first method which applies chemical processes and materials that are nominally available within a natural setting and the second method which adopts laboratory synthesis methods as a replacement for natural processes that may improve reaction times, reaction yields, or enhance convenience of demonstration.

In some embodiments, the formation of a sequence final product can either be performed in a random way or in a directed way. In a directed manner, the target nucleotide sequence is specified, and then, during the assemble step, the binary molecular substitutes of chrysene may be arranged according to the encoding schemes described herein such as those coding provided in FIGS. 5(a) and (b).

The formation of the starting molecules may begin with the halogenation of a substrate core such as chrysene. The core may be di, tri, or tetra substituted dependent on if a catalyst, substrate, or initiator is being synthesized. The halogenated material may be then turned into a phenolic compound via reaction replacing the halogens are each replaced with a hydroxyl group. The hydroxyl groups may then be used to form ethoxylated alcohol at the originally halogenated positions.

An exemplary halogenation process is bromination of the core. Bromination may occur in a flask with the unsubstituted core (e.g., chrysene) dissolved in a suitable solvent such as trimethyl phosphate. The mixture may be heated (e.g., to from 30° C.-100° C. such as 60° C.). Once heated, bromine may then be added dropwise, and the reaction mixture heated more (e.g., to more than 100° C. (e.g., 100° C.-200° C., 100° C.-150° C., 120° C.) for a period of time for the reaction to occur. The period of time may alter the end product. For example, (6,12)-dibromochrysene is present first (e.g., in a day). Next, (3,6,12)-tribromochrysene may be formed in the second to third day for a brief period, and finally the (3,6,9,12)-tetrabromochrysene molecule results. The reaction mixture does not proceed further (but may also be stopped after formation of the tetra substituted core).

The conversion of the brominated side-groups to the ethoxylated alcohol surfactants may be accomplished by replacement of the halogen groups with hydroxyl groups (e.g., conversion to a phenolic compound) which may then be converted to an ethoxylated alcohol. This can be performed by taking the mixture of the halogenated core (e.g., di, tri, or tetra substituted bromochrysene) in a solvent mixture of CuI NaOMe (e.g., from 10%-40% NaOMe by weight such as 28% NaOMe by weight) in MeOH over dimethylfuromide (e.g., at greater than 100° C. such as 120° C. to replace the halogenated groups with a methoxy group. Next $BBr_3$, DCM may convert the methoxy to a hydroxy (e.g., and prepare the phenolic compound). Ethyl bromoacetate converts may be used to convert hydroxyl groups to ethoxy ethanoic ester, which when combined with LAH, THE may convert the material to ethoxylated alcohol substituted core (e.g., on chrysene at the (6,12); (3,6,12); or (3,6,9,12) carbon locations).

In particular embodiments, the ethoxylated alcohol substrates/catalysts may be used to encode information and/or synthesize a sequence of nucleotides. For example, to develop the sequence, when a mixture of ethoxylated catalysts and substrates are phosphorylated with $POCl_3$ and tetramethylpiperidine (TMP) with a proton sponge, heterodimers may be formed. For example, the substrate and catalyst may have the structure:

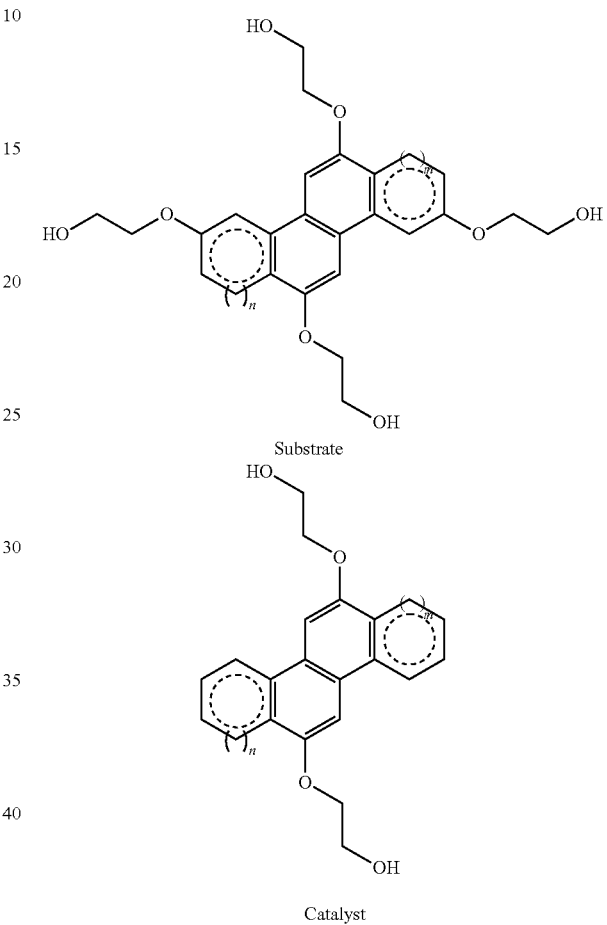

Substrate

Catalyst

These catalysts and substrates may self-assemble in the suitable reaction environment into Aligned and Unaligned forms. Self-assembly may be controlled by solvent such that the differences in solubility between substrate and catalyst in the solvent. For example, using chrysene as the core structure, (6,12) and (3,6,9,12) substituted chrysenes may preferentially dimerize because of comparatively lower steric hindrance and higher solubility relative to the alternative homodimer forms of (6,12); (3,6,9,12); or (3,6,12) substituted chrysene. The assembly of the heterodimers, in a suitable reaction environment (e.g., $POCl_3$ and tetramethylpiperidine (TMP) with a proton sponge), may result in a linked sequence through the (6,12) connections forming phosphodiester linkages between adjacent chrysene-based molecules to form a heterodimer. Each reaction vessel may also be stabilized into a sequence with π-stacking stabilizing the heterodimers (or conjugated substrate/catalyst pairs). This π-stacked arrangement or sequence is performed preferably before the phosphorylation process. It may be developed as a one pot synthesis in which reactive hydrophobic domains are dispensed throughout a hydrophilic environment.

The transformation from the sequence of substituted chrysene to DNA and RNA is accomplished preferentially through anerobic means. Oxidative cleavage may open the core rings (typically one or both of the terminal optionally aromatic core rings) which may begin the conversion. Oxidative cleavage may be performed under anerobic conditions through nitroarene chemistry using the (6,12) substituted core (e.g., (6,12) substituted chrysene) as the aromatic catalyst to induce regioselective ring opening of the substrate as an effective oxygen transfer agent through interaction with reactants including $NO_2$. (See FIG. 13(f) of example 8.)

The reaction mixture may be run in acidic conditions such as with aqueous concentrations of, for example, nitric acid ($HNO_3$), sulfuric acid ($H_2SO_4$), phosphoric acid ($H_3PO_4$), and/or ammonia ($NH_3$) and at a temperature of, for example, 30° C. to 120° C. To form nitroarene, nitric acid and concentrated sulfuric acid may be used on the chrysene-based substrate. The stabilizing sidechains enable milder conditions with the subsequent additions of $NO_2$ groups requiring aggressive temperature as the reaction proceeds. Sulfuric acid may be added to the reaction in in its concentrated form to induce the acidic conditions. Metal of palladium as a catalyst may be used to promote ring closure and imine formation as has been reported, such as in Yu, Bangkui et al., *J. Am. Chem. Soc.* 142.43 (2020): 18341-18345, which is hereby incorporated by reference in its entirety, consistent with the cleavage and reformation with nitrogen incorporation in ring structures. ZnO and Mg are other choices for metal co-reactants. Photochemical stimulation may occur through application of UV light, purple light, white LED light, light having a wavelength (or $\lambda_{max}$) of 365 nm to 440 nm may be deployed. Electromagnetic radiation for photochemical stimulation of reaction mixtures may have a radiant flux of, for example, 100 to 600 $W/m^2$. Alternative wavelengths are useful in accelerating the reaction including the use of other visible and UV light wavelengths. In various embodiments, the light may have a spectrum similar to sunlight.

In some embodiments, nitroarene based oxidative cleavage may occur in the presence of acetonitrile. The addition of acetonitrile, such as disclosed in Wise, D, et al. *J. Am. Chem. Soc* 144.34 (2022): 15347-15442, which is hereby incorporated by reference, may be advantageous in several nitroarene chemical reactions of the present disclosure. The reaction may proceed over the course of, for example, 1 minute-1 week (e.g., two or more minutes to two or more days) and optionally include a triggering step of aromatic ring opening of the substrate core. Ring opening may initiate the cascade reaction. Furthermore, to improve reaction yield, an electrochemical gradient may be held in the reaction medium to, for example, assist with the nitrogen insertion. Nitrogen insertion may increase the atom number of the resultant rings after the initiating rings are opened through the oxidative cleavage process. The addition of molecular oxygen, a carbonate such as $K_2CO_3$ and methanol solvent may also improve the conditions for oxidative cleavage. In some embodiments, degassing the reaction mixture of molecular oxygen may afford running a more anerobic process and enhance regioselectivity.

Oxidative cleavage occur via ozonolysis with an ozone generation source followed by reductive workup. In some embodiments, oxidative cleavage may be accomplished with Lemieux-Johnson method using $OsO_4$ or $KMnO_4$ followed by $NaIO_4$. Reactants may include water, ozone, permanganates ($KMnO_4$), phosphates such as ammonium phosphate and sodium phosphates, alcohols such as methanol, carbonates such as $K_2CO_3$, ammonia, nitrates, nitric acid, sulfuric acid, phosphoric acid, and ammonium salts such as ammonium halides.

After the initial oxidation, the reaction typically proceeds to completion as the reaction environment is constrained both spatially, due to the π-electron connectivity of adjacent molecular objects, and constrained chemically, through the hydrophobic core of the aromatic molecules surrounded by a hydrophilic environment. As explained herein, aromaticity is maintained and may involve a transformation from eighteen π-electrons in one molecule (e.g., of four aromatic rings) to sixteen π-electrons in two separate molecules having three total rings, wherein the two separate molecules typically also are connected to a sugar-ring each, of which the two π-electrons of the eighteen π-electrons are used in its formation, and which affords hydrophilicity of the compound during synthesis.

Therefore, the present disclosure provides for the development of the synthesis environment for breaking aromatic rings through oxidative cleavage in a regioselective manner. These synthesis environments may provide sufficient free nitrogen for insertion into the molecular arrangement which may achieve sufficient planarity and aromaticity.

Formation and Separation of Nucleic Acid and Phospholipid Bilayer Materials

Figure 9A:
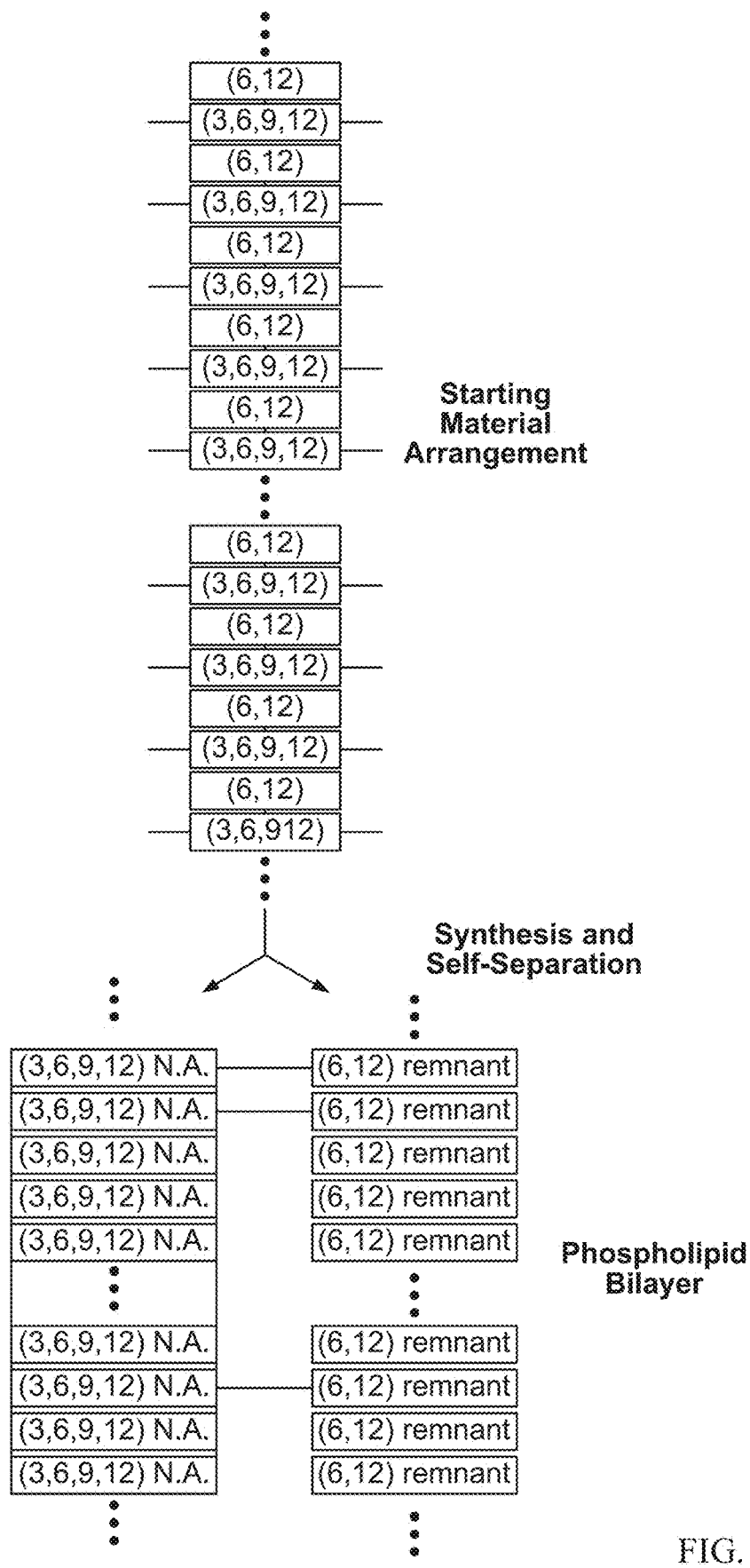
FIG. 9(a) is a schematic of a stack of reaction vessels converting to separated nucleotides (DNA and/or RNA) and catalyst remnants (which, following removal of the intercalated product, may form phospholipids (and consequently, cellular membranes).

To prevent degradation and to serve as a reaction chamber for protein synthesis after development of RNA and DNA, it is typically necessary to have a cellular membrane. The processes of synthesis of DNA and/or RNA described herein also includes the materials and mechanisms for the formation of a cellular membrane. Methods are therefore also provided for the generation of phospholipids using the syntheses from substrate/catalyst pairings described herein. In FIG. 9(a), a schematic for the transformation of the catalyst as a remnant of the formation of the DNA and RNA nucleotides is depicted. This catalyst remnant may form phospholipid bilayer materials. Thus, a cellular construct is available via the synthetic schema provided in the present application that may enable the RNA formed to initiate an instruction set to establish the cell for cellular division and propagation of the instruction set encoded by DNA. The separation process into nucleic acid and phospholipid products may be induced by double-strand separation for RNA products, by an inversion process for DNA products, and by single-strand separation for hybrid RNA/DNA products In FIG. 9(b), exemplary phospholipids for which may form a bilayer of the (6,12)-disubstituted chrysene remnants formed and ejected during nucleic acid synthesis are shown. The orientation and head groups depend upon the nucleic acid pairing. For example, in DNA synthesis, three carbons are removed for the C-G pairing, while only two carbons are removed for the T-A pairing since one carbon is used for the methyl group on thymine. In addition, one side of the catalyst polycyclic core has the two carbon or three carbon remnants from the substrate synthesis as the end group (e.g., resulting in isopropoxy or ethoxy end groups). The other side may have a hydroxyl as an end-group which is linked with adenine or separated from guanine. From left to right, FIG. 9(b) shows the catalyst remnants (in basic form, as the reduction generally results in nitrogen insertions) formed in concert with DNA with A-T, C-G, T-A, and G-C, respectively. Note that the removal of the carbons from the tetrasubstituted chrysene are extracted from the same side for all four nucleotides, irrespective of whether it is the purine or pyrimidine that comprises the 5' strand. For example, the extraction of the three carbons from the original substrate chrysene happens to the 'right' independent of whether guanine is at 5' or cytosine is at 5'.

Figure 9C:
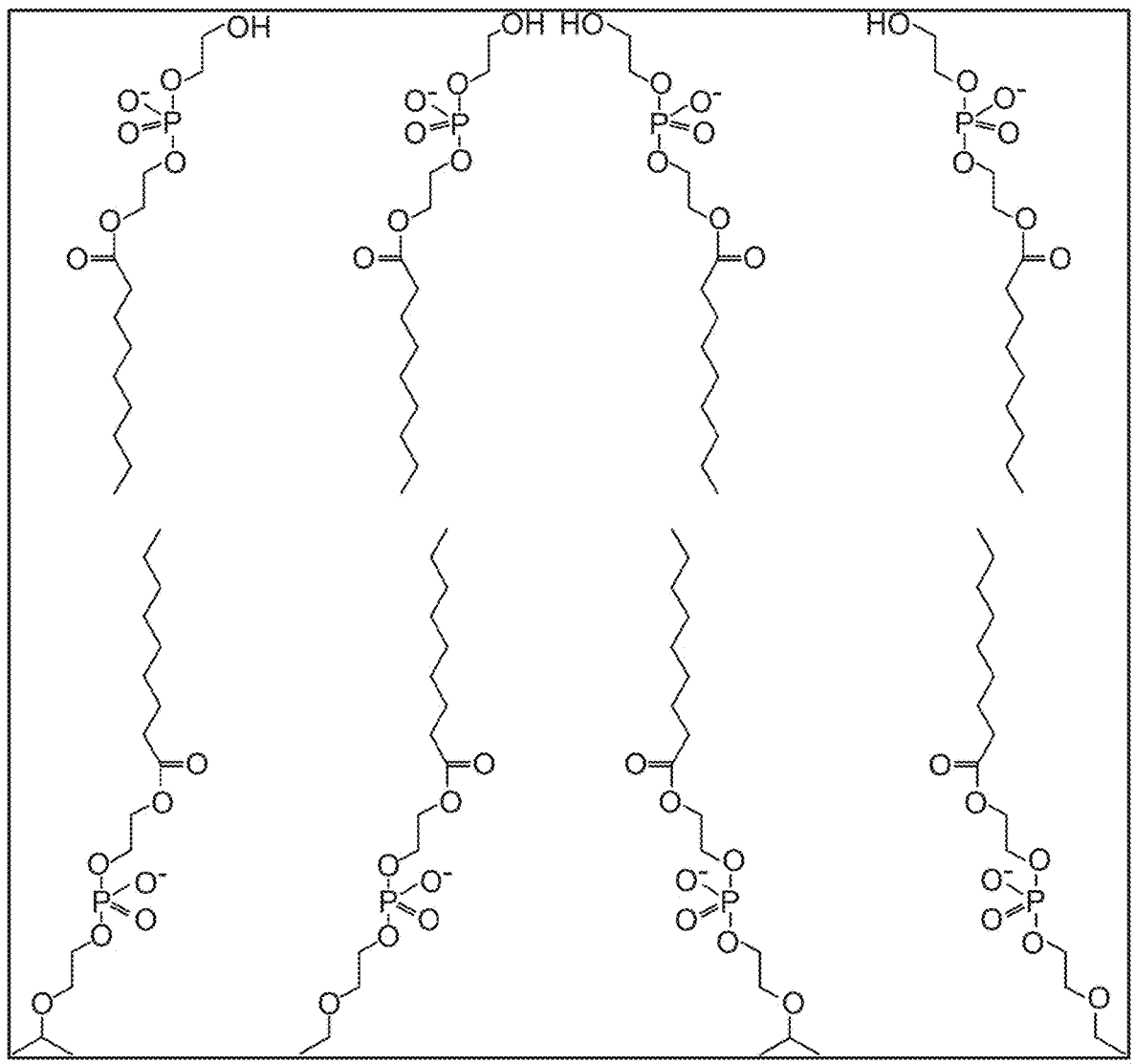
FIG. 9(c) illustrates the final phospholipids that may formed from the catalyst phospholipids following sequential reaction steps to form separate and saturate the primer cores.

Saturated phospholipids may be formed through several oxidative cleavages of the phospholipid remnants comprising the catalyst core. For example, chrysene includes 18 carbons. Repeated oxidative cleavages of phospholipid remnants may result in two phospholipids having the structure such that the acetyl core carbons are present in the terminal saturated acetal. The sum of carbons in the terminal saturated acetal groups may be 18. Repeated oxidative cleavage of a Cn core (e.g., "n" referring to the number of carbons in the core such as from 15-25, chrysene would be a $C_{18}$ core) may result, for example, in a first and second phospholipid each having the structure $HOCH_2CH_2OP(OH)_2OCH_2CH_2$—$R_1$, wherein $R_1$ is independently a $C_m$ saturated hydrocarbon and m is independently an integer from 1 to 1-n such that m1 (the m in $C_m$ for the first phospholipid)+m2 (the m in $C_m$ for the second phospholipid) sum to n. FIG. 9(c) provides exemplary phospholipids formed following multiple oxidative cleavages of a chrysene core phospholipids remnants where the rings of the catalyst core a separated to establish nine carbon linear chains on both phospholipids. Additional organization is possible of the phospholipid structure, such as the introduction of reduced forms of chrysene akin to cholesterol insertions, as well as the combination of saturated and unsaturated extensions from the phospholipid structures.

Methods to generate phospholipids may also include forming independent homodimers of the (6,12)-disubstituted catalysts. These methods may be useful for creation of general populations of the cellular construct. Furthermore, in some embodiments, amino acid syntheses are available all through the decomposition of the (6,12) disubstituted chrysene catalyst (see Example 11).

As the phosphodiester linkage of the catalyst to adenine of RNA remains after synthesis, linkage of the RNA molecule to specific positions of the cellular membrane may be designed. This is appropriate for an encoded mapping between the phospholipid bilayer material and RNA. This encoded signal mechanism is useful for sending coordination information from a membrane to the genetic material during the first cellular divisions.

Figure 10:
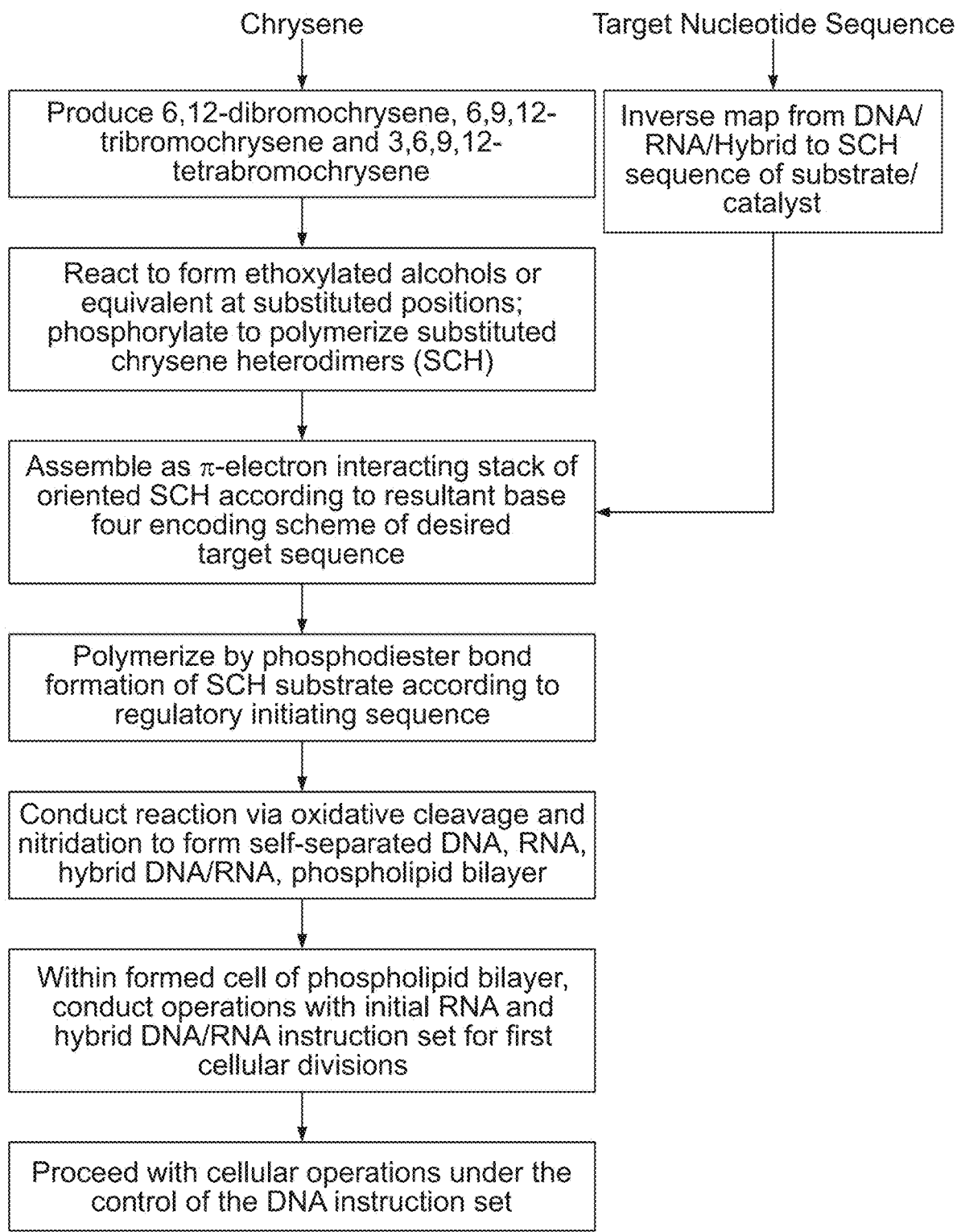
FIG. 10 provides an exemplary flow from an identified substrate/catalyst primer core (chrysene) for the possible encoding and syntheses of DNA/RNA or hybrid structure.

In FIG. 10, the overall exemplary flow for design and process synthesis is presented using chrysene as the polycyclic core for substrate/catalyst/initiators. As shown in FIG. 10, a procedure of the present disclosure, such as a laboratory procedure may involve the bromination or halogenation of chrysene to produce the (3,6)-dibromochrysene; (3,6,12)-tribromochrysene; and (3,6,9,12)-tetrabromochrysene products. Ethoxylated alcohols may then substituted at the halogenated (e.g., bromine) positions using the halogen as the leaving group. These surfactant sidechains that enhance molecular solubility of catalysts/substrates/initiators in polar protic solvents and are of the required structure for the formation of nucleic acids. Through π-electron stacking, a series of substituted chrysene heterodimers are prepared according to the orientation and alignment coupling (e.g., using the code of FIG. 5. The assembly can either be of a random sequence (see Example 18) or can be designed to produce a predetermined sequence (see Example 19).

The solution in which the sequence is synthesized is typically rich in nitrogen containing species (e.g., contains more than 20% by weight nitrogen containing species such as ammonia). A reaction then takes place to convert the assembly into a combination of DNA and RNA sequences, as well as hybrid DNA/RNA sequences. The reaction typically follows a stepwise procedure of oxidative cleavage followed by nitrogen insertion and ring closure steps. The alignment of the catalyst to the substrate determines the nucleobases synthesized. The directionality and hence code that is applied is determined through the tri-substituted chrysene molecules present in the reaction vessel stack. The specific chemical steps to induce the reactions, particularly oxidative cleavage, may be performed via an anerobic chemistry route (which is consistent with the atom economy demonstrated in the reaction sequence). For example, oxidative cleavage may be performed through photon-enhanced nitroarenes set-up through aromatic catalyst π-coupled with the substrate. Alternatively, ozonolysis or metal-based oxides can be deployed for oxidative cleavage. Electrochemical gradients can assist with nitrogen insertion.

During the nucleic acid product formation, the phospholipids may be produced as a cell membrane, and thus the composite cell can proceed to implement the instruction set provided by the RNA sequence, as well as the DNA/RNA composite product. This RNA instruction set is typically used for the first few cellular divisions at which point the DNA takes control and implements its instruction set for the cell. The hybrid set of DNA/RNA may be useful to implement the genetic code through the formation of ribosomal units.

Applications

Applications for the techniques described herein have utility in several fields including informatics, regenerative medicine, genome synthesis, artificial totipotent stem cell therapy, and life synthesis. These also relate to several areas of chemical reactions including conducting reactions in chemically and spatially constrained areas and polymerization of polyaromatic compounds. The process also relates to areas of nanotechnology including computation, display, and information processing.

Typically, the treatment of a disease, disorder, or condition (e.g., the conditions described herein such as those associated with infection) is an approach for obtaining beneficial or desired results, such as clinical results. Compounds and biological material as described herein may be used for the treatment of a disease disorder or condition in a subject in need thereof by applying or administering the compound or biological material to the subject. The compound or biological material may be present in, for example, a pharmaceutical composition. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

In terms of their form, compositions of this invention may include solutions, emulsions (including microemulsions), suspensions, creams, lotions, gels, powders, or other typical solid or liquid compositions used for application to skin and other tissues where the compositions may be used. Such compositions may contain: additional antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals. In certain embodiments, the composition of the invention is formulated with the above ingredients so as to be stable for a long period of time, as may be beneficial where continual or long-term treatment is intended.

In order to treat, prevent, or prevent recurrence of diseases, disorders, or conditions as discussed herein, the composition of the present disclosure may be administered at least once a day for at least about one week. In various embodiments, the composition is administered at least twice a day for at least two days. In certain embodiments, the composition is administered approximately daily, at least daily, twice a week, weekly, or for about one month. In certain embodiments, the composition of the invention is administered for several months, such as at least two months, six months, or about one year or longer. The invention is further suited for long-term use, which may be particularly beneficial for preventing recurring infection, or for preventing infection or conditions in at-risk or susceptible patients, including immune compromised patients. Such long-term use may involve treatment for at least two years, three years, four years, or even five or more years.

In another aspect, the composition of the invention is a kit, which contains the compositions of the present disclosure packaged to facilitate dispensing and/or applying the composition to affected or susceptible regions. The packaging or dispenser may include a bottle, tube, spray bottle, or other dispenser. In certain embodiments of the invention, the composition is packaged in a concentrated form, and diluted to a desired concentration upon use by the end user. Typically, in these aspects, the composition may be formulated and packaged in a manner suitable for long-term storage to maintain efficacy of the composition.

The kit may further include additional components to facilitate application of the composition to the affected area, such as, for example, a brush, sponge, cotton swab, or the like.

Alterations

This invention source materials are primarily exemplified by chrysene-based derivatives. The concepts extend to the other four-ring structures, such as pyrene, and to chrysene with other appropriate sidechains. The invention extends to polyaromatic hydrocarbons other than chrysene such as those having the structure:

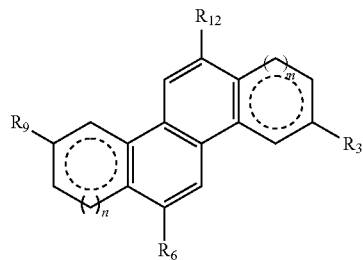

In addition, analogous to the extension of phosphodiester chains to progress from adenosine monophosphate to adenosine triphosphate, the use of multiple phosphodiester groups to the sidechains of the catalysts, substrates, and regulators (initiators) may introduce additional energy to the system of molecules, which may be useful for inducing chemical reactions.

Also included in the disclosure is the opportunity for a code that considers the unalignment of the catalyst to the substrate as the basis for protecting the unpaired ketone during the nucleotide formation process. In this embodiment, the Forward or Backward configurations would correspond to be considered as F for protective and B for non-protective. Although specified as the opposite alignment configuration, the code is as described in the primer, FIG. 1.

Figure 12A:
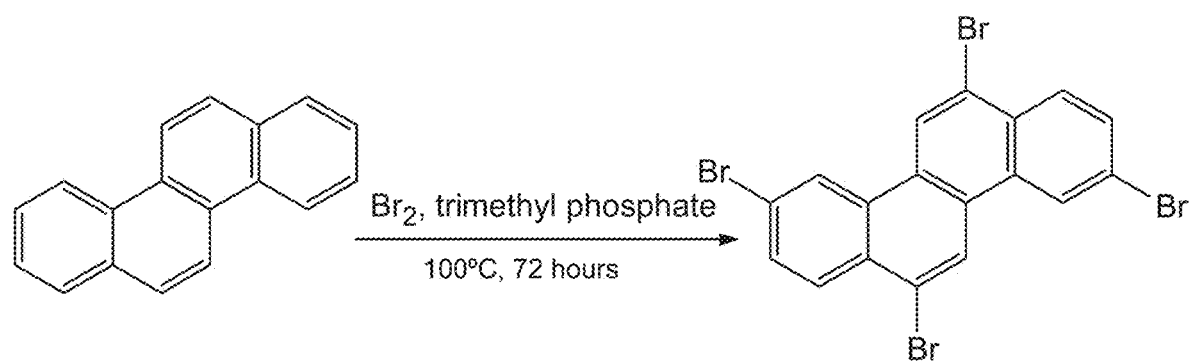
FIG. 12(a) provides an exemplary synthetic schema used to produce substrate/catalyst/initiators.
Figure 12B:
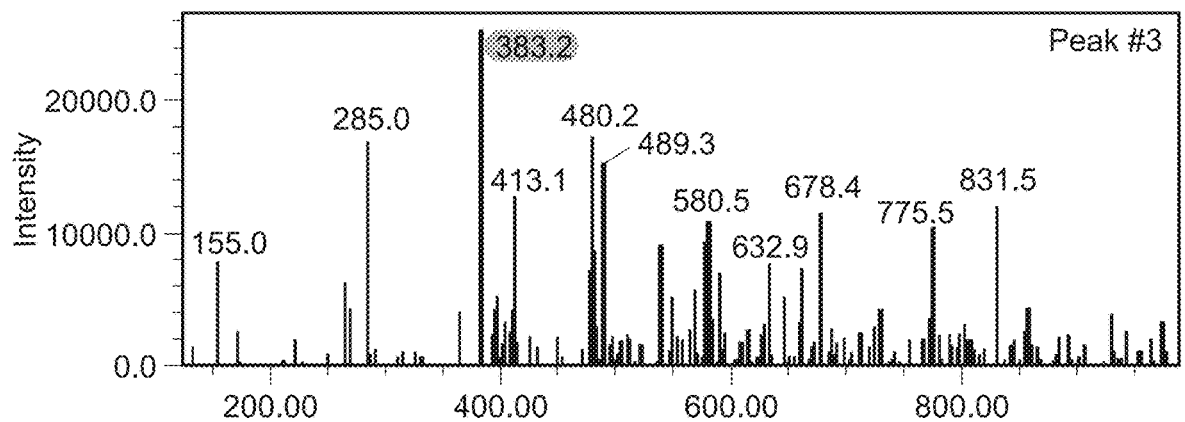
FIGS. 12(b)-(d) provide the measured liquid chromatograph mass spectroscopic (LCMS) measurements of the reaction of FIG. 12(a) illustrating the formation of catalyst (12(b)), initiator (12(c)), and substrate (12(d)).
Figure 12C:
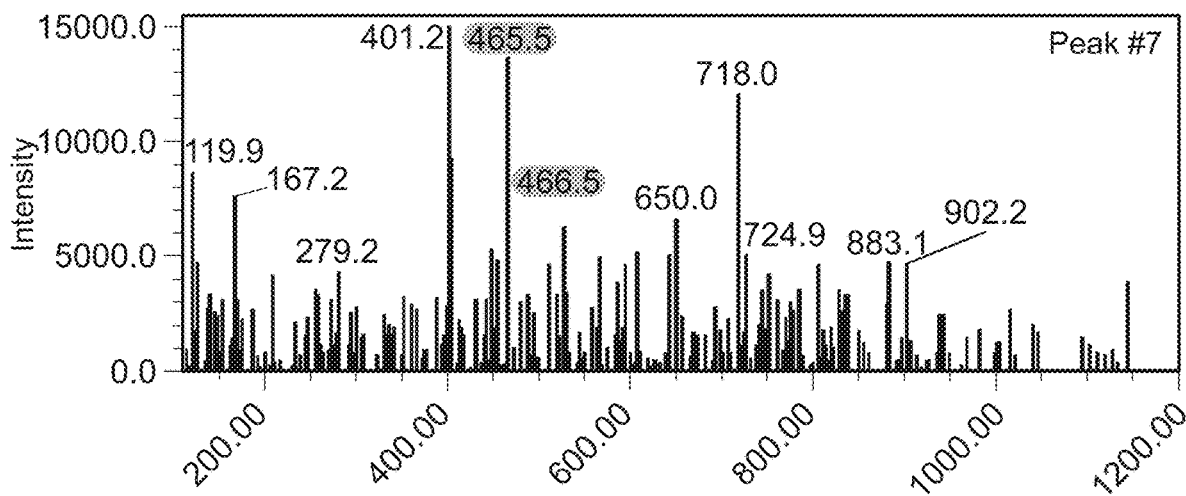
Figure 12D:
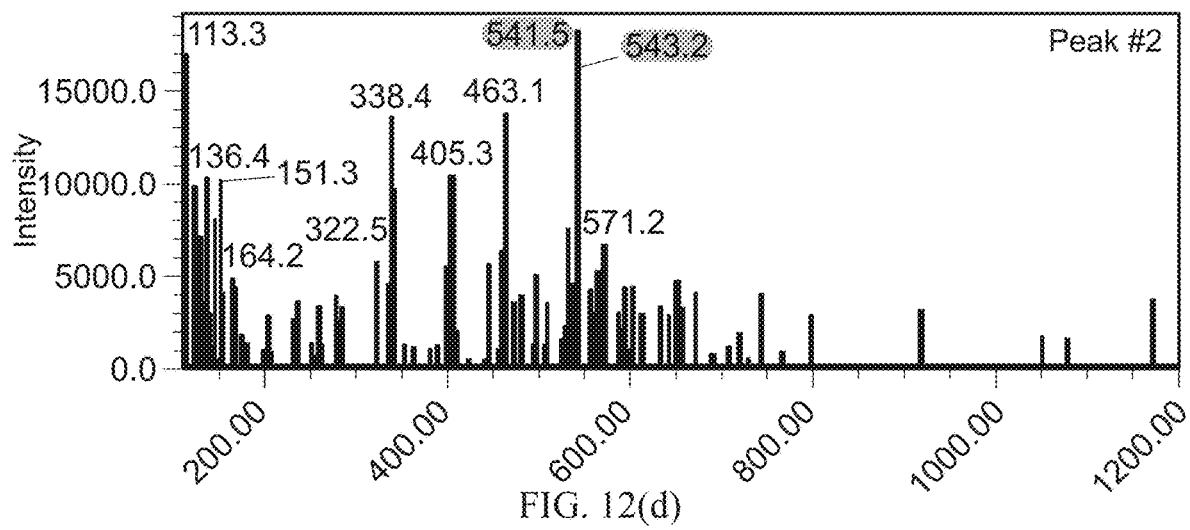
Figure 12E:
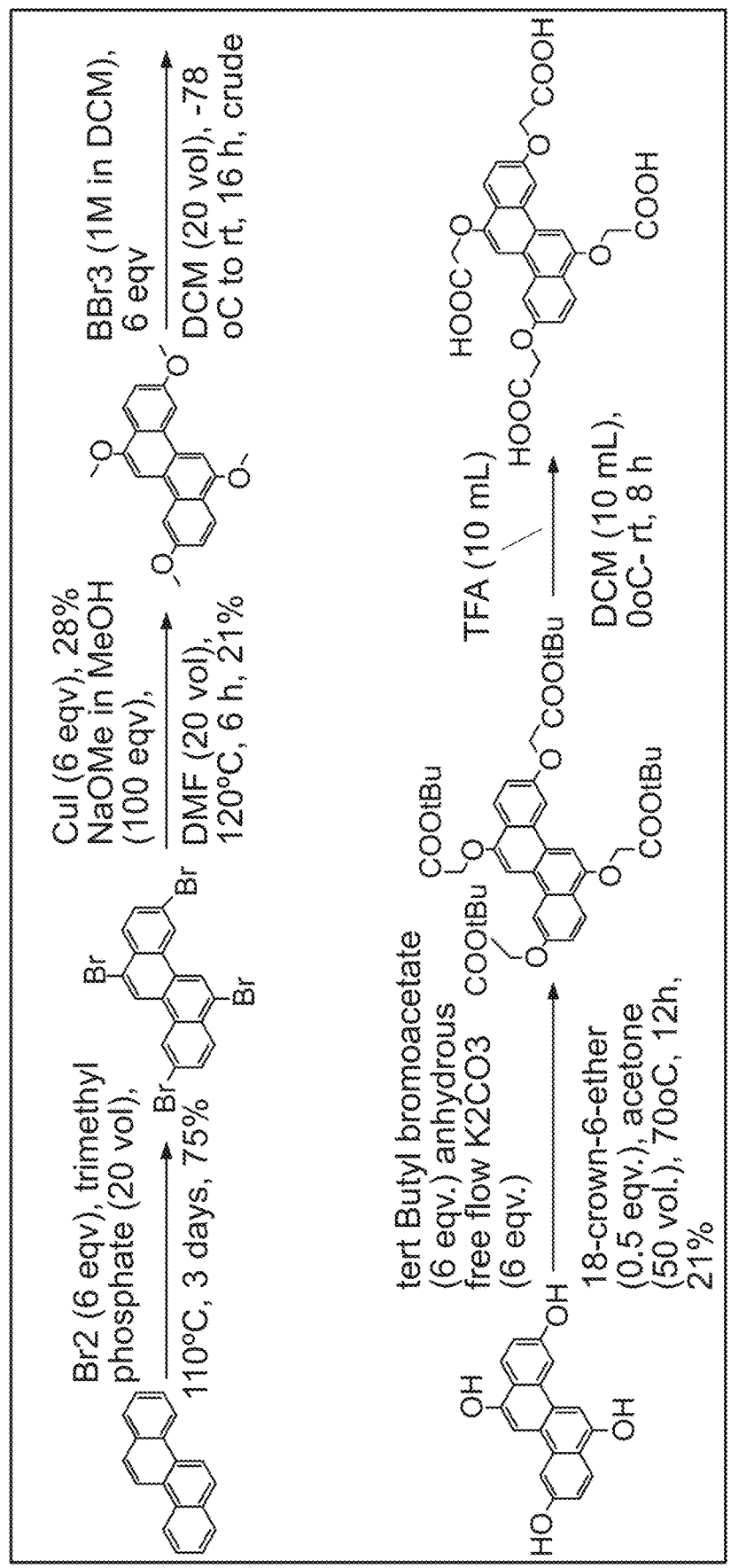
FIG. 12(e) provides an exemplary synthetic schema used to produce substrate/catalyst/initiators.
Figure 12F:
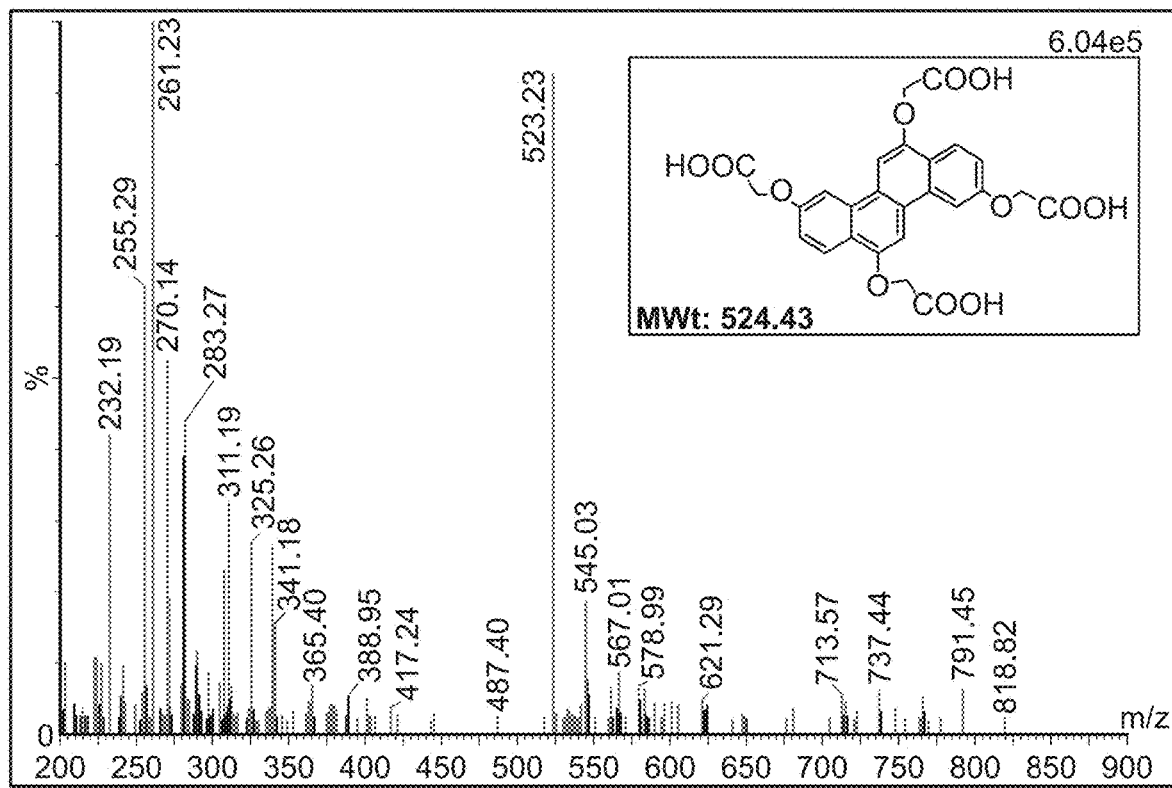
FIG. 12(f) provides the measured liquid chromatograph mass spectroscopic (LCMS) measurements of substrate prepared by the synthesis in FIG. 12(e).
Figure 12G:
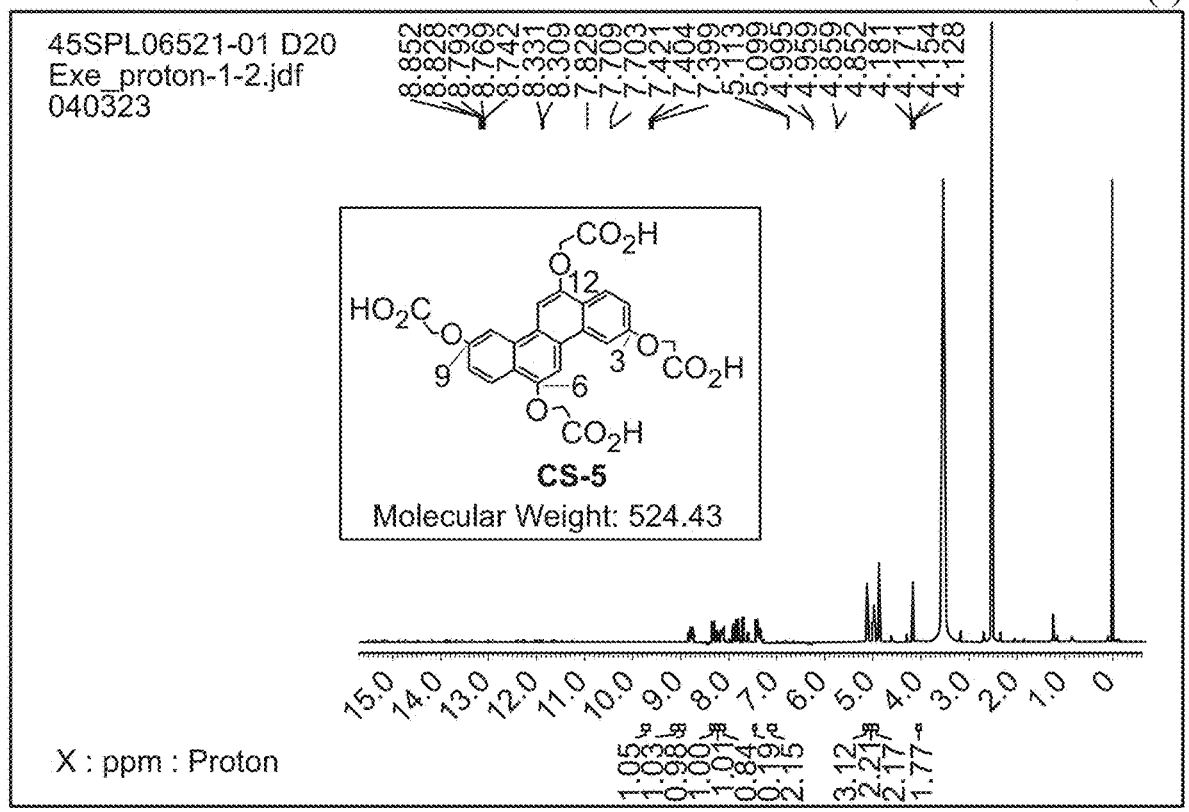
FIG. 12(g) provides the measured nuclear magnetic resonance (NMR) measurements of the substrate prepared by the reaction of FIG. 12(e).
Figure 12H:
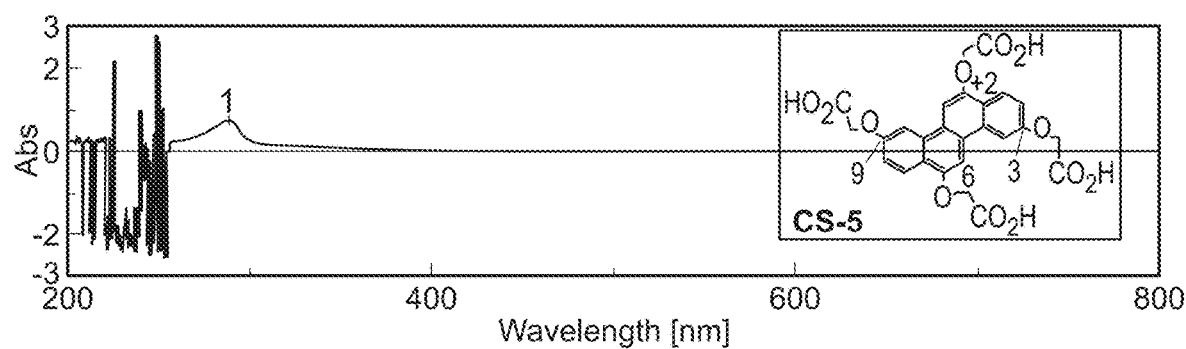
FIG. 12(h) provides the UV/Vis absorbance spectra of the substrate prepared by the reaction of FIG. 12(e).
Figure 12I:
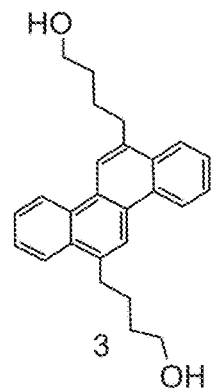
FIG. 12(i) illustrates the structure of an exemplary catalyst synthesized for further study.
Figure 12J:
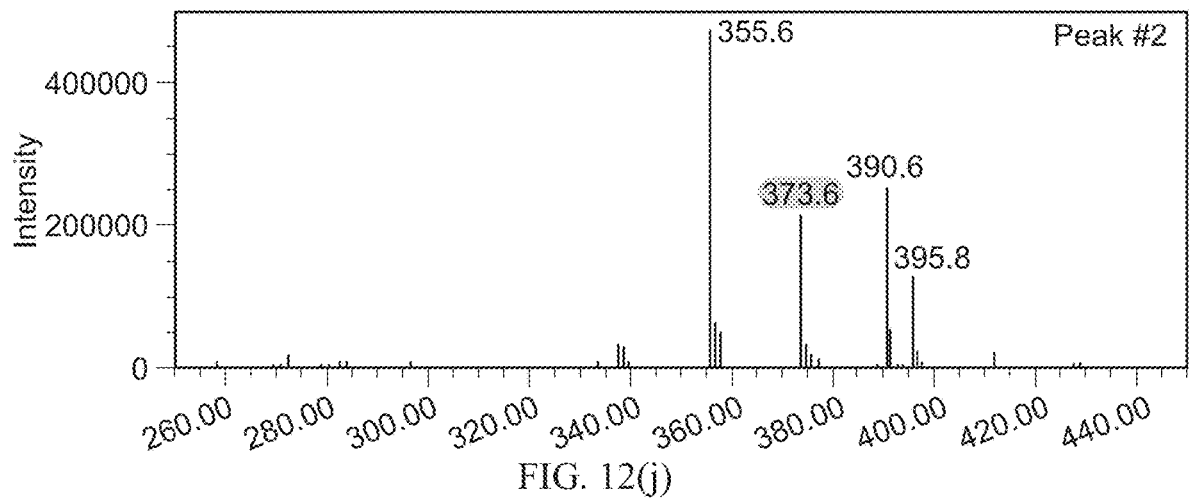
FIG. 12(j) provides the LCMS taken of the catalyst of FIG. 12(j).
Figure 12K:
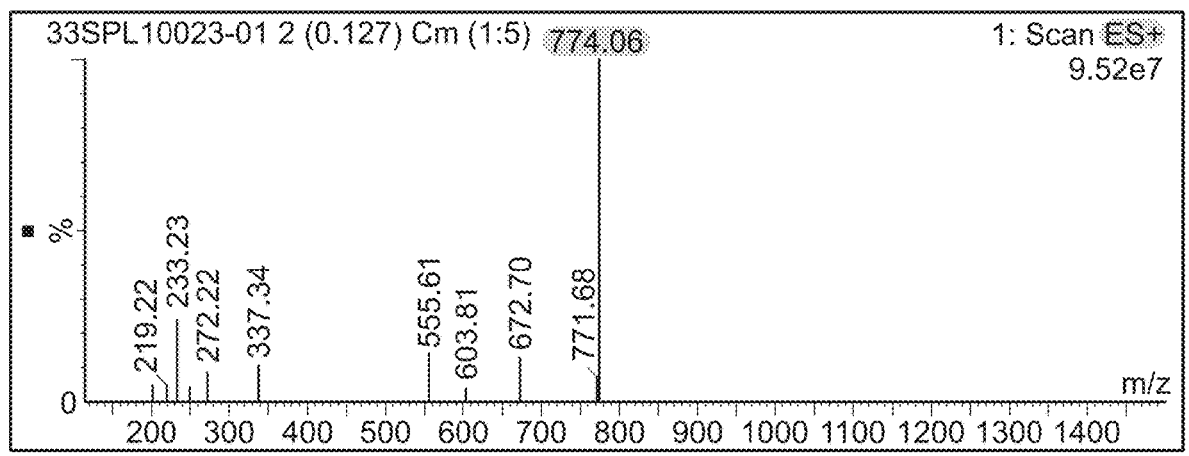
FIG. 12(k) provides the LCMS taken of the substrate of the phosphorylated catalyst of FIG. 12(j) and FIGS. 12(l) and 12(m) provide NMR spectra of the phosphorylated spectra.
Figure 12L:
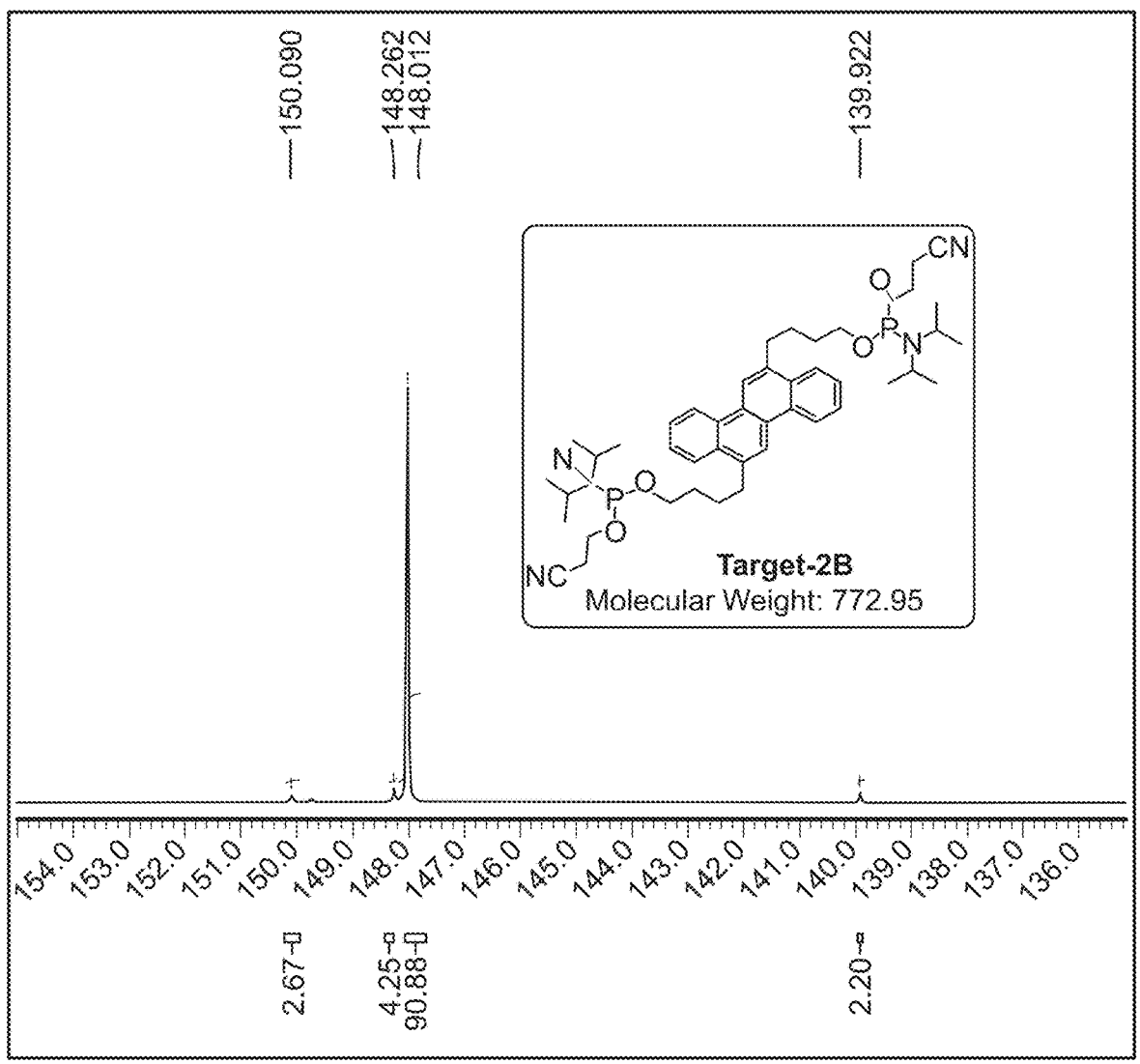
FIG. 12 (FIG. 12(a)-(q)) details the formation of substrate and catalysts and experimental results of those chemical syntheses.
FIG. 12(n) provides NMR and mass spectra of the progression in forming the catalyst (structure inset) and FIG. 12(o) provides NMR and mass spectra of a phosphorylated catalyst (structure inset).
FIG. 12(p) provides LCMS spectra of π-electron stacking of phosphorylated and non-phosphorylated catalyst.
FIG. 12(q) provides LCMS spectra of synthesized 1,9-disubstituted chrysene, which addresses alternative configurations of the catalyst and substrate for pharmaceutical applications.

The disclosure also includes reagents and intermediates of the reactions, for example, phosphoramidites (such as those associated with spectra in FIGS. 12(k) and 12(l)) are useful to produce monomers leading to the linkages which enable phosphodiester chain or binding. The synthetic methods may also include the synthesis for homodimer formations of catalyst/catalyst (e.g., 6,12-disubstituted chrysene) and substrate/substrate (e.g., 3,6,9,12-tetrasubstituted chrysene). These homodimer formations, which may considered to be supportive biological materials and result in formation of additional useful compounds such as non-encoded phospholipids (and membranes thereof) and amino acids. The present disclosure also includes polymerization of the phosphodiester linkage with triphosphate transition to monophosphate which thereby would issue additional energy to achieve the ring formation processes of the nucleotides.

EXAMPLES

Towards improving clarity in the principles and practices of the present disclosure, the following examples are presented. These are not to be considered as a limitation to the scope of the claimed embodiments. SCH denotes Substituted Chrysene Heterodimer to represent the association of 2,2'-(chrysene-6,12-diylbis(oxy))bis(ethan-1-ol) and 2,2',2'',2'''-(chrysene-3,6,9,12-tetrayltetrakis(oxy))tetrakis(ethan-1-ol) coupled through a monophosphate at the (6,12) positions as shown in FIG. 4(b).

Example 1: Encoding Target DNA Sequence into an SCH Sequence

To illustrate the encoding of a target DNA sequence into a sequence of substituted chrysene heterodimers (SCH), the encoding tables of FIG. 5 were used to convert information from the DNA into the encoded information of a sequence of SCH's. A random sequence of 13 nucleotides was generated and the resultant 26 encoding molecules, comprised of 13 SCH pairs, which comprise the same information at the randomly generated sequence. As can be seen, the length of the encoding sequence for DNA is twice as long since it is comprised of two molecules of which each is a binary object.

Target→TGAAA TTCCG ATA
Output→FFFBBBBBBB FFFFBFBFFB BBFFBB

Example 2: Decoding an Input SCH Sequence to an Output DNA Sequence

Given a sequence of substituted chrysene heterodimers, the corresponding DNA nucleotide sequence was determined through the use of the encoding table of FIG. 5(b). In this case, sequential pair of SCH was compared within the table to its associated DNA nucleotide, of which 2 letters for SCH will result in 1 letter for the DNA nucleotide sequence. Here, the 26 encoding substituted chrysene heterodimers will result in 13 DNA nucleotides. The map of SCH to DNA is useful for designing an encoded sequence, assembling the sequence, and/or initiating a chemical reaction to produce an equivalent relation of DNA nucleotides, expressed as follows in which SCH is the input and DNA is the output.

Target→FBBBFBFFFB BFBFBFBBBB FFBBBF= GAGTG CCCAA TAC→output

Example 3: Decoding an Input SCH Sequence to an Output RNA Sequence

As in the case of DNA, a decoding of an input SCH sequence to an RNA sequence was accomplished with the use of the encoding table of FIG. 5(a). The following relation indicates this mapping from SCH to RNA, with the reduction in length due to the base two representation of each molecule comprising SCH. The header sequence or initiation point directs the code towards DNA or RNA.

BBBFBFBBFF FBFFBBFBFB BBFBFF= UGGUA CAUCC UCA

Example 4: Regulatory Sequences

In FIG. 5(c), the information for directing the sequence as to the implementation code, RNA, DNA or hybrid, is upstream and downstream of the processed segment is provided. The use of an initiator (e.g., 2,2',2''-(chrysene-3, 6,12-triyltris(oxy))tris(ethan-1-ol)) to direct the sequence of SCH to produce the RNA or DNA configuration, or as a hybrid, is shown. It is noted that the reaction vessel formed from a heterodimer of initiator (2,2',2''-(chrysene-3,6,12-triyltris(oxy))tris(ethan-1-ol)) and catalyst (2,2'-(chrysene-6,12-diylbis(oxy))bis(ethan-1-ol)) is different due to the lack of a substituted sidechain at the 12 position of the substrate.

After reactivity of this regulatory reaction vessel, the result is a 5'-cap structure for RNA, which can be used as a signal to initiate translation. It is also noted that the triphosphate association of the 5'-cap structure on mRNA is consistent with the method of initiating polymerization through phosphorylation of the 3,9 sidechains of the sequence of tetrasubstituted chrysene.

In addition, regulation is provided by sequences of the (3,9) polymerization induced by the sequential orientation of 2,2',2'',2'''-(chrysene-3,6,9,12-tetrayltetrakis(oxy))tetrakis (ethan-1-01). For example, consider the repetitive sequence:

TTTTAAAAA

In this sequence, the orientation of the entry point at the downstream position of AAAAA is consistent with a 5'-RNA configuration; and likewise, the upstream condition of TTTT has AAAA on the 3' side, and thus on the reverse strand, the preferred orientation is also of a 5' to 3' RNA configuration.

Example 5: Hybrid DNA:RNA Encoding

With the upstream regulatory sequence coding for DNA at 5' and a downstream regulatory sequence coding on the antiparallel side of the molecule and encoding for RNA and 5', the result is a hybrid DNA/RNA. An example is presented below in which the decoding was performed by using the table of FIG. 5(b) to decode for DNA running in the 5' to 3' direction, and using the table of RNA running on the antiparallel 5' to 3' direction (end of the encoding string to the beginning of the encoding string).

$$FFBBFBFFFB\ BBFBBFFFBB\ BFBFBB = \begin{bmatrix} TAGTG & ACCTA & CCA \\ AUCAC & UCGAU & GGU \end{bmatrix}$$

Example 6: Simulation of Base-Four π-Electron Stacked Structure

Figure 11A:
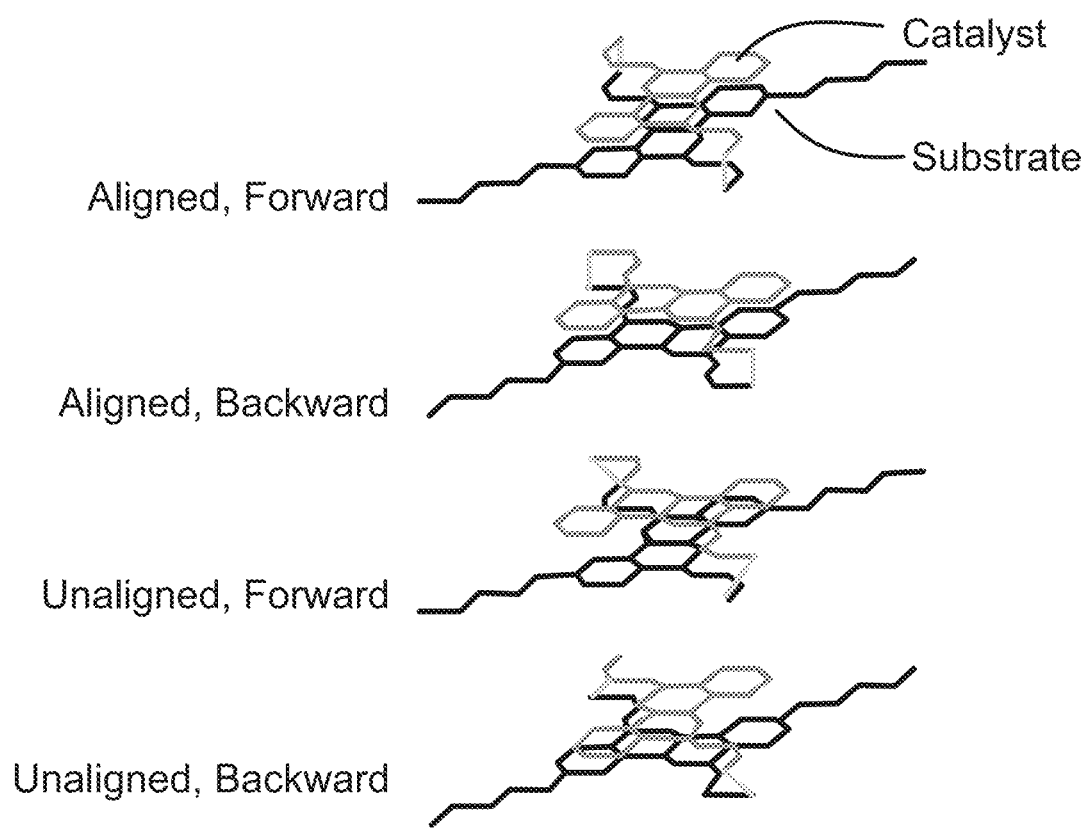
FIG. 11(a) illustrates the four different orientations of reaction vessels for information storage and transcription.

Simulation of the catalyst-substrate combination in the formation of base-four structure enabled through π-electron stacking was performed. FIG. 11(a) illustrates the bond structure of the four reaction vessels used in the simulation as well as the identifiers of the ring structures as to the absolute position of the substrate, and the relative orientation of the catalyst, both linked through the (6,12) phosphodiester bond. The code, whether DNA, RNA, or hybrid, is determined through the orientation of the catalyst to substrate, as well as the orientation of the substrate to the stack, depending upon the regulatory sequence (or initiator orientation). For a 5' RNA sequence, the code for this structure would be AUGC.

Figure 11B:
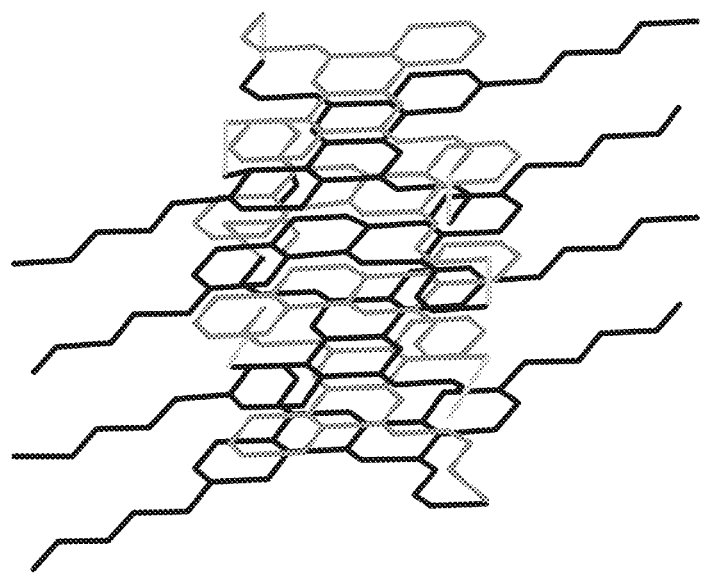
FIG. 11(b) provides a perspective view of a stacked version of these reaction vessels and FIG. 11(c) is a side view highlighting the phosphodiester bonds made between catalyst and substrate in each reaction vessel in their stacked orientation.
Figure 11C:
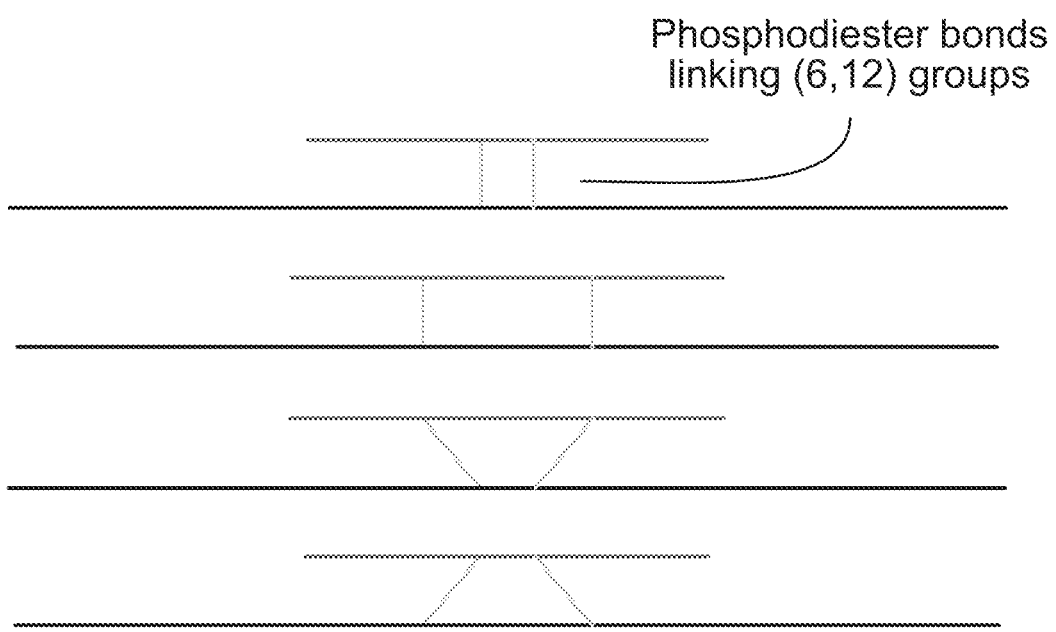
Figure 11D:
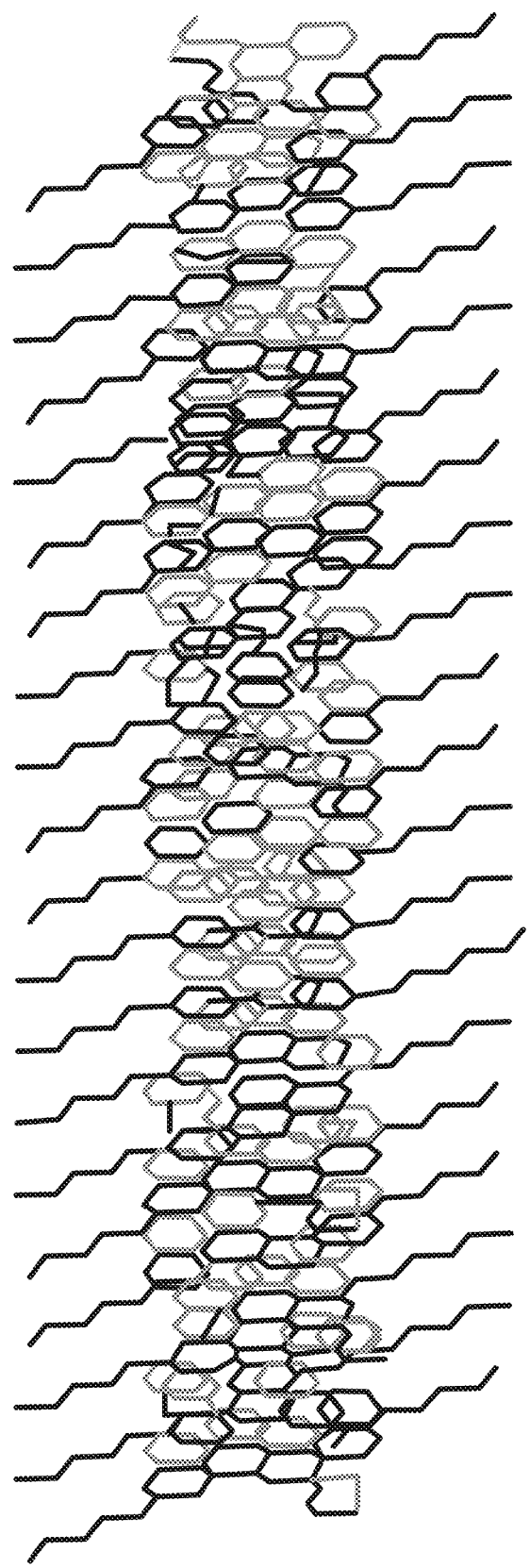
FIG. 11(d) provides a perspective view of a stacked version of many reaction vessels and FIG. 11(e) is a side view highlighting the phosphodiester bonds made between catalyst and substrate in each of these reaction vessel in their stacked orientation.
Figure 11E:
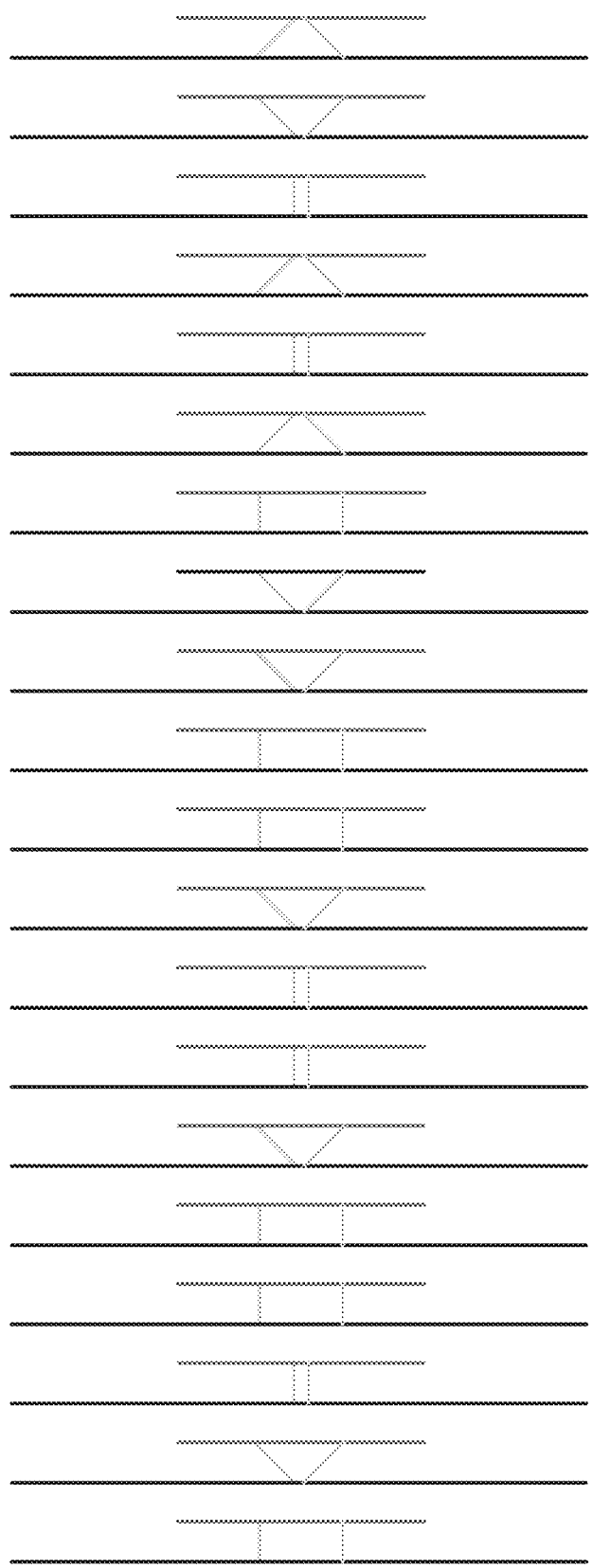

The alignment determines whether the resultant structure has two or three intramolecular bonds, while the regulatory sequence determines which side of the molecule, the polymerization will take place, and thus determine whether a purine or pyrimidine is the 5' structure as dictated by the entry position of the sugar ring. FIG. 11(b) illustrates the bond structure of the π-electron stacking showing a hydrophobic core and hydrophilic sidechains. The side-view of this structure is presented in FIG. 11(c). As can be seen, the phosphodiester linkage geometry is indicative of the four reaction vessels enabled by the catalyst-substrate structure to produce a base-four encoding functional molecular structure. Thus, for the four structures, the phosphodiester linkage configuration on the (6,12) combination is indicative of an encoded A-U; U-A; G-C; C-G for an RNA/RNA sequence. Longer sequences are demonstrated for twenty random SCH structures in FIG. 11(d) with the side-view shown in FIG. 11(e), of which the resultant nucleotide can be determined by evaluating the position of the phosphodiester linkage. The density of the hydrophobic core and the wire-like coupling of the π-electron stacking are features that become more apparent in stacked structures.

Example 7: Experimental Development of Materials

In FIG. 12(a), the reaction of bromine with chrysene over 72 hours is provided. The progression of the reaction mixture was monitored over time. It was observed that the natural progression of the reaction is that first 6,12-dibromochrysene is formed in which the dibrominated chrysene appears nearly simultaneously with the monobromide version, as there is little monobromide compound identified. The LCMS match plot taken at twenty-four hours reaction time is presented in FIG. 12(b). As can be seen, a molecule in the reaction mixture has a m/z of 383.2 which matches the dibrominated chrysene product.

Next 3,6,12-tribromochrysene appears, and the LCMS match plot at forty-eight hours is presented in FIG. 12(c) with a peak at m/z=465.5 which correlates with the tribrominated chrysene. Thereafter, the product 3,6,9,12-tetrabromochrysene is present in the LCMS at seventy-two hours as identified in FIG. 12(d) having a m/z peak at 541.5-543.2. The yield was 74 mol %.

These three materials are available and were used for further processing to develop ethoxylated alcohols as sidechains for polymerization by phosphodiester linkages, and subsequently reactivity to open the aromatic rings for triggering a stepwise cascade reaction to form nucleotide pairs.

In FIG. 12(e), the reaction sequence used to produce ethoxylated acid sidechains from tetra substituted chrysene is shown. The LCMS result confirming that the ethoxylated acid is on each of the sidechains is indicated in FIG. 12(f). To transform to an alcohol, the phenolic compound was applied with ethyl bromo acetate and lithium aluminum hydride (LAH). In FIG. 12(g) provides the proton NMR of synthesized 3,6,9,12-tetrasubstituted chrysene with oxyacetic acid sidechains indicating a successful run. Chrysene is a chromophore and is thus sensitive to UV-VIS spectroscopy of which FIG. 12(h) shows a peak at 288.5 nm which likely indicates an influence of the sidechains on the absorption spectra of chrysene that has a nominal absorption of 265-270 nm per NIST.

Figure 12M:
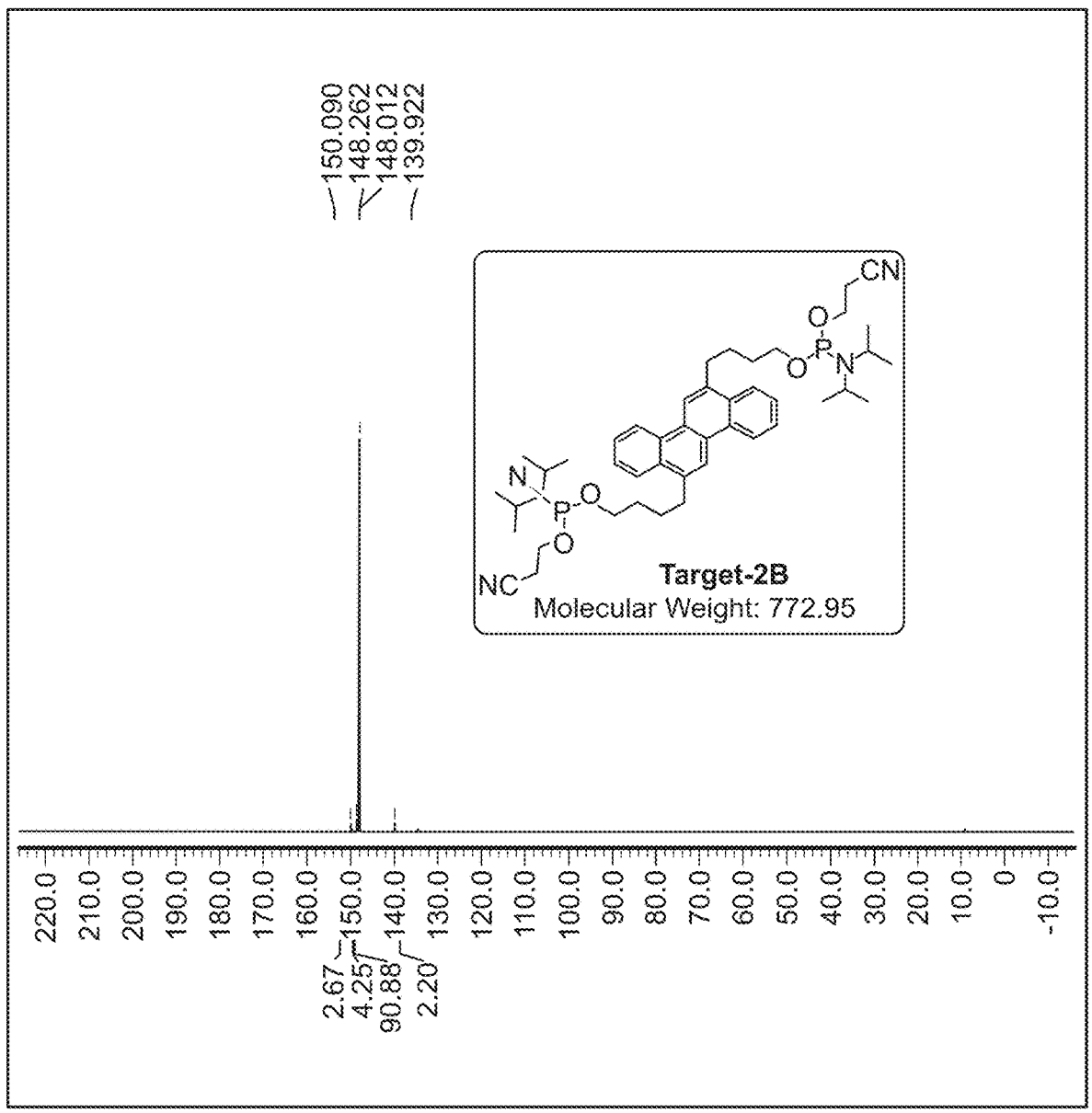
Figure 12N:
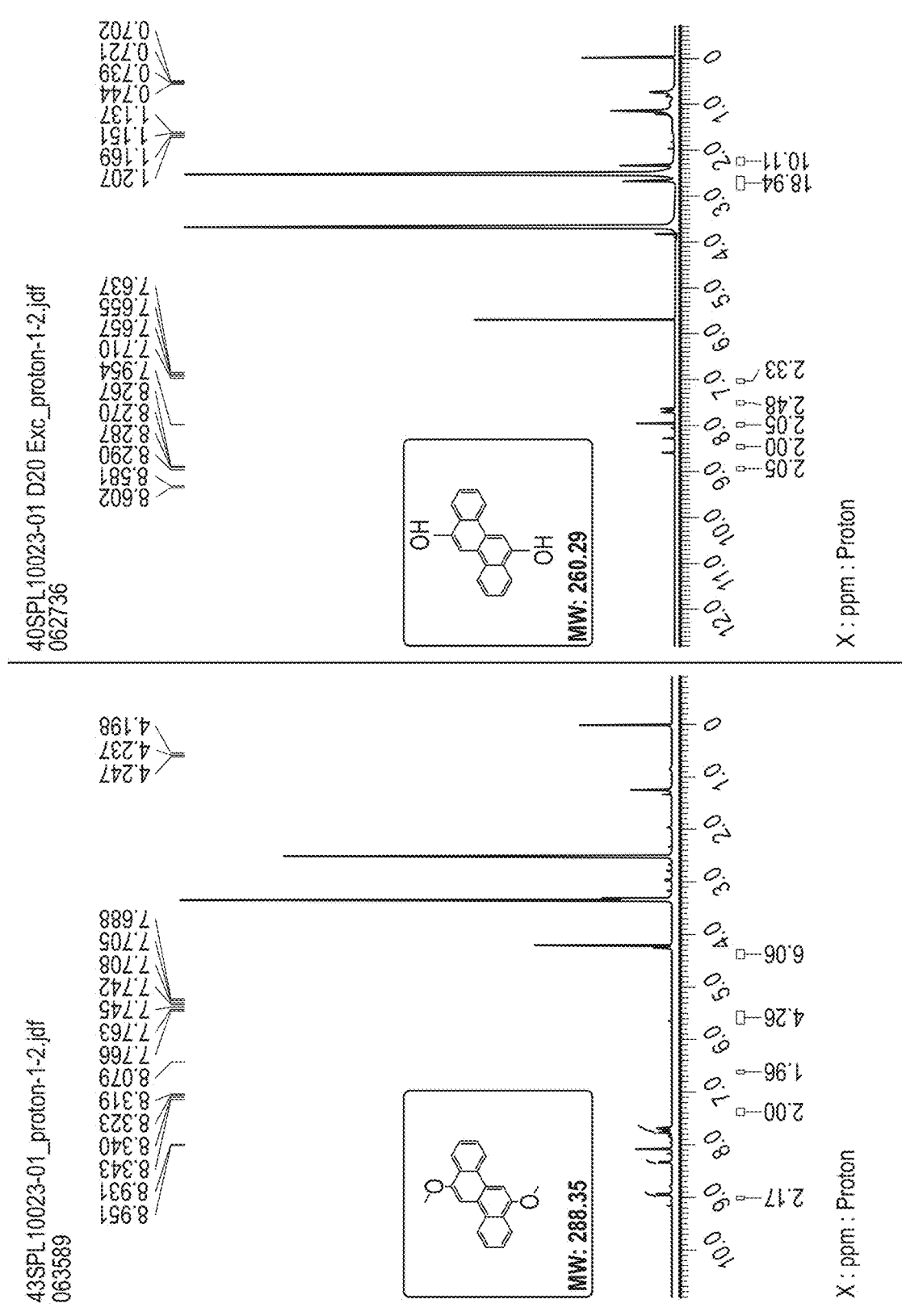
Figure 12N:
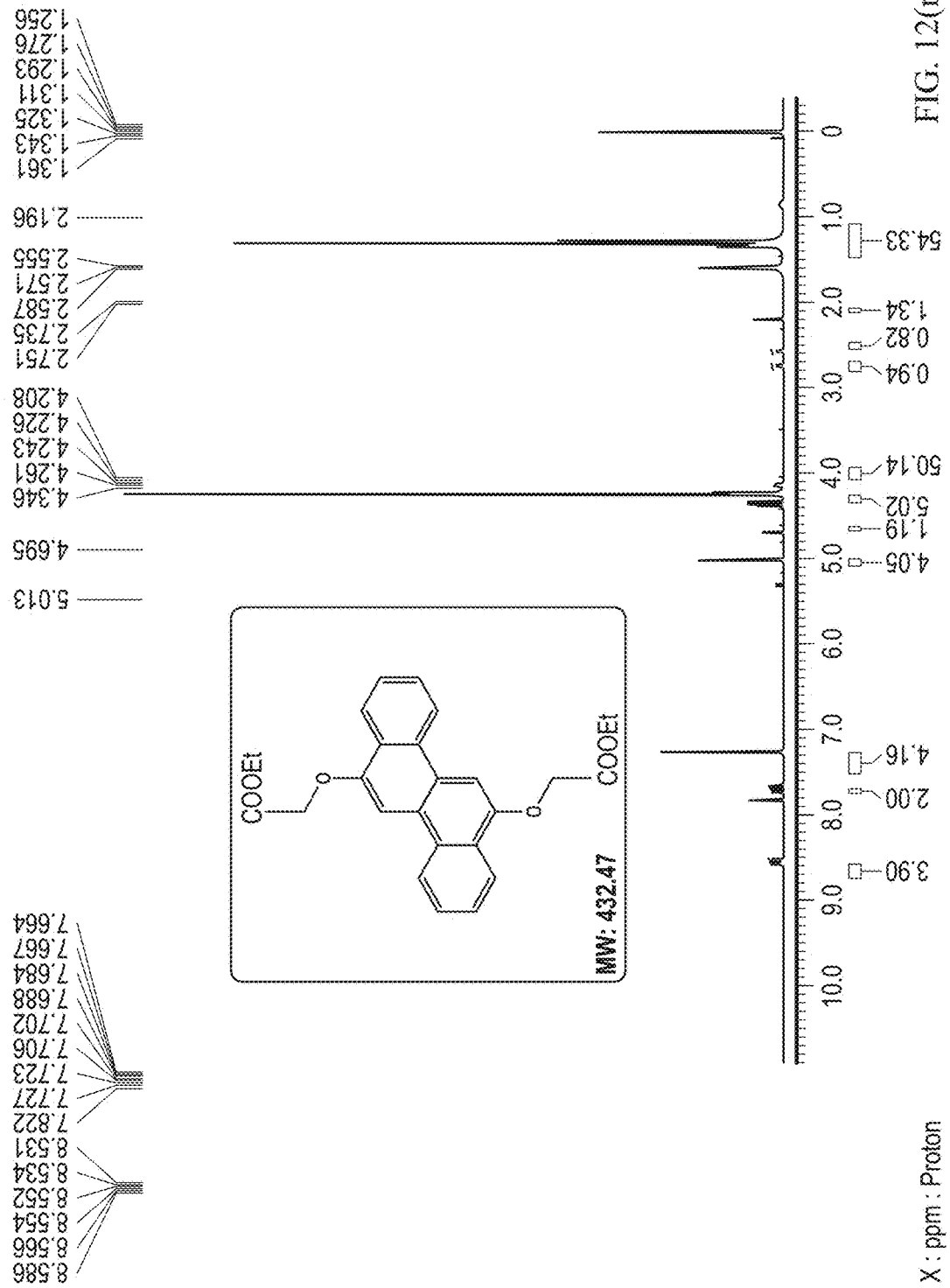
Figure 12N:
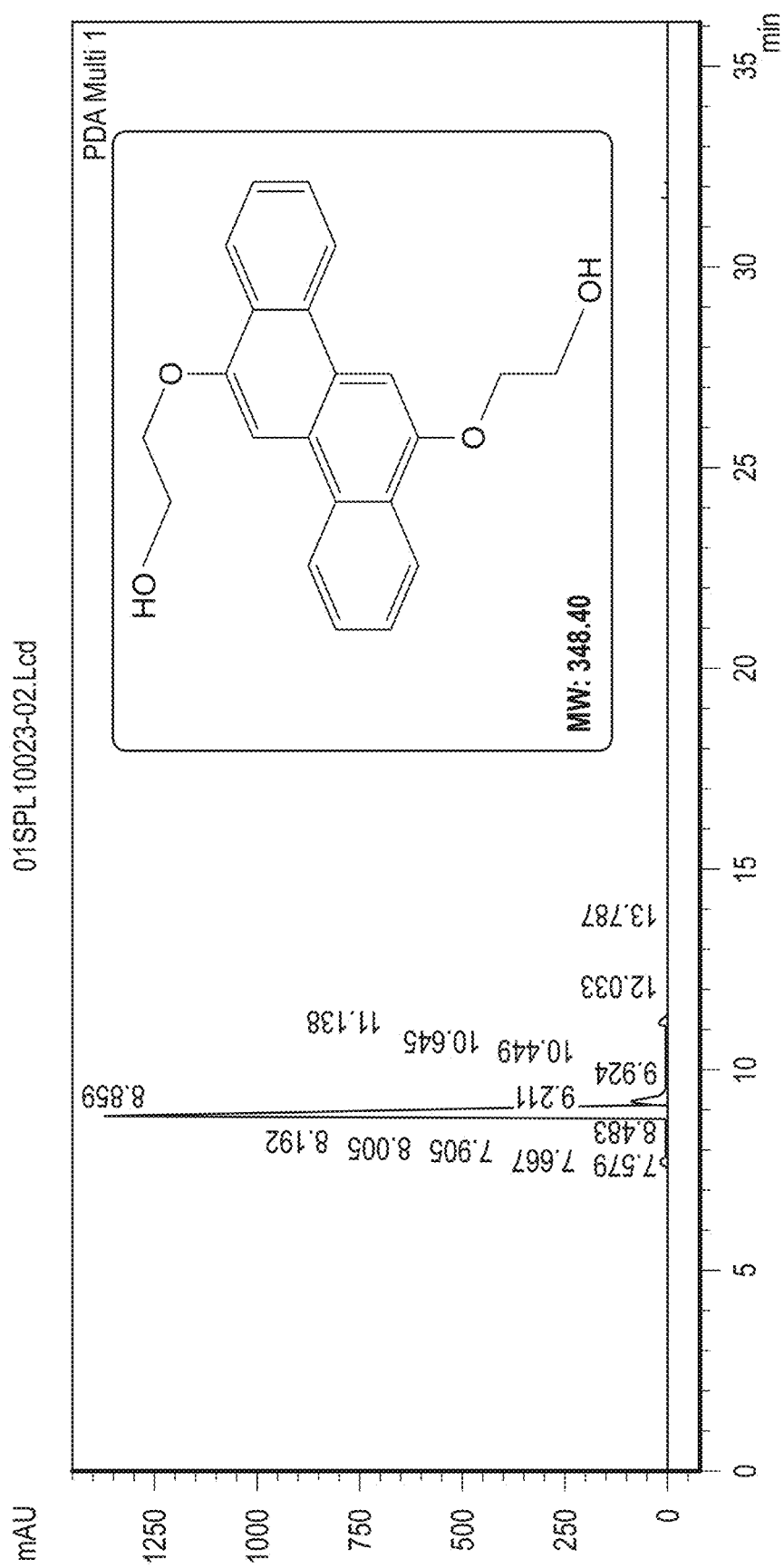

In FIG. 12(i), a 6,12-disubstituted chrysene is shown with butanol sidechains. This compound was synthesized using a Sonogashira reaction of chrysene with 3-butyn-1-ol over a $PdCl_2(PPh_3)_2$ catalyst with CuI added and triethanolamine utilized. FIG. 12(j) is an LCMS match plot of the synthesized 6,12-disubstituted chrysene having butanol sidechains after hydrogenation of the alkyne through a Pd/C catalyst and stirred for twelve hours. This material was then phosphorylated through a phosphoramidate process to provide the LCMS plot shown in FIG. 12(k) and the NMR plots shown for the 6,12-dibutonalphosphoramidate chrysene shown in FIGS. 12(l) and 12(m). FIG. 12(n) provides NMR spectra for the progression of catalyst syntheses performed.

FIG. 12(n) depicts data illustrating the observed progression of steps to form the 6,12 ethoxy alcohol chrysene. Starting from dibromochrysene, dimethoxy chrysene was formed, followed by diphenol chrysene, then diethoxy ethyl ester chrysene proceeding to the product using LAH/THF. The isolation of the product yielded 89%.

Figure 12O:
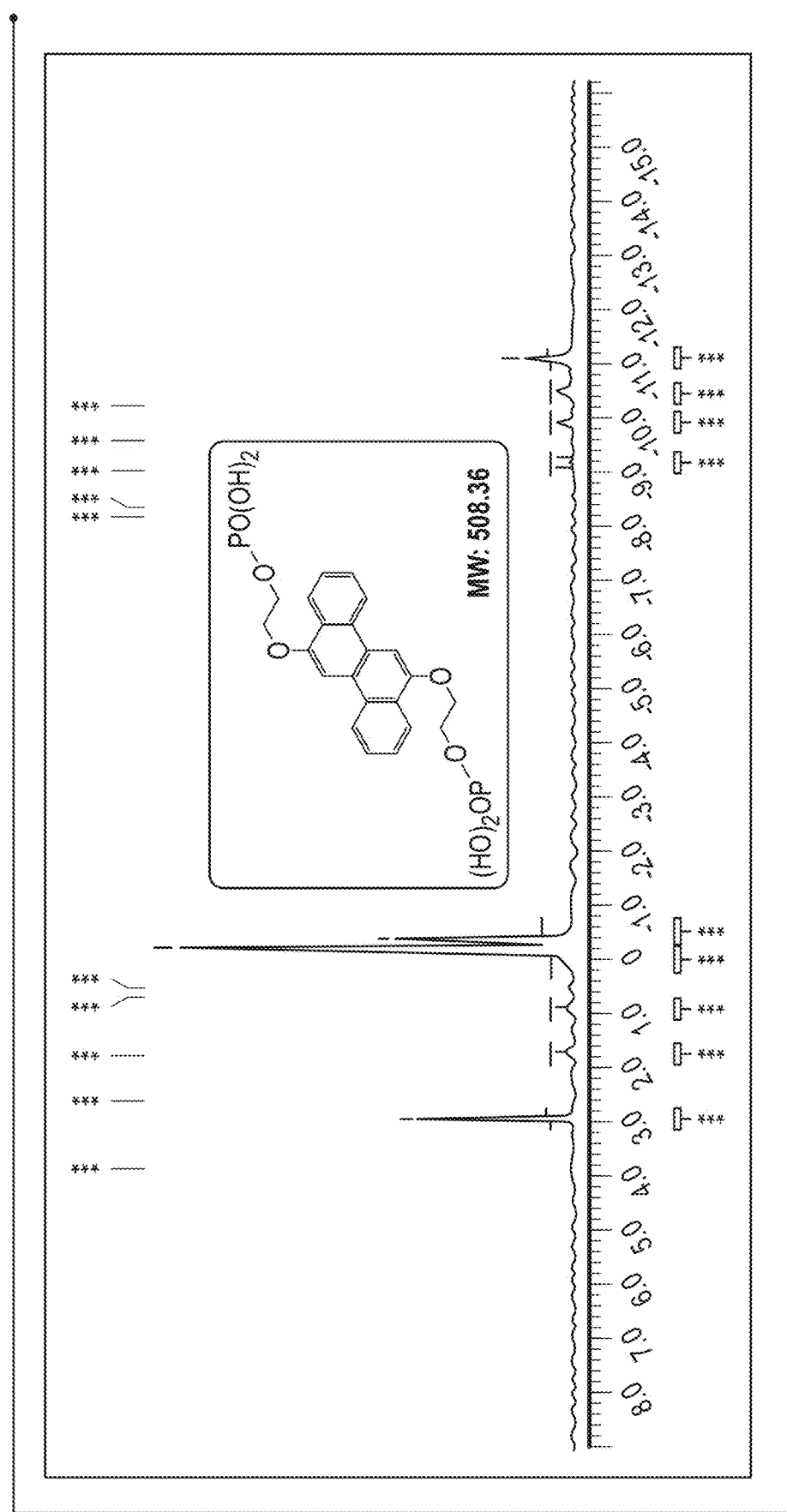
Figure 12O:
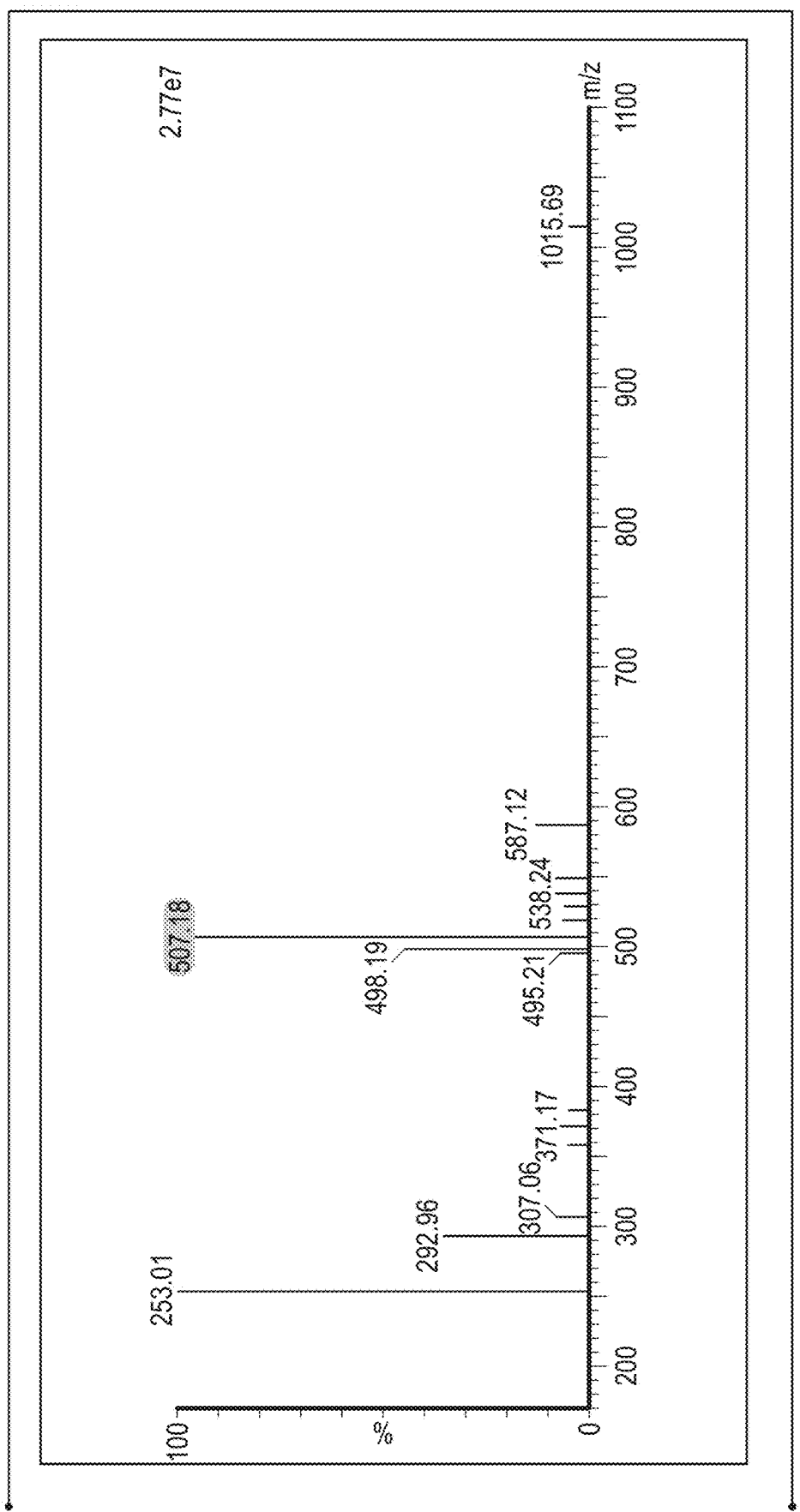

In FIG. 12(o), the phosphorylation of 6,12 ethoxy alcohol chrysene is shown in NMR spectrum measurement along with LC mass spectrometry. The phosphorylation was conducted with POCl3 and TMP achieving a yield of 78.3%. Also noted was the stacking of two phosphorylated 6,12 ethoxy alcohol molecules as indicated by a signal of a mass of 1015.69.

Figure 12P:
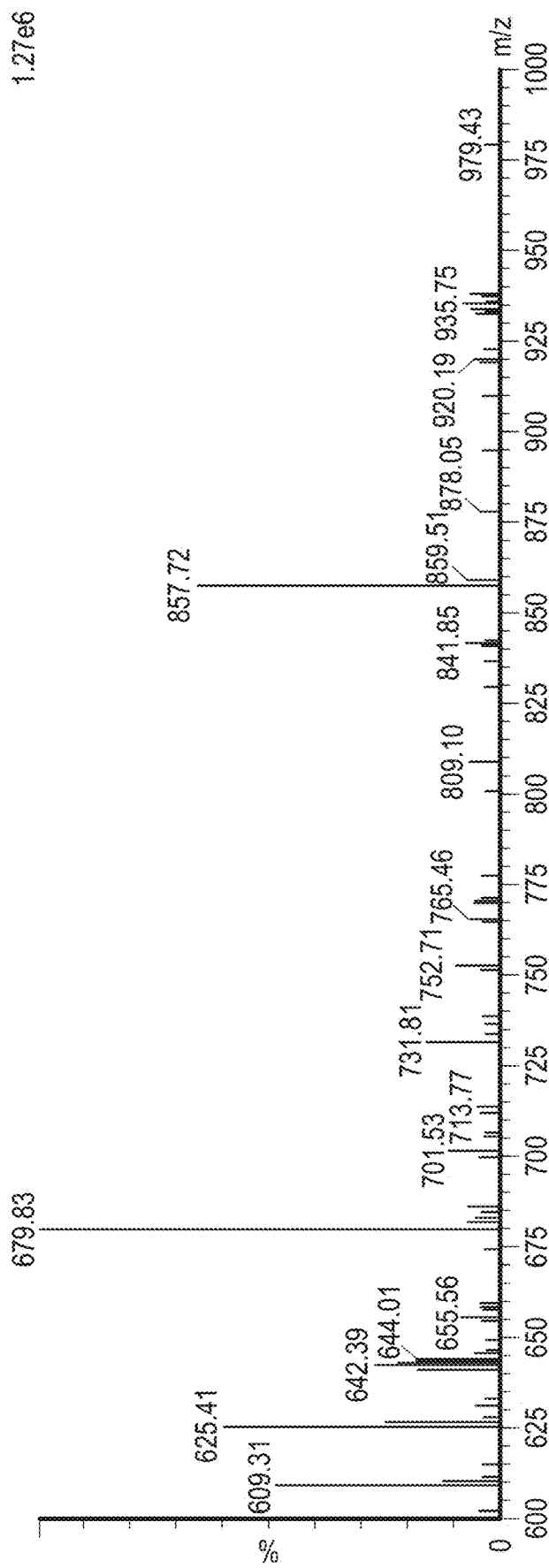
Figure 12Q:
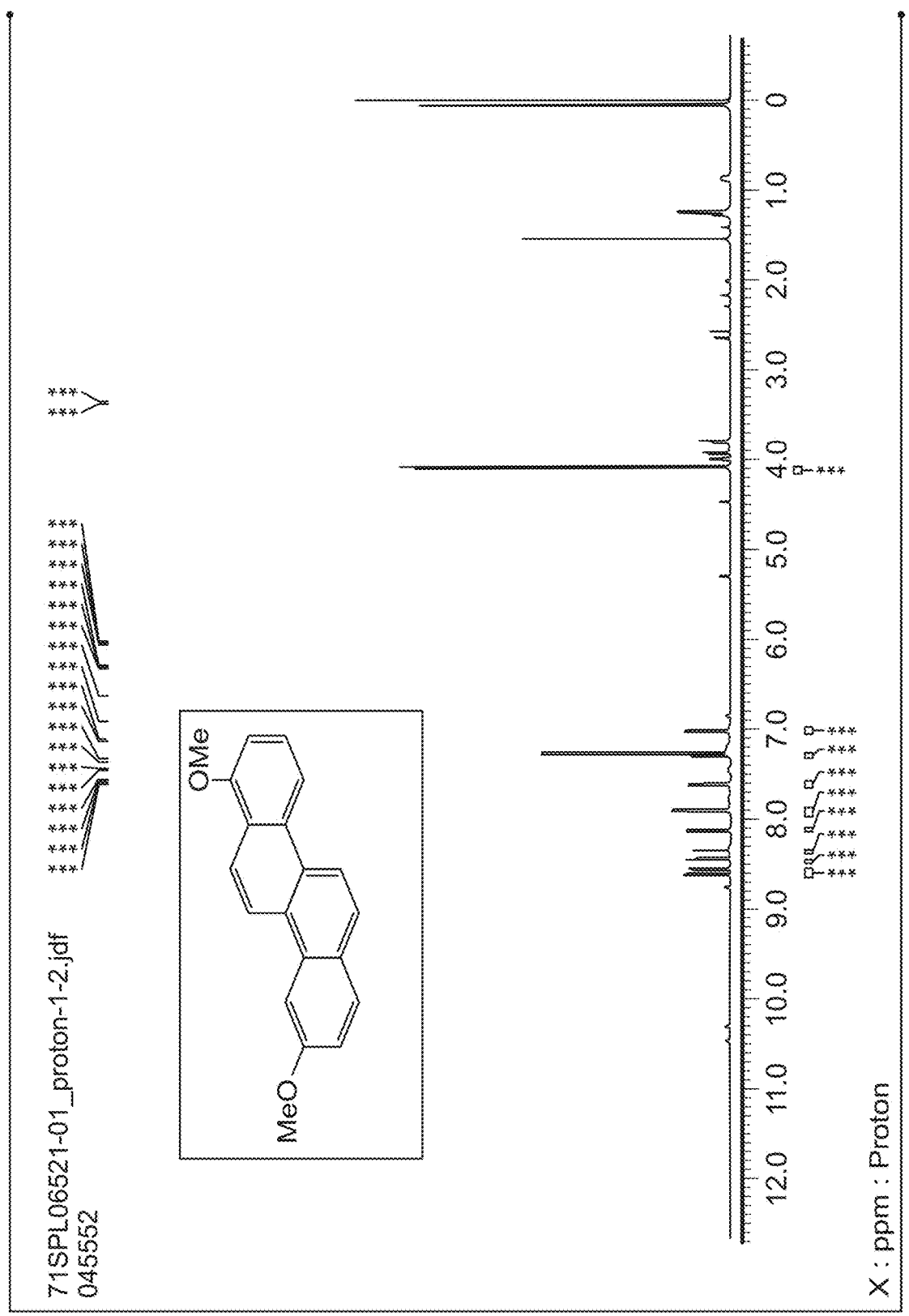
Figure 12Q:
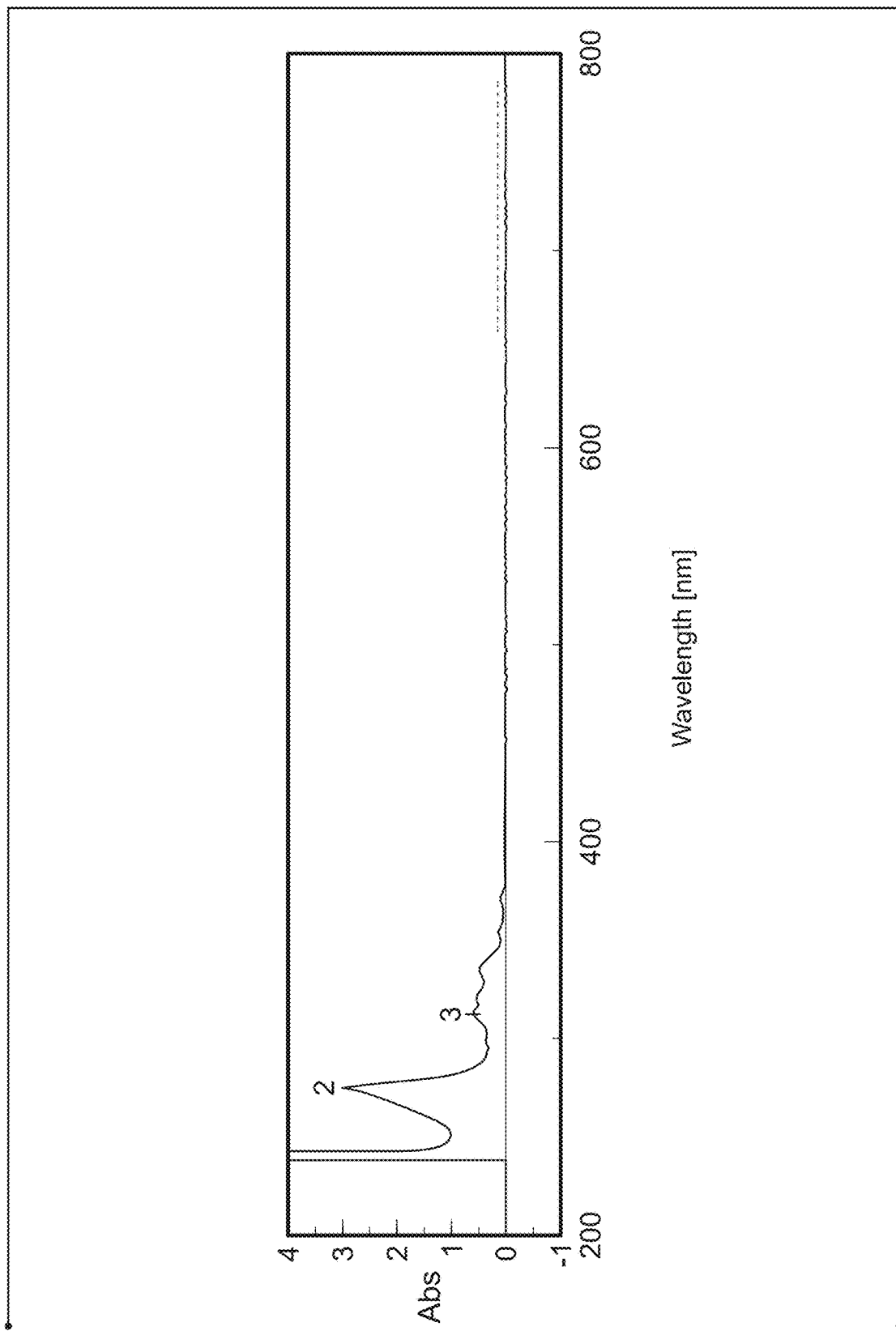

The encoding schemes are developed using substitutions of chrysene at the 3,6,9,12 positions. For pharmaceutical product development, the association of the substituted positions related to the prototype configurations of cortisol and testosterone (e.g., FIG. 1(c)) was noted with the correspondence of binding equivalency of the substituted sidechain as indicated in FIG. 3. To extend the range of molecules that can retain the binding equivalency outside of the 3,6,9,12 positions while providing alternative entry positioning, synthesis methods were developed for placement of functional groups at specific positions other than the natural set of 3,6,9,12. FIG. 12(p) shows LCMS spectra suggesting π-electron stacking of phosphorylated catalyst and non-phosphorylated catalyst demonstrating an interaction at the 6,12 position with a peak at 857.72. In FIG. 12(q), the molecule 1,9-dimethoxy chrysene is shown for NMR spectra and for UV absorption. This result demonstrates a procedure of the formation of substitutes at alternative sites spatially consistent with the sidechains of testosterone-like steroid pharmaceuticals.

Example 8: Modeling and Simulation

Figure 13A:
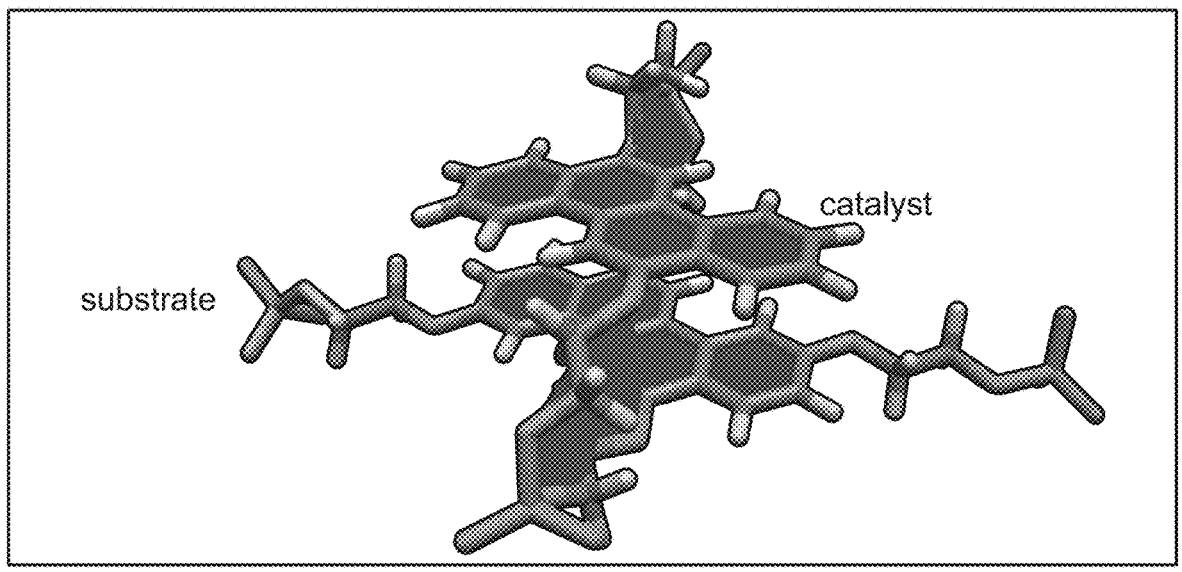
FIG. 13(a) provides a ball and stick model of a substrate catalyst reaction vessel (or SCH complex) and 13(b) provides the electron density map of this complex.
Figure 13B:
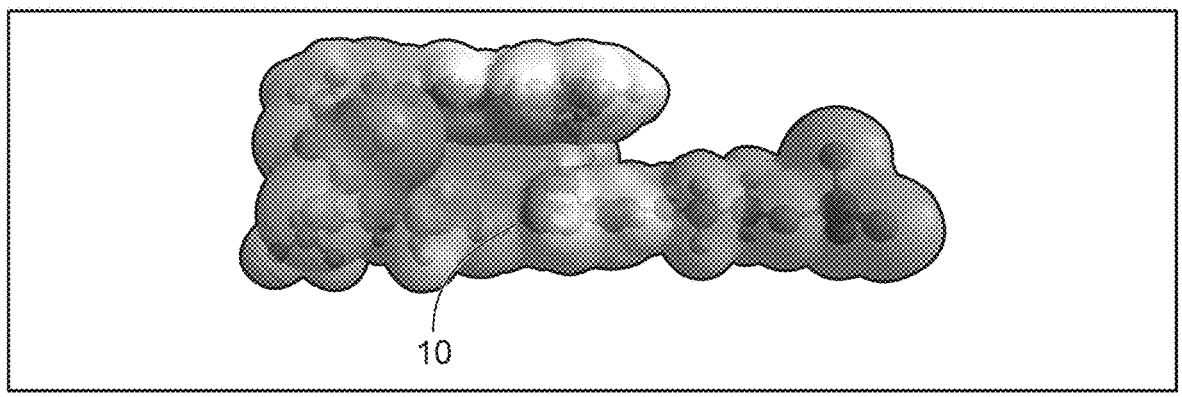
FIG. 13 (FIG. 13(a)-(f)) provide illustrations of SCH complexes and stacks of SCH complexes.
FIG. 13(c) provides the ball and stick model for a stack of SCH complexes and 13(d) provides the electron density may of this stack.
FIG. 13(e) provides a ball and stick model of an SCH complex intermediate having a substrate having undergone several reaction steps such as oxidative cleavage prior to formation of the nucleotide pairing.
FIG. 13(f) relates to the formation of a nitroarene in an aligned catalyst substrate pairing through association of nitric acid and the catalyst in a position consistent with the subsequent oxidative cleavage of the substrate to initiate ring-opening to form the sugar-ring. As can be seen, the electropositive nitrogen core of the nitric acid may be attracted to a carbon on the catalyst (e.g., a carbon adjacent to the $R_{6S}$ or $R_{12S}$ group) and the corresponding oxygen groups may be attracted to vicinal carbons on the substrate to initiate oxidative cleavage and formation (and possible base pairing).

The (3,6,9,12)-tetrasubstituted chrysene is polymerized with (6,12)-disubstituted chrysene to form an SCH (substituted chrysene heterodimer), which is a basis structure to construct the sequence. In FIG. 13(a), an aligned SCH is illustrated whereby the 6,12 connections are phosphorylated to form an inner ring spanning the catalyst and substrate. The ends of the substrate are exposed and available for further processing such as by oxidative cleavage of the outer rings, as well as the inner rings. In FIG. 13(b), the electropositive region 10 of the substrate is indicated whereby oxidative cleavage is targeted to open the outer ring. There are three other electropositive regions on the substrate: one for the other outer ring, and two for the inner ring.

Figure 13C:
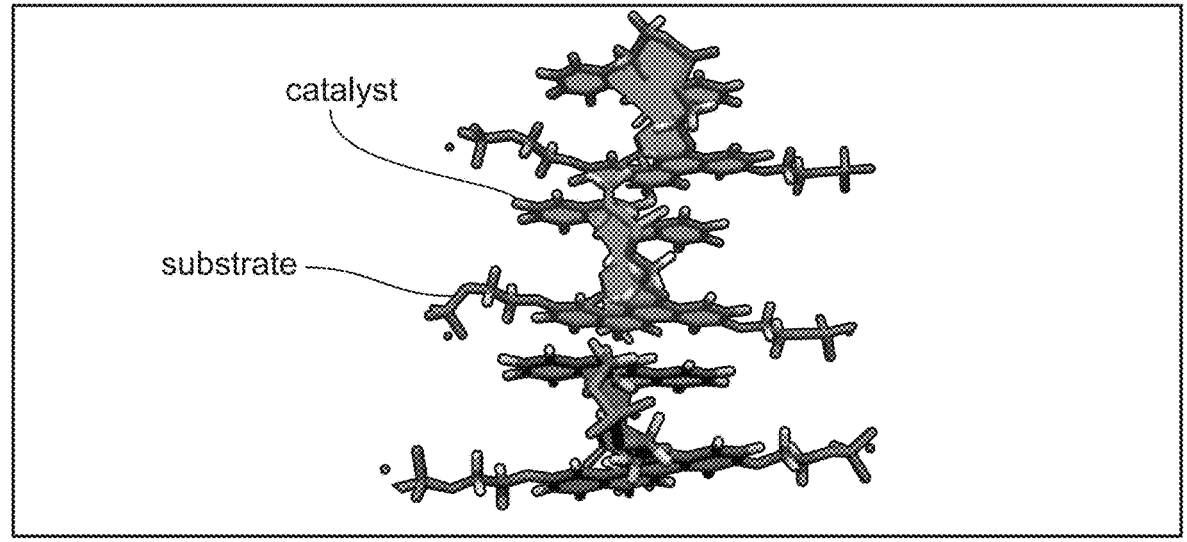
Figure 13D:
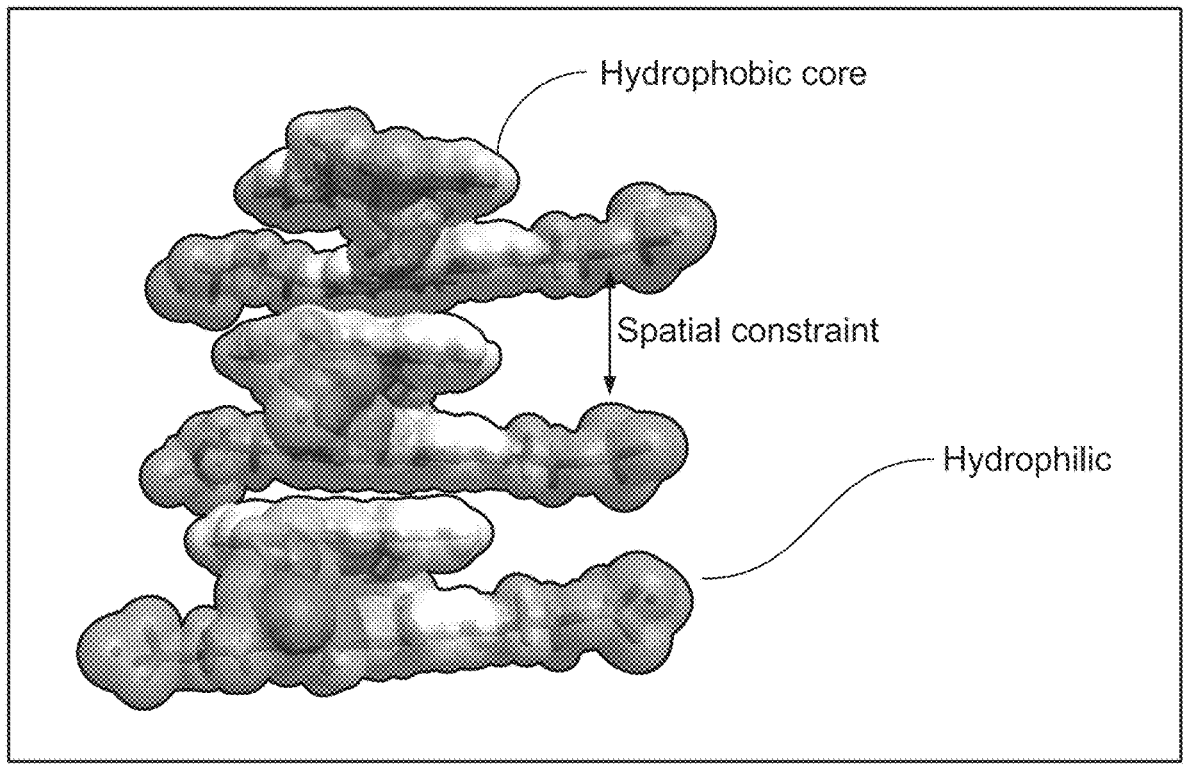

FIG. 13(c), a simulation of π-electron stacked substituted chrysene heterodimer, shows three unaligned SCH with the code of FBFBFB. As can be seen, phosphorylated ethoxylated alcohols extend away from the core chrysene, and therefore are available for interaction and formation of phosphodiester linkages between each adjacent substrate/catalyst pair. FIG. 13(d) shows the electrostatic potential of the three π-stacked SCH. The core of the molecule is hydrophobic whereas the extensions are hydrophilic. The interior space is constrained. Thus, the overall molecular structure creates a chemically and spatially constrained system from which chemical reactions can be run in a controlled manner. The simulations were prepared using the Avogadro simulation software program deploying an MMFF94 force field and steepest gradient convergence algorithm.

Figure 13E:
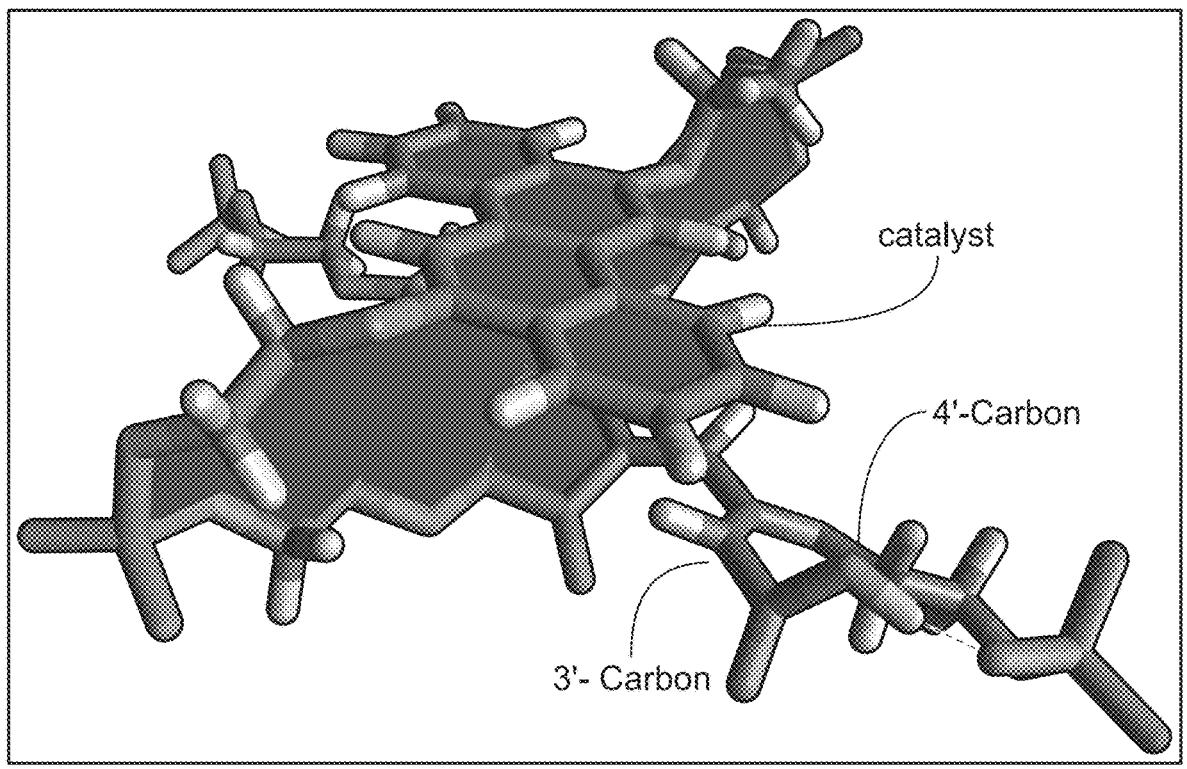
Figure 13F:
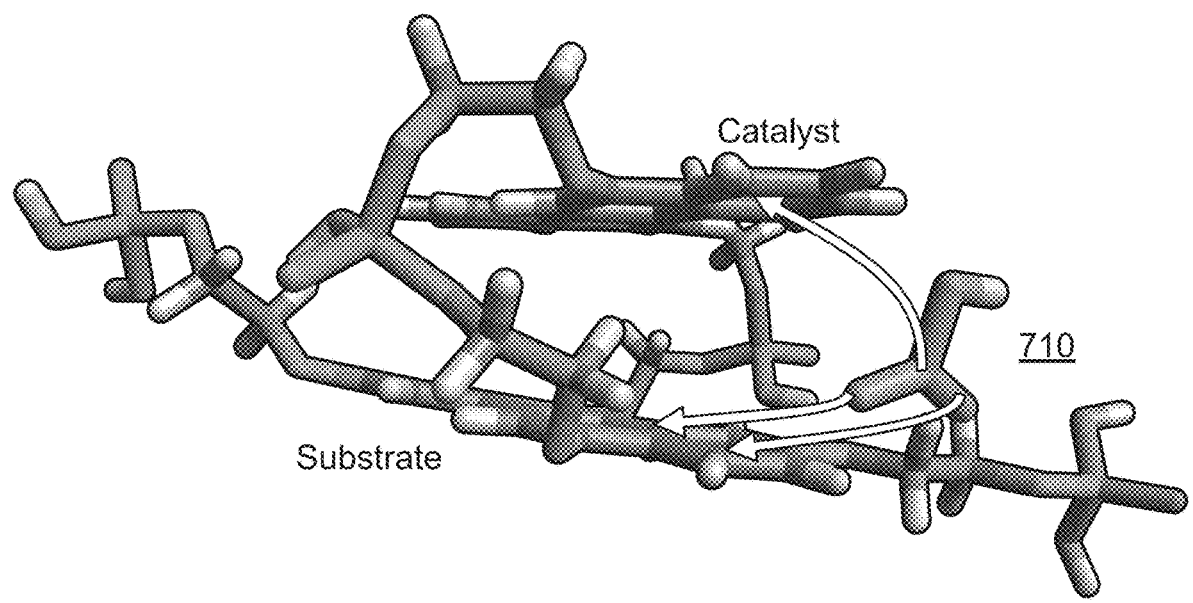

To simulate sugar-ring closure, SCH compounds as a π-electron stacked assembly are processed by applying an oxidative cleavage, preferably under green chemistry conditions using anerobic procedures with a mixture of ammonia, sulfuric acid, nitric acid, water, phosphoric acid, and a metal such as zinc oxide or magnesium under visible light. Other methods of oxidative cleavage are also described herein including ozonolysis. As modeled in FIG. 13(e) using the Avogadro simulation program, the nitric acid induces oxygen transfer and ring opening of the outer rings, which then migrate towards the phosphorous compound and bring the 3' and 4' carbon in close association for carbon-carbon bonding using the oxygen of the carboxylic acid, which was formed from the oxidative cleavage action, as a leaving group. The inner rings show strain, as does the opened outer ring, which induces nitrogen insertion and ring closures, followed by sidechain development based upon the alignment configuration of the catalyst and substrate to form the final product of DNA, RNA, or hybrid, which also depends upon the direction of polymerization. FIG. 13(f) uses the Avogadro simulation program to indicate the formation of the nitroarene through reaction nitric acid 710 with the catalyst. Subsequently, the oxygen atoms of nitric acid associate with the substrate in an oxidative cleavage to open the ring structure for the formation of the sugar-ring.

Example 9: Alteration of Source Material and (6,12) Substitution

Figure 14A:
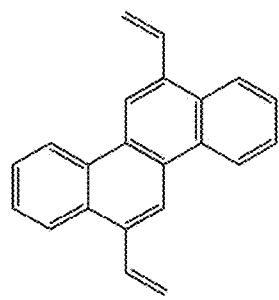
FIG. 14 (FIG. 14(a)-(f)) provides additional set of exemplary catalyst (e.g., 14(a))/substrate (e.g., 14(b))/initiators.
FIGS. 14(c)-(e) provide exemplary reaction environments created by different conjugations between substrates and catalyst.
FIG. 14(f) provides exemplary side groups which may be conjugated to the primer core (e.g., suitable at $R_3$, $R_6$, $R_9$, $R_{12}$, $R_{3S}$, $R_{6S}$, $R_{9S}$, $R_{12S}$, $R_{3C}$, $R_{6C}$, $R_{9C}$, $R_{12C}$, $R_{9S}$, $R_{12S}$, $R_{6L}$, or $R_{12L}$).
Figure 14B:
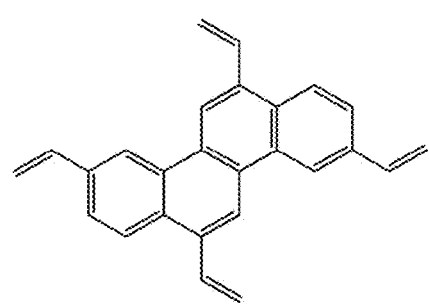

In FIG. 14(a), 6,12-divinylchrysene, and FIG. 14(b), 3,6,9,12-tetravinylchrysene, alternative source materials are provided. These materials may be arranged to form the equivalent heterodimer to follow the format of the codes presented in FIG. 5 for substituted chrysene. The advantage of the materials of FIGS. 14(a) and (b) is that these starting materials are is all carbon (and hydrogen) and may be derived from graphite, or single sheet graphene, stacked through π-electron coupling, which produces long sequences of structures through a crystalline-like starting material. The formed materials can be converted to phenols through reactions in oxidizing air at elevated temperatures. The phenolic compounds can then be converted into ethoxylated alcohols using the previously described methods. It is noted that an equivalent result in the basic divinyl-structure starting from chrysene and forming vinyl-based sidechains was demonstrated as an intermediate result for the formation of the 6,12-disubstituted chrysene structure of FIG. 12(i) by binding an alkyne through a Sonogashari reaction to dibrominated chrysene.

Figure 14C:
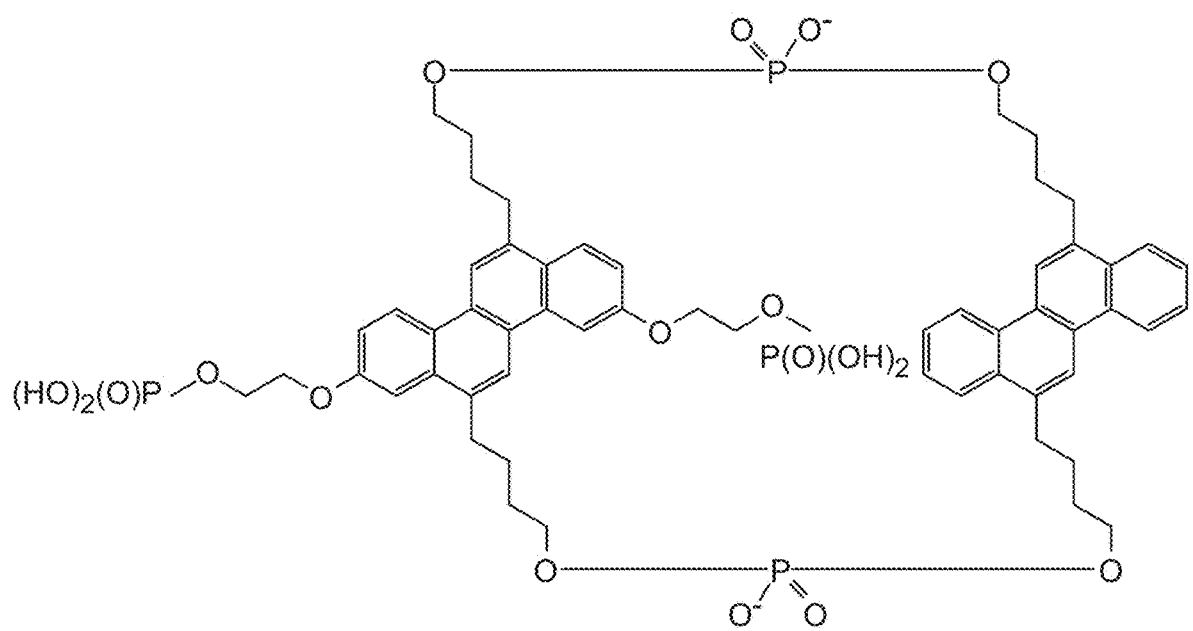
Figure 14D:
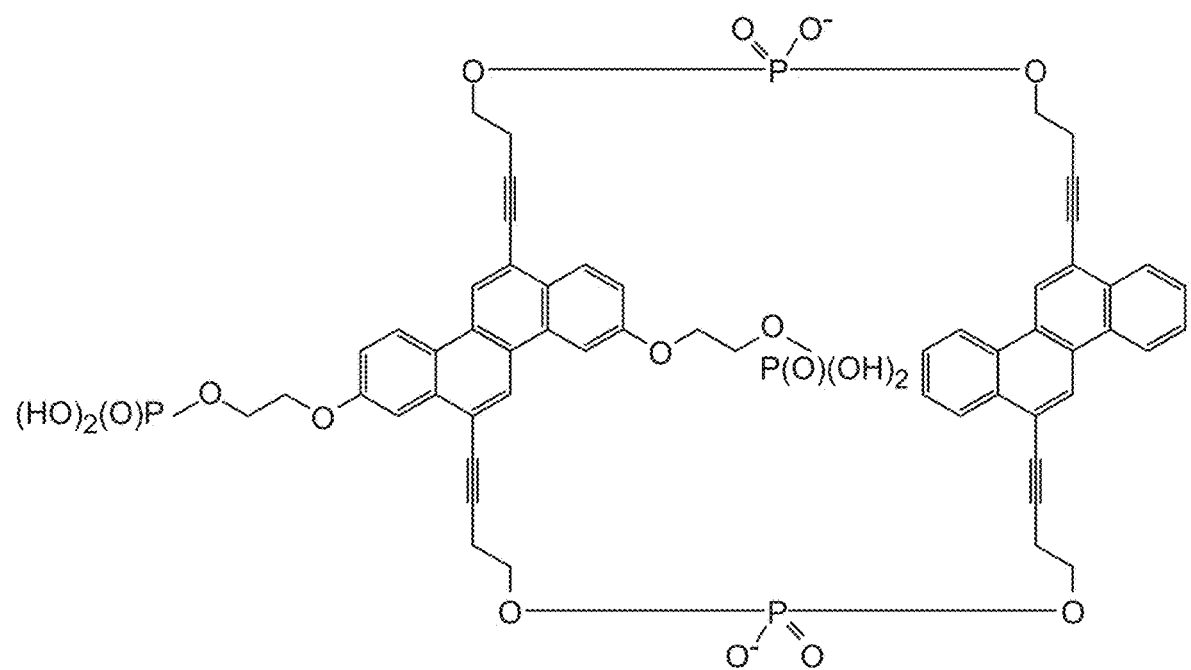
Figure 14E:
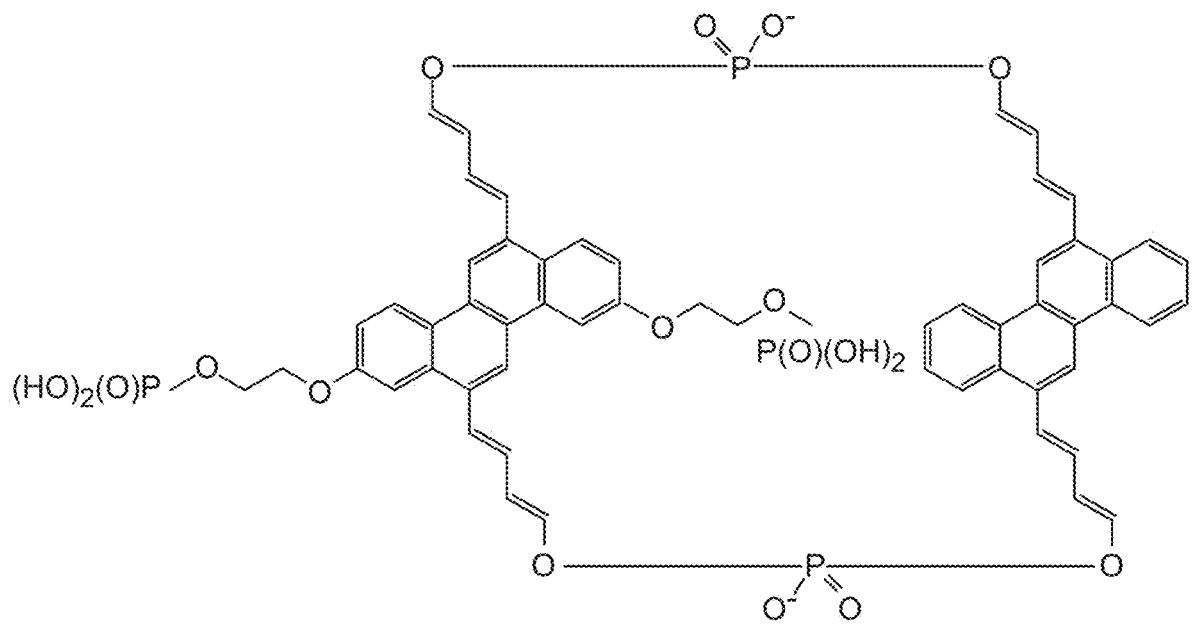

It is noted that the sidechain at the (6,12) position is not part of the DNA which is seen by review of the atom mapping results of FIG. 7. Consequently, the side groups can be modified to improve binding characteristics of SCH and regioselectivity of the oxidative cleavage reaction. One such alternation is shown in FIG. 14(c) which shows a four carbon linker to the phosphodiester linkage. This will modify the structure of the phospholipid that results as the remnant of the transformation. In addition, the incorporation of leaving groups, such as an alkene or alkyne at the 1-2 carbon position of the (6,12) sidechains as shown in FIG. 14(d), will also assist with the reaction. The integration of the entire structure with a double bond configuration as shown in FIG. 14(e) also provides additional functional groups for subsequent reactions.

Figure 14F:
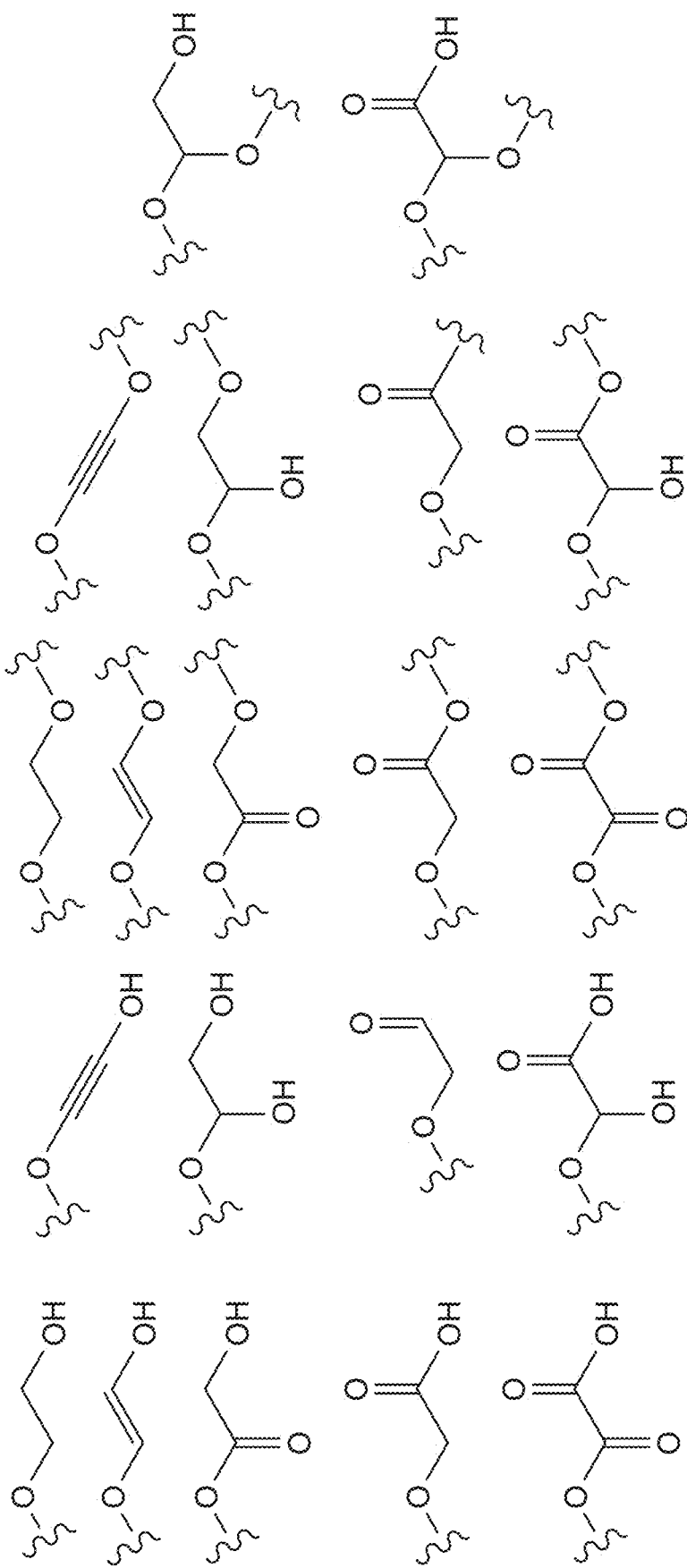

In FIG. 14(f), various types of sidechains (e.g., suitable at $R_3$, $R_6$, $R_9$, $R_{12}$, $R_{3S}$, $R_{6S}$, $R_{9S}$, $R_{12S}$, $R_{3C}$, $R_{6C}$, $R_{9C}$, $R_{12C}$, $R_{9S}$, $R_{12S}$) are presented. Of interest is the substitution of oxalate sidechain for two reasons: (1) the oxalate sidechain has a ketone group at the first carbon which can aid as a leaving group in the formation of the sugar ring; (2) the attachment of an oxalate as a dianion of charge −2 to the chrysene core enables a conjugated flow of electrons into a stack of conjugated chrysene molecules, thereby establishing contents for an electrochemical cell to provide input energy to power the oxidation and nitrogen insertion steps converting the stacked sequence of chrysene molecules into nucleic acids.

Example 10: SCH Sequence Design for Implementation of First Instruction Set

The described method is capable of producing RNA concurrently with DNA and hybrid DNA/RNA, and thus proteins for the first instruction set can be developed from RNA. One area to consider however is that for implementing the first instruction set the proteins are not available to stabilize RNA in order to perform translation. This can be resolved through efficient design of RNA in conjunction with the catalyst for implementing the first instruction set. As mentioned, the interaction of the catalyst from RNA-adenine, which is connected at the 6-position of the (6,12)-disubstituted chrysene to the carbon of RNA-adenine without a sidechain, may remain. This can be exploited therefore to stabilize RNA by maintaining a connection with the catalyst, which is a phospholipid bilayer. Thus, the catalyst and remnant after synthesis can remain attached to RNA through a sequential adenine group at the post-coding area to stabilize through association with the cellular membrane. For a long sequence of RNA-adenine, the catalyst attached to the RNA and the membrane will provide sufficient stability for translation of the RNA molecule. This approach is equivalent to the poly-A tail of mRNA. Thus, the sequence for translated RNA for implementing the first instruction set should include the SCH sequence:

FFFFFFFFFF FFFFFFFFFF FFFFFF=AAAAA AAAAA AAA

Figure 15A:
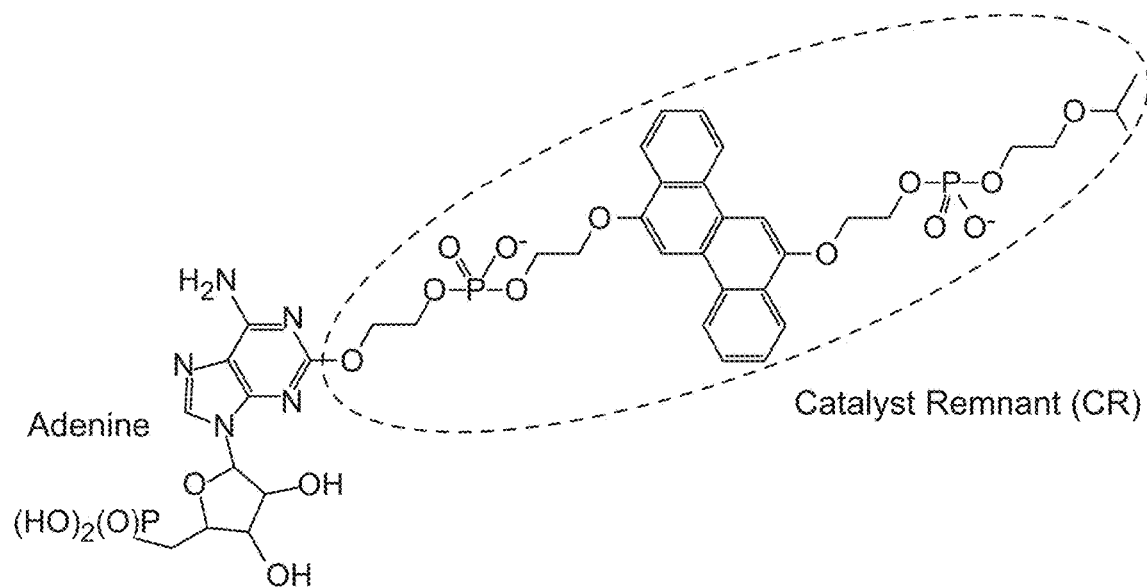
FIG. 15(a) illustrates an exemplary catalyst remnant conjugated to an Adenine.
Figure 15B:
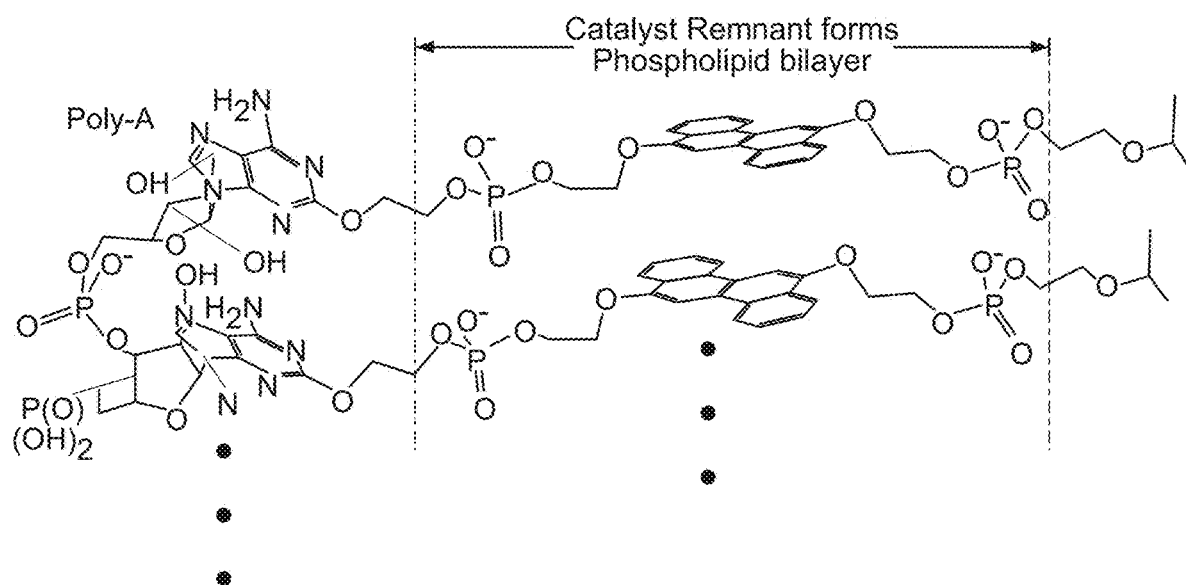
FIG. 15(b) illustrates how multiple catalyst remnant layers may be conjugated to polymers comprising adenine which may end up forming a phospholipid bilayer optionally tethered to RNA.
Figure 15C:
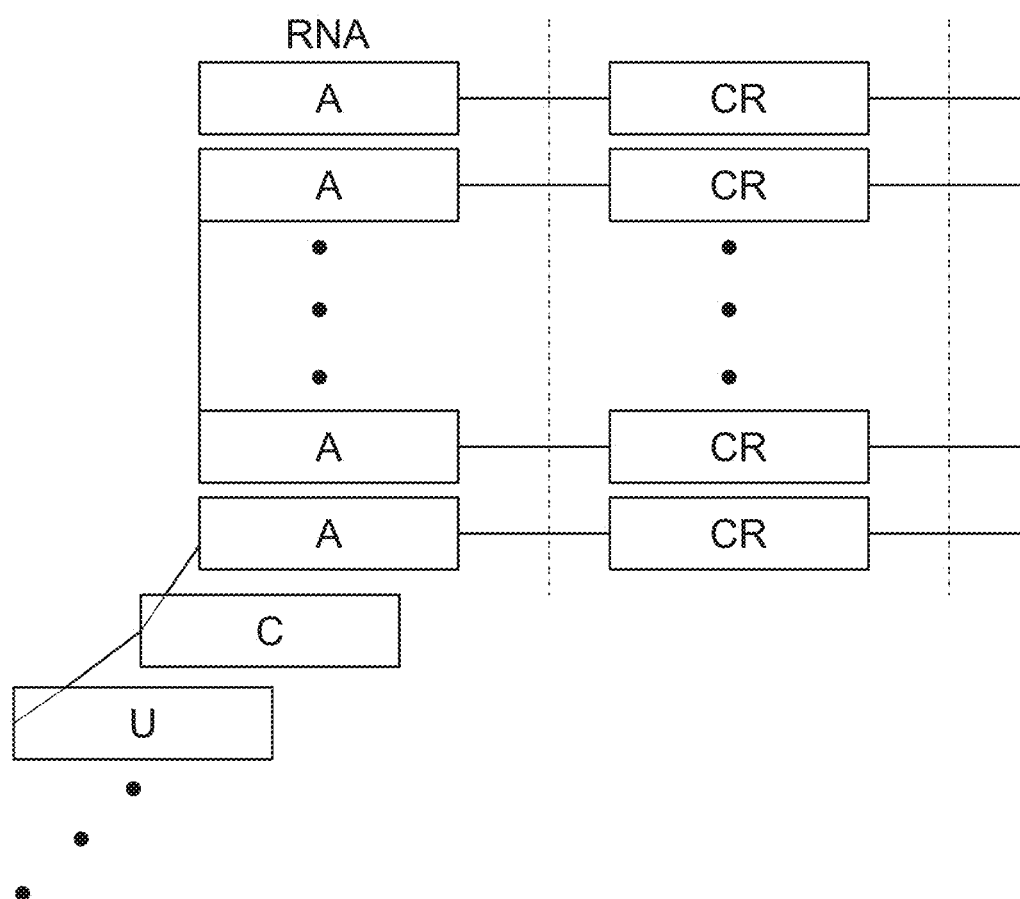
FIG. 15(c) provides a schematic for this tethering.

For implementation of the first instruction set, this relation between adenine attached to the catalyst remnant is illustrated in FIG. 15(a), which when stacked, is shown in FIG. 15(b). It is noted that the catalyst remnant forms a phospholipid bilayer and anchors the poly-A tail. The initiation of the RNA strand that is utilized for translation departing from the poly-A tail is illustrated in FIG. 15(c).

Example 11: Supportive Molecules from Homodimers of Substituted Chrysene

While the heterodimers produce the nucleic acids as well as encoded phospholipid structures for interaction with membranes, to produce the cellular structure and engage in protein synthesis, amino acids as well as non-encoded phospholipid structures are required. These materials are available from the phosphorylated homodimers of the naturally produced substituted set of chrysene molecules, comprised of 6,12-disubstituted chrysene, 3,6,12-trisubstituted chrysene, and 3,6,9,12-tetrasubstituted chrysene.

Figure 16A:
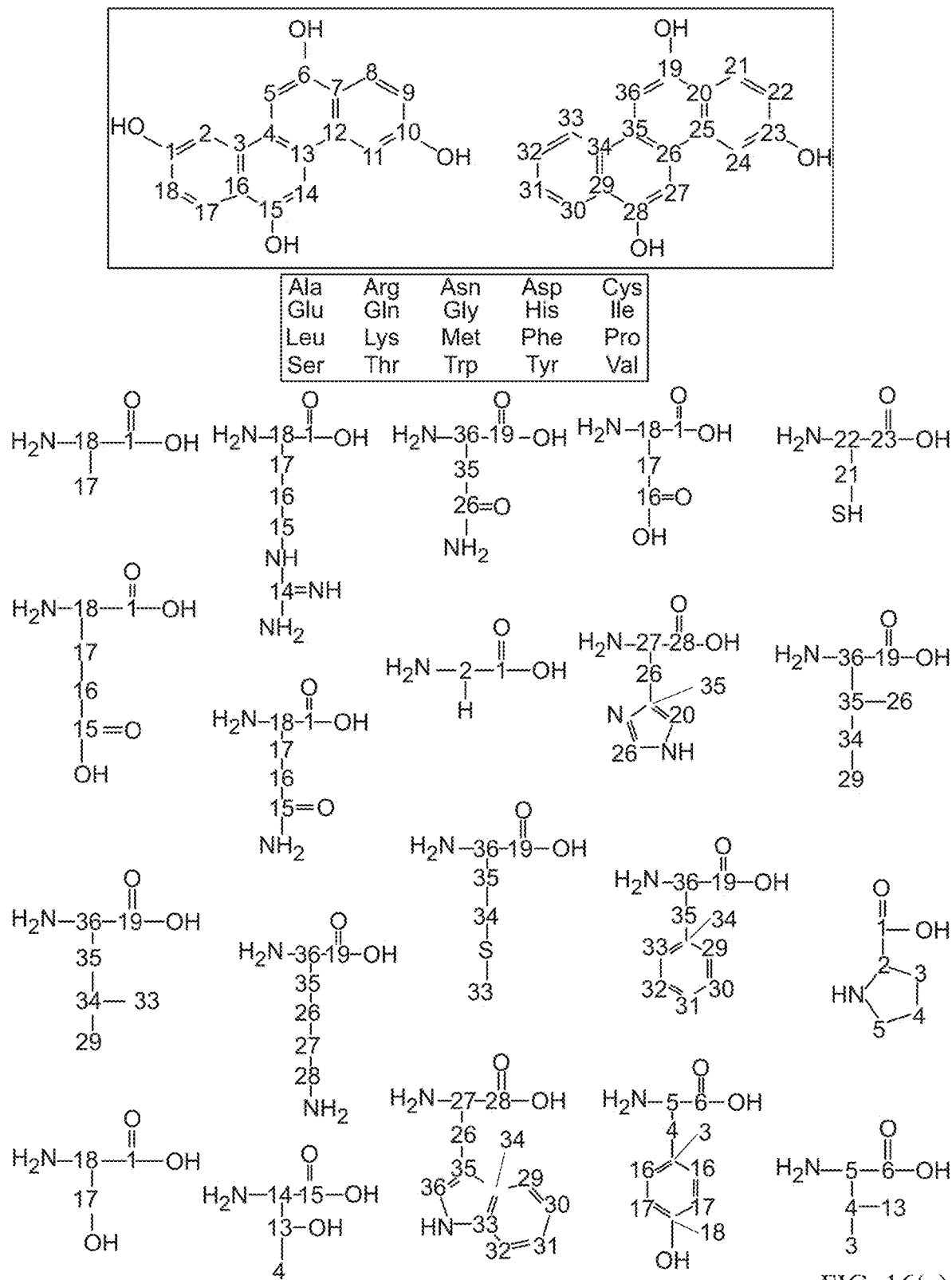
FIG. 16 (FIG. 16(a)-(b)) details an atom mapping scheme for substrate and catalyst and the corresponding amino acids (16(a)) and phospholipids such as phosphatidylcholines (16(b)) described in the present specification.
Figure 16B:
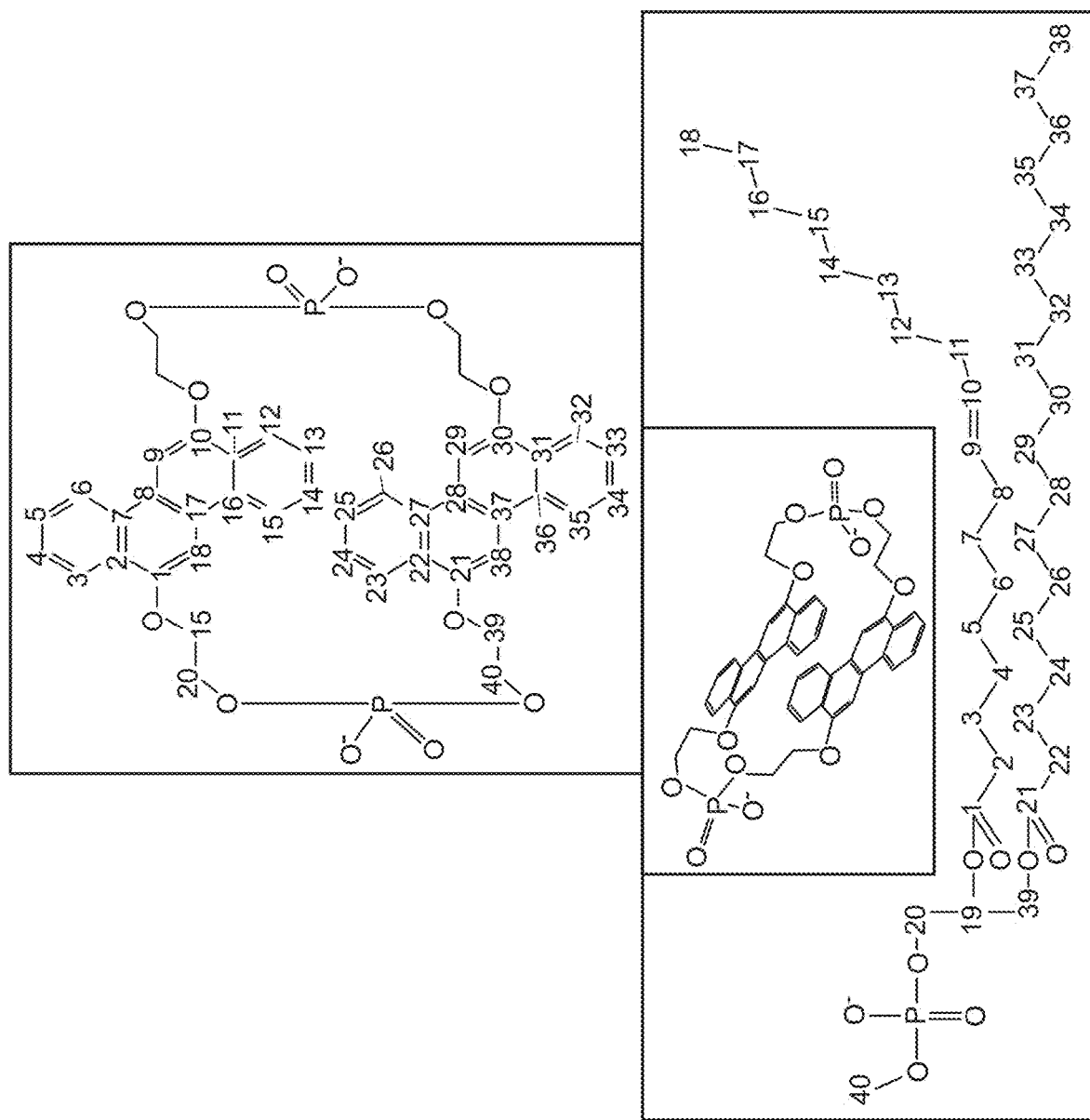

Anaerobic oxidative cleavage, reduction, and polyarene nitrogen insertion, hydroamination, and imine formation will enable these structures in a manner consistent with encoded nucleotide synthesis. In FIG. 16(a), atom mappings and resultant structures are indicated for the phosphorylated homodimer of 6,12-disubstituted chrysene, which forms the phospholipid bilayer structures that interact with the catalyst remnant associated with the adenine nucleotides. Alternative tails of the phospholipids are possible through different oxidative cleavage pathways. In FIG. 16(b), examples of atom mappings for amino acids generated from the homodimers of 3,6,12-trisubstituted chrysene and 3,6,9,12-tetrasubstituted chrysene. There are multiple pathways to produce the set of amino acids. In sum, the supporting products inducible from homodimers of a natural set of substituted chrysene combined with the encodable nucleotides from the heterodimers of substituted chrysene enable a sufficient set of biological materials for the fabrication of an initial cell.

Example 12: Application to Biosynthesis

While the developments have application in areas of genome synthesis and regenerative medicine, the method and means for the design and synthesis of encoding nucleotides and phospholipids described within have utility in many areas including in research directed towards life synthesis, informatics, or investigations into origins of life.

In FIG. 17, the design characteristics are described as a guide towards the optimization and breadth of application. The listing indicates methods and means that may be capable of more than 95% (e.g., more than 99%, 100%) efficiency in atom economy for phosphorous and carbon and less than 5% (e.g., less than 1%, 0%) for external requirements of carbon. Both nucleic acids and cellular component materials are provided by the syntheses described herein. As shown herein, encoding of the complex of substituted chrysene heterodimers is 100% encodable through the tables of FIG. 5.

It is also noted that anaerobic means of oxidative cleavage using photo-assistance with nitroarenes on polyaromatics within an electrochemical environment, as well as atom economy and self-sufficiency, enable green chemistry principles of synthesis. Aerobic chemistry can also be used for synthesis which may improve reaction times and yields.

Example 13: Application to Pharmaceuticals—Cortisol, Aldosterone Analogues

The primer identified in FIG. 1 illustrates the potential space of hydrogen bonding between the unpaired ketone of thiamine and with the hydroxyl group of cortisol. This hydrogen bonding occurs at its so-called carbon-11 position when there is alignment of the ring structures of the steroid hormone and the DNA nucleotide complementary pairs. In the developments, to utilize symmetry and naturally derived compounds, a catalyst (which has the equivalency of hydrogen bonding per cortisol) was deployed with the sidechain located on the carbon-12 position of chrysene.

Figure 18A:
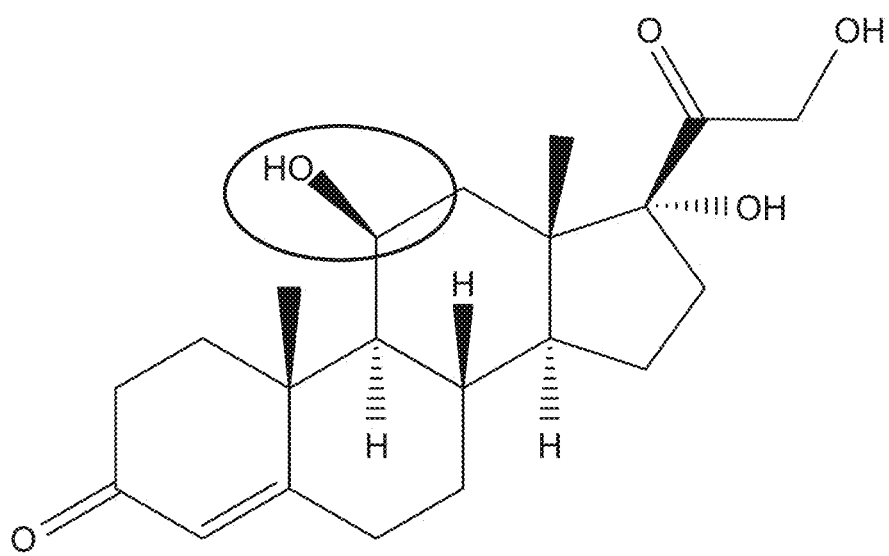
FIG. 18(a) provides a structure of cortisol which may be matched with proper substitution to the catalyst of FIG. 18(b) (both circled).
Figure 18B:
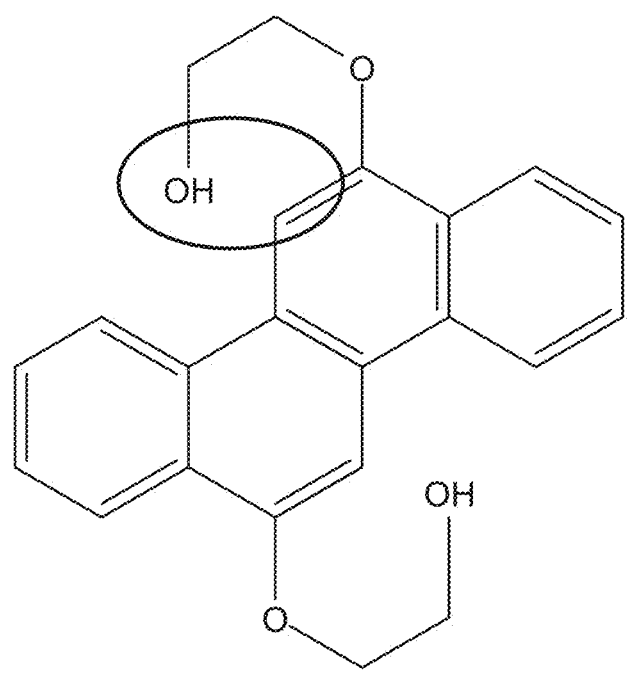
FIG. 18 (FIG. 18(a)-(q)) details various pharmacological effects and efficacy relationships afforded by comparing the substrates and catalysts with steroid molecules.
FIGS. 18(c)-18(q) provide various compounds having a steroid core but functionalized in a manner that may augment efficacy of each compound. $R_1$ may be as described herein.
Figure 18C:
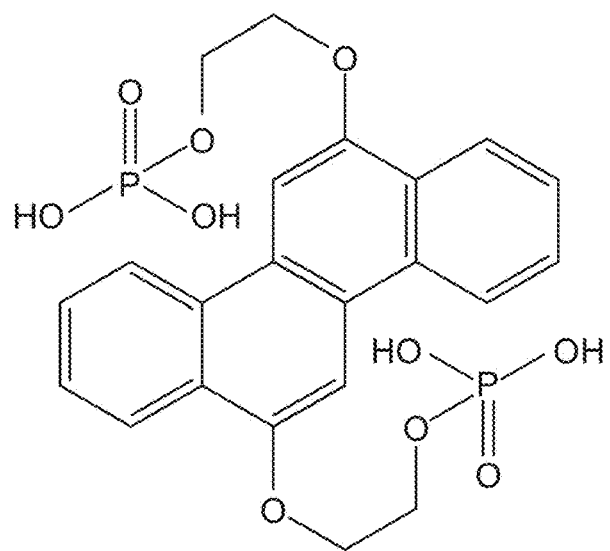
Figure 18D:
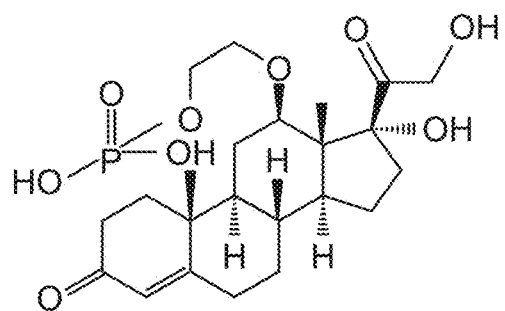
Figure 18E:
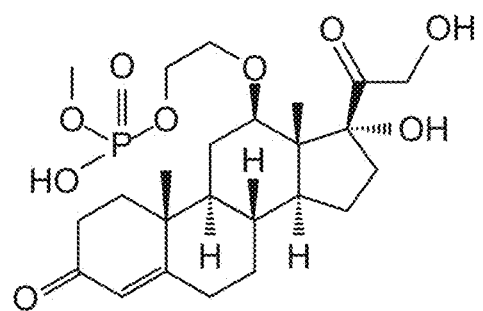
Figure 18F:
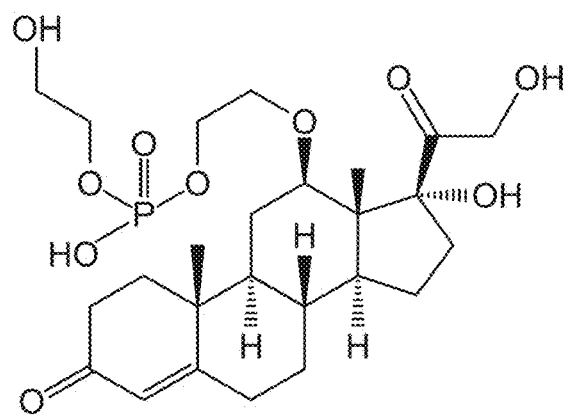
Figure 18G:
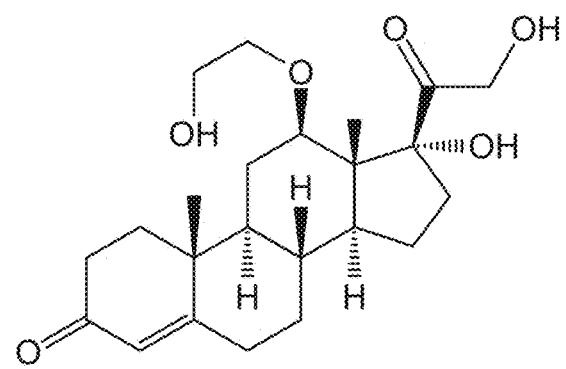
Figure 18H:
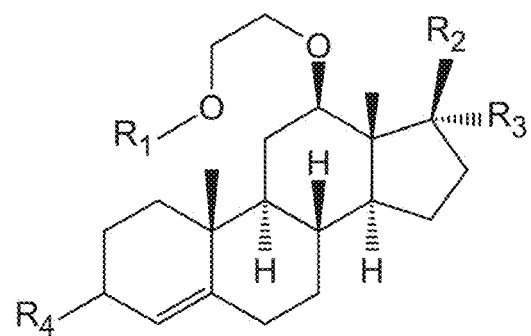
Figure 18I:
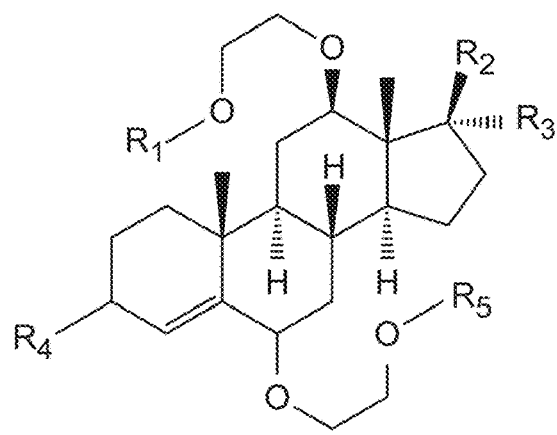
Figure 18J:
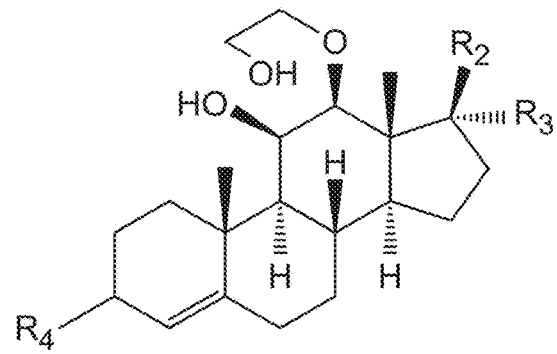
Figure 18K:
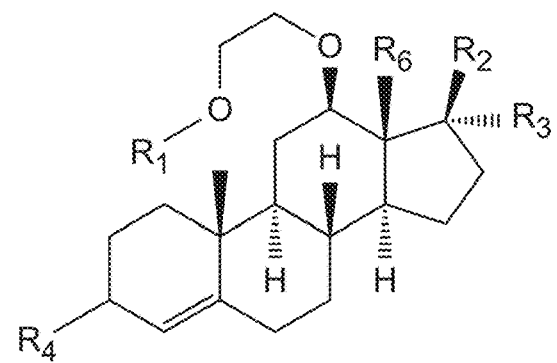

Instead of a hydroxyl group as in cortisol, the relevant sidechain for the corresponding substituted chrysene is an oxalate derivative. Moreover, when coupled to form the heterodimer, the sidechain is extended with a phosphodiester bond, which is thereby available to interact with the unpaired ketone of thiamine or uracil during its formation process of DNA and RNA, respectively. Comparing the position of the hydroxyl group for cortisol in FIG. 18(a) with the hydroxyl group of the 6,12-disubstituted chrysene as the catalyst in FIG. 18(b), the relation of the active oxygen group is shown as an equivalency in cortisol and in the catalyst 6,12-disubstituted chrysene. Moreover, with the availability of a phosphorous group to couple the catalyst to the substrate as shown in FIG. 18(c), an enhancement exists to divert the ketone group to couple with the catalyst linkage, thereby preventing formation of the amine group on adenine resultant in the T-A or U-A nucleotide pairing.

To relate the potential space of pharmaceutical equivalency between the primer structures and the catalyst, structural analysis demonstrated a correlation between the spatial positioning of the unpaired ketone and steroid hormones was one of efficacy in terms of the potential intermolecular bond strength shown in the examples of FIG. 1(d)-(g). Consequently, because of the spatial relation between the hydroxyl group of the sidechain at the 12 position of chrysene and the hydroxyl group of the carbon-11 position of cortisol, similar intermolecular interactions and thus efficacy is expected.

Figure 18L:
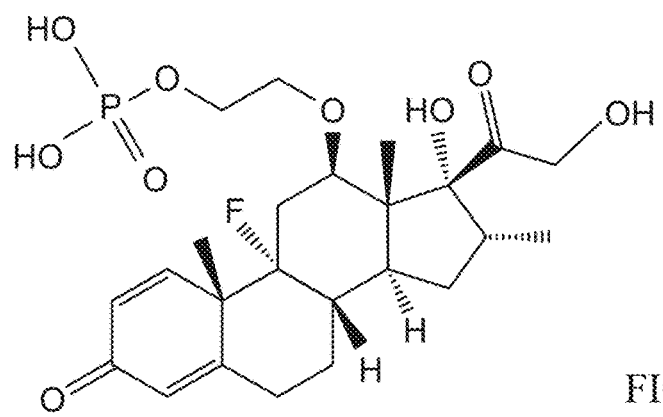
Figure 18M:
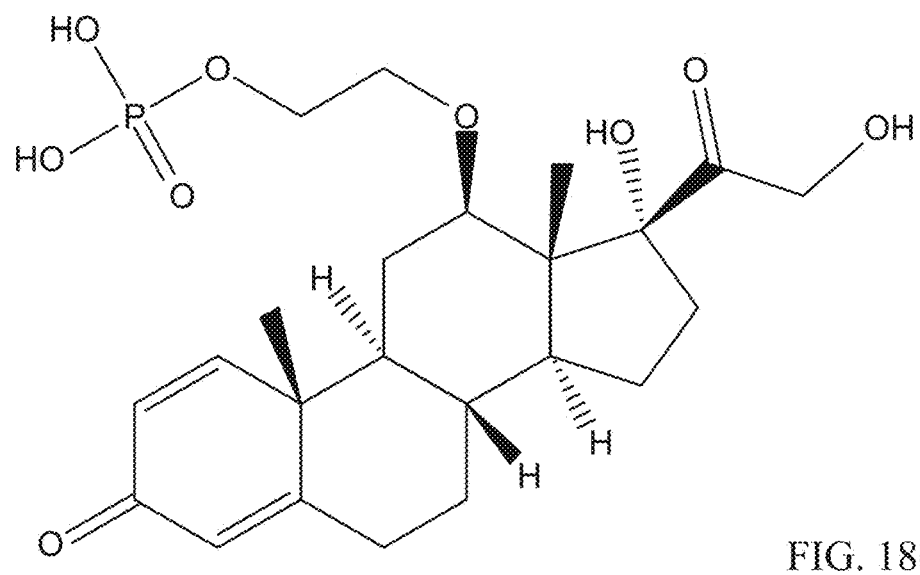

Thus, in FIG. 18(d)-(k), a series of molecules are presented that can show pharmaceutical efficacy. These molecules leverage stabilizing chains of cortisol at the outer rings, but maintain the same stereochemistry of the steroid molecule. The advantage of the approach of applying the functional group on carbon-12 is that additional tuning, such as in potency or elimination, can be adjusted by manipulating the design of this sidechain. Manipulation of this sidechain may occur other than the ring-based structures, such as with dexamethasone or prednisolone deploying fluorine or double-bonds, which is shown in FIGS. 18(l)-(m). Such ring structures are also available for tuning the chrysene derivative molecule for efficacy. In a preferred embodiment, the four aromatic ring staggered structure of chrysene is deployed with oxalate alcohol side chains at the 3,9,12 positions. First alternatives of said embodiment may involve the reduction of aromaticity from one or more rings.

Figure 18N:
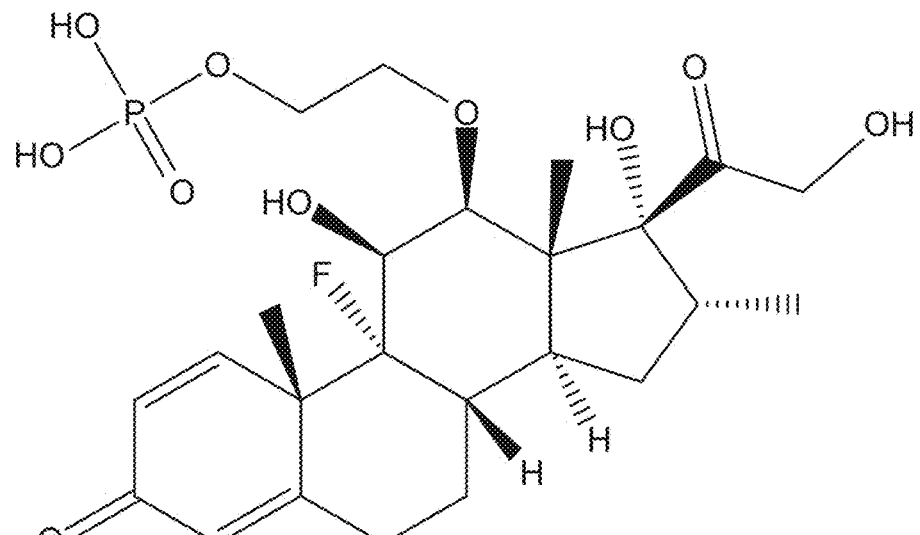
Figure 18O:
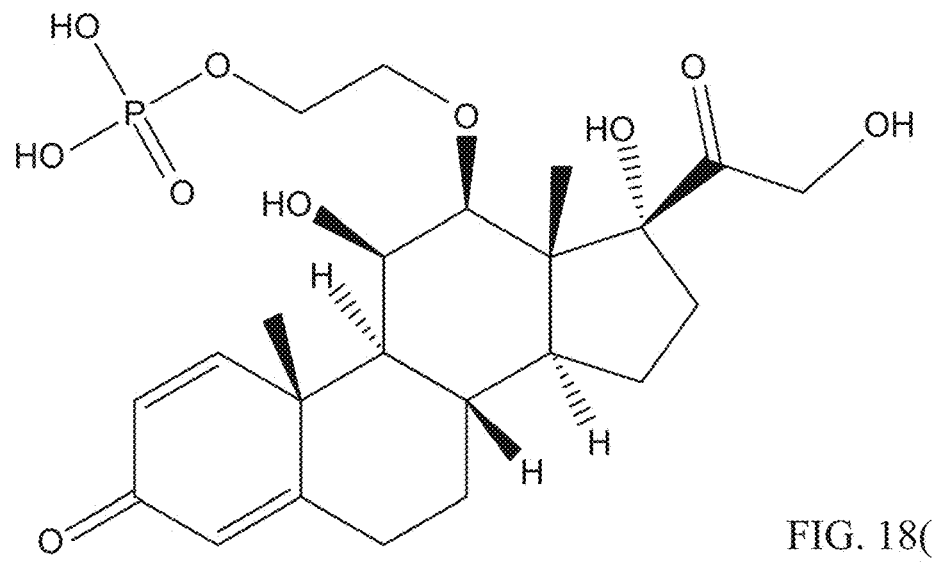
Figure 18P:
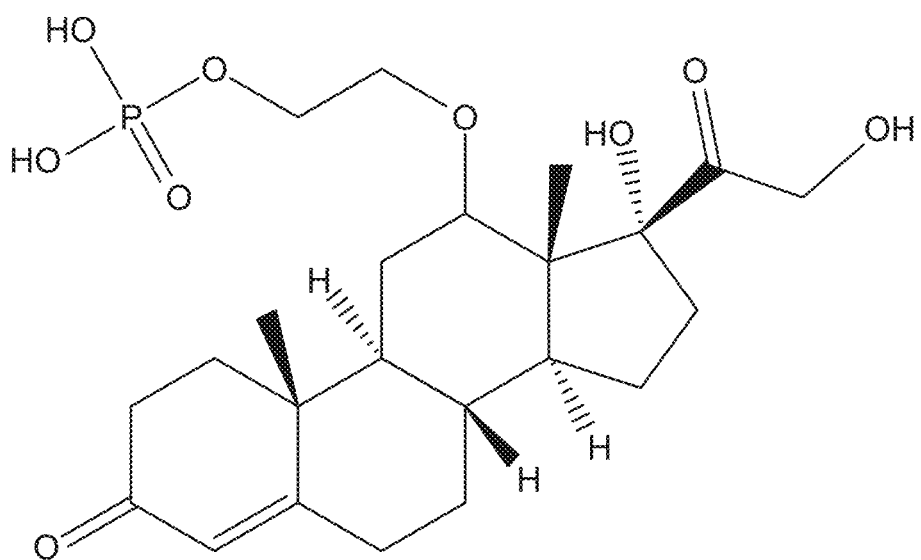
Figure 18Q:
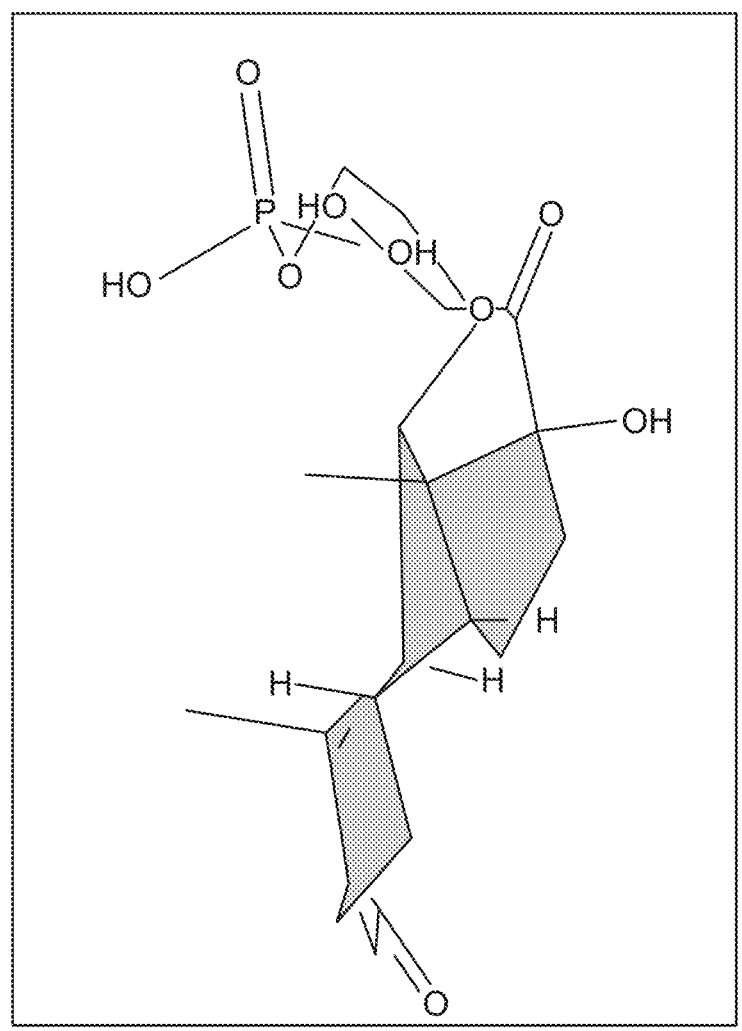

In FIG. 18(n)-(o), the results are generalized to additional groups on the external rings. FIG. 18(p)-(q) indicates that the substituted group at the 12-carbon position can be evaluated either on the same side as the hydroxyl group or on the reverse side, due to the rotation afforded by the ethoxy alcohol group.

Example 14: Application to Pharmaceuticals—Testosterone, Estrogen Analogs

In addition to cortisol, the primer of FIG. 1 illustrated that intermolecular hydrogen bonding was not necessary between testosterone-like hormones and the cytosine-guanine pairings because three hydrogen bonds are already available to connect the nucleotide pairing. For the practical implementation of the code of substituted chrysene, the catalyst went unaligned to the substrate. The phosphorylated ethoxy alcohol sidechains are nonetheless available to influence the formation of the three hydrogen bonds, along with the end-elements.

Figure 19A:
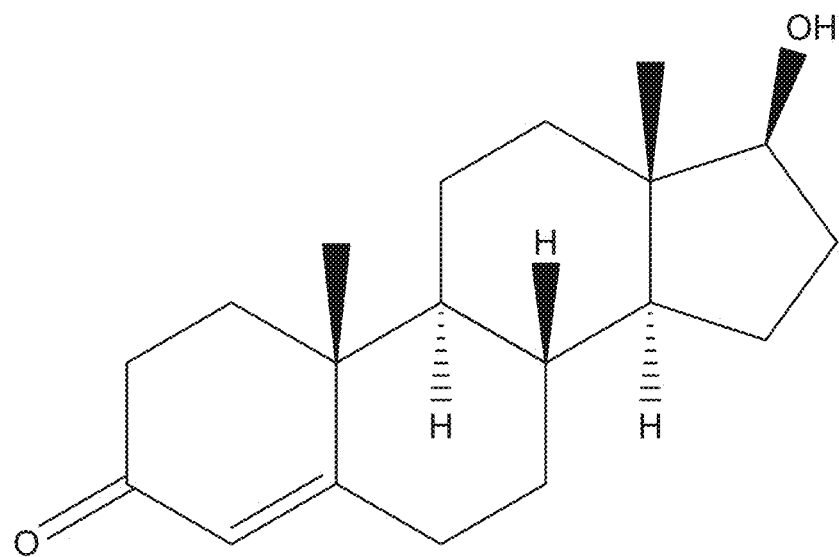
FIG. 19(a) provides a structure of testosterone which may be functionalized to, for example, increase efficacy by promotion of binding to various substrates (including the substrates of the present disclosure or other biological substrates).
Figure 19B:
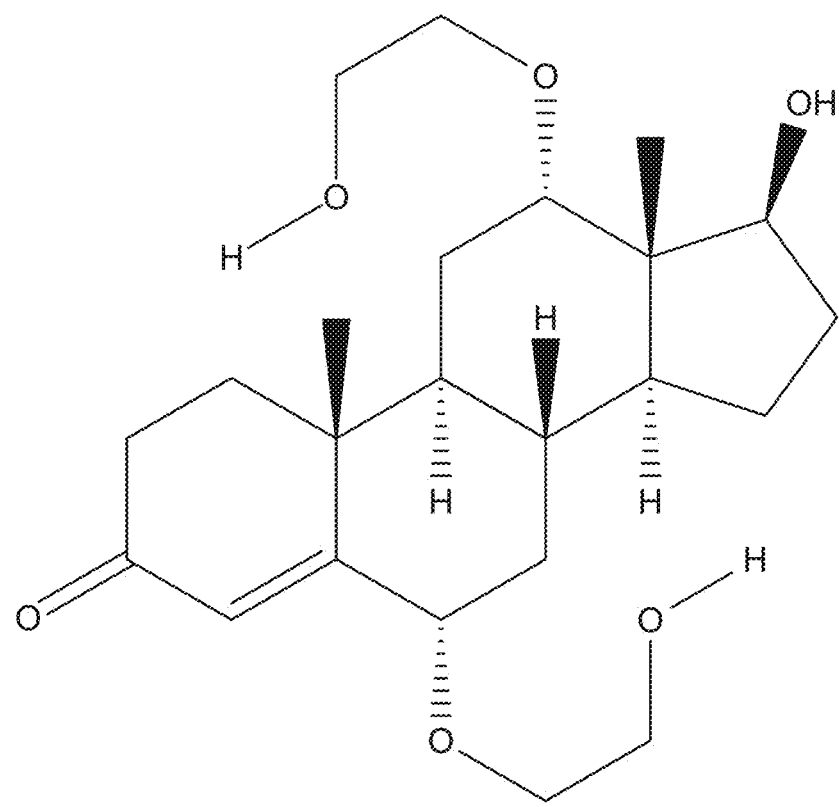
FIGS. 19(b)-(f) provide various compounds having a steroid core but functionalized in a manner that may augment efficacy of each compound. $R_1$ may be as described herein.
Figure 19C:
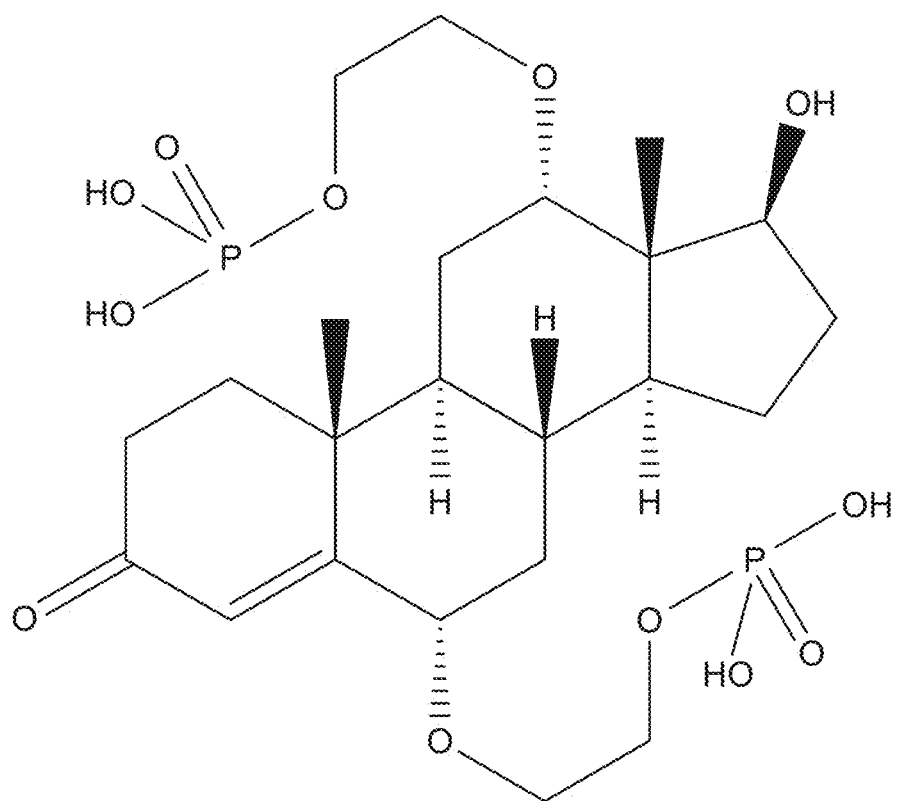
Figure 19D:
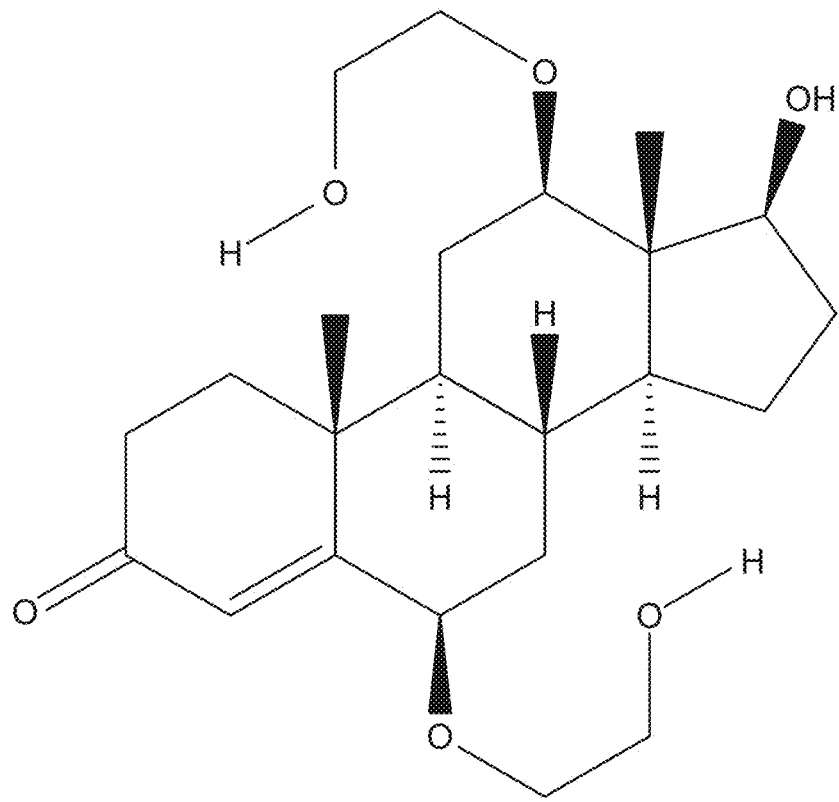
Figure 19E:
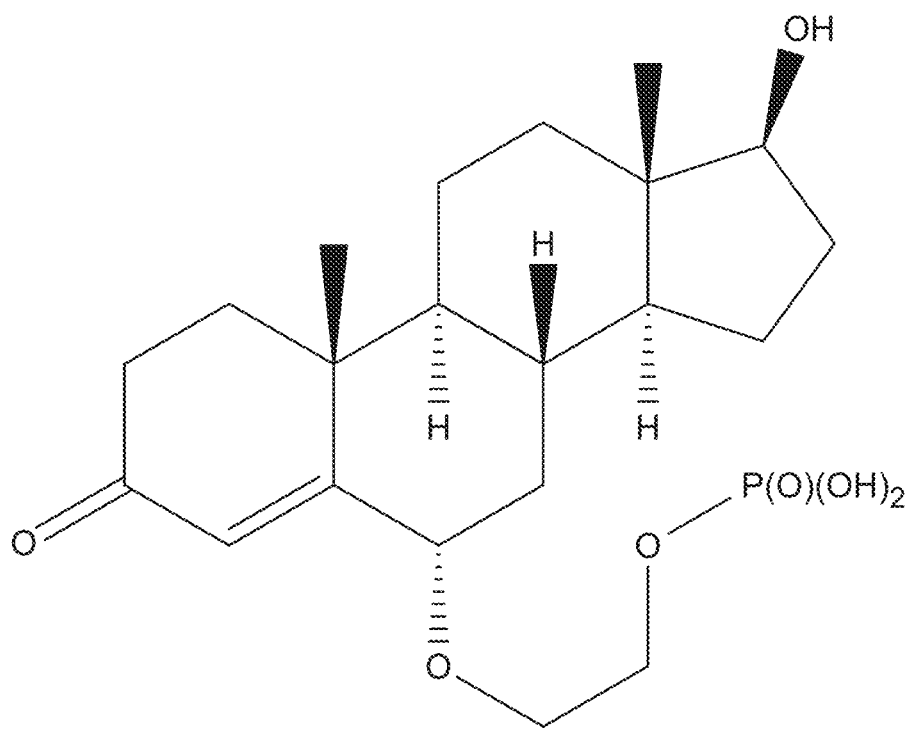
Figure 19F:
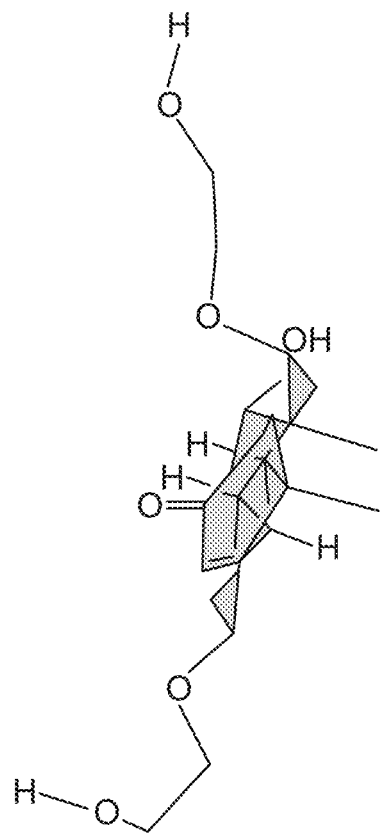

Without wishing to be bound by theory, the bonding of testosterone to the androgen receptor could have a pocket available for an unaligned catalyst of which the sidechains at the 6,12 positions are available to alter the interaction of testosterone with the androgen receptor as proxy for interaction directly with the CG pairing. As with cortisol, in the case of testosterone, shown in FIG. 19(a), sidechains at the 6,12 positions as shown in FIG. 19(b) modulate the strength of association between the hormone and the dinucleotide pairing. Various alternatives are shown in FIGS. 19(c)-(e) that could alter the bond strength of the hydrogen bond couplings. In FIG. 19(f), the spatial orientation of the 6,12 groups are shown corresponding to FIG. 19(b). The tuning of the sidechains along the 6,12 coupling is useful to adjust efficacy and to reduce side-effects.

In similar fashion to cortisol and to testosterone, the structural configurations of aldosterone and estrogen can be augmented at the 6,12 carbon positions with ethoxy alcohol sidechains to modulate the performance and the side-effects. Phosphorylation, and additional groups, along with stereochemistry in positioning the sidechains are available as tuning parameters to further amplify or attenuate the interaction of the sidechain and by proxy the nucleotide pairings. The end-groups may be adjusted as well in conjunction with the 6,12 sidechains. In a preferred embodiment, the four aromatic ring staggered structure of chrysene is deployed with oxalate alcohol side chains at the 3,9 positions.

Example 15: Application to Pharmaceuticals—Single Site Intercalation of Nucleic Acid Sequences The methodology of intercalating DNA sequences with molecules is used in chemotherapy, for example to reduce the progression of protein processing through transcription or replication to reduce cancerous cells out of control. Common materials used to achieve this result include doxorubicin and other anthracycline molecules. This approach uses a linear sequence of rings, generally four arranged in a linear fashion, to intercalate the DNA strand, while a bulky side chain locks the linear portion and halts strand processing. It is an effective approach, however, is generally indiscriminate and methods to reduce the side effects are sought.

Figure 20A:
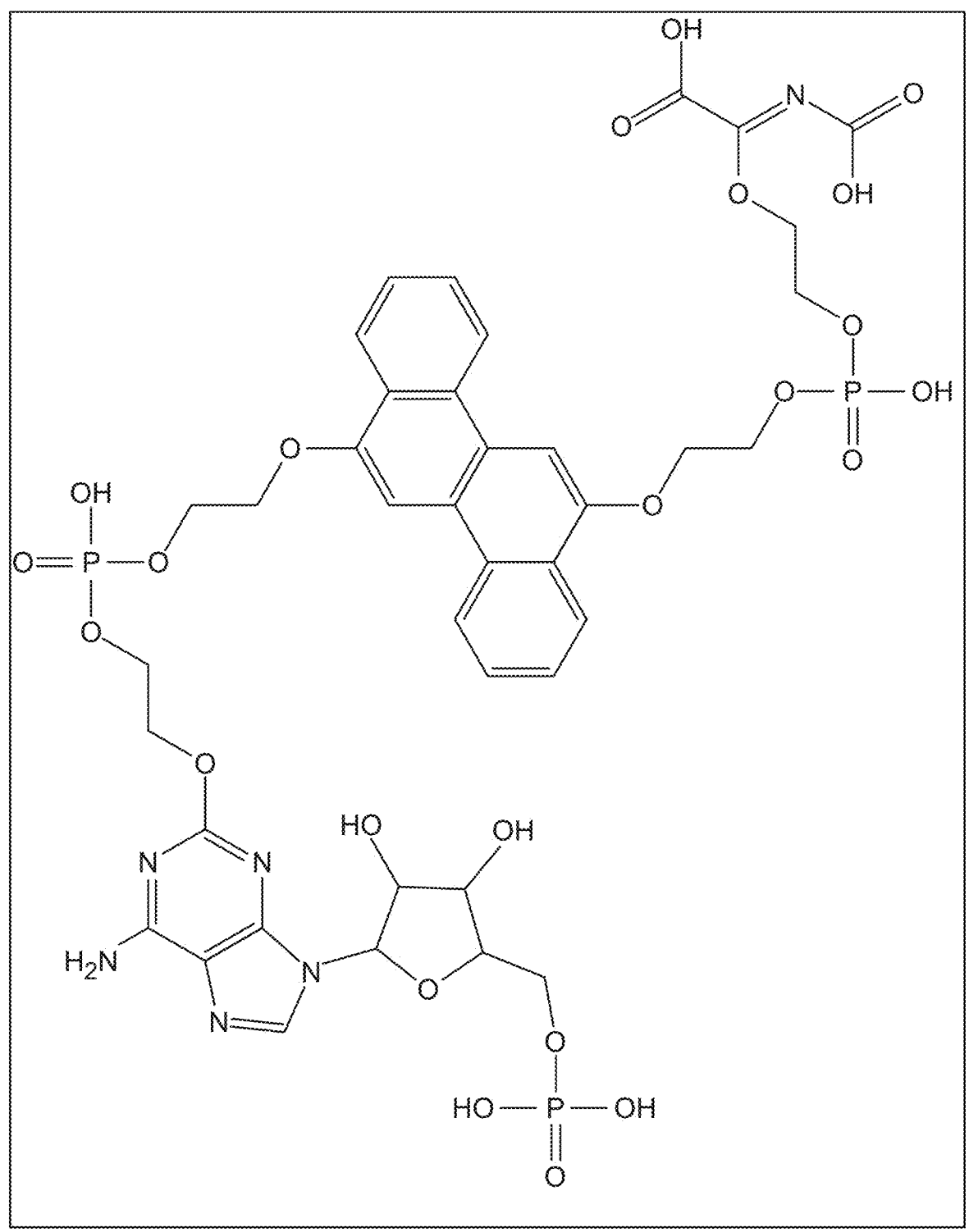
FIGS. 20(a)-(e) illustrate an exemplary catalyst remnant conjugated to an Adenine ($R_1$ may be as described herein).
Figure 20B:
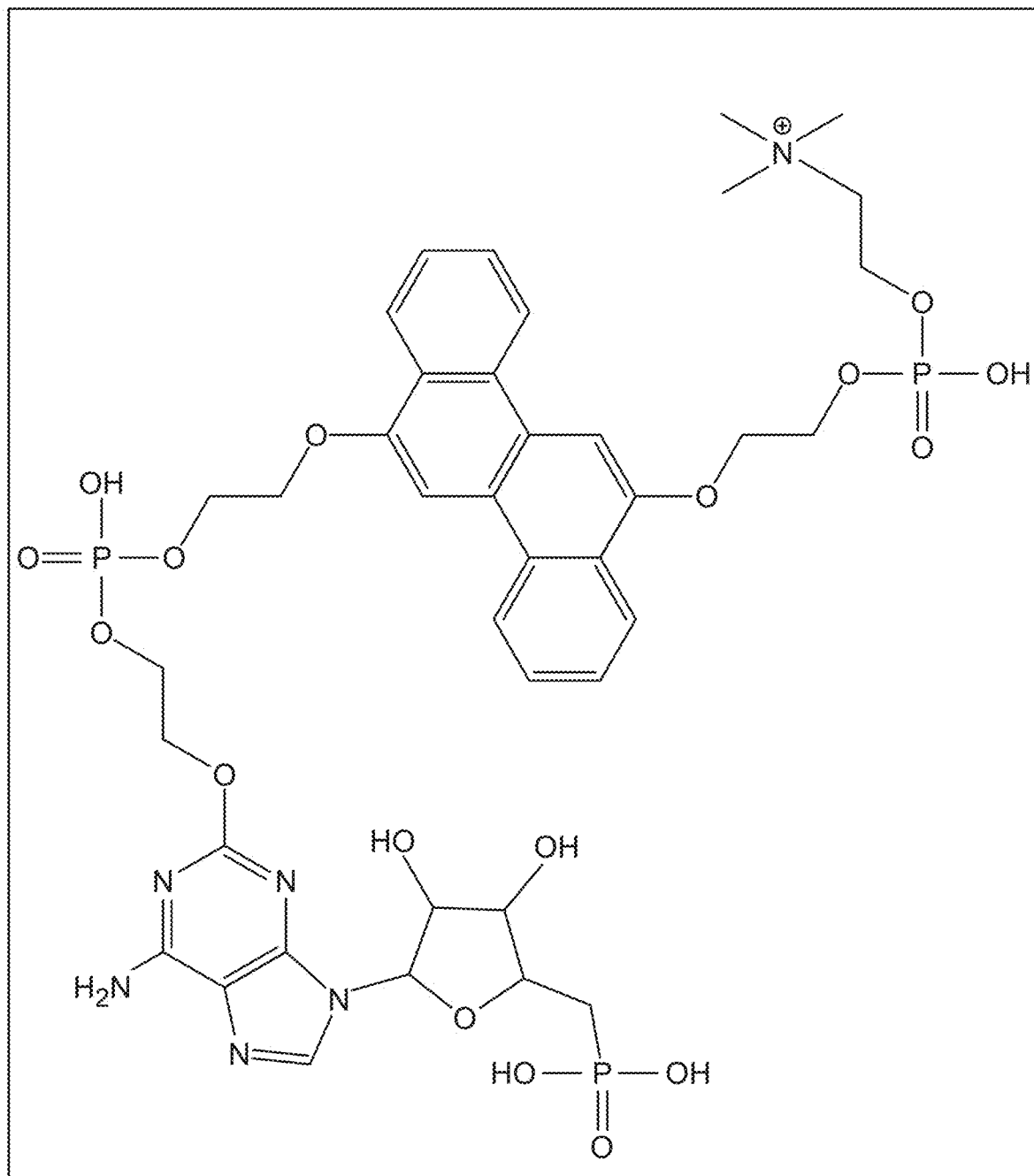
Figure 20C:
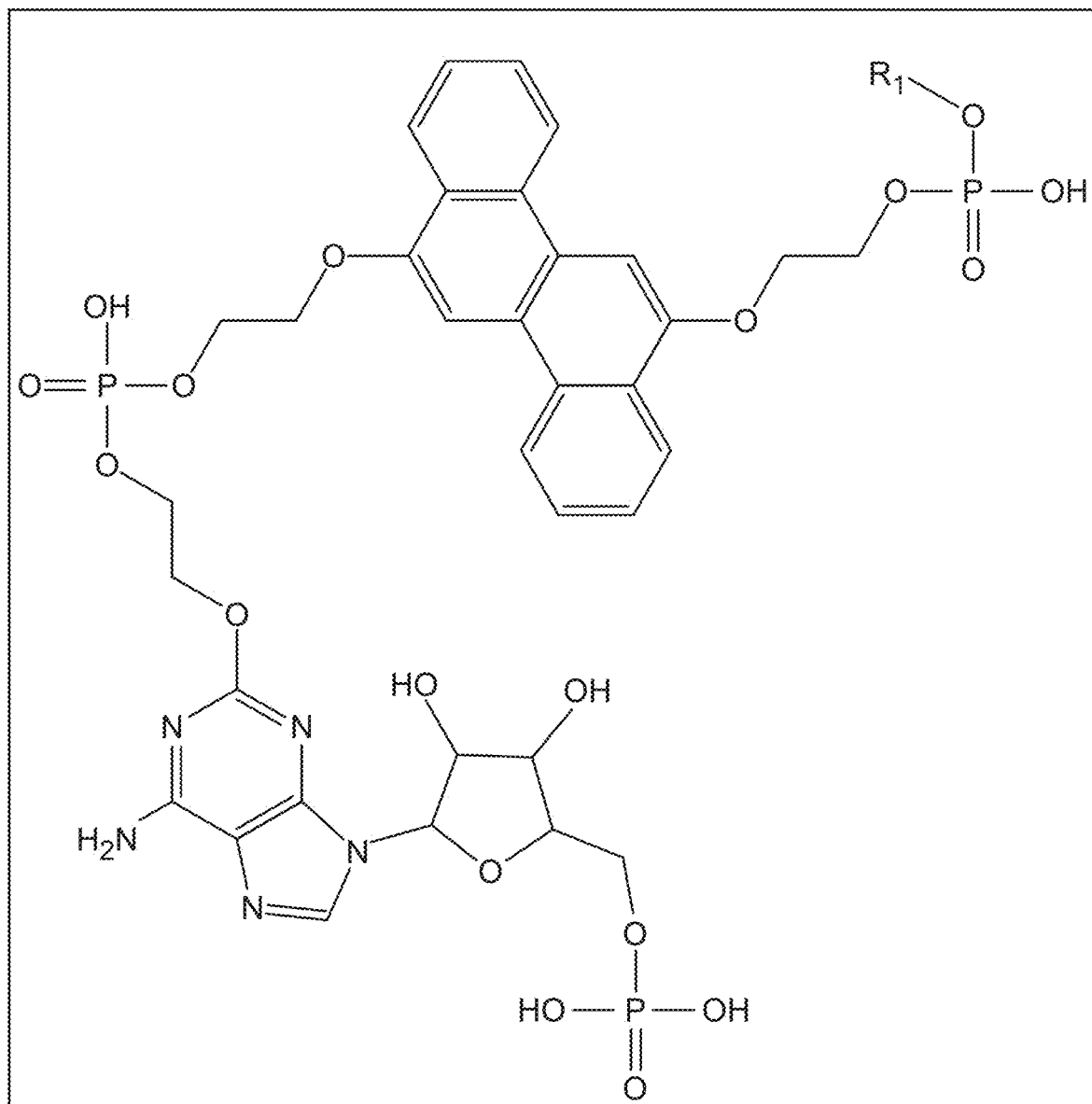
Figure 20D:
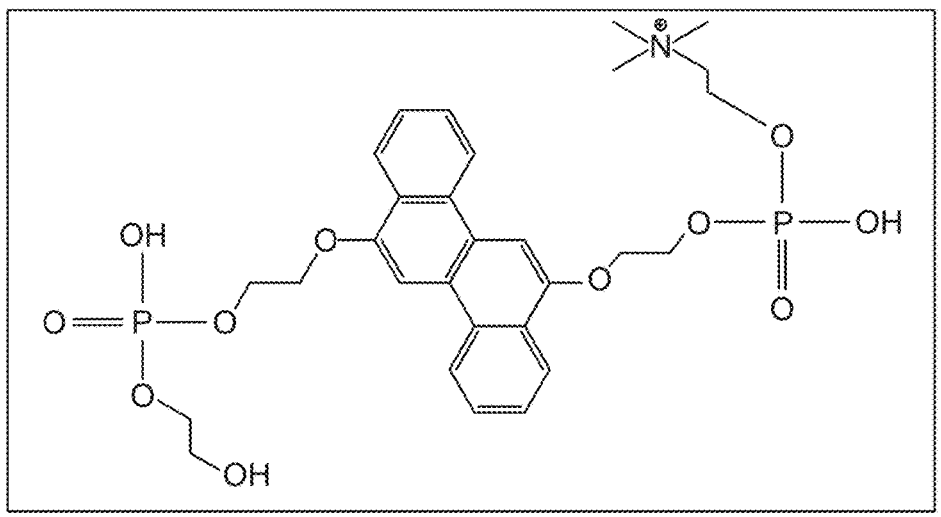
Figure 20E:
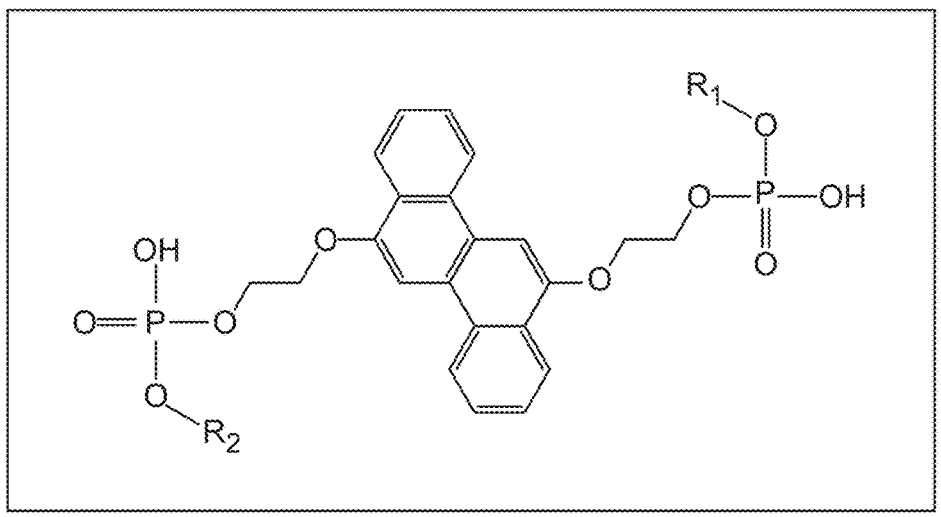
Figure 20F:
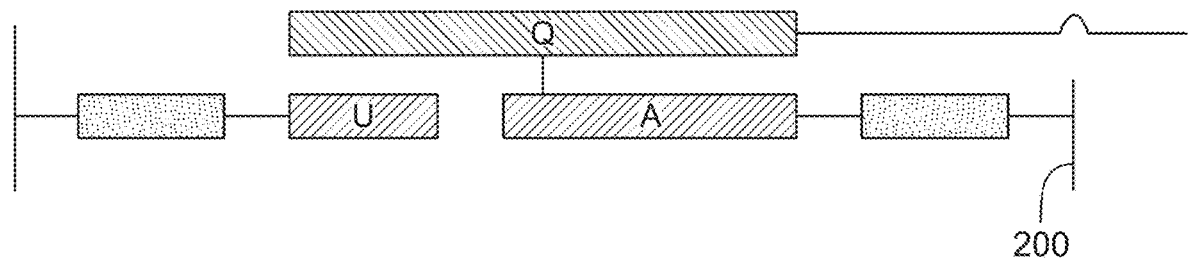
FIG. 20(f) is a schematic indicating the catalyst remnant (Q) binding to Adenine (A) formed from a substrate encoded to form the Adenosine (A)/Uracil(U) pair of RNA.

The methodology of synthesizing RNA and DNA described herein from primer cores (e.g., chrysene) which provide a natural method of intercalating and locking nucleic acid sequences. The synthesis of the RNA strand produces for each adenine in a sequence a covalently attached chrysene unit with head group, as shown in FIG. 20(a) for a single unit, and generalized as to the choline head group in FIG. 20(b), or a generalized head group as depicted in FIG. 20(c). The attached group to adenine is depicted in FIG. 20(d) and generalized in FIG. 20(e). This single unit is capable of pairing with the cytosine nucleobase in a single-strand RNA, and through the attached chrysene unit intercalates the formed double strand. The anchoring sidechain of the chrysene unit can then interact with the phospholipid membrane to stabilize the unit for subsequent removal, of which the intercalated structure is depicted in FIG. 20(f). In the schematic, 100 denotes a single-strand RNA uracil nucleobase interacting with adenine nucleotide 200, of which the intercalating unit Q is conjugated with the paired nucleobases, and in which is in turn conjugated with a phospholipid bilayer 300.

Figure 21:
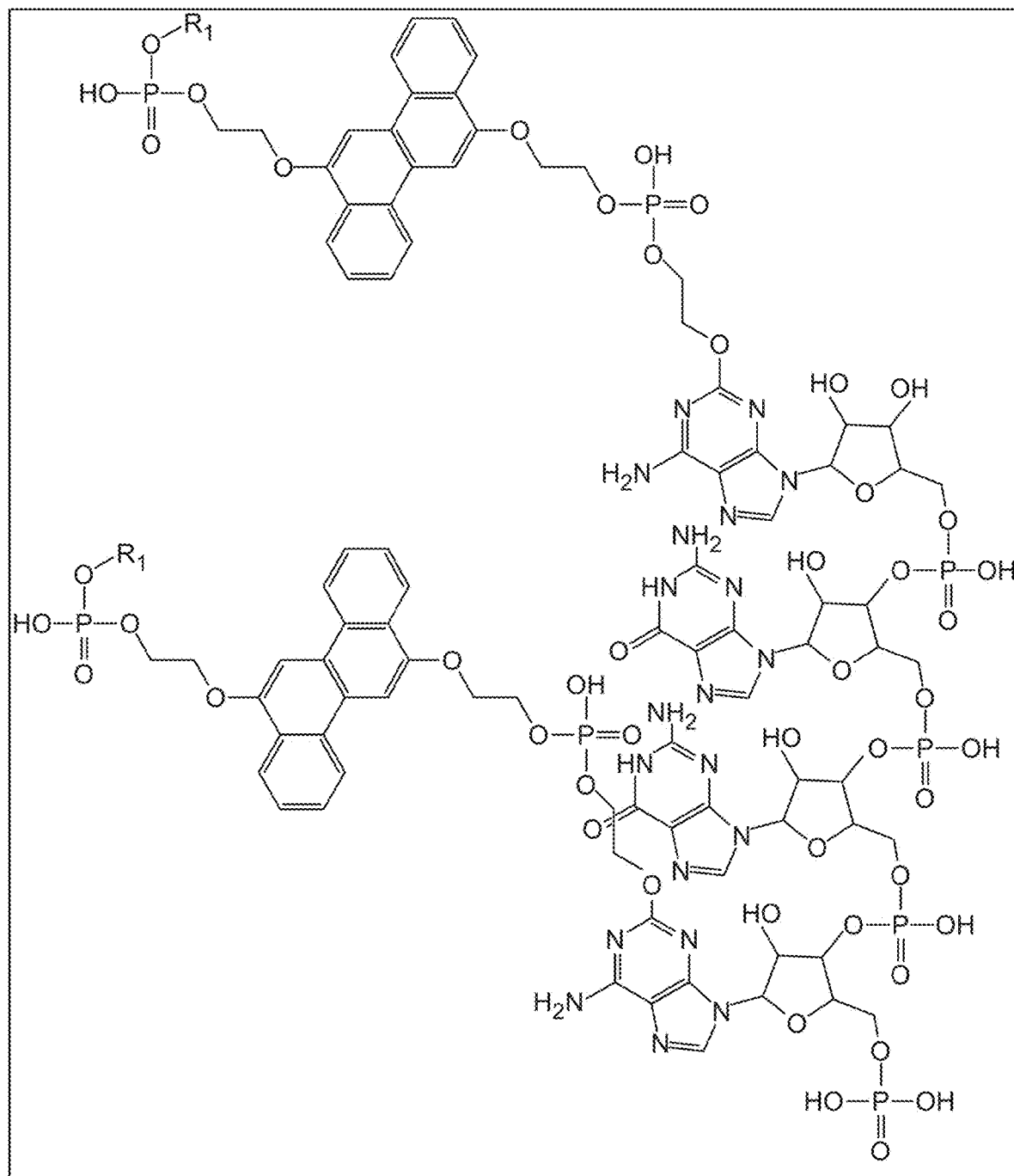
FIG. 21 provides an exemplary RNA molecule having the sequence AGGA, wherein each adenine is conjugated to a substrate phospholipid remnant.

Example 16: Application to Pharmaceuticals—Intercalation of Nucleic Acid Sequences The approach of single nucleobase intercalation can be extended to a targeted nucleic acid sequence in which a strand is deployed wherein each adenine is bound to an intercalating unit. In FIG. 21, a sequence is shown of AGGA, of which each A is associated with the chrysene unit with the linkers comprised of a two carbon phosphodiester. This structure forms an intercalating unit that can associate with single-strand RNA of reference, which can for example be affiliated with a neoplasm or a viral infection. Similar methodology may be developed for DNA strands.

Figure 22:
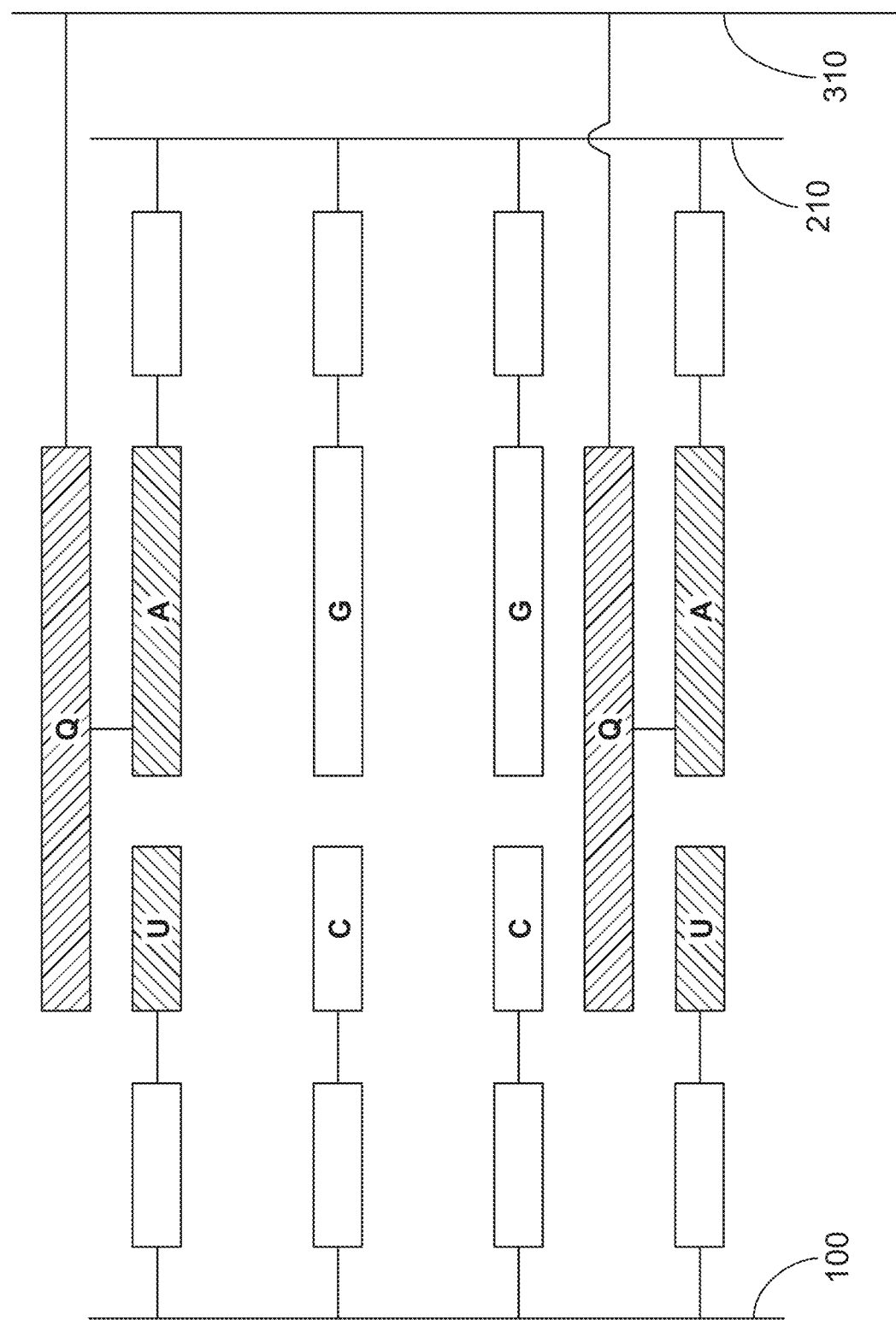
FIG. 22 provides a schematic for the targeted intercalation process afforded by the present disclosure.

Sequential intercalation of which a targeted sequence is indicated in FIG. 21 and FIG. 22 for the AGGA sequence. Item 100 is the RNA single strand sequence which is to be intercalated by 210, of which each adenine possesses its intercalating chrysene unit Item Q. In turn, the chrysene intercalating unit is connected through its head group (e.g., choline) into the surface of a phospholipid membrane Item 310 to stabilize the overall RNA unit. The intercalation of the nucleic acid can prevent its propagation, and the stabilization with a phospholipid membrane can aid in its removal.

In addition to single-strand RNA, the approach is applicable to double-strand DNA, especially during periods of replication when the single-strand is exposed for more direct interaction with the adenine nucleobase and thymine. By targeting a nucleic acid sequence, rather than a single nucleotide, precision intercalation results and can be applied to target pathogens as well as cancerous cells.

Example 17: Application to Cell-Based Therapies—Encoded Cellular Membrane

With the binding of the phospholipid structure to the adenine nucleobase at the carbon-2 position, the ribonucleic acid sequence for the first replication may attach into the phospholipid membrane. Thus, a spatial mapping between the cellular membrane and the initial instruction set is established. This relationship may then be applied to organize the initial condition of a physical cytoskeleton construct between the cellular membrane and the nucleic acid, permitting the communication of signals from the external environment into the genome. Consequently, the result is a spatially encoded cellular membrane that is correlated with its genomic contents. Applications include morphogenesis in which the spatial orientation of the cellular construct is set through a mapping with the replicating nucleic acid. This mapping is useful for cell-based therapies in which the genomic contents are combined within a programmable cellular enclosure to induce a targeted function.

Example 18: Random Generation of an Intercalated Sequence

Figure 23A:
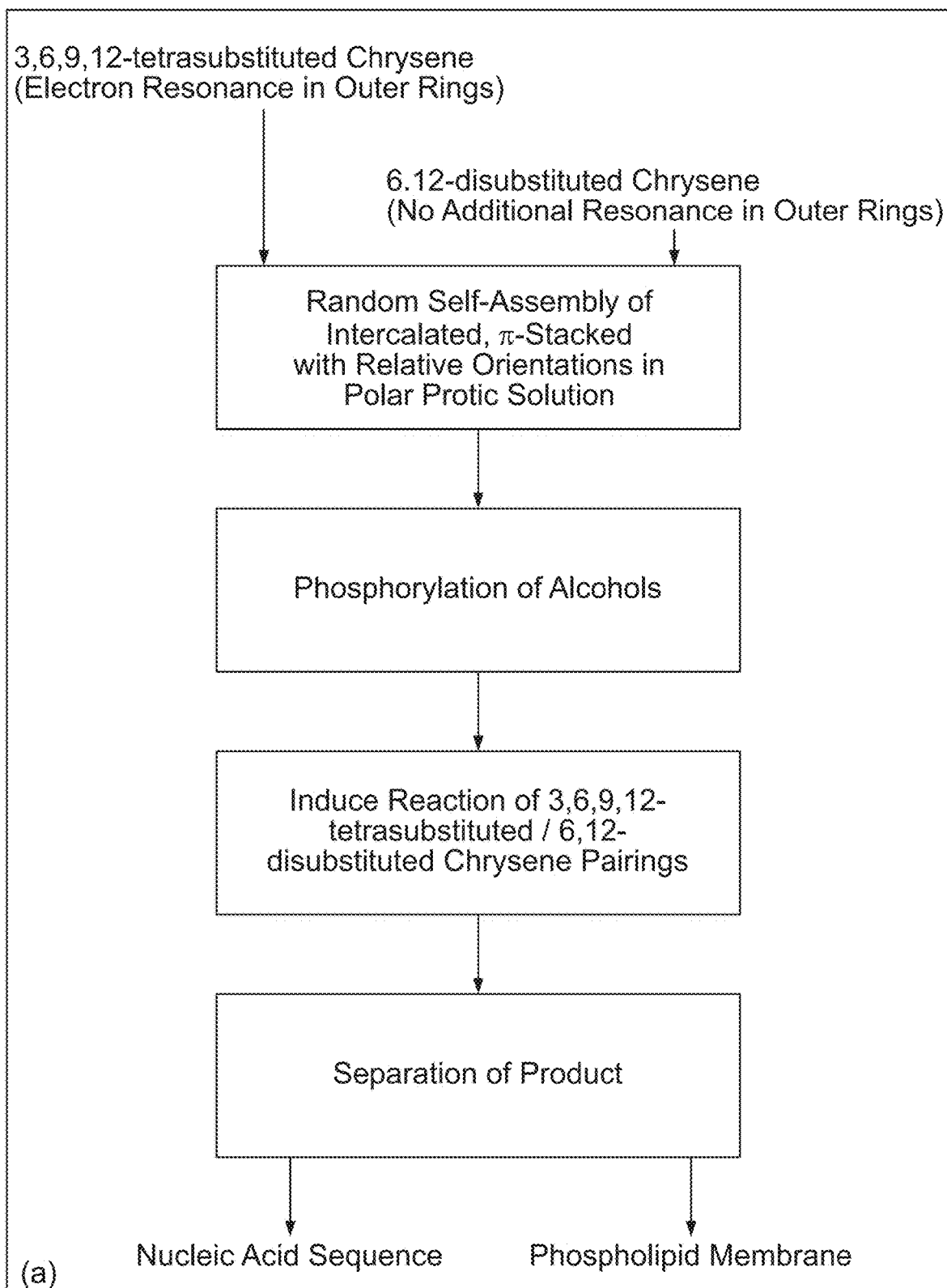
FIG. 23(a) provides flow chart for the encoding of a random sequence including the synthesis of the reaction vessels and resultant substrate/catalyst separation to form a nucleic acid sequence and a phospholipid membrane.

The formation of an intercalated sequence of 3,6,9,12-tetrasubstituted chrysene and 6,12-disubstituted chrysene is achievable through random self-assembly. Self-assembly may occur due to the differences in electrostatic potential of the outer rings of the chrysene base structure of the two molecules. Resonance structures of an ethoxy group substituted on the chrysene enable an electron donating characteristic of the outer rings of 3,6,9,12-tetrasubstituted chrysene relative to 6,12-disubstituted chrysene, which do not have sidechains on the outer rings. A flow chart illustrating this procedure is provided in FIG. 23(a).

Figure 23B:
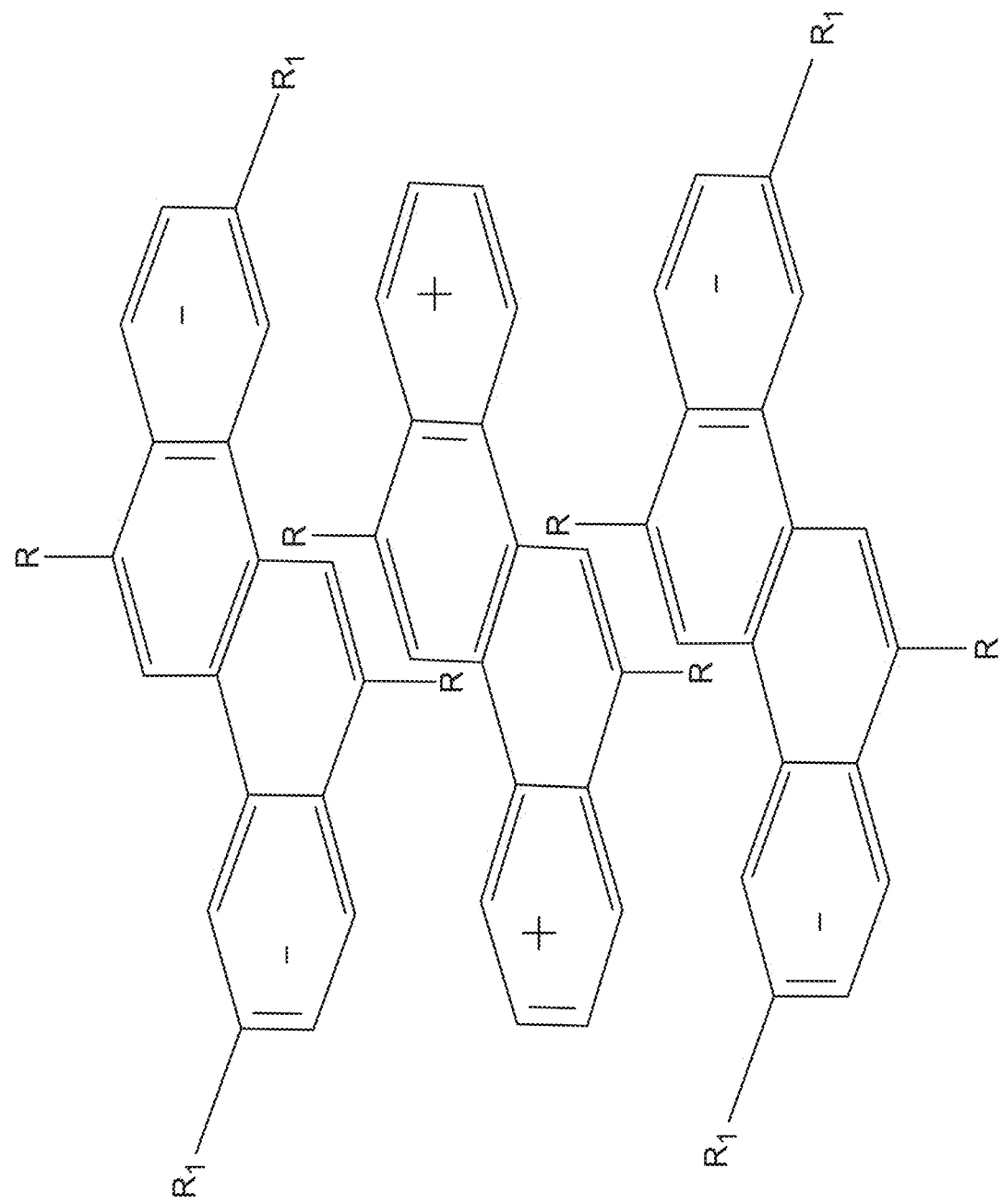
FIG. 23(b) provides an exemplary stack of substrates mediated by self-assembly. In the figure, $R_1$ and R may be independently at each occurrence similar to $R_3$, $R_6$, $R_9$, $R_{12}$, $R_{3S}$, $R_{6S}$, $R_{9S}$, $R_{12S}$, $R_{3C}$, $R_{6C}$, $R_{9C}$, $R_{12C}$, $R_{9S}$, $R_{12S}$, $R_{6L}$, and $R_{12L}$ as described herein.

Thus, the self-assembled pi-stacking of the structures will favor an intercalated format with the electropositive rings interleaved between electronegative rings, which is illustrated in FIG. 23(b). Moreover, steric hindrance of the sidechains of the outer rings may be avoided by having the interleaved 6,12-disubstituted chrysene intercalated between substrates. The alignment of the rings is a tradeoff between stabilization provided by overlapping p-orbitals compared to the steric hindrance off the adjacent 6,12-pairings.

After intercalation, phosphorylation of adjacent pairings and of the outer sidechains produces a heterodimeric system of structures. This heterodimeric system, after reaction, produce a nucleic acid sequence according to the codes provided herein. The electrostatic potential differences of the two molecules can be enhanced through selection of alternative sidechains, especially at the two carbon units, of which a double bond would further improve resonance effects on the outer rings. In addition, electron withdrawing groups can be added to the outer rings of disubstituted chrysene to aid in achieving an intercalated sequence, which afterwards can be removed. Because it is a self-assembled process, long random nucleotide sequences are possible, of which random genomes may be feasible. The process flow diagram for this procedure is presented in FIG. 23(a). An advantage of a random generation of intercalated sequence is that long genomes are possible which take little cost and time to produce. These sequences can then be reacted to determine if useful protein structures result.

Example 19: Directed Generation of an Intercalated Sequence

In addition to a random orientation of the intercalated sequence to produce a resultant nucleic acid sequence, methods to induce a targeted sequence are available by linking the structures through the alcohol end groups. It is noted that the usual procedures applying phosphonamidites to construct oligonucleotides are available for designing methods of directed sequence construction. The advantages however of the planar carbon construct of the catalyst and substrate can find use for optimizing the directed sequence manufacturing mechanism, such as molecular constructs inert to the ultraviolet radiation of high-resolution photolithography.

Figure 24A:
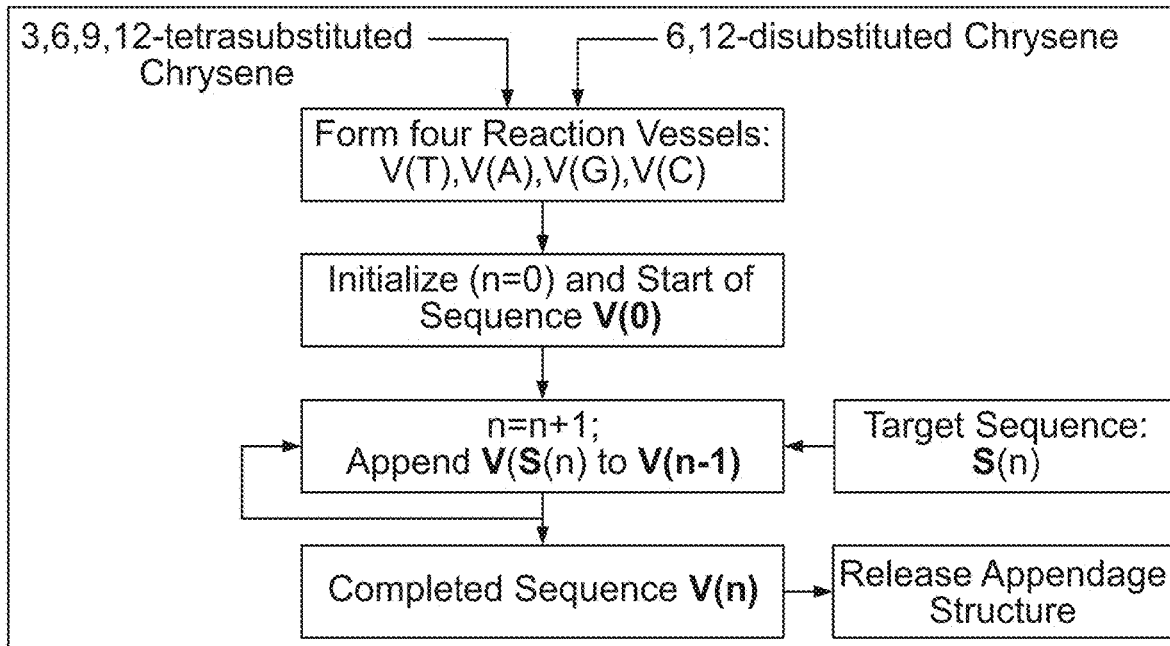
FIG. 24(a) provides a flow diagram for construction of the reaction vessels and ordering of the reaction vessels in a manner to form the sequence.
Figure 24B:
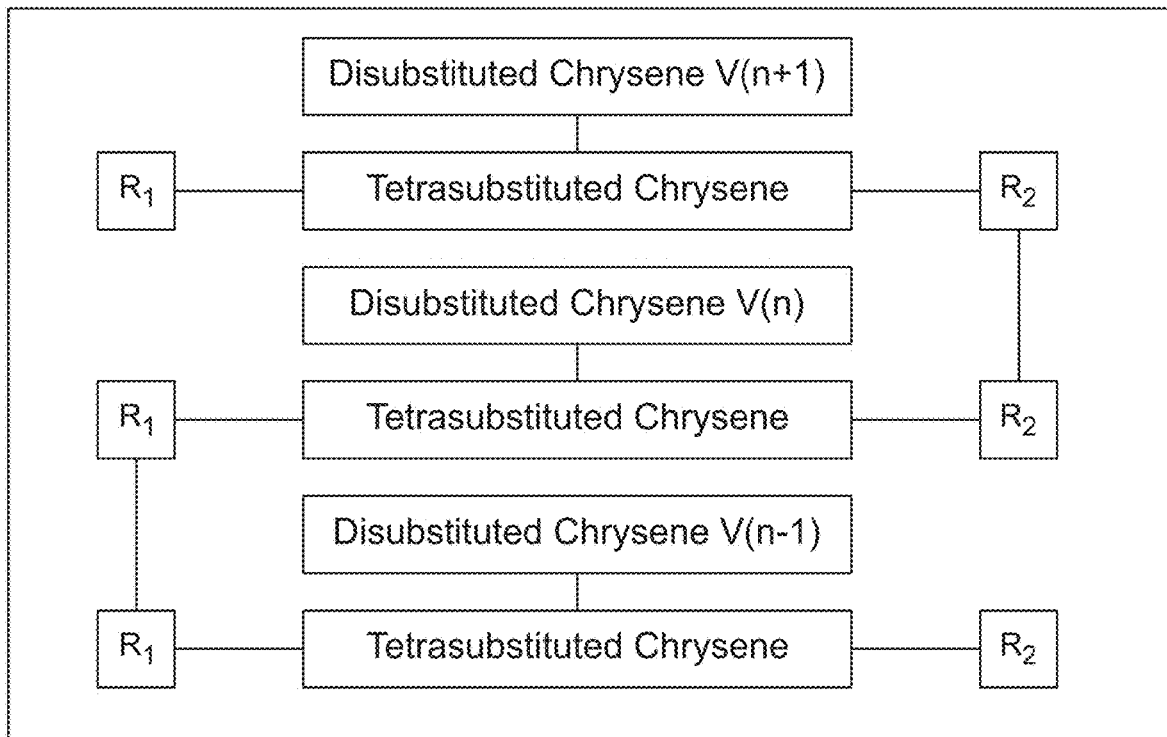
FIG. 24(b) details specific constructions available for the substrate and catalyst (by manipulation of the side-chains identified here as $R_1$ and $R_2$ (which may be, independently, $R_3$, $R_6$, $R_9$, $R_{12}$, $R_{3S}$, $R_{6S}$, $R_{9S}$, $R_{12S}$, $R_{3C}$, $R_{6C}$, $R_{9C}$, $R_{12C}$, $R_{9S}$, or $R_{12S}$) chosen in a manner to afford the proper stack using the process of FIG. 24(a).

To arrange for the proper orientation and molecule, the 3,6,9,12-tetrasubstituted chrysene and 6,12-disubstituted chrysene are coupled into four configurations based on orientation, and then linked heterostructure are coupled in a sequence according to the specified codes of FIG. 5. FIG. 24(a) depicts a general procedure to produce a designed sequence. The heterodimeric structures are first formed as a set V(T), V(A), V(G), V(C) for DNA implementation and then assembled according to a target sequence S(n) such that when formed as V(n) after reaction the target sequence is the result. The sequence can be installed by binding the substrate at alternating segments at the 3 or 9 positions of the substrate using for example, two different phosphonamidite schemes. This configuration is presented in FIG. 24(b). At the conclusion of the directed assembly steps, the interactions at the 3 and 9 positions can be released and the overall structure reset to proceed with reaction cascade to form the target sequence.

Figure 25A:
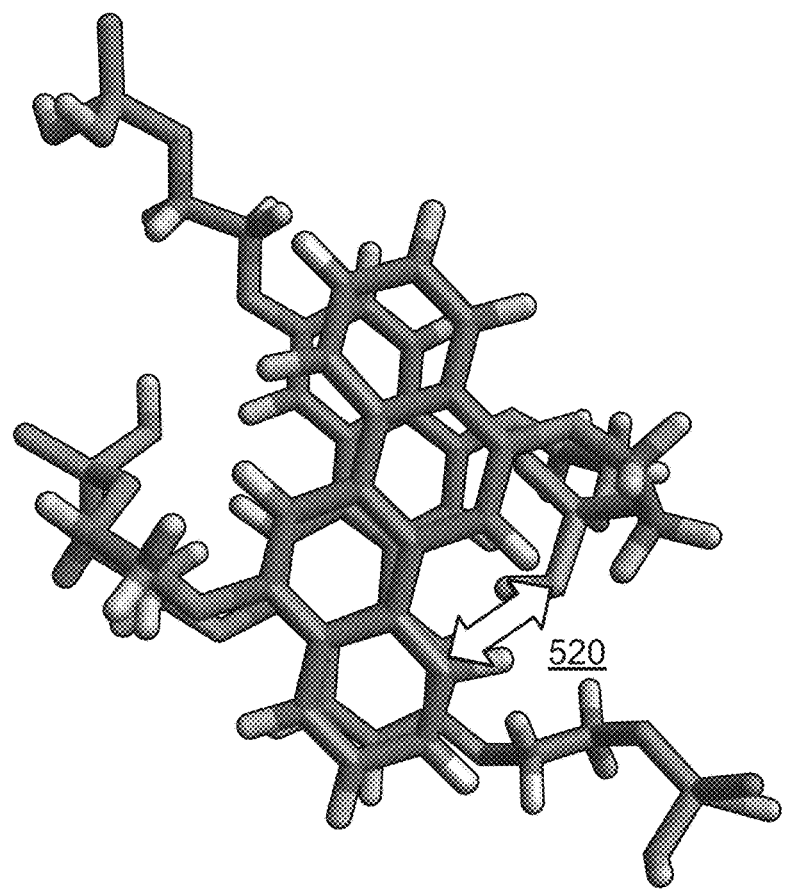
FIG. 25(a) illustrates a top-down view with arrow indicating the distance between interactive elements for an aligned configuration, which is associated with an adenine-thymine or thymine-adenine result.
Figure 25B:
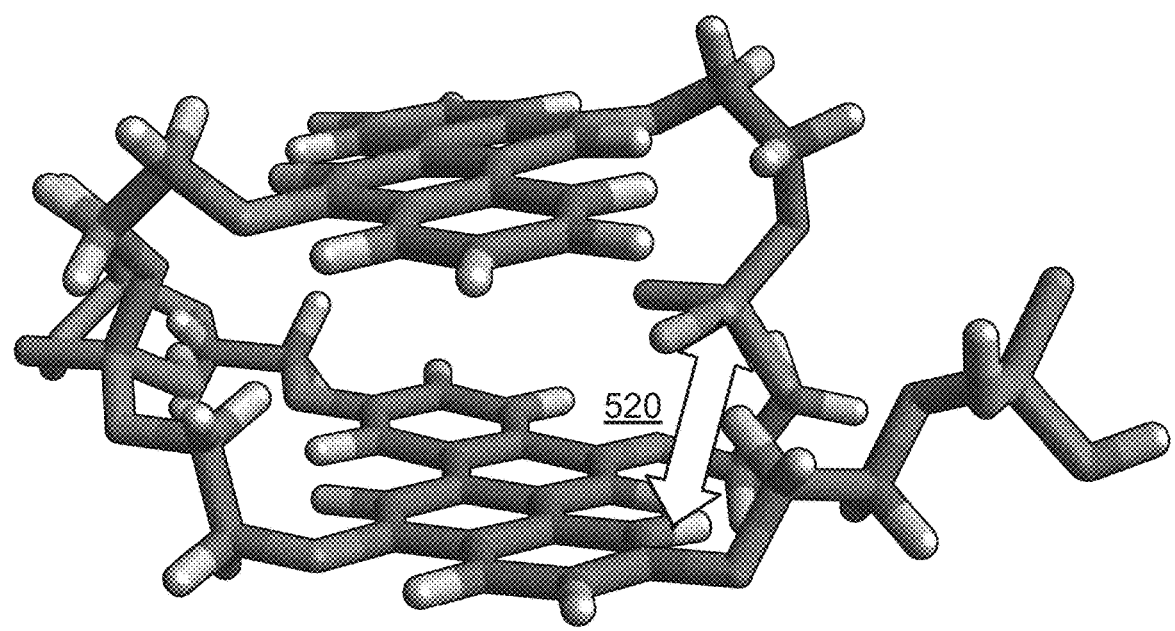
FIG. 25(b) shows a cross-section view of the aligned configuration.
Figure 25C:
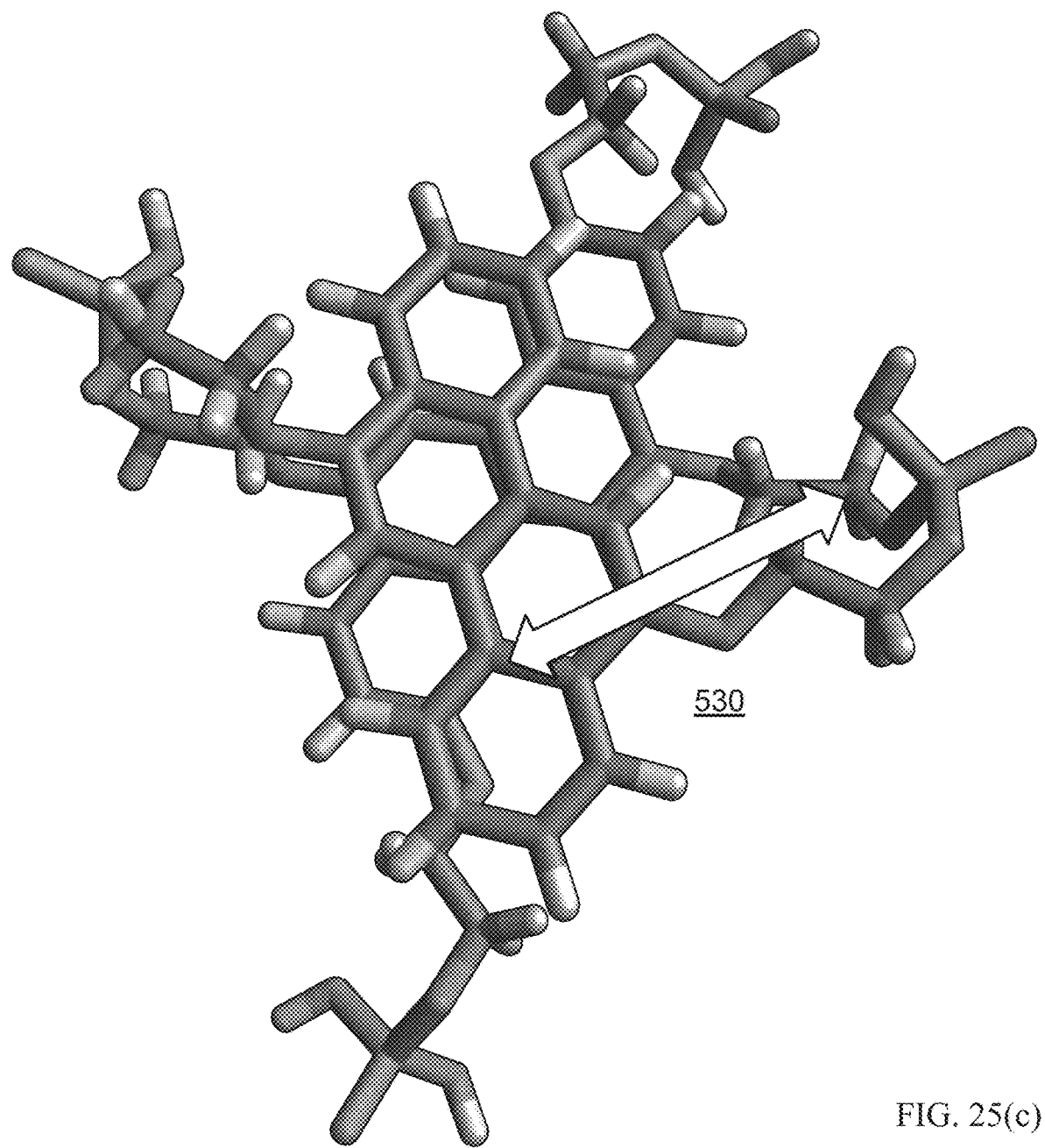
FIG. 25(c) illustrates a top-down view with arrow indicating the longer distance between the potentially interactive elements for an unaligned configuration, which is associated with the guanine-cytosine or cytosine-guanine result.
Figure 25D:
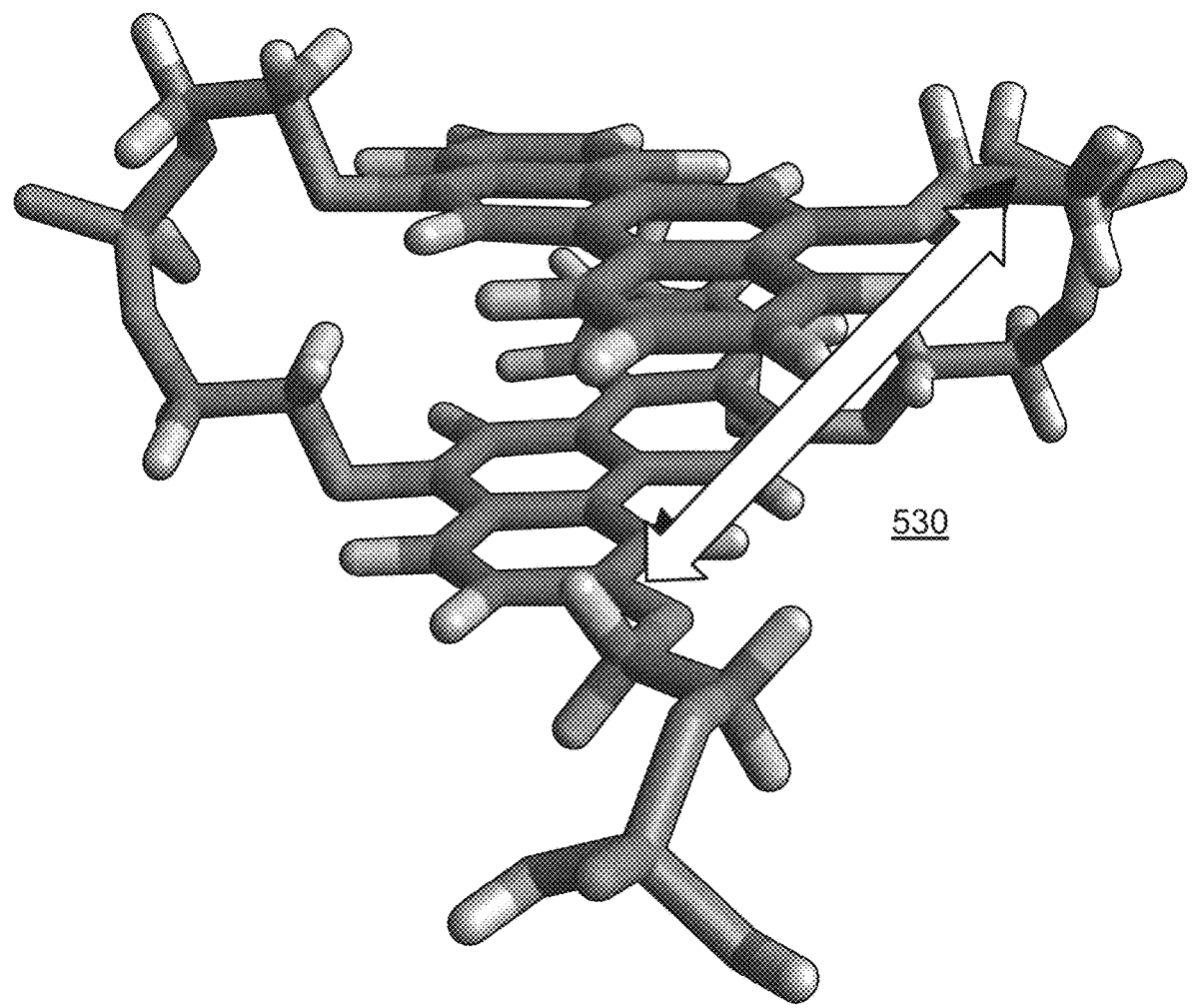
FIG. 25(d) shows a cross-section view of the unaligned configuration.

Example 20: Directed A-T/T-A or G-C/C-G Synthesis Through Alignment or Unalignment of the Catalyst and Substrate Ring Structures The intermolecular spatial organization of the ring structure of the substrate to catalyst determines whether the configuration results in three-hydrogen bonds as in cytosine-guanine or in two-hydrogen bonds as in thymine-adenine, of which its code was presented in FIG. 1(h). Consistent with that code, in FIG. 3 it was shown that the orientation of the side-group at the (6,12) position is consistent with the catalyst effectively providing the third hydrogen-bond instead of adenine during the formation of thymine. In FIG. 25, models are presented illustrating differences between aligned and unaligned configurations in the ability to form independent reaction vessels that interact with the formative transformation of the substrate to the final nucleotide pairing. In FIG. 25(a), a top-down view of the aligned configuration is shown. Arrow 510 indicates a distance of 3.8 Å from a carbon atom position, from which the unpaired ketone group of the thymine is positioned, and an oxygen atom position, from which the associated hydrogen bonding interacts with the ketone group of thymine during its synthesis. Arrow 510 represents a distance between interactive elements between substrate and catalyst in an aligned configuration, which may be associated with an adenine-thymine or thymine-adenine result. FIG. 25(b) shows the corresponding cross-section view of the aligned configuration and the associated measurement. This interactive distance is due to the alignment of both the substrate and catalyst of which the side-group at the 6 or 12 position can achieve the same orientation by both bending without opposition towards substrate. For comparison with the unaligned configuration, FIG. 25(c) illustrates a top-down view with arrow indicating the longer distance of 7.9 Å between the potentially interactive elements for an unaligned configuration, which is associated with the guanine-cytosine or cytosine-guanine result. FIG. 25(d) shows a cross-section view of the unaligned configuration. The unaligned configuration is not able to achieve a level of interaction between the substrate and catalyst because the side-groups are configured in opposing direction and the coupled side-group is not able to bend towards the substrate together, rather projecting outwards.

SPECIFIC EMBODIMENTS

Non limiting specific embodiments (SE) are provided below. Each embodiment is considered explicitly disclosed and may be combined with any other embodiment or disclosure.

SE 1. A compound having the structure:

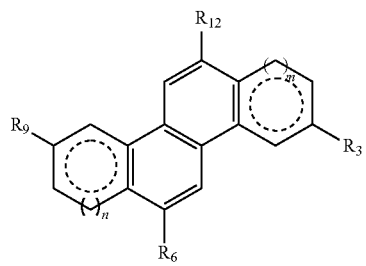

wherein the dotted circles independently indicate optional aromaticity, m and n are independently 0 (i.e., a bond) or 1, $R_3$, $R_6$, $R_9$, and $R_{12}$ are independently hydrogen, halogen (e.g., F, Cl, Br), hydroxylalkyl (e.g., $C_{1-6}$ hydroxyalkyl) optionally substituted with hydroxy or —COOH, hydroxylalkoxy (e.g., optionally unsubstituted $C_{1-6}$ hydroxyalkoxy such as hydroxylethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), —OCH$_2$COOH, —OCOCH$_2$OH, —O(CH$_2$)$_{1-6}$O(P(O)(OH)(O))$_{0-6}$(CH$_2$)$_{1-6}$OR, and at least one (e.g., at least two, at least three) of $R_3$, $R_6$, $R_9$, and $R_{12}$ is not hydrogen, or $R_6$ and/or $R_{12}$ may be optionally:

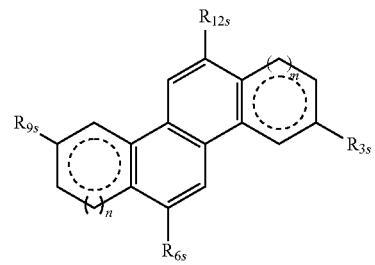

$R_{3s}$, $R_{6s}$, $R_{9s}$, and $R_{12s}$ are independently hydrogen, halogen (e.g., F, Cl, Br), hydroxylalkyl (e.g., $C_{1-6}$ hydroxyalkyl) optionally substituted with hydroxy or —COOH, hydroxylalkoxy (e.g., optionally unsubstituted $C_{1-6}$ hydroxyalkoxy such as hydroxylethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), —OCH$_2$COOH, —OCOCH$_2$OH, —O(CH$_2$)$_{1-6}$O(P(O)(OH)(O))$_{0-6}$(CH$_2$)$_{1-6}$OR; and R is independently at each occurrence hydrogen, alkyl (e.g., lower alkyl, $C_{1-6}$ alkyl), or acyl (e.g., $C_{1-20}$ acyl, $C_{1-6}$ acyl); or salts (e.g., alkali salts such as sodium salts or lithium salts, alkaline earth salts, quaternary ammonium salts, pyridinium salts) thereof.

SE 2. The compound according to SE 1, wherein $R_3$, $R_6$, $R_9$, and $R_{12}$ are independently hydrogen, hydroxylalkyl (e.g., $C_{1-6}$ hydroxyalkyl), hydroxylalkoxy (e.g., $C_{1-6}$ hydroxylalkoxy such as hydroxylethoxy), or hydroxylpolyethyleneoxy (e.g., —O(CH$_2$CH$_2$O)$_n$OH, where n is from 1 to 20 or from 1 to 8 or from 1 to 6).

SE 3. The compound according to SE 1 or 2, wherein $R_6$ and $R_{12}$ are not hydrogen.

SE 4. The compound according to any one of SEs 1-3, wherein $R_9$ is not hydrogen.

SE 5. The compound according to any one of SEs 1-4, wherein $R_3$ and $R_9$ are hydrogen.

SE 6. The compound according to any one of SEs 1-4, wherein $R_3$, $R_6$, $R_9$, and $R_{12}$ are hydroxylalkoxy (e.g., $C_{1-6}$ hydroxylalkoxy such as hydroxylethoxy).

SE 7. The compound according to any one of SEs 1-6, wherein $R_{3s}$ and $R_{9s}$ are hydrogen.

SE 8. The compound according to any one of SEs 1-7, wherein said compound is:

2,2'-(chrysene-6,12-diylbis(oxy))bis(ethan-1-ol), 2,2',2''-(chrysene-3,6,12-triyltris(oxy))tris(ethan-1-ol), 2,2',2'',2'''-(chrysene-3,6,9,12-tetrayltetrakis(oxy))tetrakis(ethan-1-ol), 6,12-dibromochrysene, 3,6,12-tribromochrysene, or 3,6,9,12-tetrabromochrysene.

SE 9. The compound according to any one of SEs 1-8, for use in forming a π-electron stacked sequence of molecules to contain a base two or base four information set, wherein each member of the information set is determined by the relative intramolecular spatial positioning of the aromatic rings.

SE 10. A system comprising a first compound comprising a first polycyclic aromatic ring structure and a second compound comprising a second polycyclic aromatic ring structure, wherein the π structures of the first and second polycyclic aromatic rings interact (e.g., overlap, bond) to form a heterodimer, wherein the interaction between the π structures can have at least two different orientations of the heterodimer (e.g., Aligned, Unaligned).

SE 11. The system according to SE 10, wherein the first compound has the structure:

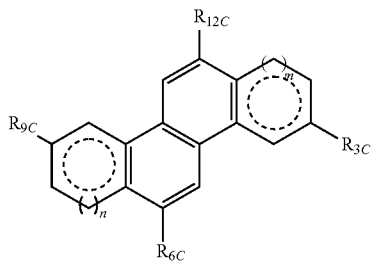

wherein the dotted circles independently indicate optional aromaticity, m and n are independently 0 (i.e., a bond) or 1, $R_{3C}$, $R_{6C}$, $R_{9C}$, and $R_{12C}$ are independently hydrogen, halogen (e.g., F, Cl, Br), hydroxylalkyl (e.g., $C_{1-6}$ hydroxyalkyl) optionally substituted with hydroxy or —COOH, hydroxylalkoxy (e.g., optionally unsubstituted $C_{1-6}$ hydroxyalkoxy such as hydroxylethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), —OCH$_2$COOH, —OCOCH$_2$OH, —O(CH$_2$)$_{1-6}$O(P(O)(OH)(O))$_{0-6}$(CH$_2$)$_{1-6}$OR, and at least three of $R_{3C}$, $R_{6C}$, $R_{9C}$, and $R_{12C}$ is not hydrogen, and R is independently at each occurrence hydrogen, alkyl (e.g., lower alkyl, $C_{1-6}$ alkyl), or acyl (e.g., $C_{1-20}$ acyl, $C_{1-6}$ acyl); or salts (e.g., alkali salts such as sodium salts or lithium salts, alkaline earth salts, quaternary ammonium salts, pyridinium salts) thereof, and the second compound has the structure:

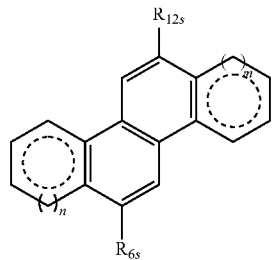

wherein $R_{3s}$, $R_{6s}$, $R_{9s}$, and $R_{12s}$ are independently hydroxylalkyl (e.g., $C_{1-6}$ hydroxyalkyl) optionally substituted with hydroxy or —COOH, hydroxylalkoxy (e.g., optionally unsubstituted $C_{1-6}$ hydroxyalkoxy such as hydroxylethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), oxalate (—OC(O)C(O)OH), —OCOCH$_2$OH, or —O(CH$_2$)$_{1-6}$(OP(O)(OH))$_{0-3}$O(CH$_2$)$_{1-6}$OR, and R is independently at each occurrence hydrogen, alkyl (e.g., lower alkyl, $C_{1-6}$ alkyl), or acyl (e.g., $C_{1-20}$ acyl, $C_{1-6}$ acyl); or salts (e.g., alkali salts such as sodium salts or lithium salts, alkaline earth salts, quaternary ammonium salts, pyridinium salts) thereof.

SE 12. The system according to SE 10 or 11, wherein the first compound is 2,2',2''-(chrysene-3,6,12-triyltris(oxy))tris(ethan-1-ol), or 2,2',2'',2'''-(chrysene-3,6,9,12-tetrayltetrakis(oxy))tetrakis(ethan-1-ol), and the second compound is 2,2'-(chrysene-6,12-diylbis(oxy))bis(ethan-1-ol).

SE 13. The system according to any one of SEs 10-12, wherein the heterodimer is a first heterodimer and the system further comprises a second heterodimer, wherein the π structures of the first and second heterodimer interact (e.g., overlap, bond) such that the interaction between the π structures of the first and second heterodimers can have at least four different orientations between the heterodimers (e.g., Aligned, Forward; Aligned, Backward; Unaligned, Forward; and Unaligned, Backward).

SE 14. A method of creating the information for a base two or base four code sequence comprising orienting a first molecule comprising a first polycyclic aromatic ring structure with a second molecule comprising a second polycyclic aromatic ring structure such that π structures of the first and second polycyclic aromatic rings interact (e.g., overlap, bond) to form a heterodimer, wherein the interaction between the π structures can have at least two different orientations of the heterodimer; and each member of the base two or base four code sequence is created by one of the at least two different orientations of the heterodimer.

SE 15. The method according to SE 14, wherein the first and second polycyclic aromatic ring structure each comprise four planar fused aromatic rings and no plane of symmetry perpendicular to the planar fused aromatic rings (e.g., $C_{2h}$ symmetry), the first polycyclic aromatic ring structure being substantially parallel to the second polycyclic aromatic ring structure in the heterodimer, and one of the at least two different orientations of the heterodimer, if viewed from a plane parallel to the planar fused aromatic rings, is a) the first molecule oriented with two rings above and to the left and two rings at the bottom and to the right, and the second molecule oriented with two rings at the top and to the right and two rings toward the bottom and to the left (e.g., G-C, C-G);

b) the first molecule oriented with two rings at the top and to the left and two rings toward the bottom and to the right, and the second molecule oriented with two rings at the top and to the left and two rings toward the bottom and to the right (e.g., U-A, A-U).

SE 16. The method according to SE 14 or 15, wherein the first molecule is 2,2'-(chrysene-6,12-diylbis(oxy))bis(ethan-1-ol) or analog thereof and the other molecule is 2,2',2'',2'''-(chrysene-3,6,9,12-tetrayltetrakis(oxy))tetrakis(ethan-1-ol) or analog thereof.

SE 17. The method according to any one of SEs 14-16, wherein a base four code sequence is created by the relative orientations of two adjacent heterodimers.

SE 18. The method according to SE 17, wherein the first molecule is 2,2'-(chrysene-6,12-diylbis(oxy))bis(ethan-1-ol) or analog and the second molecule is 2,2',2''-(chrysene-3,6,12-triyltris(oxy))tris(ethan-1-ol) or analog, and the positional orientation of the 3' hydroxyethanoxy sidechain of the second molecules sets the base four code and the relative orientation of the adjacent heterodimer (e.g., the 5' direction the next heterodimer in a DNA or RNA sequence).

SE 19. A method of producing a base four molecule by inducing reaction from a heterodimer or from an intercalated or conjugated set of heterodimers each formed by π stacking of one (e.g., when $R_6$ and $R_{12}$ are conjugated to one another), two compounds according to any one of SEs 1-9, or the system of any one of SEs 10-13, wherein the reaction comprises at least one of:
a) oxidative cleavage,
b) formation of carbon carbon rings (e.g., for closure of sugar-rings),
c) nitrogen insertions,
d) formation of N—C bonds for closure of inner rings,
e) oxygen and/or nitrogen side group modifications, and
f) catalyst-substrate separations.

SE 20. The method according to SE 19, the heterodimer is formed from orienting 2,2'-(chrysene-6,12-diylbis(oxy))bis(ethan-1-ol) or analog thereof with 2,2',2'',2'''-(chrysene-3,6,9,12-tetrayltetrakis(oxy))tetrakis(ethan-1-ol) or analog thereof.

SE 21. The method according to SE 19, wherein said set of intercalated heterodimers is formed from orienting 2,2',2''-(chrysene-3,6,12-triyltris(oxy))tris(ethan-1-ol) or analog thereof with 2,2'-(chrysene-6,12-diylbis(oxy))bis(ethan-1-ol) or analog thereof to form a first heterodimer;
orienting 2,2'-(chrysene-6,12-diylbis(oxy))bis(ethan-1-ol) or analog thereof with 2,2',2'',2'''-(chrysene-3,6,9,12-tetrayltetrakis(oxy))tetrakis(ethan-1-ol) or analog thereof to form a second heterodimer, and
inducing π-stacking between the first and second heterodimer.

SE 22. The method according to any one of SEs 20-21, wherein said base four molecule is DNA or RNA or hybrid DNA/RNA,
the intercalated set of heterodimers is formed by pi stacking a tri or tetra substituted aromatic ring from one heterodimer with a di substituted aromatic ring from the adjacent heterodimer, and
the reaction is initiated by oxidative cleavage of the tri or tetra substituted aromatic ring system of two adjacent heterodimers, and reaction proceed via a reaction cascade to produce at least two nucleotide pairs having a catalyst comprising di substituted aromatic polycyclic ring system intercalated therebetween.

SE 23. The method according to SE 22, wherein the base four molecule is DNA and at least one member of the two nucleotide pairs is thymine, wherein the DNA is formed through a rotation of the nucleotide pair such that the motion of the methyl group of thymine ejects the catalyst from between the two nucleotide pairs.

SE 24. The method according to SE 22, wherein the substituent at the 3 or 12 position of each heterodimer is phosphorylated and conjugated to the adjacent heterodimer via the 3 or 12 position via a sugar ring.

SE 25. The method according to SE 24, wherein said base four molecule is RNA formed through the hydroxylation of the 2' carbon of the sugar ring which results in separation of the nucleotide from the catalyst by strand separation.

SE 26. The method according to any one of SEs 19-25, wherein each heterodimer of the intercalated set of heterodimers is an independent reaction vessel, wherein each reaction vessel may have four possible configurations (relative from one of the outermost heterodimers) to form a base four code relative to an initiation sequence established by a first heterodimer (e.g., an initiator/catalyst heterodimer), and oxidative cleavage induces a cascade reaction that produces nucleotide pairs in each reaction vessel dependent on the configuration of the reaction vessel and the initiation sequence, in which A-U at 5' is (e.g., Forward, Forward), G-C is (e.g., Backward, Forward), U-A is (e.g., Backward, Backward) and C-G is (e.g., Forward,Backward) for RNA positioning of catalyst and substrate in the sequence, and the opposite code holds for DNA in which T-A is (e.g., Forward, Forward), C-G is (e.g., Backward,Forward), A-T is (e.g., Backward,Backward) and G-C is (e.g., Forward,Backward).

SE 27. The method according to SE 26, wherein the reaction vessels comprise a set of at least four possible configurations which thereby form a base four code in which DNA and RNA represent a composite hybrid double strand with DNA nucleotides on one strand and RNA nucleotides on the other strand.

SE 28. The method according to any one of SEs 19-27 wherein the two compounds are a substrate π stacked with a catalyst, wherein in the substrate, $R_3$, $R_6$, $R_9$, and $R_{12}$ are each not hydrogen and, in the catalyst, $R_3$ and $R_9$ are hydrogen,
wherein the catalyst is phosphorylated at $R_6$ and $R_{12}$ and the catalyst separated from the substrate forms a phospholipid bilayer following the reaction and/or
the substrate is phosphorylated at the $R_3$, $R_6$, $R_9$, and $R_{12}$ which form a nucleic acid backbone following the reaction.

SE 29. A polymer comprising the monomer:

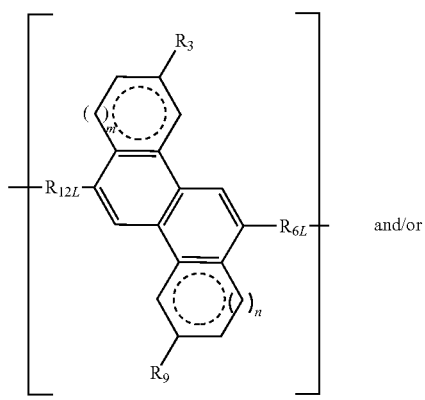 and/or

-continued

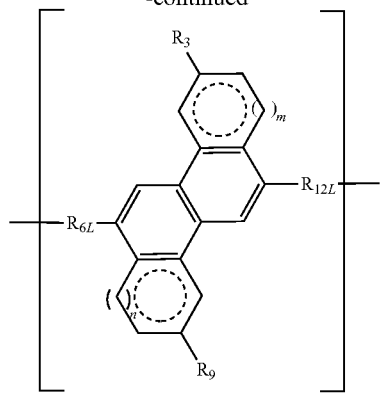

wherein the dotted circle indicates optional aromaticity,
m and n are independently 0 (i.e., a bond) or 1,
p and q are independently 1-6, $R_{6L}$, and $R_{12L}$ are independently —O(CH$_2$)$_{1-6}$O—, —OCH$_2$COO—, —OCOCH$_2$O—, —O(CH$_2$)$_{1-6}$OP(O)(OH)O(CH$_2$)$_{1-6}$O—, $R_3$ and $R_9$ are independently hydrogen, halogen (e.g., F, Cl, Br), hydroxylalkyl (e.g., C$_{1-6}$ hydroxyalkyl) optionally substituted with hydroxy or —COOH, hydroxylalkoxy (e.g., optionally unsubstituted C$_{1-6}$ hydroxyalkoxy such as hydroxylethoxy or hydroxyethenoxy or hydroxyethynoxy) optionally substituted with hydroxy or —COOH, hydroxylpolyethyleneoxy (e.g., —O(CH$_2$CH$_2$O)$_n$OH, where n is from 1 to 20 or from 1 to 8 or from 1 to 6), —OCH$_2$COOH, —OCOCH$_2$OH, —O(CH$_2$)$_{1-6}$O(P(O)(OH)(O))$_{0-6}$ (CH$_2$)$_{1-6}$OR; and R is independently at each occurrence hydrogen, alkyl (e.g., lower alkyl, C$_{1-6}$ alkyl), or acyl (e.g., C$_{1-20}$ acyl, C$_{1-6}$ acyl); or salts (e.g., alkali salts such as sodium salts or lithium salts, alkaline earth salts, quaternary ammonium salts, pyridinium salts) thereof.

SE 30. The polymer according to SE 29 wherein the polymer is capped by a tri substituted polycyclic aromatic (e.g., 6, 9, 12 substituted chrysene), wherein the 9 position is conjugated to the polymerized monomer (e.g., to form the two indicated orientations).

SE 31. The polymer according to SE 29 or 30, wherein the polymer comprises one or more monomers having the structure:

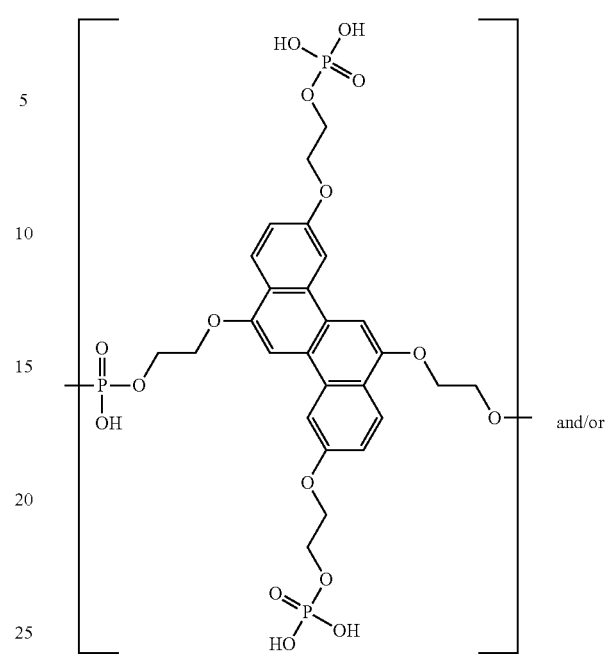

and/or

SE 32. The polymer according to SE 29 or 30, wherein the polymer comprises one or more monomers having the structure:

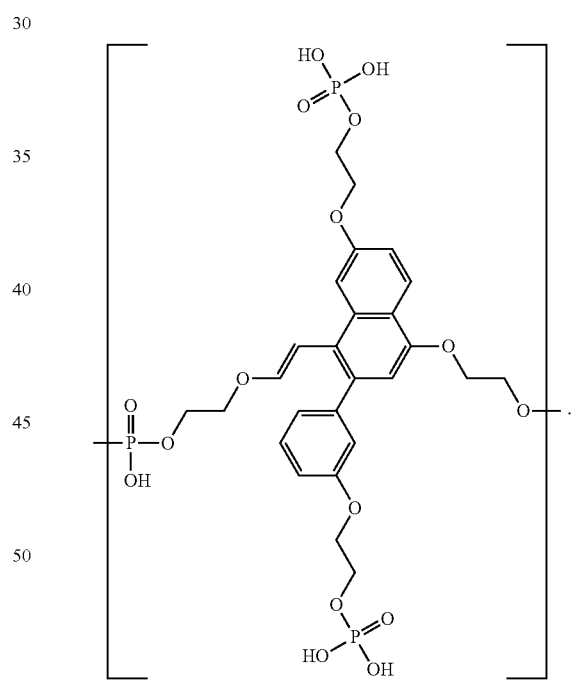

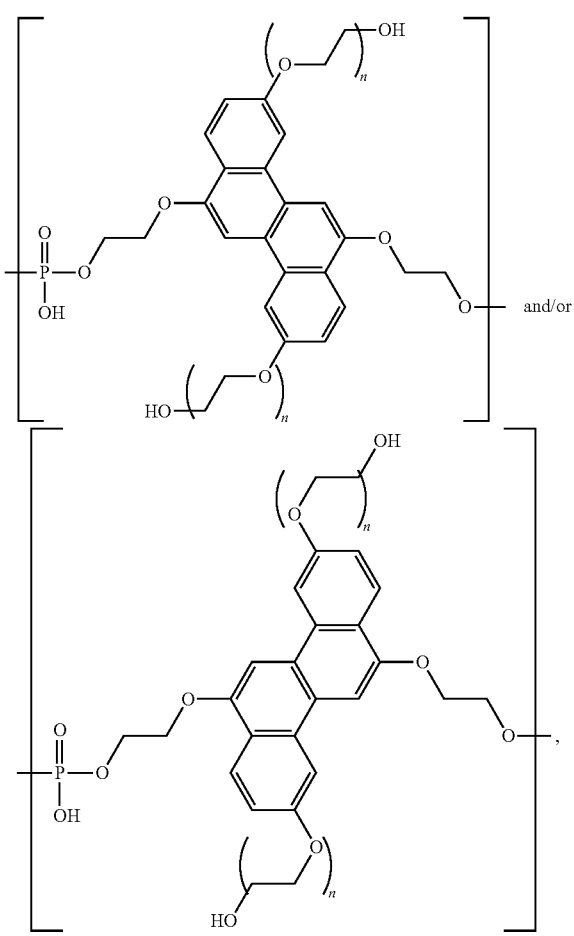

wherein n is independently selected at each occurrence from 1-6.

SE 33. A compound having the structure:

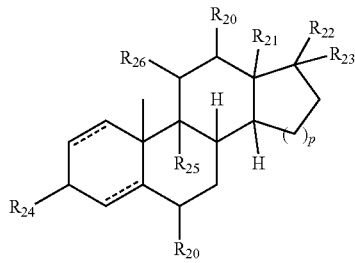

wherein the dashed lines represent optionally double bonds, and at least one of the dashed bonds is a double bond; p is 0 (i.e., it is a bond) or 1;

R$_{20}$ is independently at each occurrence hydrogen, hydroxylalkoxy (e.g., C$_{1-6}$ hydroxyalkoxy such as —OCH$_2$CH$_2$OH or —OCH$_2$CH$_2$CH$_2$OH), or —OCH$_2$CH$_2$OP(O)OHOR; wherein at least one R$_{20}$ group is not hydrogen;

R$_{21}$ is hydrogen, methyl or —OH;

R$_{22}$ is hydrogen, —OH, or —C(O)CH$_2$OH;

R$_{23}$ is hydrogen or —OH;

R$_{24}$ is =O (there is no geminal hydrogen on the carbon) or hydroxylalkoxy (e.g., C$_{1-6}$ hydroxyalkoxy such as —OCH$_2$CH$_2$OH or —OCH$_2$CH$_2$CH$_2$OH);

R$_{25}$ is hydrogen or fluorine;

R$_{26}$ is hydrogen or —OH, and

R is alkyl (e.g., C$_{1-4}$ alkyl) optionally substituted with —OH; or pharmaceutically acceptable salts thereof.

SE 34. The compound according to SE 33, wherein said compound has the structure:

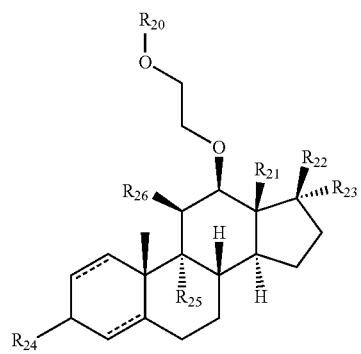

SE 35. The compound according to SE 33, wherein said compound has the structure:

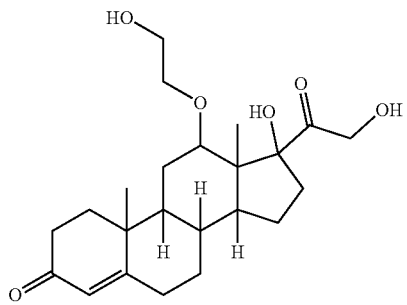

17-hydroxy-17-(2-hydroxyacetyl)-12-(2-hydroxy-ethoxy)-10,13-dimethyl-1,2,6,7,8,9,10,11,12,13,14,15,16,17-tetradecahydro-3H-cyclopenta[a]phenanthren-3-one SE 36. The compound according to SE 33, wherein said compound has the structure:

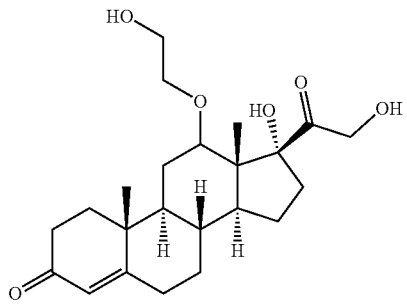

(8R,9S,10R,13R,14S,17R)-17-hydroxy-17-(2-hy-
droxyacetyl)-12-(2-hydroxyethoxy)-10,13-dimethyl-
1,2,6,7,8,9,10,11,12,13,14,15,16,17-tetradecahydro-
3H-cyclopenta[a]phenanthren-3-one SE 37. The compound according to SE 33, wherein said compound has the structure:

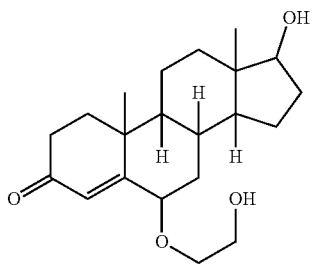

17-hydroxy-6-(2-hydroxyethoxy)-10,13-dimethyl-1,
2,6,7,8,9,10,11,12,13,14,15,16,17-tetradecahydro-
3H-cyclopenta[a]phenanthren-3-one SE 38. The compound according to SE 33, wherein said compound has the structure:

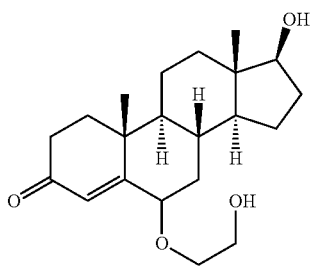

(8R,9S,10R,13S,14S,17S)-17-hydroxy-6-(2-hy-
droxyethoxy)-10,13-dimethyl-1,2,6,7,8,9,10,11,12,
13,14,15,16,17-tetradecahydro-3H-cyclopenta[a]
phenanthren-3-one SE 38A. A compound having the structure:

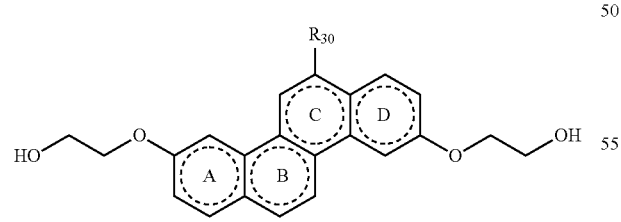

wherein rings A, B, C, and D are each independently saturated or unsaturated (e.g., each are optionally aromatic), and $R_{30}$ is hydrogen or —OCH$_2$CH$_2$OH.

SE 38AA. The compound according to SE 38A, wherein the number of double bonds in at least one of Rings A, B, C, or D is decreased as compared to the aromatic version thereof.

SE 38AB. The compound according to SE 38AB having the structure:

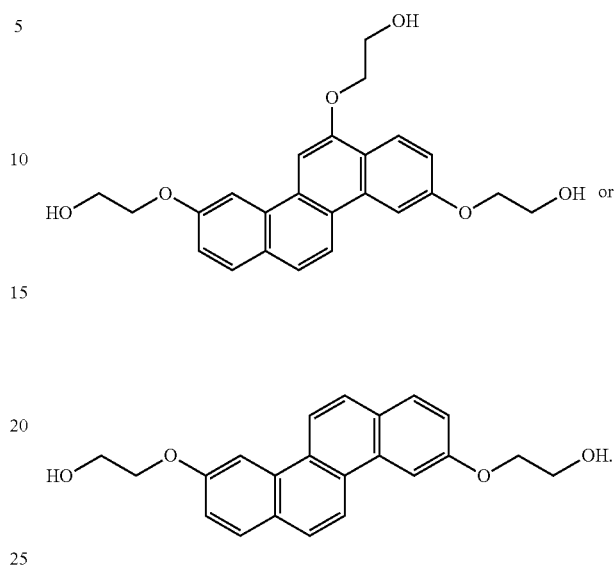

SE 39. A compound having the structure:

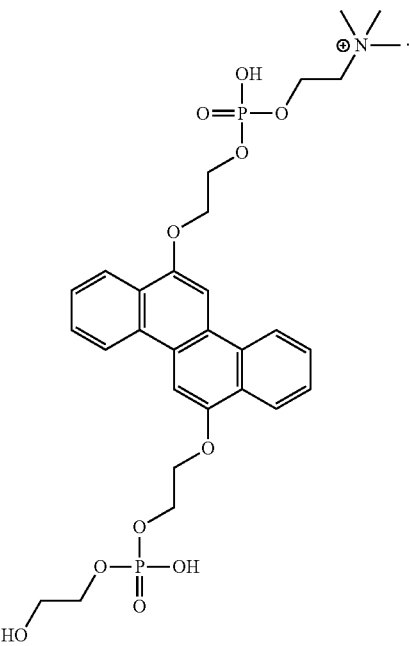 [SMILES: C[N+](C)(C)CCOP(=O)(O)OCCOc1cc2c3ccccc3c(OCCOP(=O)(O)OCCO)cc2c2ccccc12]

SE 40. A compound having the structure:

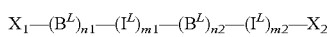

wherein n1 and n2 are independently 0-15;

m1 and m2 are independently at each occurrence 0-15 and at least one of m1 or m2 is greater than 1;

$B^L$ has the structure:
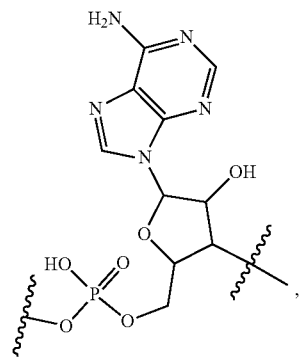
(A$^L$)
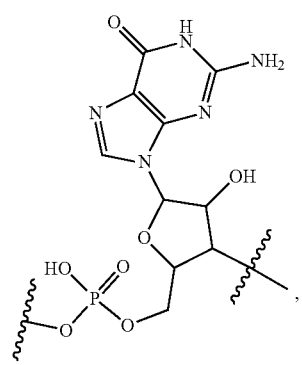
(G$^L$)
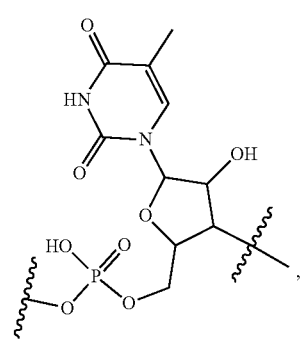
(T$^L$)
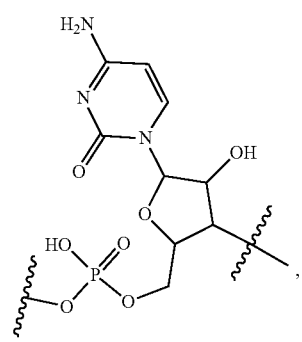
(C$^L$)
-continued
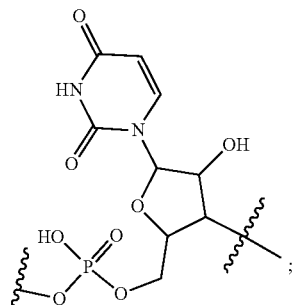
(U$^L$)
$I^L$ has the structure:
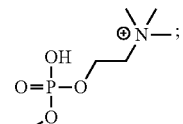
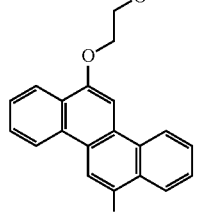
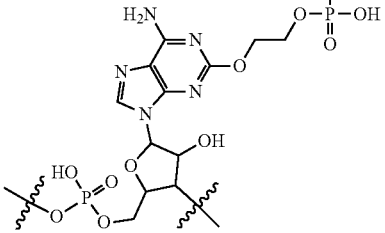
$X_1$ has the structure:
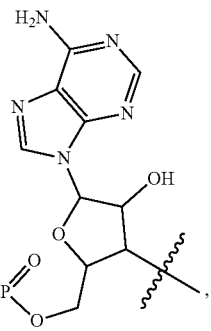
(A$_1$)

(G₁)
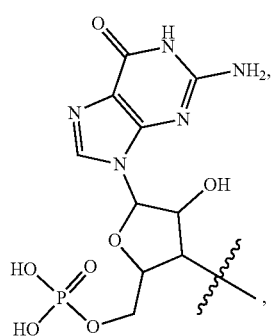
(T₁)
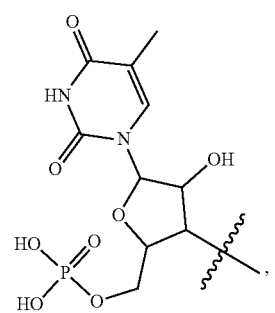
(C₁)
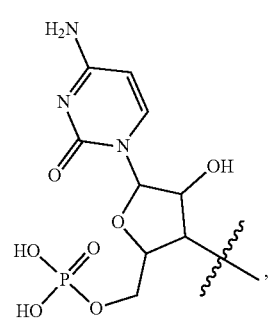
(U₁)
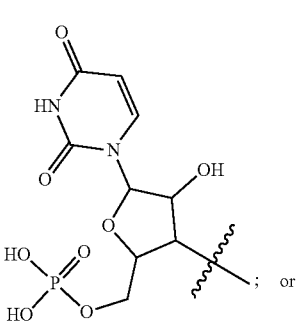
; or
(I₁)
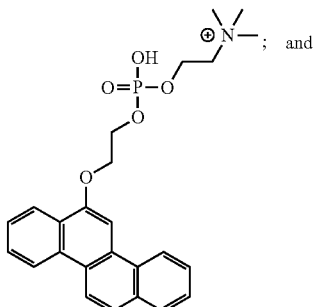
; and
$X_2$ has the structure:
(A₂)
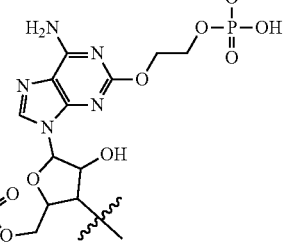
(G₂)
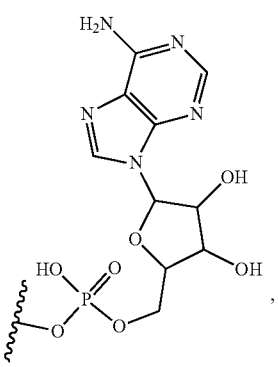

(T₂)
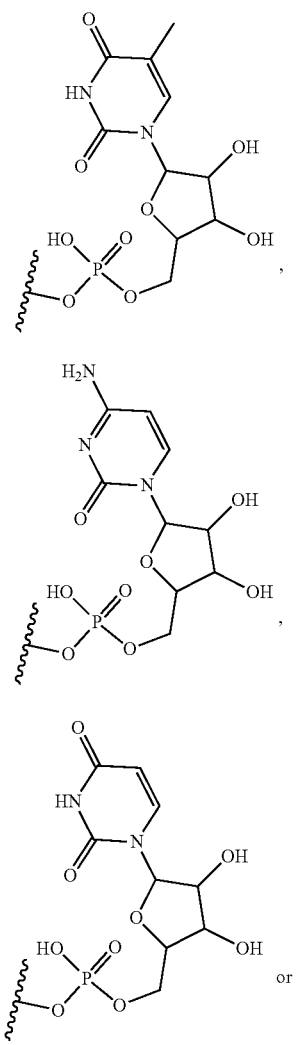
(C₂)
(U₂)
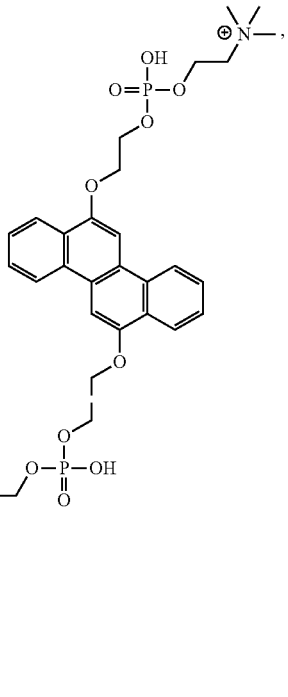
where the wavy bond indicates conjugation to the adjacent moiety;
or pharmaceutically acceptable salts thereof.
SE 41. The compound according to SE 40, wherein the compound has the structure ($I_1$—($C^L$)$_2$—$I_2$):
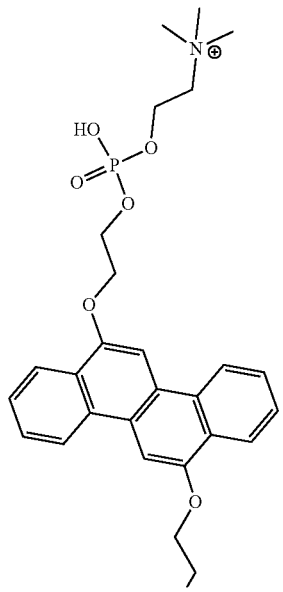
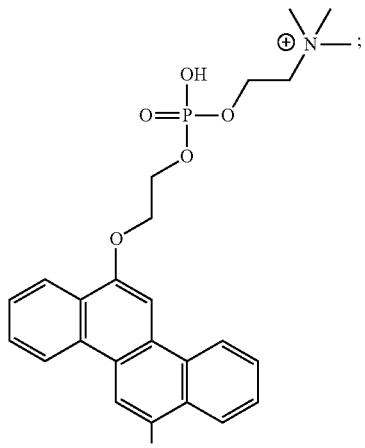

-continued

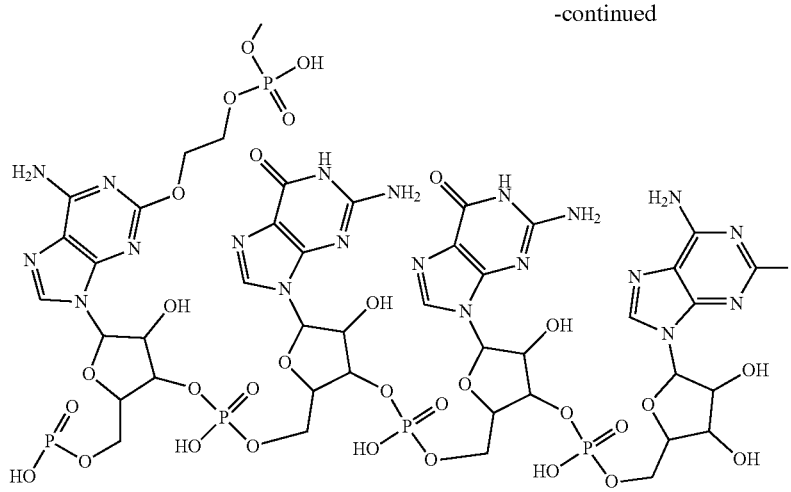

42. The compound according to SE 40, wherein m1+m2+n1+n2 is less than or equal to 16.

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications and variances which fall within the scope of the appended claims.

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

The invention claimed is:

1. A compound having the structure:

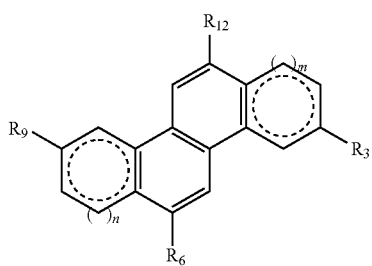

wherein the dotted circles independently indicate optional aromaticity, m and n are independently 0 or 1, $R_3$, $R_6$, $R_9$, and $R_{12}$ are independently hydrogen, hydroxyalkyl optionally substituted with hydroxy or —COOH, saturated $C_{2-6}$ hydroxyalkoxy optionally substituted with hydroxy or —COOH, hydroxypolyethyleneoxy, —OCH$_2$COOH, —OCOCH$_2$OH, —O(CH$_2$)$_{1-6}$O(P(O)(OH)(O))$_{0-6}$(CH$_2$)$_{0-6}$OR, and at least one of $R_3$, $R_6$, $R_9$, and $R_{12}$ is not hydrogen, or $R_6$ and/or $R_{12}$ may be optionally:

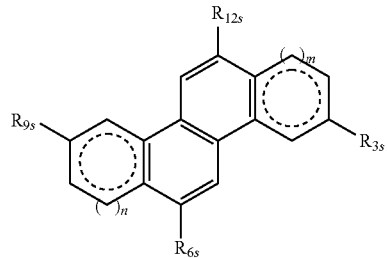

$R_{3s}$, $R_{6s}$, $R_{9s}$, and $R_{12s}$ are independently hydrogen, halogen hydroxyalkyl optionally substituted with hydroxy or —COOH, hydroxyalkoxy optionally substituted with hydroxy or —COOH, hydroxypolyethyleneoxy, —OCH$_2$COOH, —OCOCH$_2$OH, —O(CH$_2$)$_{1-6}$O(P(O)(OH)(O))$_{0-6}$ (CH$_2$)$_{1-6}$OR; and R is independently at each occurrence hydrogen, alkyl, or acyl; or salts thereof.

2. The compound according to claim 1, wherein $R_3$, $R_6$, $R_9$, and $R_{12}$ are independently hydrogen, hydroxyalkyl, hydroxyethoxy, or hydroxypolyethyleneoxy.

3. The compound according to claim 1, wherein $R_6$ and $R_{12}$ are not hydrogen.

4. The compound according to claim 1, wherein $R_9$ is not hydrogen.

5. The compound according to claim 1, wherein $R_3$ and $R_9$ are hydrogen.

6. The compound according to claim 1, wherein $R_3$, $R_6$, $R_9$, and $R_{12}$ are saturated $C_{2-6}$ hydroxyalkoxy.

7. The compound according to claim 1, wherein $R_{3s}$ and $R_{9s}$ are hydrogen.

8. The compound according to claim 1, wherein said compound is:
2,2'-(chrysene-6,12-diylbis(oxy))bis(ethan-1-ol),
2,2',2''-(chrysene-3,6,12-triyltris(oxy))tris(ethan-1-ol), or
2,2',2'',2'''-(chrysene-3,6,9,12-tetrayltetrakis(oxy))tetrakis(ethan-1-ol).

9. The compound according to claim 1, for use in forming a π-electron stacked sequence of molecules to contain a base two or base four information set, wherein each member of the information set is determined by the relative intramolecular spatial positioning of the aromatic rings.

* * * * *